(12) United States Patent
Standring et al.

(10) Patent No.: US 7,928,086 B2
(45) Date of Patent: Apr. 19, 2011

(54) β-L-2'-DEOXYNUCLEOSIDES FOR THE TREATMENT OF RESISTANT HBV STRAINS AND COMBINATION THERAPIES

(75) Inventors: David Standring, Milton, MA (US); Jean-Pierre Sommadossi, Cambridge, MA (US); April L. Patty, Medford, MA (US); Maria Seifer, Clinton, MA (US)

(73) Assignee: Novartis AG, Basel (CH)

( * ) Notice: Subject to any disclaimer, the term of this patent is extended or adjusted under 35 U.S.C. 154(b) by 1121 days.

(21) Appl. No.: 11/651,353

(22) Filed: Jan. 9, 2007

(65) Prior Publication Data

US 2008/0182814 A1 Jul. 31, 2008

Related U.S. Application Data

(63) Continuation of application No. 10/662,641, filed on Sep. 15, 2003, now Pat. No. 7,186,700.

(60) Provisional application No. 60/410,675, filed on Sep. 13, 2002.

(51) Int. Cl.
*A01N 43/04* (2006.01)
*A61K 31/70* (2006.01)
*A61K 31/715* (2006.01)

(52) U.S. Cl. .............. 514/49; 514/42; 514/43; 514/50; 514/51

(58) Field of Classification Search .................. None
See application file for complete search history.

(56) References Cited

U.S. PATENT DOCUMENTS

| | | | |
|---|---|---|---|
| 4,916,122 A | 4/1990 | Chu et al. | |
| 4,957,924 A | 9/1990 | Beauchamp | |
| 5,190,926 A | 3/1993 | Chu et al. | |
| 5,194,654 A | 3/1993 | Hostetler et al. | |
| 5,223,263 A | 6/1993 | Hostetler et al. | |
| 5,256,641 A | 10/1993 | Yatvin et al. | |
| 5,411,947 A | 5/1995 | Hostetler et al. | |
| 5,463,092 A | 10/1995 | Hostetler et al. | |
| 5,532,246 A | 7/1996 | Belleau et al. | |
| 5,539,116 A | 7/1996 | Liotta et al. | |
| 5,543,389 A | 8/1996 | Yatvin et al. | |
| 5,543,390 A | 8/1996 | Yatvin et al. | |
| 5,543,391 A | 8/1996 | Yatvin et al. | |
| 5,554,728 A | 9/1996 | Basava et al. | |
| 5,559,101 A | 9/1996 | Weis et al. | |
| 5,565,438 A | 10/1996 | Chu et al. | |
| 5,567,688 A | 10/1996 | Chu et al. | |
| 5,587,362 A | 12/1996 | Chu et al. | |
| 5,939,402 A | 8/1999 | Weis et al. | |
| 6,025,335 A | 2/2000 | Weis et al. | |
| 6,194,391 B1 | 2/2001 | Schinazi et al. | |
| 6,242,187 B1 | 6/2001 | Capon et al. | |
| 6,245,749 B1 | 6/2001 | Schinazi et al. | |
| 6,265,181 B1 | 7/2001 | Dong et al. | |
| 6,297,222 B1 | 10/2001 | von Borstel et al. | |
| 6,395,716 B1 | 5/2002 | Gosselin et al. | |
| 6,444,652 B1 | 9/2002 | Gosselin et al. | |
| 6,566,344 B1 | 5/2003 | Gosselin et al. | |
| 6,569,837 B1 | 5/2003 | Gosselin et al. | |
| 2003/0083306 A1 | 5/2003 | Imbach et al. | |

FOREIGN PATENT DOCUMENTS

| | | |
|---|---|---|
| EP | 0350287 | 1/1990 |
| EP | 0352248 | 1/1990 |
| EP | 0494119 | 7/1992 |
| EP | 0355131 | 9/1996 |
| JP | 06-293645 | 10/1994 |
| WO | WO 89/02733 | 4/1989 |
| WO | WO 89/03838 | 5/1989 |
| WO | WO 90/00555 | 1/1990 |
| WO | WO 91/16920 | 11/1991 |
| WO | WO 91/18914 | 12/1991 |
| WO | WO 91/19721 | 12/1991 |
| WO | WO 92/08727 | 5/1992 |
| WO | WO 92/15308 | 9/1992 |
| WO | WO 92/18517 | 10/1992 |
| WO | WO 93/00910 | 1/1993 |
| WO | WO 94/20523 | 9/1994 |
| WO | WO 94/26273 | 11/1994 |
| WO | WO 95/07086 | 3/1995 |
| WO | WO 96/11204 | 4/1996 |
| WO | WO 96/13512 | 5/1996 |
| WO | WO 96/15132 | 5/1996 |
| WO | WO 96/40164 | 12/1996 |
| WO | WO 00/09531 | 2/2000 |
| WO | WO 01/04358 | 1/2001 |
| WO | WO 01/96353 | 12/2001 |
| WO | WO 02/00613 | 1/2002 |

OTHER PUBLICATIONS

Delaney et al., J. Hepatology, 2002, 36(suppl 1): 89, abstract 309.*
Ahmed, S.N.S., et al., "Early Detection of Viral Resistance by Determination of Hepatitis B Virus Polymerase Mutations in Patients Treated by Lamivudine for Chronic Hepatitis B," *Hepatology*, 32(5):1078-1088 (Nov. 2000).
Allen, M.I., et al., "Identification and characterization of mutations in hepatitis B virus resistant to lamivudine," *Hepatology*, 27(6):1670-1677 (Jun. 1998).
Arner, E.S.J., et al., "Mammalian Deoxyribonucleoside Kinases," *Pharm. Ther.*, 67(2), 155-186 (1995).
Berk, A.J., et al., "A Genetically Distinct Tymidine Kinase in Mammalian Mitochondria," *J Biol Chem*, 248(8):2722-2729 (1973).

(Continued)

*Primary Examiner* — Traviss C McIntosh, III
(74) *Attorney, Agent, or Firm* — Ann R. Pokalsky, Esq.; Dilworth & Barrese, LLP

(57) ABSTRACT

It has been discovered that β-L-2'-deoxynucleosides are active against drug-resistant hepatitis B virus with mutations. A method for treating lamivudine resistant HBV (M552V) in a host is provided that includes administering a β-L-2'-deoxynucleoside or its pharmaceutically acceptable salt, ester or prodrug. In addition, a method for preventing lamivudine resistant HBV (M552V) mutation from occurring in a naïve host is provided that includes administering a β-L-2'-deoxynucleoside or its pharmaceutically acceptable salt, ester or prodrug. A method for preventing and/or suppressing the emergence of the HBV double mutant (L528M/M552V) in a host is also provided that includes administering a β-L-2'-deoxynucleoside or its pharmaceutically acceptable salt, ester or prodrug.

32 Claims, 17 Drawing Sheets

OTHER PUBLICATIONS

Bestwick, R.K., et al., "Selective Expansion of Mitochondrial Nucleoside Triphosphate Pools in Antimetabolite-treated HeLa Cells," *J. Biol. Chem.*, 257(16):9300-9304 (1982).

Bloch, A., et al., "The Role of the 5'-Hydroxyl Group of Adenosine in Determining Substrate Specificity for Adenosine Deaminase," *J. Med. Chem.*, 10(5):908-12 (Sep. 1967).

Bridges, E.G., et al., "Characterization of a dCTP Transport Activity Reconstituted from Human Mitochondria," *J. Biol. Chem.*, 274(8):4620-4625 (Feb. 19, 1999).

Bridges, E.G., et al., "Identification of a novel mitochondrial dNTP carrier and its interaction with anti-HIV nucleoside analogs," *Proc. Am. Assoc. Cancer Res.*, 38:62, Abstract 414 (Mar. 1997).

Bridges, E.G., et al., "Inhibition of Mammalian DNA Polymerase-Associated 3' to 5' Exonuclease Activity by 5'-Monophosphates of 3'-Azido-3'-Deoxythymine and 3'-Amino-3'-Deoxythymidine," *Biochemical Pharmacology*, 45(8):1571-1576 (1993).

Bryant, M.L., et al., "Antiviral L-Nucleosides Specific for Hepatitis B Virus Infection," *Antimicrobial Agents and Chemotherapy*, 45(1):229-235 (Jan. 2001).

Chang, C.N., et al., "Deoxycytidine Deaminase-resistant Stereoisomer is the Active Form of (−)-2',3'-thiacytidine in the Inhibition of Hepatitis B Virus Replication," *Journal of Biological Chemistry*, 267(20):13938-13942 (Jul. 15, 1992).

Chang, C.-N., et al., "Biochemical Pharmacology of (+)- and (−)-2'3'-Dideoxy-3'-thiacytidine as Anti-hepatitis B Virus Agents," *J Biol Chem*, 267(31), 22414-22420 (Nov. 5, 1992).

Chariot, P., et al., "Zidovudine-induced mitochondrial disorder with massive liver steatosis myopathy, lactic acidosis, and mitochondrial DNA depletion," *J. Hepatology*, 30:156-160 (1999).

Chayama, K., et al., Emergence and takeover of YMD motif mutant hepatitis B virus during long-term lamivudine therapy and re-takeover by wild type after cessation of therapy, *Hepatology*, 27(6):1711-1716 (Jun. 1998).

Chen, M.S., et al., "Characterization of Pyrimidine Deoxyribonucleoside Kinase (Thymidine Kinase) and Thymidylate Kinase as a Multifunctional Enzyme in Cells Transformed by Herpes Simplex Virus Type 1 and in Cells Infected with Mutant Strains of Herpes Simplex Virus," *J Virol.*, 30(3):942-945 (Jun. 1979).

Chen, C.-H., et al., "Delayed Cytotoxicity and Selective Loss of Mitochondrial DNA in Cells Treated with the Anti-human Immunodeficiency Virus Compound 2',3'-Dideoxycytidine," *J. Biol. Chem.*, 264(20):11934-11937 (Jul. 15, 1989).

Chen, C.-H., et al., "The Role of Cytoplasmic Deoxycytidine Kinase in the Mitochondrial Effects of the Anti-human Immunodeficiency Virus Compound 2',3'-Dideoxycytine," *J. Biol. Chem.*, 267(5):2856-2859 (Feb. 15, 1992).

Cui, L., et al., "Effect of Nucleoside Analogs ion Neurite Regeneration of Mitochondrial DNA Synthesis in PC-12 Cells," *J. of Pharmacology and Experimental Therapeutics*, 280(3):1228-1234 (1997).

Das, et al., "Molecular Modeling and Biochemical Characterization Reveal the Mechanism of Hepatitis B virus Polymerase Resistance to Lamivudine (3TC) and Emtricitabine (FTC)," *Journal of Virology*, 75(10):4771-4779 (May 2001).

Davis, A.F., et al., "In Situ Localization of Mitochondrial DNA Replication in Intact Mammalian Cells," *J Cell Biol*, 135(4), 883-893 (Nov. 1996).

Davisson, V.J., et al., "Synthesis of Nucleotide 5'-Diphosphates from 5'-O-Tosyl Nucleosides," *J Org. Chem.*, 52(9):1794-1801 (1987).

Delaney, "Cross-Resistance Testing of Antihepadnaviral Compounds using Novel Recombinant Baculoviruses which Encode Drug-Resistant Strains of Hepatitis B Virus," *Antimicrobial Agents and Chemotherapy*, 45(6):1705-1713 (Jun. 2001).

Delaney, W.E., Huiling Y, Westland CE, et al., "In vitro cross resistance testing of adefovir, entecavir, and α-L-thymidine (LDT) against drug-resistant strains of HBV," *Hepatology*, 34(No. 4, pt 2):628A, abstract #1825 (2001).

Doong, S.-L., et al., "Inhibition of the replication of hepatitis B virus in vitro by 2',3'-dideoxy-3'-thiacytidine and related analogues," *Proc. Natl. Acad. Sci. USA*, 88:8495-8499 (Oct. 1991).

Du, J., et al., Synthesis, "Anti-Human Immunodeficiency Virus and Anti-Hepatitis B Virus Activities of Novel Oxaselenolane Nucleosides," *J. of Med. Chem.*, 19(40):2991-2993 (Sep. 12, 1997).

Dutschman, G.E., et al., "Metabolism of 2',3'-dideoxy-2',3'-didehydro-β-L-(−)5-Fluorocytidine and Its Activity in Combination with Clinically Approved Anti-Human Immunodeficiency Virus β-D-(+) Nucleoside Analogs in Vitro," *Antimicrobial Agents and Chemotherapy*, 42(7), 1799-1804 (Jul. 1998).

Fu, L., et al., "Role of Additional Mutations outside the YMDD Motif of Hepatitis B Virus Polymerase in L-(−)-SddC (3TC) Resistance," *Biochemical Pharmacology*, 57(12):1351-1359 (1999).

Furman, P.A., et al., "The Anti-Hepatitis B Virus Activities, Cytotoxicities, and Anabolic Profiles of the (−) and (+) Enantiomers of cis-5-Fluoro-1-[2-(Hydroxymethyl)-1,3-oxathiolane-5-yl]-Cytosine" *Antimicrobial Agents and Chemotherapy*, 36(12):2686-2692 (Dec. 1992).

Gauthier, "Quantitation of Hepatitis B Viremia and Emergence of YMDD Variants in Patients with Chronic Hepatitis B Treated with Lamivudine," *The Journal of Infection Diseases*, 180, 1757-1762 (Dec. 1999).

Gilead FDA Advisory Committee Briefing Document. "Adefovir dipivoxil for the treatment of chronic hepatitis B," NDA 21-449, Table 1, p. 12, (Jul. 5, 2002).

Gosselin, G., et al., "Synthesis and Antiviral Evaluation of α-L-Xylofuranosyl Nucleosides of the Five Naturally Occurring Nucleic Acid Bases," *Journal of Heterocyclic Chemistry*, 30:1229-1233 (Oct.-Nov. 1993).

Hernandez-Santiago, B., et al., "Pharmacology of α-L-Thymidine and β-L-2'-Deoxycytidine in HepG2 Cell and Primary Human Hepatocytes: Relevance to Chemotherapeutic Efficacy against Hepatitis B Virus," *Antimicrobial Agents and Chemotherapy*, 46(6) 1728-1733 (Jun. 2002).

Hoard, D.E., et al., "Conversion of Mono- and Oligodeoxyribonucleotides to 5'-Triphosphates," *J. Am. Chem. Soc.*, 87(8):1785-1788 (Apr. 20, 1965).

Holy, A., "Nucleic Acid Components and Their Analogs. CLIII. Preparation of 2'-deoxy-L-Ribonucleosides of the Pyrimidine Series," *Collect. Czech. Chem. Commun.*, 37(12):4072-4087 (1972).

Hostetler, K.Y., et al., "Synthesis and Antiretroviral Activity of Phospholipid Analogs of Azidothymidine and Other Antiviral Nucleosides," *J. Biol Chem*, 265(11):6112-6115 (Apr. 15, 1990).

Hostetler, K.Y., et al., "Greatly Enhanced Inhibition of Human Immunodeficiency Virus Type 1 Replication in CEM and HT4-6C Cells by 3'-Deoxythymidine Diphosphate Dimyristoylglycerol, A Lipid Prodrug of 3'-Deoxythymidine," *Antimicrob Agents Chemother.*, 36(9):2025-2029 (Sep. 1992).

Imai, K., et al., "Studies on Phosphorylation. IV. Selective Phosphorylation of the Primary Hydroxyl Group in Nucleosides." *J. Org. Chem.*, 34(6):1547-1550 (Jun. 1969).

Jones, R.J., et al., "Mini Review: Nucleotide prodrugs," *Antiviral Research*, 27:1-17 (1995).

Jurovcik, W., et al., "Metabolism of pyrimdine L-nucleosides," *Nucleic Acids Research*, 3(8), 2143-2154 (Aug. 1976).

Korba, B.E., et al., "A cell culture assay for compounds which inhibit hepatitis B virus replication," *Antiviral Res.*, 15:217-228 (1991).

Krayevsky, A.A., et al., "Can a Substrate Enantiomer Be a Substrate for the Same Enzyme?," *Molecular Biology*, 30(5, Part 1):585-591 (1996).

Krayevsky, A.A., et al., "Should the Asymmetry of Enzymatic Active Centers Always Correlate with the Asymmetry of their Substrates?," *J. Biomolecular Structure & Dynamics*, 14(2):225-230 (1996).

Kucera, L.S., et al., "Novel membrane-interactive ether lipid analogs that inhibit infectious HIV-1 production and induce defective virus formation," *AIDS Res. Hum. Retroviruses*, 6:491-501 (1990).

Labenz, J., et al., "Analysis of the TK Enzyme Complex Induced by HSV Types 1 and 2 by Means of Isoelectric Focusing and Polyacyrlamide Gel Electrophoresis," *Arc. Virol.*, 71:235-249 (1982).

Lin, T.-S., et al., "Synthesis and Biological Evaluation of 2',3'-Dideoxy-L-pyrimidine Nucleosides as Potential Antiviral Agents against HIV and HBV," *J. Med. Chem.*, 37:798-803 (1994).

Lin, T.-S., et al., "Synthesis of Several Pyrimidine L-Nucleoside Analogues as Potential Antiviral Agents," *Tetrahedron Letters*, 51(4):1055-1068 (1995).

Lin, T.D., et al., "Design and Synthesis of 2',3'-Dideoxy-2',3'-didehydro-β-L-cytidine (β-L-d4C) and 2',3'-Dideoxy-2',3'-didehydro-β-L-5-fluorocytidine (β-L-Fd4C), Two Exceptionally Potent Inhibitors of Human Hepatitis B Virus (HBV) and Potent Inhibitors of Human Immunodeficiency Virus (HIV) in Vitro," *J. Med. Chem.*, 39(9):I757-1759 (Apr. 26, 1996).

Maga, G., et al., "Lack of stereospecificity of suid pseudorabies virus thymidine kinase," *Biochem. J.*, 294(2):381-385 (Sep. 1, 1993).

Mansour, T.S., et al., "Stereochemical Aspects of the Anti-HCMV Activity of Cytidine Nucleoside Analogues," *Antiviral Chemistry & Chemotherapy*, 6(3):138-142 (1995).

Melegari, M., et al., "Hepatitis B virus mutants associated with 3TC and famciclovir administration are replication defective," *Hepatology*, 27(2):628-633 (Feb. 1998).

Nakayama, C., et al., "Synthetic Nucleosides and Nucleotides. XX. Synthesis of Various 1-β-Xylofuranosyl-5-Alkyluracils and Related Nucleosides," *Nucleosides & Nucleotides*, 1(2):139-146 (1982).

Norbeck, D.W., et al., "A new 2',3'-dideoxynucleoside prototype with in vitro activity against HIV," *Tetrahedron Letters*, 30(46):6263-6266 (1989).

Ono, S.K., et al., "The polymerase L528M mutation cooperates with nucleotide binding-site mutations, increasing hepatitis B virus replication and drug resistance," *J. Clin. Investig.*, 107:449-455 (2001).

Ono-Nita, S.K., et al., "YMDD Motif in Hepatitis B Virus DNA Polymerase Influences on Replication and Lamivudine Resistance: A Study by in Vitro Full-Length viral DNA Transfection," *Hepatology*, 29(3):939-945 (Mar. 1999).

Ono-Nita, S.C., et al., "Susceptibility of lamivudine-resistant hepatitis B virus to other reverse transcriptase inhibitors;" *The Journal of Clinical Investigation*, 3(12):1635-1640 (Jun. 1999).

Pan-Zhou, X.-R., et al., "Differential Effects of Antiretroviral Nucleoside Analogs on Mitochondrial Function in HepG2 Cells," *Antimicrobial Agents and Chemotherapy*, 44(3):496-03 (Mar. 2000).

Placidi, I., et al., "Cellular pharmacology of β-L-thymidine and β-L-2'-deoxycytidine in HepG2 cells and primary rat, monkey and human hepatocytes," *Antivir. Ther.*, 4(Suppl.4):46-47, abstract A122 (*3rd Int. Conf. Ther. Vir. Hepatitis*) (1999).

Robins, M.J., et al., "Purine nucleosides. XXIX. The synthesis of 2'-deoxy-L-adenosine and 2'-deoxy-L-guanosine and their α anomers," *J. Org. Chem.*, 35(3):636-639 (Mar. 1970).

Robins, M.J., et al., "Selective Deoxygenation and Modification at C2' of Nucleosides," *Nucleic Acids Research Symposium Series*, vol. 11, pp. 1-4, Kyoto, Japan, Nov. 24-26, 1982, A.E. Pritchard (ed.), IRL Press, Ltd., Oxford, England, 1982 [Chemical Abstracts Service, No. 98:10767u].

Robins, M.J., et al., "Nucleic Acid Related Compounds. 42. A General Procedure for the Efficient Deoxygenation of Secondary Alcohols. Regiospecific and Stereoselective Conversion of Ribonucleosides to 2'-Deoxynucleosides," *J. Am. Chem. Soc.*, 105:4059-4065 (1983).

Saneyoshi, M., et al., "Synthetic Nucleosides and Nucleotides. XIII. Stannic Chloride Catalyzed Ribosylation of Several 6-Substituted Purines." *Chem. Pharm. Bull.*, 27:2518-2521 (1979).

Schinazi, R.F., et al., "Effect of Combinations of Acylovir with Vidarabine or its 5'-Monophosphate on Herpes Simplex Viruses in Cell Culture and in Mice," *Antimicrobial Agents and Chemotherapy*, 22(3):499-507 (Sep. 1982).

Schinazi, R.F., et al., "Selective Inhibition of Human Immunodeficiency Viruses by Racemates and Enantiomers of cis-5-Fluoro-1-[2-(Hydroxymethyl)-1,3-Oxathiolane-5-yl] Cytosine," *Antimicrobial Agents and Chemotherapy*, 36(11):2423-2431 (Nov. 1992).

Seifer, M., Hamatake R, Bifano M, Standring DN. "Generation of replication-competent hepatitis B virus nucleocapsids in insect cells," *J. Virol.*, 72(4):2765-2776 (Apr. 1998).

Seigne'Res, B., et al., "Duck hepatitis B virus polymerase gene mutants associated with resistance to lamivudine have a decreased replication capacity in vitro and in vivo," *J. Hepatol.* 34:114-122 (2001).

Shuto, S., et al., "A facile one-step synthesis of 5'-phosphatidylnucleosides by an enzymatic two-phase reaction," *Tetrahedron Letters*, 28(2):199-202 (1987).

Söderlund, J.C.F., "Mitochondrial versus cytosolic activities in deoxyribonucleoside salvage enzymes," in *Purine and Pyrimidine Metabolism in Man VIII*, A. Shota & M. Taylor (Eds.), Plenum Press, New York, 1995, pp. 201-204.

Spadari, S., et al., "L-Thymidine is Phosphorylated by Herpes Simplex Type 1 Thymidine Kinase and Inhibits Viral Growth," *J. Med. Chem.*, 35(22):4214-4220 (1992).

Stuyver, L. J., et al., "Nomenclature for antiviral-resistant human hepatitis B virus mutations in the polymerase region," *Hepatology* 33(3):751-757 (Mar. 2001).

Tyrsted, G., et al., "Inhibition of the synthesis of 5-phosphoribosyl-1-pyrophosphase by 3'-deoxy-adenosine and structurally related nucleoside analogs." *Biochim. Biophys. Acta.*, 155(2):619-622 (Feb. 26, 1968).

Verri, A., et al., "Lack of enantiospecificity of human 2'-deoxycytidine kinase: relevance for the activation of β-L-deoxycytidine analogs as antineoplastic and antiviral agents," *Molecular Pharmacology*, 51(1):132-138 (Jan. 1997).

Verri, A., et al., Relaxed Enantioselectivity of Human Mitochondrial Thymidine Kinase and Chemotherapeutic Uses for L-Nucleoside Analogues, *Biochem. J.*, 328(1):317-230 (Nov. 15, 1997).

Von Janta-Lipinski, M., et al., "Newly Synthesized L-Enantiomers of 3'-Fluoro-Modified β-2'-Deoxyribonucleoside 5'-Triphosphates Inhibit Hepatitis B DNA Polymerase but not the Five Cellular DNA Polymerases α, β, γ, δ, ε Nor HIV-1 Reverse Transcriptase," *J. Medicinal Chemistry*, 41(12):2040-2046 (May 21, 1998).

Wang, L., et al., "Recovery of Liver Sinusoidal Endothelial Cell Function over Time after Hypothermic Preservation in Rat Orthotopic Liver Transplantation," AASLD abstracts published in *Hepatology*, 24(No. 4, Pt. 2):431A, Abstract No. 1219 (1996).

Ying, C., et al., "Inhibition of the replication of the DNA polymerase M550V mutation variant of human Hepatitis B Virus by adefovir., tenofovir, L-FMAU, DAPD, penciclovir and lobucavir," *J. Viral Hepatitis*, 7:161-165 (2000).

Zedeck, M.S., et al., "Inhibition of the steroid-induced synthesis of D5-3-ketosteroid isomerase in *Pseudomonas testosterone* by a new purine deoxyribonucleoside analog: 6-chloro-8-aza-9-cyclopentylpurine," *Mol. Pharmacol.*, 3(4):386-395 (1967).

Zhang, W., et al., "Removal of Silyl Protecting Groups from Hydroxyl Functions with Ammonium Fluoride in Methanol." *Tetrahedron Letters*, 33(9):1177-1180 (1992).

Zhu, Y.-L., et al., "Inhibition of Replication of Hepatitis B Virus by Cytallene in Vitro," *Antimicrobial Agents and Chemotherapy*, 41(8):1755-1760 (Aug. 1997).

Zhu, Y.-L., et al., "Anti-Hepatitis B Virus Activity and Metabolism of 2',3'-dideoxy-2',3'-didehydro-β-L-(−)-5-Flurocytidine," *Antimicrobial Agents and Chemotherapy*, 42(7):1805-1810 (Jul. 1998).

Zhu, C., et al., "Incorporation of Nucleoside Analogs into Nuclear or Mitochondrial DNA Is Determined by the Intracellular Phosphorylation Site," *J Biol Chem*, 275(35):26727-26731 (2000).

Zoulim, F., et al., "Drug therapy for chronic hepatitis B: Antiviral efficacy and influence of hepatitis B virus polymerase mutations on the outcome of therapy," *J. Hepatology*, 29:151-168 (1989).

Zoulim, F., "Evaluation of novel strategies to combat hepatitis B virus targeting [sic] wild-type and drug-resistant mutants in experimental models," *Antivir. Chem. Chemother.*, 12(Suppl. 1):131-142 (2001).

Supplemental Partial European Search Report from EP03770334, Nov. 7, 2007, Idenix (Cayman) Limited.

Bridges et al., "Antiviral Activity of Beta-L-Thymidine and Beta-L-2'-Deoxycytidine in the Woodchuck Model of Chronic Hepatitis B Infection," Antiviral Research, 46(1):A62 (2000).

Chin et al., "In Vitro Susceptibilities of Wild-Type or Drug-Resistant Hepatitis B Virus to (−)-Beta-D-2,6-Diaminopurine Dioxolane and 2'-Fluoro-5-Methyl-Beta-L-Arabinofuranosyluracil," Antimicrobial Agents and Chemotherapy, 45(9):2495-2501 (2001).

Delany et al., "Lamivudine-Resistant HBV is Cross-Resistant to L-dT and L-dC in Vitro," Journal of Hepatology, 36(1):89 (2002).

Dunkle, "HEP DART 2001—Frontiers in Drug Development for Viral Hepatitis, Therapies for Chronic HBV Infection," IDrugs, 5(2):138-140 (2002).

Juodawlkis et al., "Synergistic Antiviral L-Nucleosides Specific for Hepatitis B Virus Infection," Antiviral Research, 50(1):A43 (2001).

Liu et al., "Hepatitis B Virus Resistance to Lamivudine and its Clinical Implications," Antiviral Chemistry & Chemotherapy, 13(3):143-155 (2002).

Raney et al., "Agents in Clinical Development for the Treatment of Chronic Hepatitis B," Expert Opinion on Investigational Drugs, 12(8):1281-1295 (2003).

Sorbera et al, "Telbivudine: Anti-HBV Agent," Drugs of the Future, 28(9):870-879 (2003).

Standring et al., "Antiviral Beta-L-Nucleosides Specific for Hepatitis B Virus Infection," Antiviral Chemistry & Chemotherapy, 12(Supp. 1):119-129 (2001).

Yuen et al., "Current and Future Antiviral Agents for Chronic Hepatitis B," Journal of Antimicrobial Chemotherapy, 51(3):481-485 (2003).

* cited by examiner

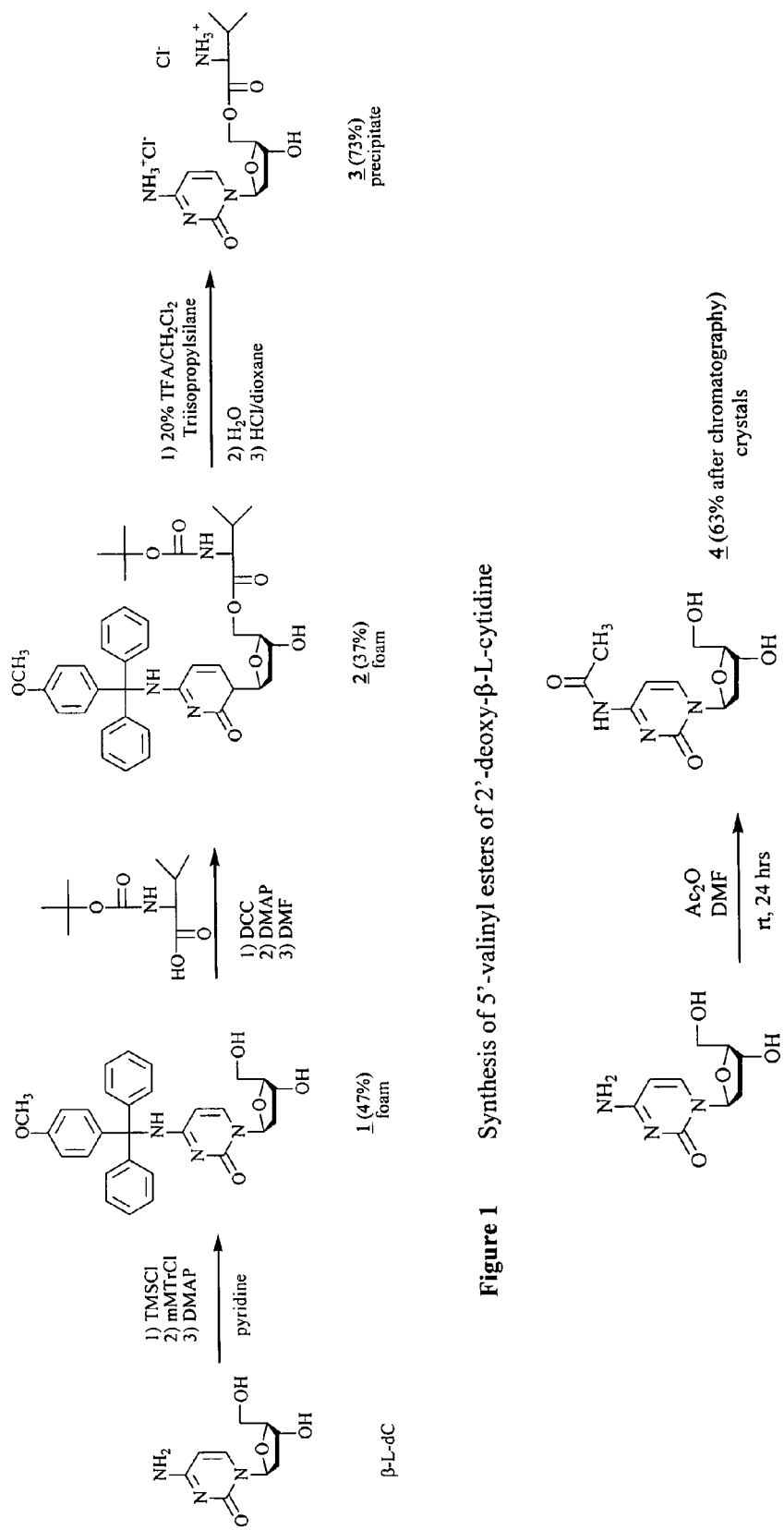
Figure 1  Synthesis of 5'-valinyl esters of 2'-deoxy-β-L-cytidine
Figure 2  Synthesis of $N^4$-acetyl-2'-deoxy-β-L-cytidine

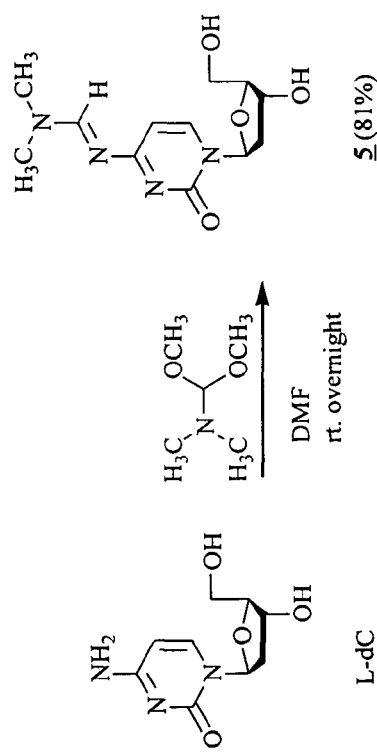
Figure 3 Synthesis of $N^4$-[(dimethylamino)methylene]-2'-deoxy-β-L-cytidine
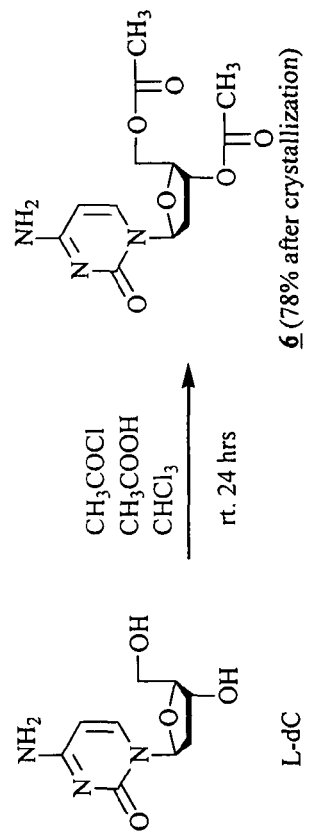
Figure 4 Synthesis of 3',5'-di-O-acetyl-2'-deoxy-β-L-cytidine

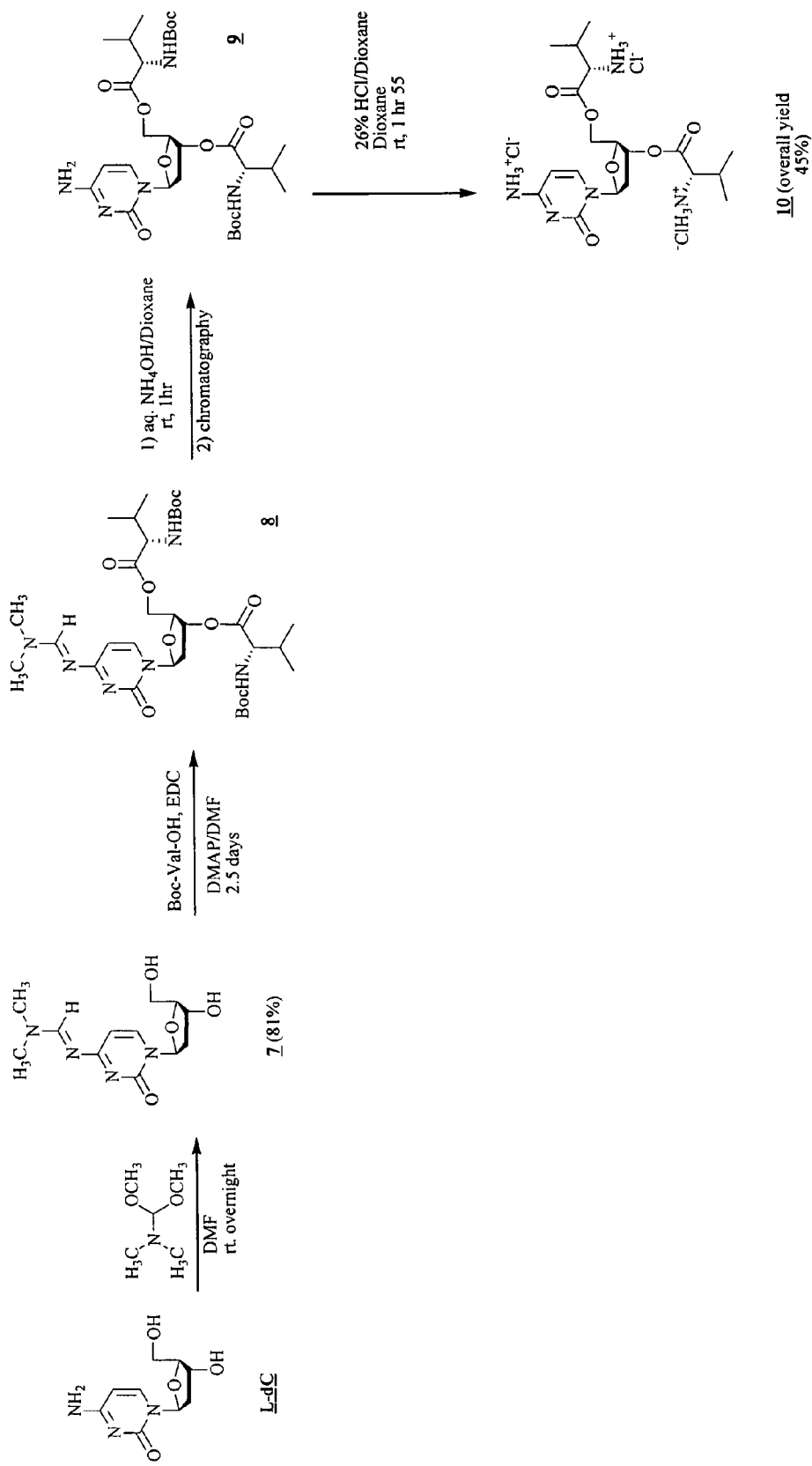
Figure 5    Synthesis of 3',5'-di-O-valinyl esters of 2'-deoxy β-L-cytidine

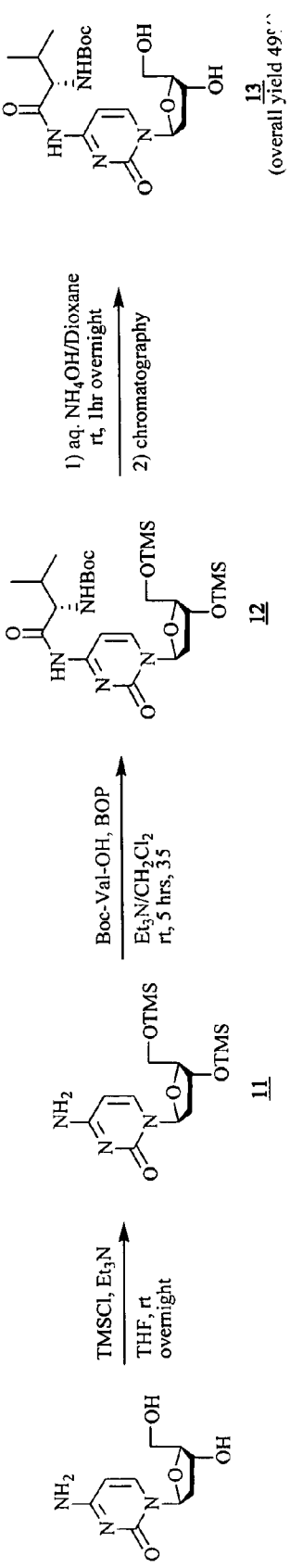
Figure 6 Synthesis of $N^4$-Boc-valinyl ester of 2'-deoxy-β-L-cytidine
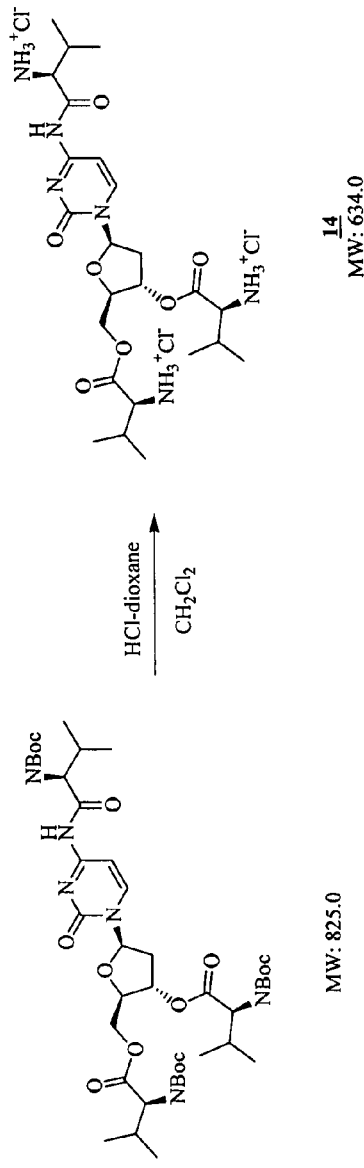
Figure 7 Synthesis of 3',5',$N^4$-tri-(L-valinyl)-L-2'-deoxycytidine

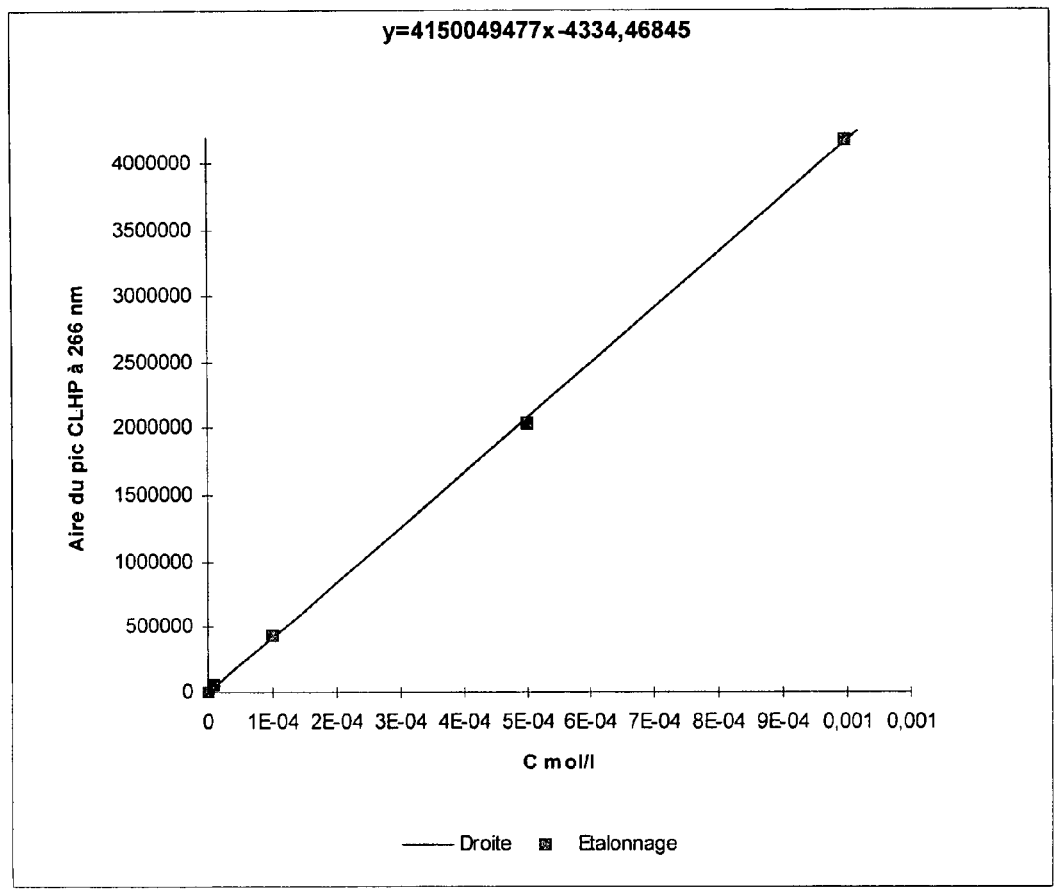
Figure 8a    Solubility Calibration Curve for D-dC

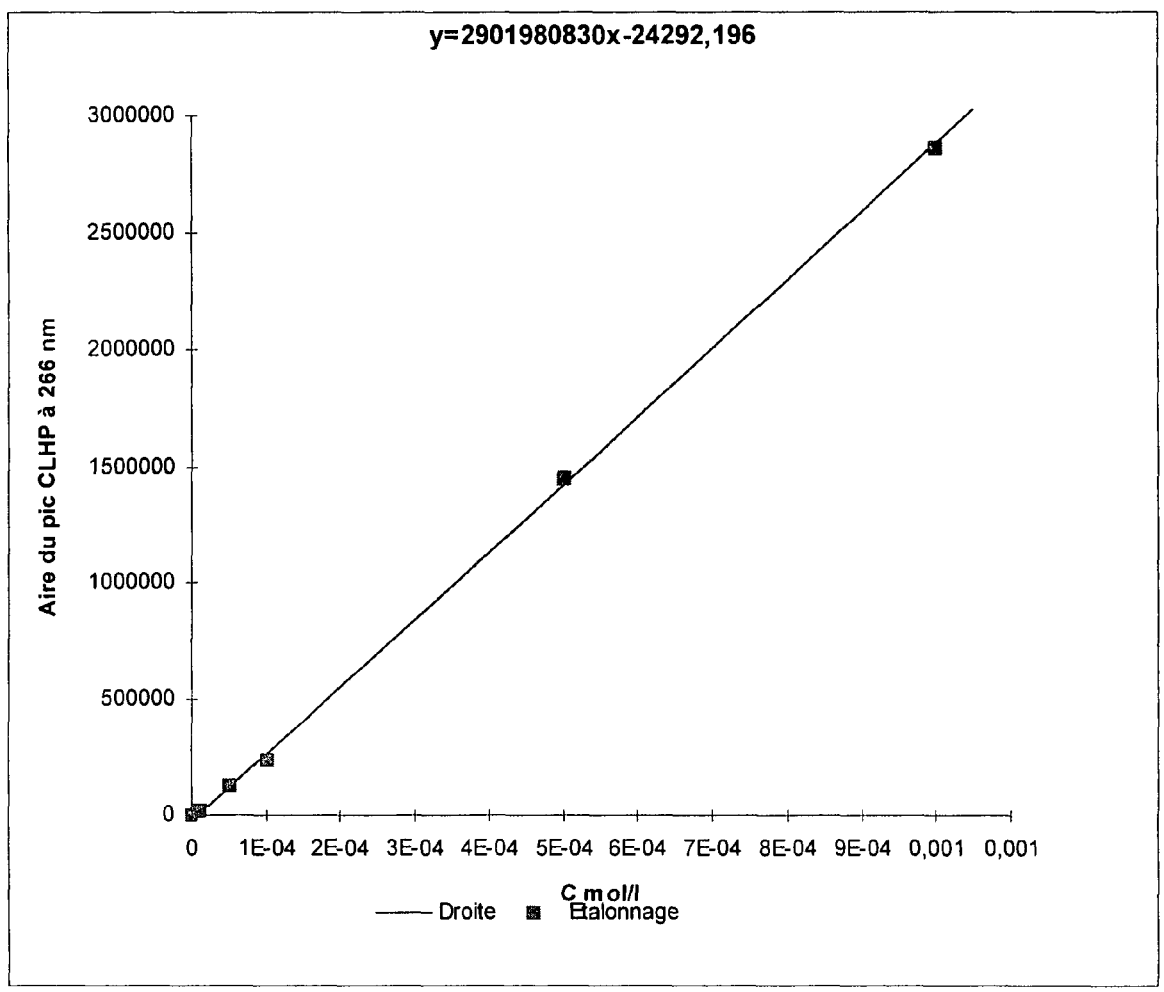
Figure 8b   Solubility Calibration Curve for the 3',5'-Divalinyl Ester of L-dC

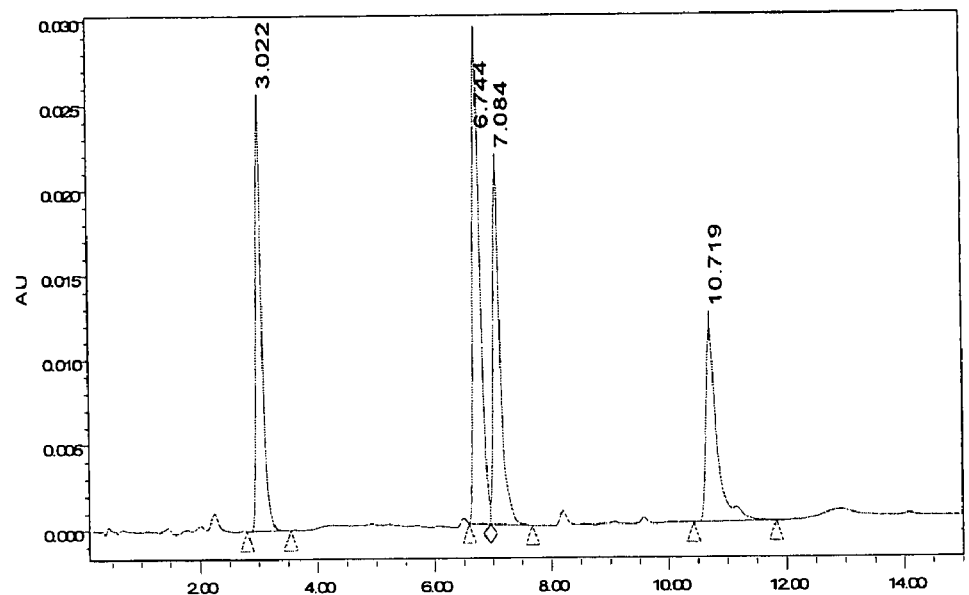
Figure 9a  HPLC profile – 7.5 hours at pH of 7.42

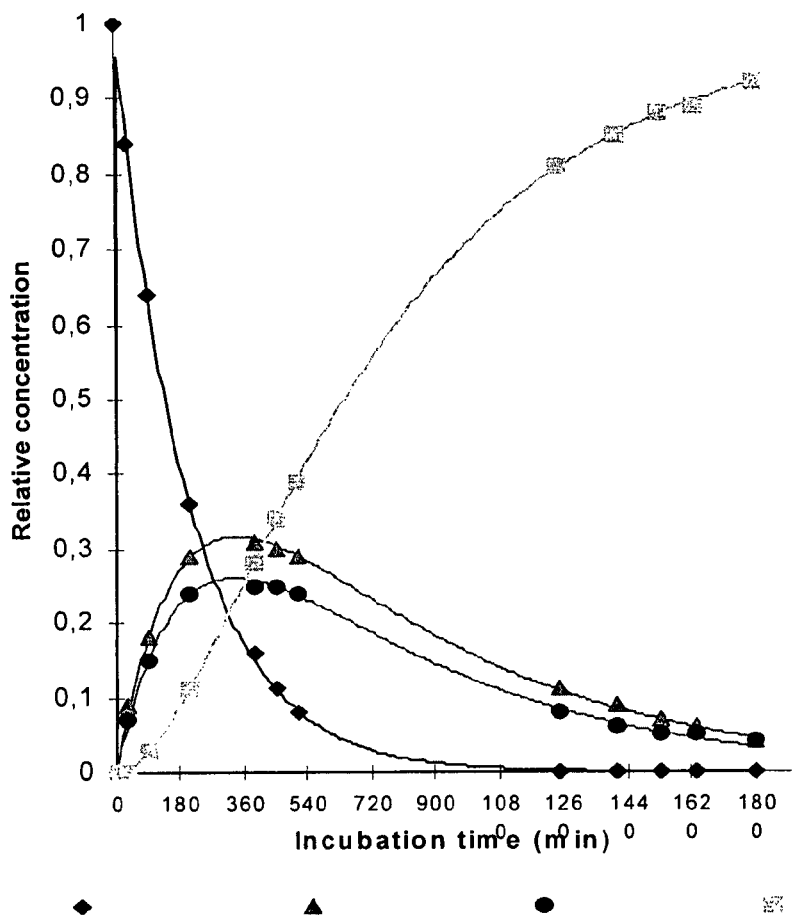
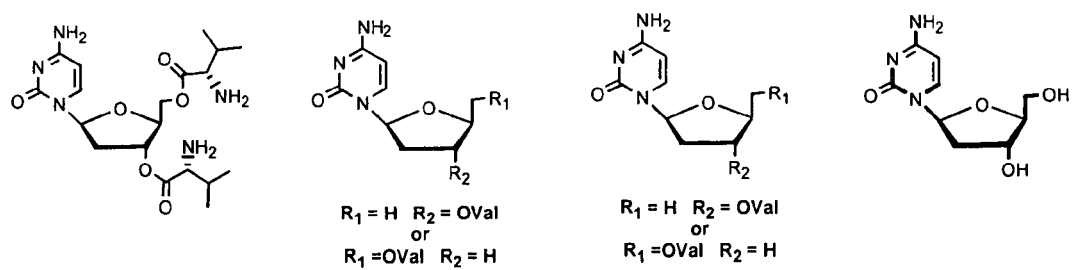
Figure 9b   Kinetics curves at pH of 7.42

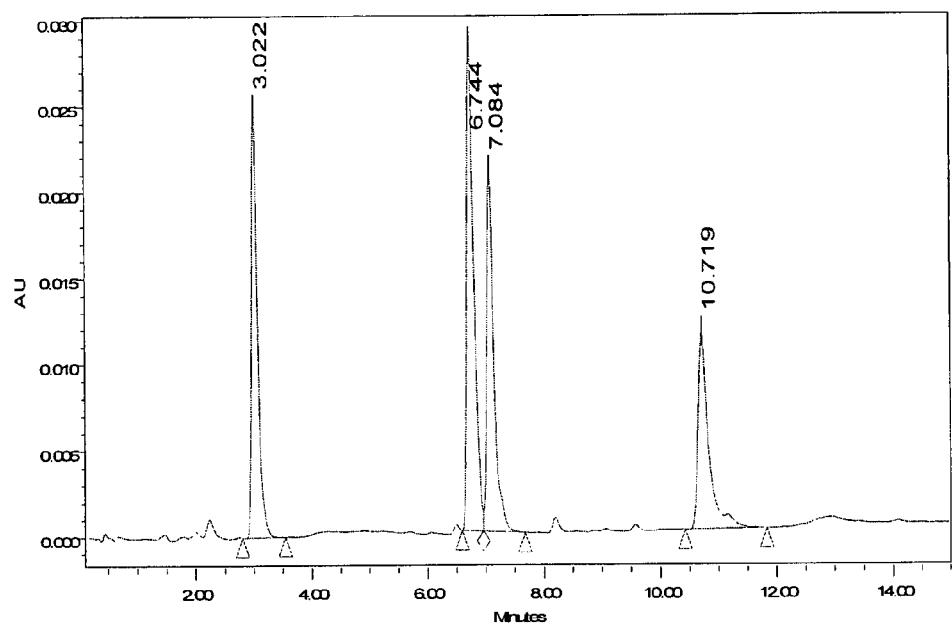
Figure 10a  HPLC profile – 5.33 hours at pH of 7.20

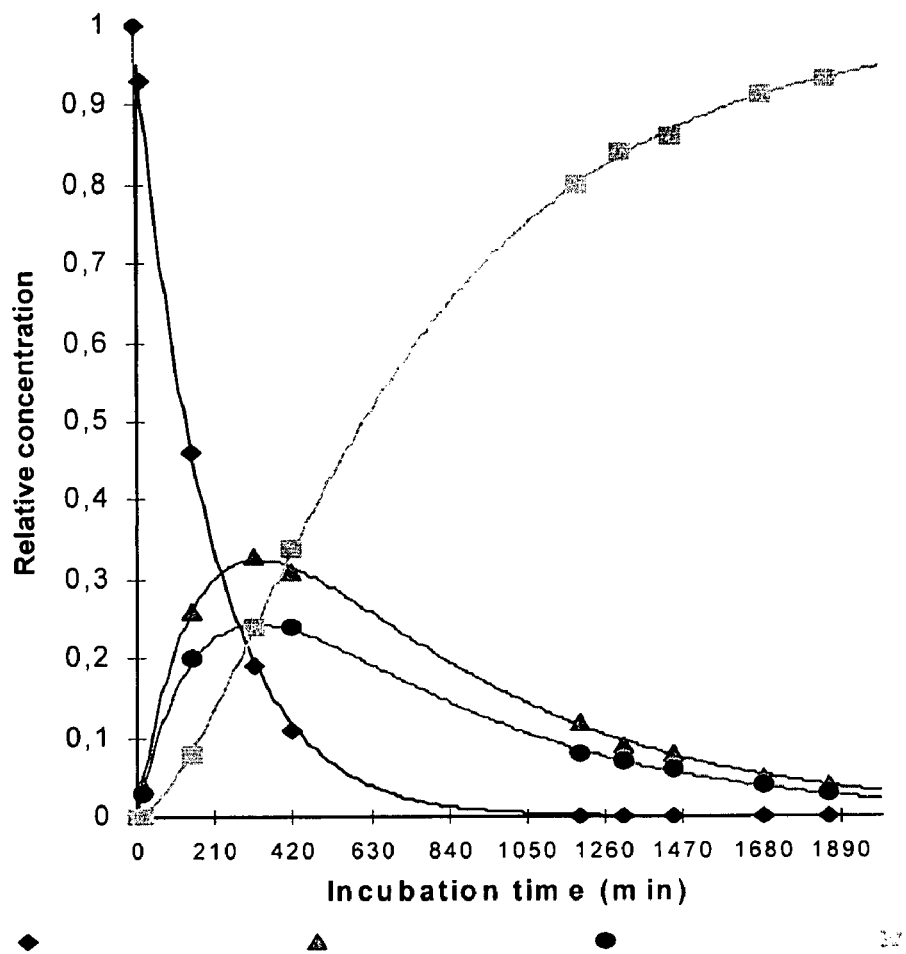
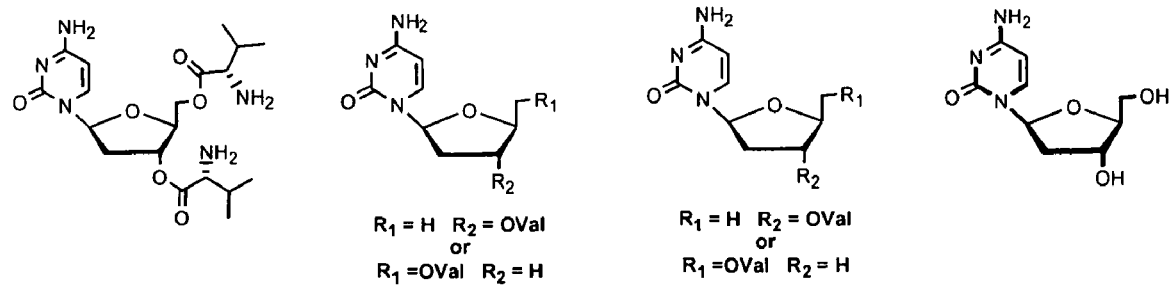
Figure 10b    Kinetics Curves at pH of 7.20

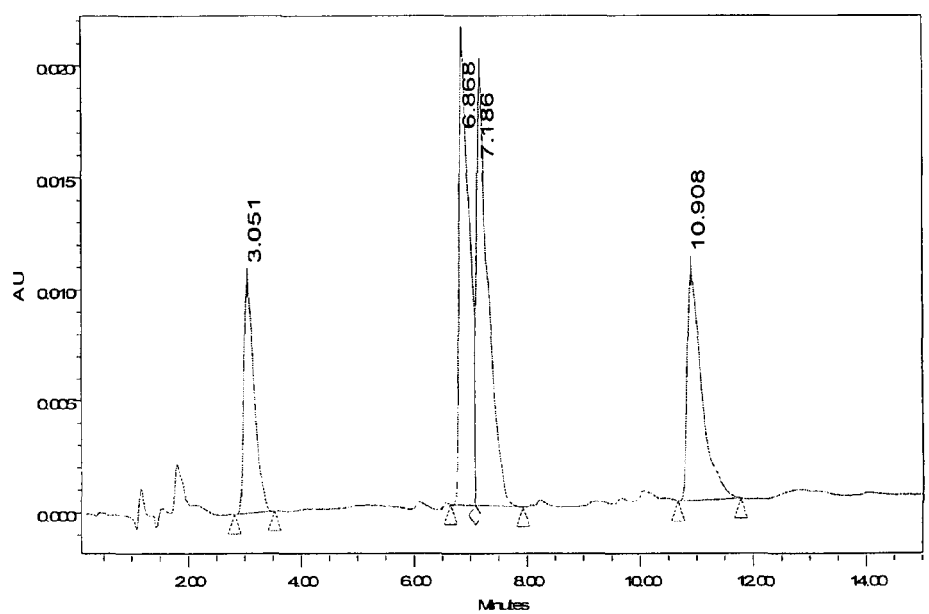
Figure 11a  HPLC profile – 95.7 hours at pH of 4.51

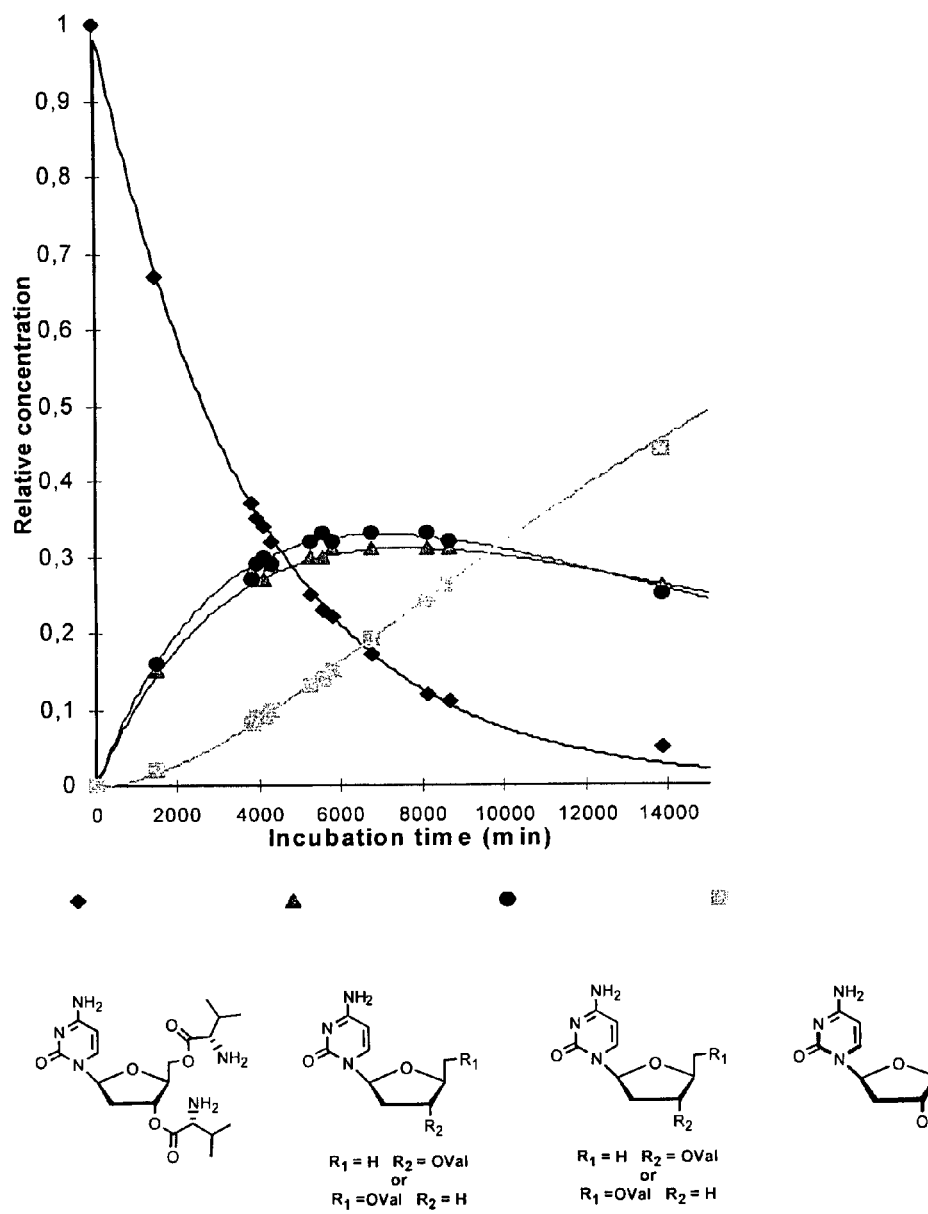
Figure 11b   Kinetics curves at pH of 4.51

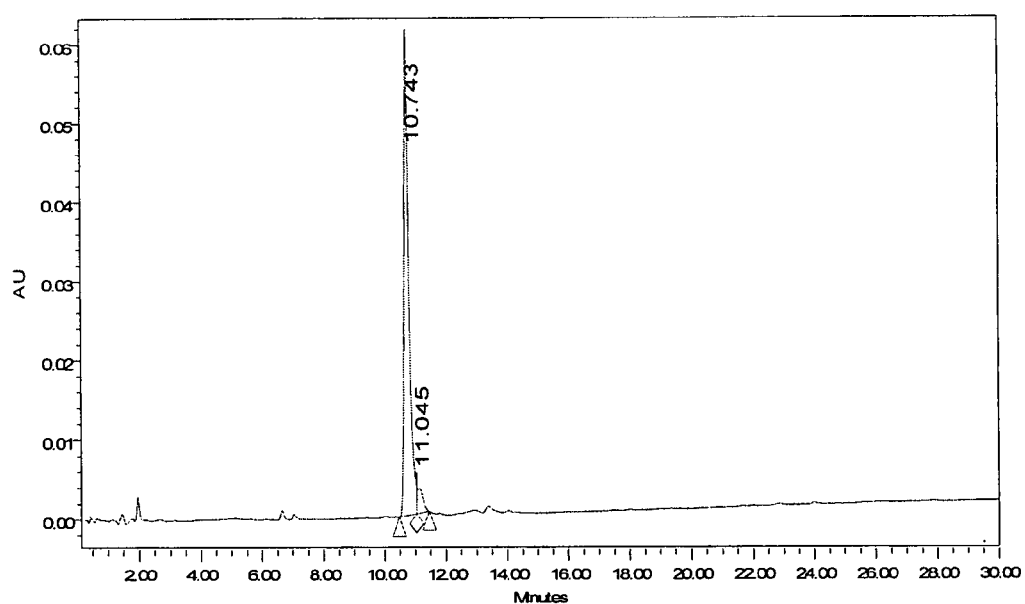
Figure 12      HPLC profile – 48 hours at pH of 1.23

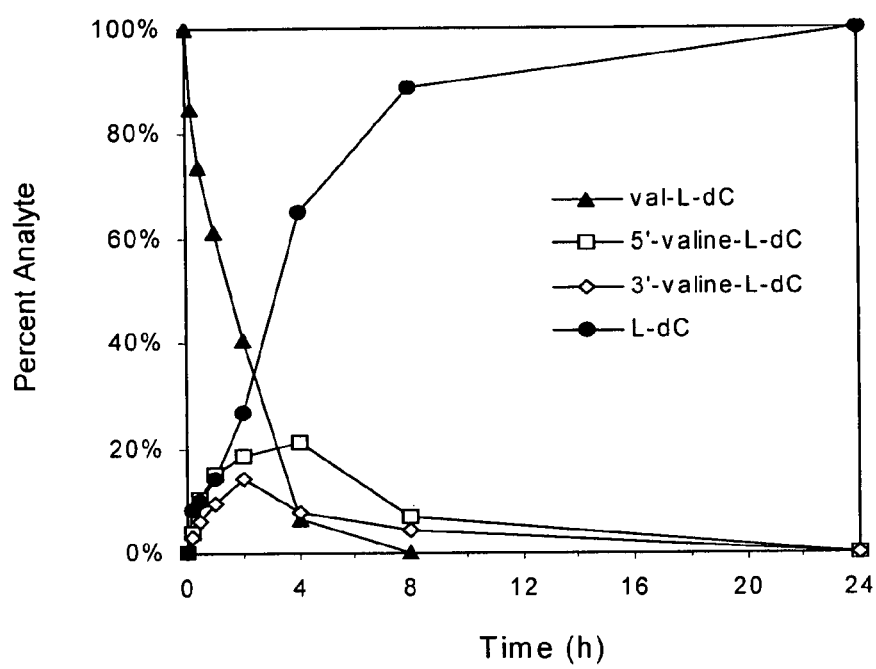
Figure 13 *In Vitro* Metabolism of 3',5'-Dival-L-dC in Human Plasma

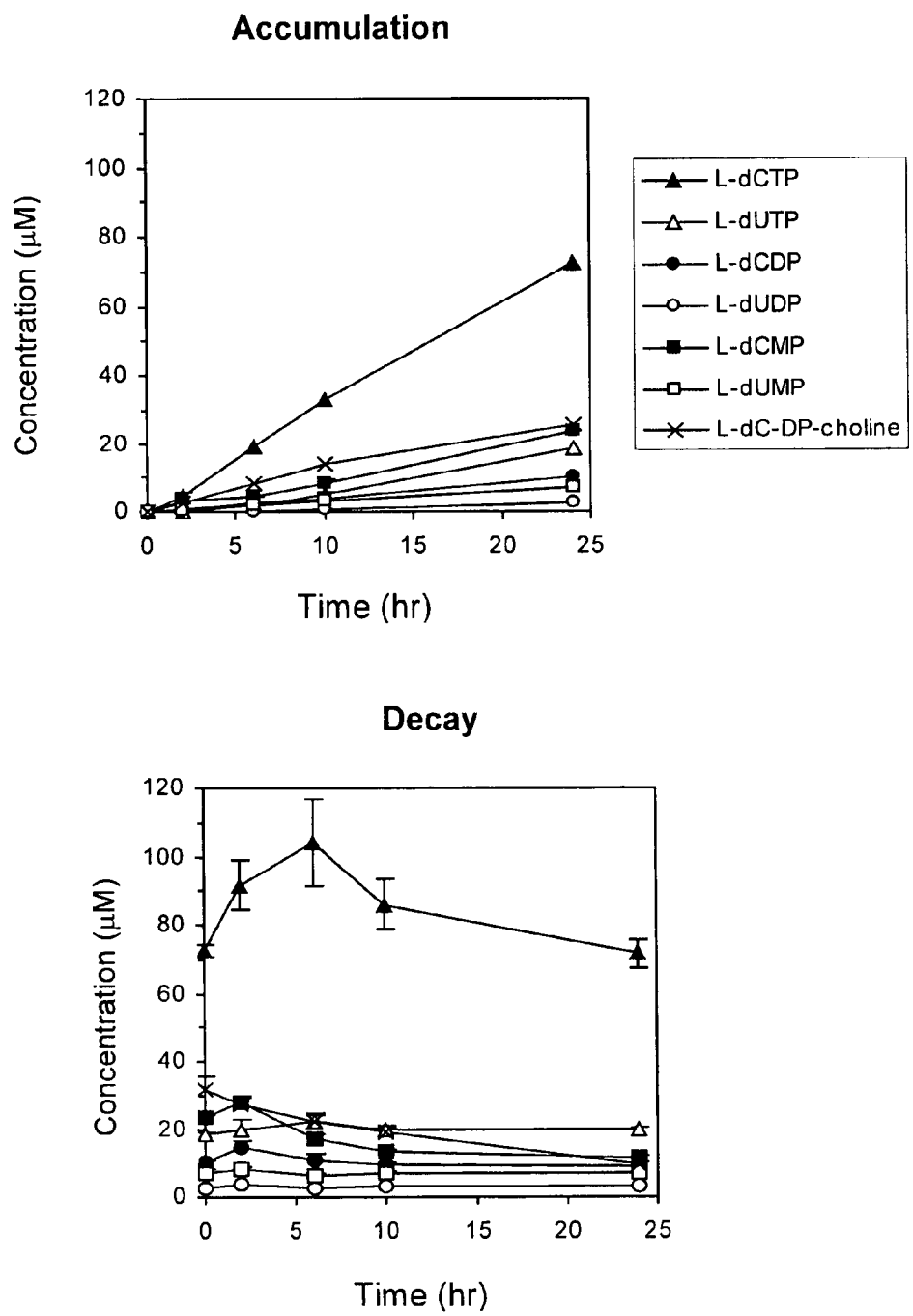
Figure 14 Intracellular Metabolism of L-dC in HepG2 Cells

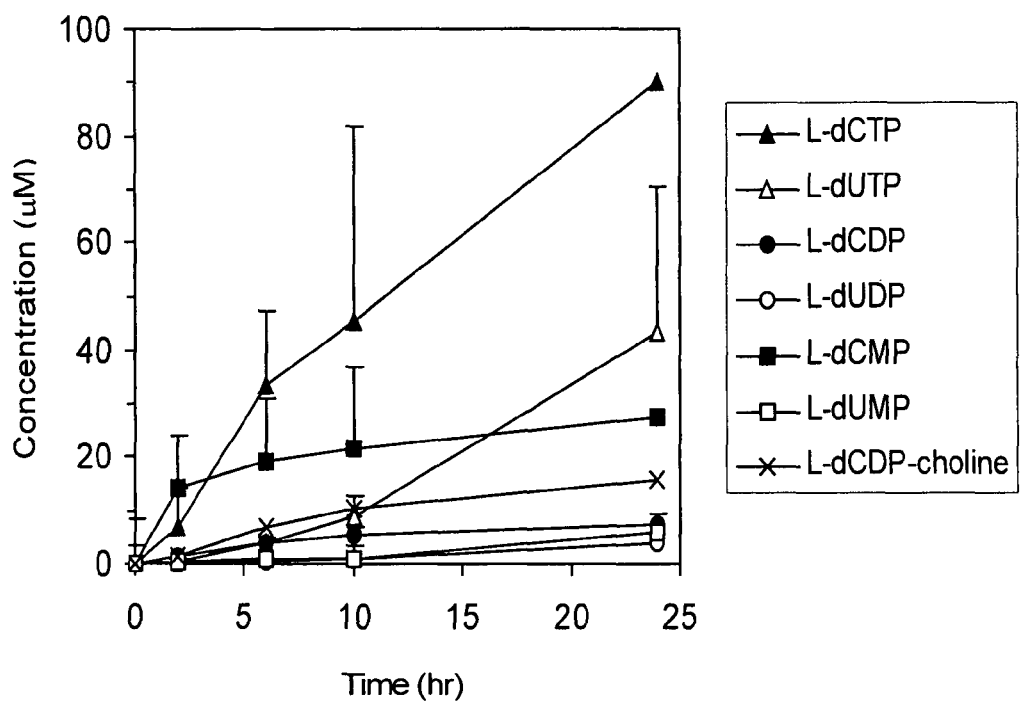
Figure 15    Intracellular Metabolism of L-dC in Primary Human Hepatocytes

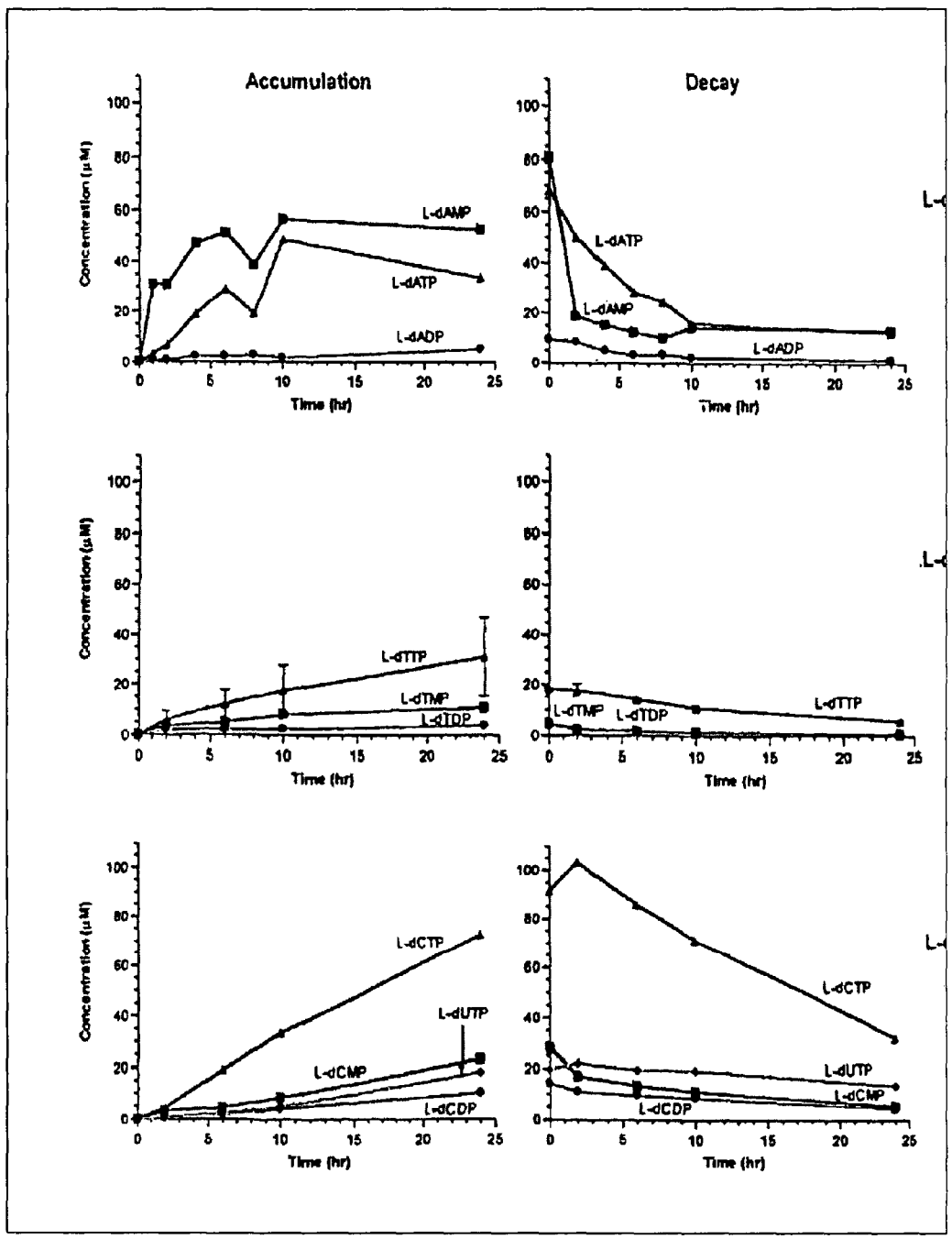
Figure 16    Accumulation and Decay of L-dA, L-dT, and L-dC in HepG2 Cells.

β-L-2'-DEOXYNUCLEOSIDES FOR THE TREATMENT OF RESISTANT HBV STRAINS AND COMBINATION THERAPIES

CROSS REFERENCE TO RELATED APPLICATIONS

This application is a continuation U.S. Ser. No. 10/662,641, filed on Sep. 15, 2003, now U.S. Pat. No. 7,186,700 which claims priority to Provisional Application No. 60/410,675, filed Sep. 13, 2002.

FIELD OF THE INVENTION

The present invention includes 2'-deoxy-β-L-nucleosides for the treatment of hepatitis B strains that exhibit resistance to known anti-HBV drugs, as well as combination therapties with 2'-deoxy-β-L-nucleosides with immunomodulators.

BACKGROUND OF THE INVENTION

Hepatitis B virus ("HBV") is second only to tobacco as a cause of human cancer. The mechanism by which HBV induces cancer is unknown, although it is postulated that it may directly trigger tumor development, or indirectly trigger tumor development through chronic inflammation, cirrhosis and cell regeneration associated with the infection.

Hepatitis B virus has reached epidemic levels worldwide. After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed. Patients typically recover from acute viral hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. Chronic persistent hepatitis can cause fatigue, cirrhosis of the liver and hepatocellular carcinoma, a primary liver cancer. In western industrialized countries, high risk groups for HBV infection include those in contact with HBV carriers or their blood samples. The epidemiology of HBV is in fact very similar to that of acquired immunodeficiency syndrome, which accounts for why HBV infection is common among patients with AIDS or HIV-associated infections. However, HBV is more contagious than HIV.

To date, only three drugs have been approved by the FDA for the treatment of chronic HBV infection: interferon alpha, 3TC (Epivir, lamivudine) and adefovir dipivoxil (Hepsera® Gilead Sciences).

FDA Approved Drugs for HBV:

| Drug Name | Drug Class | Company | FDA Status |
|---|---|---|---|
| Intron A (interferon α-2b) | interferon | Schering-Plough | FDA-approved |
| 3TC (lamivudine; Epivir-HBV) | nucleoside analogue | GlaxoSmithKline | FDA-approved |
| Adefovir dipivoxil | nucleotide analogue | Gilead Sciences | FDA-approved |

Interferon Alpha

A manufactured form of interferon is used to treat hepatitis B. This treatment involves the administration of interferon by injection for about four months.

Not all patients respond to interferon, and sometimes retreatment is necessary. In clinical studies, only 45% of patients who were treated for hepatitis B with A (Interferon alpha-2b, recombinant, Schering Corporation) for Injection had no evidence of the hepatitis B virus in their blood over time. In addition, most patients have difficulty tolerating interferon treatment, which causes severe flu-like symptoms, weight loss, and lack of energy and stamina.

3TC

The (−)-enantiomer of BCH-189 (2',3'-dideoxy-3'-thiacytidine), also known as 3TC (Epivir, lamivudine) is an antiviral drug that is active against both HIV and HBV. It belongs to the class of drugs called nucleoside analog reverse transcriptase inhibitors (NRTI), which work by blocking production of the reverse transcriptase enzyme that HIV and HBV need in order to replicate. 3TC was originally developed for the treatment of HIV, however, researchers discovered that 3TC also works against the hepatitis B virus. In December 1998, the U.S. Food and Drug Administration (FDA) approved Epivir HBV for the treatment of hepatitis B virus infection.

Although 3TC efficiently inhibits HBV replication, the slow kinetics of viral elimination during 3TC therapy (Nowak, M., S. Bonhoeffer, et al. 1996. *Proc. Natl. Acad. Sci. USA* 93:4398-4402) and the spontaneous viral genome variability lead to the emergence of drug-resistant mutants which carry mutations affecting the reverse transcriptase (RT) domain (Mason, W. S., J. Cullen, et al. 1998. *Virology* 245: 18-32. Nafa, S., S. Ahmed, et al. 2000. *Hepatology* 32:1078-1088; Melegari, M., P. P. Scaglioni, and J. R. Wands. 1998 *Hepatology* 27:628-633.; Seigneres, B., C. Pichoud, et al. 2000. *J. Infect. Dis.* 181:1221-1233). Approximately 50% of treated patients develop viral resistance after 3 years of treatment with 3TC (Leung, N. W., C. L. Lai, et al. 2001. *Hepatology* 33:1527-1532). Resistance to nucleoside analogs is associated with substitutions in the nucleic acid sequence of the polymerase gene causing changes in the amino acid sequence of the HBV RT, notably in the YMDD motif within the catalytic site. The most common polymerase variant is the rtL180M-plus-M204V change (according to the recent genotype-independent nomenclature for HBV drug-resistant variants) (Stuyver, L. J., S. A. Locarnini, et al. 2001. *Hepatology* 33:751-757) that associates a mutation in the catalytic site (rtM204V) with a compensatory mutation in the B domain of the RT (rtL180M) which provides a higher replication capacity to the catalytic site variant (Allen, M. I., M. Deslauriers, et al. 1998. *Hepatology* 27:1670-1677. Chayama, K., Y. Suzuki, et al. 1998. *Hepatology* 27:1711-1716. Melegari, M., P. P. Scaglioni, and J. R. Wands. 1998. *Hepatology* 27:628-633. Ono, S. K., N. Kato, et al. 2001. *J. Clin. Investig.* 107:449-455. Seigneres, B., S. Aguesse-Germon, et al. 2001. *J. Hepatol.* 34:114-122).

Adefovir dipivoxil (Hepsera)

On Sep. 20, 2002, the U.S. Food and Drug Administration approved adefovir dipivoxil for the treatment of chronic hepatitis B. HEPSERA™ is the tradename for adefovir dipivoxil, a diester prodrug of adefovir. Adefovir is an acyclic nucleotide analogue of adenosine monophosphate that inhibits the hepatitis B virus (HBV) DNA polymerase by competing with the natural substrate deoxyadenosine triphosphate and by causing DNA chain termination after its incorporation into viral DNA. The chemical name of adefovir dipivoxil is 9-[2-[bis[(pivaloyloxy)methoxy]phosphinyl]methoxy]-ethyl]adenine. Adefovir is phosphorylated to the active metabolite, adefovir diphosphate, by cellular kinases. See, for example, U.S. Pat. Nos. 5,641,763 and 5,142,051, entitled, N-phosphonylmethoxyalkyl derivatives of pyrimidine and purine bases and a therapeutical composition therefrom with antiviral activity.

Resistant HBV Strains

Lamivudine is an L-nucleoside for the treatment of HBV that frequently results in the selection of resistant strains of virus that can discriminate between the unnatural L-nucleoside and the D-nucleoside, the natural substrates, and in particular the single mutants, YMDD mutant (M5521 or M552V) and L528M, and the double mutant (L528M/M552V). See U.S. Pat. Nos. 6,242,187 and 6,265,181; and International Publication No. WO 01/04358. See also: Ahmed et al. "Early Detection of Viral Resistance by Determination of Hepatitis B Virus Polymerase Mutations in Patients Treated by Lamivudine for Chronic Hepatitis B" *Hepatology,* 2000, 32 (5), 1078-1088; Ono et al. "The polymerase L528M mutation cooperates with nucleotide binding-site mutations, increasing hepatitis B virus replication and drug resistance" *Journal of Clinical Investigation*, February 2001, 107 (4), 449-455; Allen "Identification and Characterization of Mutations in Hepatitis B Virus Resistant to Lamivudine" *Hepatology,* 1998, 7 (6), 1670-1677; Das et al. "Molecular Modeling and Biochemical Characterization Reveal the Mechanism of Hepatitis B virus Polymerase Resistance to Lamivudine (3TC) and Emtricitabine (FTC)" *Journal of Virology*, May 2001, 75 (10), 4771-4779; Delaney "Cross-Resistance Testing of Antihepadnaviral Compounds using Novel Recombinant Baculoviruses which Encode Drug-Resistant Strains of Hepatitis B Virus" *Antimicrobial Agents and Chemotherapy*, June 2001, 45 (6), 1705-1713; Fu "Role of Additional Mutations outside the YMDD Motif of Hepatitis B Virus Polymerase in L-(-)-SddC (3TC) Resistance" *Biochemical Pharmacology,* 1998, 55 (10), 1567-1572; Fu "Sensitivity of L-(-)-2',3'-Dideoxythiacytidine Resistant Hepatitis B Virus to Other Antiviral Nucleoside Analogues" *Biochemical Pharmacology,* 1999, 57 (12), 1351-1359; Gauthier "Quantitation of Hepatitis B Viremia and Emergence of YMDD Variants in Patients with Chronic Hepatitis B Treated with Lamivudine" *The Journal of Infection Diseases*, December 1999, 180, 1757-1762; Kioko "YMDD Motif in Hepatitis B Virus DNA Polymerase Influences on Replication and Lamivudine Resistance: A Study by In Vitro Full-Length viral DNA Transfection" *Hepatology*, March 1999, 29 (3), 939-945; Kioko "Susceptibility of lamivudine-resistant hepatitis B virus to other reverse transcriptase inhibitors" *The Journal of Clinical Investigation*, June 1999, 3 (12), 1635-1640; Zoulim "Drug therapy for chronic hepatitis B: antiviral efficacy and influence of hepatitis B virus polymerase mutations on the outcome of therapy" *Journal of Hepatology,* 1998, 29, 151-168; and Ying et al. *J. Viral Hepat., March* 2000, 7 (2), 161-165.

In controlled clinical studies of lamivudine (100 mg qd) administered to HBV-infected patients, the prevalence of YMDD-mutant HBV was 14 to 32% after one year of treatment and as much as 58% after two to three years of treatment. Mutant virus was associated with evidence of diminished treatment response relative to lamivudine-treated patients without YMDD mutations. Ono et al. *The Journal of Clinical Investigation,* 2001, 107 (4), 449-455.

Genotypic analysis of viral isolates obtained from patients with renewed HBV replication while receiving lamivudine suggests that a reduction in HBV sensitivity to lamivudine is associated with mutations resulting in a methionine to valine or isoleucine substitution in the YMDD motif of the catalytic domain of HBV polymerase (position 552) and a leucine to methionine substitution at position 515 or 528 (depending on the genotype/subtype of HBV).

At the present time, there is no cell-based HBV infection system that can be used to assess the activity of antiviral agents against cells infected with lamivudine-resistant HBV isolates from patients. The duck HBV (DHBV) in vitro model has not proved useful to select drug-resistant mutations because the primary duck hepatocytes used in this model cannot be sustained for more than a few weeks in cell culture. The relevance of selection of drug-resistant mutants in the woodchuck in vivo model is dubious because the spectrum of lamivudine-resistant mutants in the woodchuck does not match that identified in HBV-infected patients.

Interferons

Interferon is a protein made naturally by the body to modulate the immune system and to regulate other cell functions. The main classes of interferons are interferon alpha, interferon beta, interferon gamma, interferon omega and interferon tau. Interferons can be modified to increase stability in vivo, such modifications include pegylation, or other means to enhance the stability of the molecule.

Examples of the interferon alpha class of interferons include interferon alpha-2a, interferon alpha-2b, pegylated interferon alpha-2a, pegylated interferon alpha-2b ROFERON®-A (interferon alpha-2a, Roche), PEGASYS® (pegylated interferon alpha-2a, Roche), INTRON®A (Interferon alpha-2b, Schering Corporation), PEG-INTRON® (pegylated Interferon alpha-2b, Schering Corporation), consensus interferon, INFERGEN (interferon alphacon-1) by InterMune, OMNIFERON (natural interferon) by Viragen, ALBUFERON by Human Genome Sciences, Oral Interferon Alpha by Amarillo Biosciences, and SuperFeron (natural human multi-subtype IFN-alpha, Genetrol, Inc.).

Other types of interferon include: interferon beta, interferon gamma, interferon tau, interferon omega, REBIF (interferon beta-1a) by Ares-Serono, Omega Interferon by BioMedicine, interferon gamma-1b by InterMune, and HuFeron (human IFN-beta, Genetrol, Inc.).

Daily treatments with α-interferon, a genetically engineered protein, have shown promise. A human serum-derived vaccine has also been developed to immunize patients against HBV. Vaccines have been produced through genetic engineering. While the vaccine has been found effective, production of the vaccine is troublesome because the supply of human serum from chronic carriers is limited, and the purification procedure is long and expensive. Further, each batch of vaccine prepared from different serum must be tested in chimpanzees to ensure safety. In addition, the vaccine does not help the patients already infected with the virus.

An essential step in the mode of action of purine and pyrimidine nucleosides against viral diseases, and in particular, HBV and HIV, is their metabolic activation by cellular and viral kinases, to yield mono-, di- and triphosphate derivatives. The biologically active species of many nucleosides is the triphosphate form, which inhibits DNA polymerase or reverse transcriptase, or causes chain termination.

A number of synthetic nucleosides have been identified that exhibit activity against HBV. As stated supra, the (-)-enantiomer of BCH-189 (2',3'-dideoxy-3'-thiacytidine), known as 3TC, has been approved for the treatment of hepatitis B. See U.S. Pat. No. 5,532,246 as well as EPA 0 494 119 A1 filed by BioChem Pharma, Inc.

Adefovir (9-{2-(phosphonomethoxy)ethyl}adenine, also referred to as PMEA or ({2-(6-amino-9H-purin-9-yl) ethoxy}methylphosphonic acid), also has been approved in the United States for the treatment of patients infected with hepatitis B virus. See, for example, U.S. Pat. Nos. 5,641,763 and 5,142,051. Resistance to adefovir treatment in patients with HBV has been noted.

β-2-Hydroxymethyl-5-(5-fluorocytosin-1-yl)-1,3-oxathiolane ("FTC"), claimed in U.S. Pat. Nos. 5,814,639 and 5,914,331 to Liotta et al., exhibits activity against HBV. See Furman et al., "The Anti-Hepatitis B Virus Activities, Cytotoxicities, and Anabolic Profiles of the (−) and (+) Enantiomers of cis-5-Fluoro-1-{2-(Hydroxymethyl)-1,3-oxathiolane-5-yl}-Cytosine" *Antimicrobial Agents and Chemotherapy*, December 1992, 2686-2692; and Cheng, et al., *Journal of Biological Chemistry*, 1992, 267 (20), 13938-13942.

U.S. Pat. Nos. 5,565,438, 5,567,688 and 5,587,362 (Chu, et al.) disclose the use of 2'-fluoro-5-methyl-β-L-arabinofuranolyluridine (L-FMAU) for the treatment of hepatitis B and Epstein Barr virus.

Penciclovir (PCV; 2-amino-1,9-dihydro-9-{4-hydroxy-3-(hydroxymethyl)butyl}-6H-purin-6-one) has established activity against hepatitis B. See U.S. Pat. Nos. 5,075,445 and 5,684,153.

Yale University and The University of Georgia Research Foundation, Inc. disclose the use of L-FDDC (5-fluoro-3'-thia-2',3'-dideoxycytidine) for the treatment of hepatitis B virus in WO 92/18517.

Other drugs explored for the treatment of HBV include adenosine arabinoside, thymosin, acyclovir, phosphonoformate, zidovudine, (+)-cyanidanol, quinacrine, and 2'-fluoroarabinosyl-5-iodouracil.

U.S. Pat. Nos. 5,444,063 and 5,684,010 to Emory University disclose the use of enantiomerically pure β-D-1,3-dioxolane purine nucleosides to treat hepatitis B.

WO 96/40164 filed by Emory University, UAB Research Foundation, and the Centre National de la Recherche Scientifique (CNRS) discloses a number of β-L-2',3'-dideoxynucleosides for the treatment of hepatitis B.

WO 95/07287 also filed by Emory University, UAB Research Foundation, and the Centre National de la Recherche Scientifique (CNRS) discloses 2'- or 3'-deoxy and 2',3'-dideoxy-β-L-pentofuranosyl nucleosides for the treatment of HIV infection.

WO96/13512 filed by Genencor International, Inc., and Lipitek, Inc., discloses the preparation of L-ribofuranosyl nucleosides as antitumor agents and virucides.

WO95/32984 discloses lipid esters of nucleoside monophosphates as immuno-suppresive drugs.

DE 4224737 discloses cytosine nucleosides and their pharmaceutical uses.

Tsai et al., in *Biochem. Pharmacol.* 1994, 48(7), 1477-81, disclose the effect of the anti-HIV agent 2'-β-D-F-2',3'-dideoxynucleoside analogs on the cellular content of mitochondrial DNA and lactate production.

Galvez, *J. Chem. Inf Comput. Sci.* 1994, 35(5), 1198-203, describes molecular computation of β-D-3'-azido-2',3'-dideoxy-5-fluorocytidine.

Mahmoudian, *Pharm. Research* 1991, 8(1), 43-66, discloses quantitative structure-activity relationship analyses of HIV agents such as β-D-3'-azido-2',3'-dideoxy-5-fluorocytidine.

U.S. Pat. No. 5,703,058 discloses (5-carboximido or 5-fluoro)-(2',3'-unsaturated or 3'-modified) pyrimidine nucleosides for the treatment of HIV or HBV.

Lin et al., discloses the synthesis and antiviral activity of various 3'-azido analogues of β-D-nucleosides in *J. Med Chem.* 1988, 31 (2), 336-340.

WO 00/3998 filed by Idenix Pharmaceuticals, Ltd. discloses methods of preparing substituted 6-benzyl-4-oxopyrimidines, and the use of such pyrimidines for the treatment of HIV.

Idenix Pharmaceuticals, Ltd. discloses 2'-deoxy-β-L-erythropentofurano-nucleosides, and their use in the treatment of HBV in U.S. Pat. Nos. 6,395,716; 6,444,652; 6,566,344 and 6,539,837. See also WO 00/09531. A method for the treatment of hepatitis B infection in humans and other host animals is disclosed that includes administering an effective amount of a biologically active 2'-deoxy-β-L-erythro-pentofuranonucleoside (alternatively referred to as β-L-dN or a β-L-2'-dN) or a pharmaceutically acceptable salt, ester or prodrug thereof, including β-L-deoxyribothymidine (β-L-dT), β-L-deoxyribocytidine (β-L-dC), β-L-deoxyribouridine (β-L-dU), β-L-deoxyribo-guanosine (β-L-dG), β-L-deoxyriboadenosine (β-L-dA) and β-L-deoxyriboinosine (β-L-dI), administered either alone or in combination, optionally in a pharmaceutically acceptable carrier. 5' and $N^4$ (cytidine) or $N^6$ (adenosine) acylated or alkylated derivatives of the active compound, or the 5'-phospholipid or 5'-ether lipids were also disclosed.

von Janta-Lipinski et al. *J. Med. Chem.*, 1998, 41 (12), 2040-2046 disclose the use of the L-enantiomers of 3'-fluoro-modified β-2'-deoxyribonucleoside 5'-triphosphates for the inhibition of hepatitis B polymerases. Specifically, the 5'-triphosphates of 3'-deoxy-3'-fluoro-β-L-thymidine (β-L-FTTP), 2',3'-dideoxy-3'-fluoro-β-L-cytidine (β-L-FdCTP), and 2',3'-dideoxy-3'-fluoro-β-L-5-methylcytidine (β-L-FMethCTP) were disclosed as effective inhibitors of HBV DNA polymerases. In addition, von Janta-Lipinski et al. discloses the biological activity of the triphosphate of β-L-thymidine (but not β-L-2'-dC) as a nucleoside inhibitor of endogenous DNA polymerases of HBV and DHBV. However, only triphosphorylated β-L-thymidine was evaluated, not the claimed unphosphorylated form, and there is no comment in the article on whether those β-L-nucleosides are phosphorylated in cells or in vivo or, more importantly, there is no comment on the efficacy of phosphorylation of β-L-thymidine in vivo. Because of this, the article does not teach that β-L-thymidine would have any hepatitis B activity in a cell or in vivo. See also WO 96/1204.

European Patent Application No. 0 352 248 A1 to Johansson et al. discloses the use of L-ribofuranosyl compounds for the treatment of hepatitis B.

Lin et al. "Synthesis of Several Pyrimidine L-Nucleoside Analogues as Potential Antiviral Agents" *Tetrahedron*, 1995, 51 (4), 1055-1068, discusses that β-L-5-iodo-2'-deoxyuridine (β-L-IUdR, compound 7) is active against herpes infection and various other DNA viruses, that BVdU and β-L-BV-ara-U are also active against herpes, β-L-BV-ara-U is active against varicella-zoster virus; and that 2',3'-dideoxy-L-azacytidine was found to be active against HBV.

US Patent Publication No. 20030083306 to Idenix Pharmaceuticals, Ltd. discloses 3'-prodrugs of 2'-deoxy-β-L-nucleosides for the treatment of HBV. See also WO 01/96353.

U.S. Pat. No. 4,957,924 to Beauchamp discloses various therapeutic esters of acyclovir.

In the Apr, 17-21, 2002 European Association for the Study of the Liver meeting in Madrid, Spain, Sühnel et al. of Gilead Sciences, Inc. presented a poster indicating that combinations of adefovir with β-L-2'deoxythymidine produce additive antiviral effects against HBV in vitro.

At the same meeting, Delaney et al. of Gilead Sciences, Inc. presented an oral presentation indicating that select strains of lamivudine-resistant HBV, i.e., HBV with a single mutation at the L528M (rtL180M) or M552I (rtM204I), or with a double mutation at L528M (rtL528M) and M552V (rtM204V), are cross-resistant to L-dT and L-dC in vitro.

Treatments for hepatitis B infection are also described in Lok and McMahon, AASLD Practice Guidelines, pp. 1225-1241 (2001), including treatment with interferons. Eastern woodchucks chronically infected with the woodchuck hepatitis virus (WHV) were used as a model of HBV infection to study the antiviral effect of 1-(2-fluoro-5-methyl-β-L-arabinofuranosyl)-uracil (L-FMAU) and WHV surface antigen vaccine. The humoral and cellular immunity associated with the combination of L-FMAU and vaccine resembled that observed in self-limited WHV infection. Menne et al., *J. Virology*, 76(11):5305-5314 (2002).

WO 98/23285 discloses a method for the treatment or prophylaxis of hepatitis B virus infections in a human or animal patient which comprises administering to the patient effective or prophylactic amounts of penciclovir (or a bioprecursor thereof such as famciclovir) and alpha-interferon.

Examples of antiviral agents that have been identified as active against the hepatitis B virus include: Agents currently in clinical development, include:

Mark Nelson, MD. Selected Highlights from Drug Development for Antiretroviral Therapies 2001 (Hep DART 2001) Dec. 16-20, 2001, Maui, Hi.; Selected Highlights from American Association for the Study of Liver Diseases 52 nd Annual Meeting (52 nd AASLD). Nov. 9-13, 2001. Dallas, Tex.; Report on Hepatitis B from Digestive Disease Week 2001; May 20-23, 2001, Atlanta, Ga.

U.S. Application No. 20020098199, published Jul. 25, 2002, discloses immunostimulatory sequences for the treatment of HBV and HCV.

U.S. Pat. No. 6,225,292, assigned to The Regents of the University of California and Dynavax Technologies Corp., discloses oligonucleotides which inhibit the immunostimulatory activity of ISS-ODN (immunostimulatory sequence oligodeoxynucleotides) as well as methods for their identification and use. The disclosed oligonucleotides of are useful in controlling therapeutically intended ISS-ODN adjuvant activity as well as undesired ISS-ODN activity exerted by recombinant expression vectors, such as those used for gene therapy and gene immunization. The oligonucleotides also have anti-inflammatory activity useful in reducing inflammation in response to infection of a host with ISS-ODN containing microbes, in controlling autoimmune disease and in boosting host Th2 type immune responses to an antigen. The

| Drug Name | Drug Class | Company | FDA Status |
|---|---|---|---|
| Intron A (interferon α-2b) | interferon | Schering-Plough | FDA-approved |
| Epivir-HBV (lamivudine; 3TC) | nucleoside analogue | GlaxoSmithKline | FDA-approved |
| Adefovir dipivoxil | nucleotide analogue | Gilead Sciences | Phase III* (NDA filed March 2002) |
| Coviracil (emtricitabine; FTC) | nucleoside analogue | Triangle Pharmaceuticals | Phase III |
| Entecavir | nucleoside analogue | Bristol-Myers Squibb | Phase III |
| Clevudine (L-FMAU) | nucleoside analogue | Triangle Pharmaceuticals | Phase II |
| ACH 126, 443 (L-Fd4C) | nucleoside analogue | Achillion Pharmaceuticals | Phase II |
| AM 365 | nucleoside analogue | Amrad | Phase II (Asia and Australia) |
| DAPD | nucleoside analogue | Triangle Pharmaceuticals | Phase II |
| LdT (telbavudine) | nucleoside analogue | Idenix | Phase II |
| XTL 001 | monoclonal antibody | XTL Biopharm | Phase II (Israel) |
| Theradigm | Immune stimulant | Epimmune | Phase II |
| Zadaxin** (thymosin) | Immune stimulant | SciClone | Phase II with Epivir-HBV |
| EHT 899 | viral protein | Enzo Biochem | Phase II (Israel) |
| HBV DNA vaccine | Immune stimulant | PowderJect (UK) | Phase I |
| MCC 478 | nucleoside analogue | Eli Lilly | Phase I (Germany) |
| valLdC (valtorcitabine) | nucleoside analogue | Idenix | Phase I |
| ICN 2001 | nucleoside analogue | ICN | Preclinical |
| Fluoro L and D nucleosides | nucleoside analogue | Pharmasset | Preclinical |
| Racivir | nucleoside analogue | Pharmasset | Preclinical |
| Robustaflavone | nucleoside analogue | Advanced Life Sciences | Preclinical |
| Post Exposure and/or Post Liver Transplant Therapies | | | |
| BayHepB | HBV immuneglobulin | Bayer (US) | FDA-approved |
| anti-hepatitis B | HBV immuneglobulin | Cangene (Canada) | NDA submitted 2001 |
| Nabi-HB | HBV immuneglobulin | Nabi | FDA-approved |

**Zadaxin: orphan drug approval in US patent also encompasses pharmaceutically useful conjugates of the oligonucleotides of the invention (including conjugate partners such as antigens and antibodies).

U.S. Pat. No. 6,589,940, assigned to Dynavax Technologies Corp., discloses immunostimulatory oligonucleotide compositions. These oligonucleotides comprise an immunostimulatory octanucleotide sequence. These oligonucleotides can be administered in conjunction with an immunostimulatory peptide or antigen. Methods for modulating an immune response upon administration of the oligonucleotide are also disclosed. In addition, an in vitro screening method to identify oligonucleotides with immunostimulatory activity is provided.

U.S. Pat. No. 6,562,798, assigned to Dynavax Technologies Corp., discloses immunomodulatory oligonucleotide compositions, including immunostimulatory hexanucleotide sequence comprising a modified cytosine. These oligonucleotides can be administered in conjunction with an immunomodulatory peptide or antigen. Methods of modulating an immune response upon administration of the oligonucleotide comprising a modified immunostimulatory sequence are also disclosed.

PCT WO 03/014316 A2, assigned to Dynavax Technologies Corp., discloses compositions and methods for immunomodulation of individuals. Immunomodulation is accomplished by administration of immunomodulatory polynucleotide/microcarrier (IMO/MC) complexes comprising 3-6 mer immunomodulatory oligonucleotides. The IMO/MC complexes may be covalently or non-covalently bound. Also disclosed are immunomodulatory compositions comprising a 3-6 mer IMO encapsulated in an MC.

PCT WO 03/000922 A2, assigned to Dynavax Technologies Corp., discloses immunomodulatory compounds and methods for immunomodulation of individuals using the immunomodulatory compounds.

PCT WO 02/052002 A2, assigned to Dynavax Technologies Corp., discloses immunomodulatory polynucleotides and methods for immunomodulation of individuals using the immunomodulatory polynucleotides.

PCT WO 01/68144 A2 and PCT WO0168143 A2 assigned to Dynavax Technologies Corp., disclose compositions and methods for immunomodulation of individuals. Immunomodulation is accomplished by administration of immunomodulatory polynucleotide/microcarrier (IMP/MC) complexes. The IMP/MC complexes may be covalently or non-covalently bound, and feature a polynucleotide comprising at least one immunostimulatory sequence bound to a biodegradable microcarrier or nanocarrier.

PCT WO 01/68117 A2, assigned to Dynavax Technologies Corp., discloses methods for the treatment of papillomavirus infections. A polynucleotide comprising an immunstimulatory sequence is administered to an individual who has been exposed to or infected by papillomavirus. The polynucleotide is not administered with papillomavirus antigen. Administration of the polynucleotide results in amelioration of symptoms of papillomavirus infection.

PCT WO 01/68078 A2, assigned to Dynavax Technologies Corp., discloses methods for the treatment of hepatitis B virus (HBV) and hepatitis C virus (HCV) infections. A polynucleotide comprising an immunostimulatory sequence is administered to an individual who has been exposed to or infected by HBV and/or HCV. The polynucleotide is not administered with a HCV or HBV antigen. Administration of the polynucleotide results in amelioration of symptoms of HBV and/or HCV infection.

PCT WO 01/68077 A3, assigned to Dynavax Technologies Corp., discloses methods of suppression, prevention, and/or treatment of infection by viruses. A polynucleotide comprising an immunostimulatory sequence (an "ISS") is administered to an individual who is at risk of being exposed to, has been exposed to or is infected with a virus. The ISS-containing polynucleotide is administered without any antigens of the virus. Administration of the ISS-containing polynucleotide results in reduced incidence and/or severity of one or more symptoms of virus infection.

PCT WO 01/12223 A2, assigned to Dynavax Technologies Corp., discloses methods of modulating an immune response to a second antigen which entail administration of a first antigen and an immunostimulatory polynucleotide. Modulation of the immune response is generally manifested as stimulation of a Th1 response.

PCT WO 00/21556 A1, assigned to Dynavax Technologies Corp., discloses anti-viral immunomodulatory compositions comprising immunostimulatory polynucleotides and HIV antigens, such as gp120. Methods for modulating an immune response upon administration of the oligonucleotide and antigen compositions are also disclosed.

PCT WO 00/16804 A1, assigned to Dynavax Technologies Corp., discloses methods of treating IgE-associated disorders and compositions for use therein. The methods are particularly useful in treatment of allergies and allergy-related disorders. The methods generally comprise administering an IgE inhibitor (such as anti-IgE antibody) and an antigen and/or immunostimulatory polynucleotide sequence (ISS). These combination methods offer significant advantages, such as allowing more aggressive therapy while reducing unwanted side effects, such as anaphylaxis.

PCT WO 99/62923 A2, assigned to Dynavax Technologies Corp., discloses oligonucleotides comprise an immunostimulatory hexanucleotide sequence comprising a modified cytosine. These oligonucleotides can be administered in conjunction with an immunomodulatory peptide or antigen. Methods of modulating an immune response upon administration of the oligonucleotide comprising a modified immunostimulatory sequence are also disclosed.

PCT WO 98/55495 A2, assigned to Dynavax Technologies Corp., discloses immunostimulatory oligonucleotide composition including immunostimulatory octanucleotide sequence. These oligonucleotides can be administered in conjunction with an immunostimulatory peptide or antigen. Methods for modulating an immune response upon administration of the oligonucleotide are also disclosed. In addition, an in vitro screening method to identify oligonucleotides with immunostimulatory activity is also disclosed.

PCT WO 03/015711 A2, assigned to Coley Pharmaceutical Group, Inc., discloses a class of immunostimulatory nucleic acids having at least two functionally and structurally defined domains. This class of combination motif immunostimulatory nucleic acids activates an immune response and is useful for treating a variety of immune related disorders such as cancer, infectious disease, and allergic disorders. The nucleic acids also stimulate activation of natural killer cells and production of type 1 interferon.

U.S. Pat. No. 6,406,705, assigned to Coley Pharmaceutical Group, Inc., discloses methods and products utilizing a synergistic combination of immunostimulatory oligonucleotides having at least one unmethylated CpG dinucleotide (CpG ODN) and a non-nucleic acid adjuvant. Such combinations of adjuvants may be used with an antigen or alone. Methods and products utilizing immunostimulatory oligonucleotides having at least one unmethylated CpG dinucleotide (CpG ODN) for induction of cellular immunity in infants are also disclosed.

U.S. Pat. No. 6,339,068, assigned to Coley Pharmaceutical Group, Inc., discloses DNA vaccine vectors that can be improved by removal of CpG-N motifs and optional addition of CpG-S motifs. In addition, for high and long-lasting levels of expression, the optimized vector should include a promoter/enhancer that is not down-regulated by the cytokines induced by the immunostimulatory CpG motifs. Vectors and methods of use for immunostimulation are provided herein. The invention also provides improved gene therapy vectors by determining the CpG-N and CpG-S motifs present in the construct, removing stimulatory CpG (CpG-S) motifs and/or inserting neutralizing CpG (CpG-N) motifs, thereby producing a nucleic acid construct providing enhanced expression of the therapeutic polypeptide.

U.S. Pat. No. 6,239,116, assigned to Coley Pharmaceutical Group, Inc., discloses nucleic acid sequences containing unmethylated CpG dinucleotides that modulate an immune response including stimulating a Th1 pattern of immune activation, cytokine production, NK lytic activity, and B cell proliferation are disclosed. The sequences are also useful a synthetic adjuvant.

U.S. Pat. No. 6,207,646, assigned to Coley Pharmaceutical Group, Inc., discloses Nucleic acids containing unmethylated CpG dinucleotides and therapeutic utilities based on their ability to stimulate an immune response and to redirect a Th2 response to a Th1 response in a subject are disclosed.

U.S. Pat. No. 6,194,388, assigned to Coley Pharmaceutical Group, Inc., discloses oligonucleotides containing unmethylated CpG dinucleotides and therapeutic utilities based on their ability to stimulate an immune response in a subject are disclosed. Also disclosed are therapies for treating diseases associated with immune system activation that are initiated by unmethylated CpG dinucleotides in a subject comprising administering to the subject oligonucleotides that do not contain unmethylated CpG sequences (i.e. methylated CpG sequences or no CpG sequence) to outcompete unmethylated CpG nucleic acids for binding. Further disclosed are methylated CpG containing dinucleotides for use antisense therapies or as in vivo hybridization probes, and immunoinhibitory oligonucleotides for use as antiviral therapeutics.

U.S. publication no. 20030091599 A1, assigned to Coley Pharmaceutical Group, Inc., discloses methods and products utilizing a synergistic combination of immunostimulatory oligonucleotides having at least one unmethylated CpG dinucleotide (CpG ODN) and a non-nucleic acid adjuvant. Such combinations of adjuvants may be used with an antigen or alone. The publication also relates to methods and products utilizing immunostimulatory oligonucleotides having at least one unmethylated CpG dinucleotide (CpG ODN) for induction of cellular immunity in infants.

PCT WO 03/031573 A2, assigned to Coley Pharmaceutical Group, Inc., discloses compositions and methods are provided to identify, characterize, and optimize immunostimulatory compounds, their agonists and antagonists, working through TLR3.

PCT WO 03/012061 A2, assigned to Coley Pharmaceutical Group, Inc., discloses methods and compositions relating to a dentritic cell expression database.

PCT WO 02/069369 A2, assigned to Coley Pharmaceutical Group, Inc., discloses immunostimulatory compositions described as CpG-like nucleic acids are provided, including nucleic acids having immunostimulatory characteristics of CpG nucleic acid, despite certain substitutions of C, G, or C and G of the CpG dinucleotide. The substitutions can include, among others, exchange of methylated C for C, inosine for G, and ZpY for CpG, where Z is Cytosine or dSpacer and Y is inosine, 2-aminopurine, nebularine, or dSpacer. Also disclosed are methods for inducing an immune response in a subject using the CpG-like nucleic acids. The methods are useful in the treatment of a subject that has or is at risk of developing an infectious disease, allergy, asthma, cancer, anemia, thrombocytopenia, or neutropenia.

PCT WO 01/95935 A1, assigned to Coley Pharmaceutical Group, Inc., discloses methods and products for inducing an immune response using immunostimulatory nucleic acids. In particular the immunostimulatory nucleic acids preferentially induce a Th2 immune response. The invention is useful for treating and preventing disorders associated with a Th1 immune response or for creating a Th2 environment for treating disorders that are sensitive to Th2 immune responses.

PCT WO 01/22990 A2, assigned to Coley Pharmaceutical Group, Inc., discloses methods and compositions for extending the clinical utility of IFN-'alpha' in the treatment of a variety of viral and proliferative disorders. Also disclosed are methods which increase the efficacy of IFN-'alpha' treatment and reduce IFN-'alpha' treatment-related side effects. In addition, methods are provides for supporting the survival and for activating natural interferon producing cells (IPCs) in vitro without exogenous IL-3 or GM-CSF.

PCT WO 01/22972 A2, assigned to Coley Pharmaceutical Group, Inc., discloses immunostimulatory nucleic acid compositions and methods of using the compositions. The T-rich nucleic acids contain poly T sequences and/or have greater than 25% T nucleotide residues. The TG nucleic acids have TG dinucleotides. The C-rich nucleic acids have at least one poly-C region and/or greater than 50% c nucleotides. These immunostimulatory nucleic acids function in a similar manner to nucleic acids containing CpG motifs. The invention also encompasses preferred CpG nucleic acids.

In light of the fact that hepatitis B virus has reached epidemic levels worldwide, and has severe and often tragic effects on the infected patient, there remains a strong need to provide new effective pharmaceutical agents to treat humans infected with the drug-resistant virus, i.e., lamivudine resistant HBV, that have low toxicity to the host.

Therefore, it is an object of the present invention to provide compounds, compositions and methods for the treatment and/or prophylaxis of a lamivudine resistant HBV infection in a host, such as human patients.

It is another object of the present invention to provide compounds, compositions and methods for the prevention of a resistant HBV mutant, for example YMDD HBV (M552V), infection in a naïve host, such as human patients.

It is still another object of the present invention to provide compounds, compositions and methods for the treatment of patients infected with a drug resistant form of HBV.

It is yet another object of the present invention to provide effective combination therapies compositions for the treatment of treatment of HBV and/or the suppression or prevention of the expression of resistant HBV strains in a patient.

SUMMARY OF THE INVENTION

It has been discovered that β-L-2'-deoxynucleosides, and in particular β-L-2'-deoxycytidine and β-L-2'-deoxythymidine, are active against drug-resistant hepatitis B virus with mutations at the 552 (M to V) codon, i.e., the 204 (M to V) codon of the reverse transcriptase region of the virus. Based on this discovery, a method for treating lamivudine resistant HBV (M552V) in a host, such as a mammal, and in particular a human, is provided that includes administering a β-L-2'-deoxynucleoside or its pharmaceutically acceptable salt, ester or prodrug. In addition, a method for preventing lamivudine resistant HBV (M552V) mutation from occurring in a naïve host, such as a mammal, and in particular a human, is provided that includes administering a β-L-2'-deoxynucleoside or its pharmaceutically acceptable salt, ester or prodrug. A method for preventing and/or suppressing the emergence of the HBV double mutant (L528M/M552V) in a host, such as a mammal, and in particular a human, is also provided that includes administering a β-L-2'-deoxynucleoside or its pharmaceutically acceptable salt, ester or prodrug.

In one embodiment, the invention provides the use of a β-L 2'-deoxynucleoside of the formula (I):

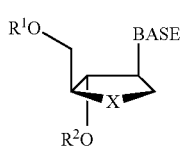

(I)

or its pharmaceutically acceptable salt, ester or prodrug thereof, wherein $R^1$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

X is O, S, $SO_2$ or $CH_2$; and

BASE is a purine or pyrimidine base that may optionally be substituted;

and all tautomers and stereoisomers thereof.

In a preferred embodiment, X is O.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl);

and all tautomers and stereoisomers thereof.

In another embodiment of the present invention, the β-L 2'-deoxynucleoside is a β-L-2'-deoxypurine of the formula:

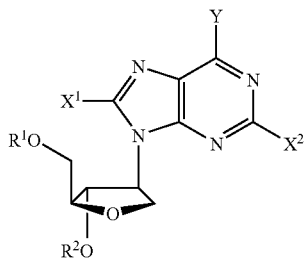

or its pharmaceutically acceptable salt, ester or prodrug thereof, wherein $R^1$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

Y is $OR^3$, $NR^3R^4$ or $SR^3$; and $X^1$ and $X^2$ are independently selected from the group consisting of H, straight chained, branched or cyclic alkyl, acyl, acetyl, butyryl, CO-alkyl, CO-aryl, CO-alkoxyalkyl, halogen, $OR^5$, $NR^5R^6$ or $SR^5$; and $R^3$, $R^4$, $R^5$ and $R^6$ are independently H, straight chained, branched or cyclic alkyl (especially cyclopropyl), dialkylaminoalkylene (in particular, dimethylaminomethylene), acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

and all tautomers and stereoisomers thereof.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl);

and all tautomers and stereoisomers thereof.

In another embodiment of the present invention, the β-L 2'-deoxynucleoside is β-L-2'-deoxypyrimidine of the formula:

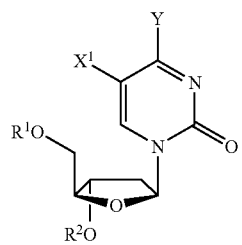

or its pharmaceutically acceptable salt, ester or prodrug thereof, wherein $R^1$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

Y is $OR^3$, $NR^3R^4$ or $SR^3$;

$X^1$ is selected from the group consisting of H, straight chained, branched or cyclic alkyl, acyl, acetyl, butyryl, CO-alkyl, CO-aryl, CO-alkoxyalkyl, halogen, $OR^5$, $NR^5R^6$ or $SR^5$; and $R^3$, $R^4$, $R^5$ and $R^6$ are independently H, straight chained, branched or cyclic alkyl (especially cyclopropyl), dialkylaminoalkylene (in particular, dimethylaminomethylene), acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

and all tautomers and stereoisomers thereof.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl);

and all tautomers and stereoisomers thereof.

In one particular embodiment, the β-L 2'-deoxynucleoside is β-L-2'-deoxycytidine of the formula:

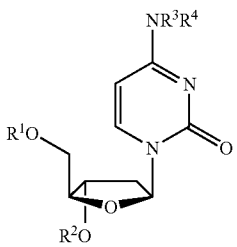

or its pharmaceutically acceptable salt, ester or prodrug thereof, wherein $R^1$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^3$ and $R^4$ are independently H, straight chained, branched or cyclic alkyl (especially cyclopropyl), dialkylaminoalkylene (in particular, dimethylaminomethylene), acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a preferred embodiment, $R^1$ and/or $R^2$ is H.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl).

In another preferred embodiment, $R^1$ and/or $R^2$ is an amino acid residue, and in particular L-valinyl.

In one embodiment, $R^3$ is hydrogen, and $R^4$ is dimethylaminomethylene.

In another embodiment, $R^3$ is hydrogen, and $R^4$ is acetyl.

In another embodiment, $R^3$ is hydrogen, and $R^4$ is L-valinyl.

In one particular embodiment, the β-L-2'-deoxycytidine is of the formula:

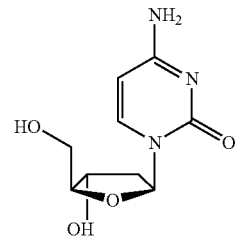

or a pharmaceutically acceptable salt, ester or prodrug thereof.

In another particular embodiment, the β-L-2'-deoxycytidine is of the formula:

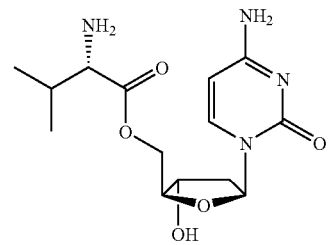

or a pharmaceutically acceptable salt thereof.

In another particular embodiment, the β-L-2'-deoxycytidine is of the formula:

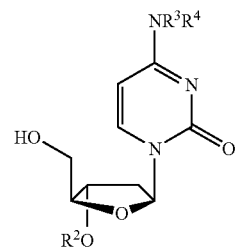

or a pharmaceutically acceptable salt, ester or prodrug thereof, wherein $R^2$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate prodrug; and $R^3$ and $R^4$ are independently H, straight chained, branched or cyclic alkyl, dialkylaminoalkylene, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate prodrug.

In yet another particular embodiment, the β-L-2'-deoxycytidine is of the formula:

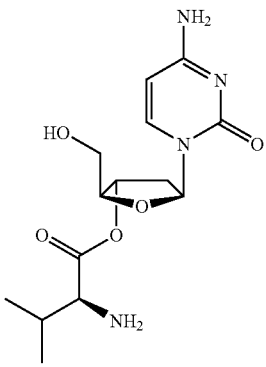

or a pharmaceutically acceptable salt thereof.

In yet another particular embodiment, the β-L-2'-deoxycytidine is of the formula:

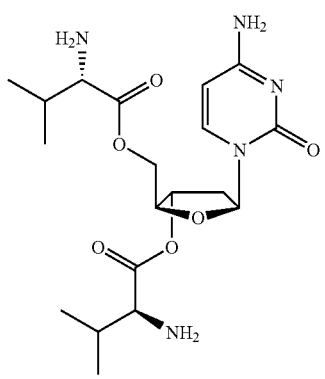

or a pharmaceutically acceptable salt thereof.

In another embodiment, the β-L 2'-deoxynucleoside is β-L-2'-deoxythymidine of the formula:

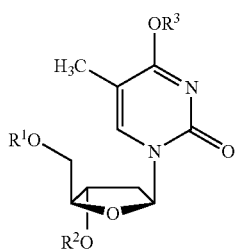

or its pharmaceutically acceptable salt, ester or prodrug thereof, wherein $R^1$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^2$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^3$ is hydrogen, straight chained, branched or cyclic alkyl (especially cyclopropyl), acyl, acetyl, butyryl, dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and all tautomers and stereoisomers thereof.

In a preferred embodiment, $R^1$ and/or $R^2$ is H.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl);

and all tautomers and stereoisomers thereof.

In another preferred embodiment, $R^1$ and/or $R^2$ is an amino acid residue, and in particular L-valinyl.

In one particular embodiment, the β-L-2'-deoxythymidine is of the formula:

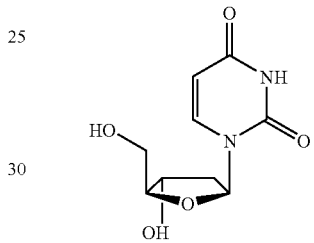

or a pharmaceutically acceptable salt, ester or prodrug thereof.

In another particular embodiment, the β-L-2'-deoxythymidine is of the formula:

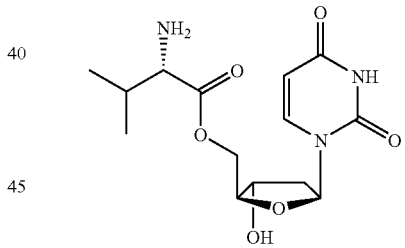

or a pharmaceutically acceptable salt thereof.

In another particular embodiment, the β-L-2'-deoxythymidine is of the formula:

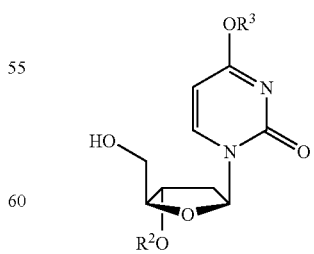

or a pharmaceutically acceptable salt, ester or prodrug thereof, wherein $R^2$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate prodrug; and $R^3$ is hydrogen, straight chained, branched or cyclic alkyl, dialkylaminoalkylene, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate prodrug.

In yet another particular embodiment, the β-L-2'-deoxythymidine is of the formula:

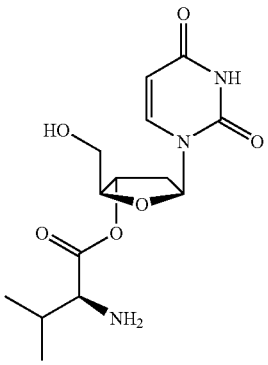

or a pharmaceutically acceptable salt thereof.

In yet another particular embodiment, the β-L-2'-deoxythymidine is of the formula:

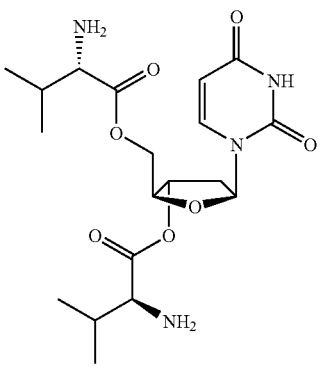

or a pharmaceutically acceptable salt thereof.

In a preferred embodiment, the β-L-2'-deoxynucleoside is at least 90% free of its opposite β-D-enantiomers.

In another embodiment, the invention includes a method for the treatment of humans infected with HBV that includes administering an HBV treatment amount of a salt, ester or prodrug of the disclosed 2'-deoxy-β-L-erythro-pentofuranonucleoside derivatives. A prodrug, as used herein, refers to a compound that is converted into the nucleoside on administration in vivo. Nonlimiting examples include pharmaceutically acceptable salt (alternatively referred to as "physiologically acceptable salts"), the 5' and $N^4$ (cytidine) or $N^6$ (adenosine) acylated (including with an amino acid residue such as L-valinyl) or alkylated derivatives of the active compound, or the 5'-phospholipid or 5'-ether lipids of the active compound.

In another embodiment, the 2'-deoxy-β-L-erythro-pentofuranonucleoside is administered in alternation or combination with one or more other 2'-deoxy-β-L-erythro-pentofuranonucleosides or one or more other compounds that exhibit activity against hepatitis B virus.

The anti-hepatitis B viral activity of the β-L-2'-deoxynucleosides provided herein, and in particular β-L-2'-dC or β-L-2'-dT, or the pharmaceutically acceptable salts, esters, phosphates or prodrugs of these compounds, can be enhanced by administering two or more of these nucleosides in combination or alternation. Alternatively, for example, one or more of the β-L-2'-deoxynucleosides provided herein, and in particular β-L-2'-dC or β-L-2'-dT, can be administered in combination and/or alternation with one or more other compounds that exhibit activity against hepatitis B virus. Nonlimiting examples include FTC, L-FMAU, DAPD, DXG, famciclovir, penciclovir, BMS-200475, bis pom PMEA (adefovir, dipivoxil), lobucavir, ganciclovir, tenofovir, Lfd4C, interferon, pegylated interferon, or ribavirin. In one embodiment, the β-L-2'-deoxynucleosides provided herein, and in particular β-L-2'-dC or β-L-2'-dT, can be administered in combination and/or alternation with 3TC.

In one embodiment, the 2'-deoxy-β-L-erythro-pentofuranonucleoside is administered in alternation or combination with one or more immunomodulators, such as a TH1 cytokine, and in particular an interferon, preferably interferon gamma for the treatment of either resistant or wild-type HBV infection.

In one embodiment of the invention, the immunomodulator is delivered in the form of a protein. In an alternate embodiment, the immunomodulator is delivered in the form of a gene or gene fragment that expresses the immunomodulator protein. In one particular embodiment of the present invention, the immunomodulator is delivered in the form of a gene or gene fragment thereof, and the delivery is mediated by an adenovirus. In one particular embodiment of the invention, the immunomodulator is interferon (such as interferon gamma), and its delivery is in the form of a gene or gene fragment that is mediated by an adenovirus.

A β-L-2'-deoxynucleoside administered in combination and/or alternation with an interferon, such as interferon alpha or interferon gamma provides superior therapy in humans against hepatitis B virus. In one embodiment, the interferon is administered in the form of a protein, typically directly into the vein or artery. In an alternate embodiment of the invention, the interferon is administered in the form of a nucleic acid, gene or gene fragment thereof that is expressed by the host. The interferon nucleic acid can be delivered to the host "naked", i.e., without a vector, or alternatively, can be delivered via a vector, including but not limited to a viral vector such as an adenovirus vector.

In one embodiment, the interferon is interferon alpha, optionally, pegylated interferon alpha. In another embodiment, the interferon alpha is selected from the group, including, but not limited to: interferon alpha-2a, interferon alpha-2b, pegylated interferon alpha-2a, pegylated interferon alpha-2b ROFERON®-A (interferon alpha-2a, Roche), PEGASYS® (pegylated interferon alpha-2a, Roche), INTRON®A (Interferon alpha-2b, Schering Corporation), PEG-INTRON® (pegylated Interferon alpha-2b, Schering Corporation), consensus interferon, INFERGEN (interferon alphacon-1) by InterMune, OMNIFERON (natural interferon) by Viragen, ALBUFERON by Human Genome Sciences, Oral Interferon Alpha by Amarillo Biosciences, and SuperFeron (natural human multi-subtype IFN-alpha, Genetrol, Inc.). In an alternate embodiment, the interferon is interferon gamma. In yet another embodiment, the interferon is interferon beta, interferon omega or interferon tau. In another embodiment, the interferon is selected from the group, including, but not limited to: REBIF (interferon beta- 1a) by Ares-Serono, Omega Interferon by BioMedicine, interferon gamma-1b by InterMune, and HuFeron (human IFN-beta, Genetrol, Inc.).

In general, during alternation therapy, an effective dosage of each agent is administered serially, whereas in combination therapy, effective dosages of two or more agents are administered together. The dosages will depend on absorption, inactivation, bio-distribution, metabolism and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. Examples of suitable dosage ranges can be found in the scientific literature and in the *Physicians Desk Reference*. Many examples of suitable dosage ranges for other compounds described herein are also found in public literature or can be identified using known procedures. These dosage ranges can be modified as desired to achieve a desired result.

BRIEF DESCRIPTION OF THE FIGURES

FIG. 1 provides non-limiting illustrative example according to the present invention of the synthesis of 5'-valinyl esters of 2'-deoxy-β-L-cytidine (β-L-dC) from 2'-deoxy-β-L-cytidine.

FIG. 2 is a non-limiting illustrative example according to the present invention of the synthesis of $N^4$-acetyl-2'-deoxy-β-L-cytidine from 2'-deoxy-β-L-cytidine.

FIG. 3 is a non-limiting illustrative example according to the present invention of the synthesis of $N^4$-[(dimethylamino)methylene]-2'-deoxy-β-L-cytidine from 2'-deoxy-β-L-cytidine.

FIG. 4 is a non-limiting illustrative example according to the present invention of the synthesis of 3',5'-di-O-acetyl-2'-deoxy-β-L-cytidine from 2'-deoxy-β-L-cytidine.

FIG. 5 is a non-limiting illustrative example according to the present invention of the synthesis of 3',5'-di-O-valinyl ester of 2'-deoxy-β-L-cytidine from 2'-deoxy-β-L-cytidine.

FIG. 6 is a non-limiting illustrative example according to the present invention of the synthesis of $N^4$-(Boc-valinyl) ester of 2'-deoxy-β-L-cytidine from 2'-deoxy-β-L-cytidine.

FIG. 7 is a non-limiting illustrative example according to the present invention of the synthesis of 3',5', $N^4$-tri-(L-valinyl)-2'-deoxy-β-L-cytidine from 3',5', $N^4$-tri-(Boc-L-valinyl)-2'-deoxy-β-L-cytidine.

FIG. 8 is a line graph depicting a standard calibration technique useful for the determination of solubility of various nucleosides. FIG. 8a is the calibration curve determined for natural β-D-deoxyribocytosine. FIG. 8b is the calibration curve determined for the 3',5'-divalinyl ester of β-L-deoxyribocytosine.

FIG. 9a is a non-limiting example of a HPLC profile used to assess the stability of the 3',5'-divalinyl ester of β-L-deoxyribocytosine at a pH of 7.42. The HPLC profile indicates the presence of the 3',5'-divalinyl ester of β-L-deoxyribocytosine along with 3 active metabolites, the 3'-valinyl ester of β-L-deoxyribocytosine, the 5'-valinyl ester of β-L-deoxyribocytosine and L-dC. FIG. 9b is a line graph depicting the relative concentrations of the 3',5'-divalinyl ester of β-L-deoxyribocytosine and its metabolites over time.

Similarly, FIGS. 10a and 11a are non-limiting examples of HPLC profiles used to assess the stability of the 3',5'-divalinyl ester of β-L-deoxyribocytosine at a pH of 7.20 and 4.51, respectively. At these pH's, the HPLC profile indicates the presence of the 3',5'-divalinyl ester of β-L-deoxyribocytosine along with 3 active metabolites, the 3'-valinyl ester of β-L-deoxyribocytosine, the 5'-valinyl ester of β-L-deoxyribocytosine and L-dC. FIGS. 10b and 11b are line graphs depicting the relative concentrations of the 3',5'-divalinyl ester of β-L-deoxyribocytosine and its metabolites over time.

FIG. 12 is a non-limiting example of a HPLC profile used to assess the stability of the 3',5'-divalinyl ester of β-L-deoxyribocytosine at a pH of 1.23. At this pH, the HPLC profile only indicates the presence of the 3',5'-divalinyl ester of β-L-deoxyribocytosine without any decomposition into any of its 3 active metabolites.

FIG. 13 is a line graph depicting the in vitro metabolism of 3',5'-divalinyl ester of β-L-deoxyribocytosine in human plasma.

FIG. 14 is a line graph depicting the intracellular metabolism of β-L-deoxyribocytosine (L-dC) in HepG2 cells.

FIG. 15 is a line graph depicting the intracellular accumulation of L-dC in primary human hepatocytes.

FIG. 16 is a graph that illustrates the metabolism of L-dA, L-dC, and L-dT in human Hep G2 cells in terms of accumulation and decay. The cells were incubated with 10 μM of compound.

DETAILED DESCRIPTION OF THE INVENTION

It has been discovered that β-L-2'-deoxynucleosides, and in particular β-L-2'-deoxycytidine and β-L-2'-deoxythymidine, are active against drug-resistant hepatitis B virus with mutation(s), and in particular, the mutation is at the 552 (M to V) codon, i.e., the 204 (M to V) codon of the reverse transcriptase region of the virus. Based on this discovery, a method for treating lamivudine resistant HBV (M552V) in a host, such as a mammal, and in particular a human, is provided that includes administering a β-L-2'-deoxynucleoside or its pharmaceutically acceptable salt, ester or prodrug. In addition, a method for preventing lamivudine resistant HBV (M552V) mutation from occurring in a naïve host, such as a mammal, and in particular a human, is provided that includes administering a β-L-2'-deoxynucleoside or its pharmaceutically acceptable salt, ester or prodrug. A method for preventing and/or suppressing the emergence of the HBV double mutant (L528M/M552V) in a host, such as a mammal, and in particular a human, is also provided that includes administering a β-L-2'-deoxynucleoside or its pharmaceutically acceptable salt, ester or prodrug.

In another embodiment, the 2'-deoxy-β-L-erythro-pentofuranonucleoside is administered in alternation or combination with one or more other 2'-deoxy-β-L-erythro-pentofuranonucleosides or one or more other compounds which exhibit activity against hepatitis B virus. In general, during alternation therapy, an effective dosage of each agent is administered serially, whereas in combination therapy, an effective dosage of two or more agents are administered together. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In another embodiment, the invention includes a method for the treatment of humans infected with HBV that includes administering an HBV treatment amount of a prodrug of the disclosed 2'-deoxy-β-L-erythro-pentofuranonucleoside derivatives. A prodrug, as used herein, refers to a compound that is converted into the nucleoside or a metabolite thereof on administration in vivo. Nonlimiting examples include the pharmaceutically acceptable salt (alternatively referred to as "physiologically acceptable salt"), the 5' and/or $N^4$ (cytidine) and/or $N^6$ (adenosine) acylated (including with an amino acid residue such as L-valinyl) or alkylated derivative of the active compound, or the 5'-phospholipid or 5'-ether lipid of the active compound.

A preferred embodiment of the present invention is a method for the treatment of HBV infections in humans or other host animals, that includes administering an effective amount of one or more of a 2'-deoxy-β-L-erythro-pentofuranonucleoside derivative selected from the group consisting of β-L-2'-deoxyadenosine, β-L-2'-deoxycytidine, β-L-2'-deoxyuridine, β-L-2'-guanosine, β-L-2'-deoxyinosine, and β-L-2'-deoxythymidine, or a pharmaceutically acceptable prodrug thereof, including a phosphate, 5' and or $N^6$ alkylated or acylated derivative, or a pharmaceutically acceptable salt thereof, optionally in a pharmaceutically acceptable carrier. The compounds of this invention either possess anti-HBV activity, or are metabolized to a compound or compounds that exhibit anti-HBV activity. In a preferred embodiment, the 2'-deoxy-β-L-erythropentofurano-nucleoside is administered substantially in the form of a single isomer, i.e., at least approximately 95% in the designated stereoconfiguration.

I. Compounds Defined by the Present Invention

In one embodiment, the invention provides the use of a β-L-2'-deoxynucleoside of the formula (I):

(I)

or its pharmaceutically acceptable salt, ester or prodrug thereof, wherein $R^1$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

X is O, S, $SO_2$ or $CH_2$; and

BASE is a purine or pyrimidine base that may optionally be substituted;

and all tautomeric and stereoisomeric forms thereof.

In a preferred embodiment, X is O.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl);

and all tautomeric and stereoisomeric forms thereof.

In a first subembodiment $R^1$ and/or $R^2$ is C(O)-alkyl (including lower alkyl) or aryl, and BASE is cytosine, protected cytosine or thymine.

In a second subembodiment $R^1$ and/or $R^2$ is C(O)-lower alkyl and BASE is cytosine, protected cytosine or thymine.

In a third subembodiment $R^1$ and/or $R^2$ is C(O)-methyl and BASE is cytosine, protected cytosine or thymine.

In a fourth subembodiment $R^1$ and/or $R^2$ is $C(O)C(R^8)(H)(NR^{10}R^{11})$, and BASE is cytosine, protected cytosine or thymine.

In a fifth subembodiment $R^1$ and/or $R^2$ is $C(O)C(R^8)(H)(NR^{10}R^{11})$, $R^8$ is isopropyl, at least one of $R^{10}$ and $R^{11}$ is hydrogen, and BASE is cytosine, protected cytosine or thymine.

In a sixth subembodiment $R^1$ and/or $R^2$ is $C(O)C(R^8)(H)(NR^{10}R^{11})$, $R^8$ is an amino acid side chain, and BASE is cytosine, protected cytosine, or thymine.

In a seventh subembodiment $R^1$ and/or $R^2$ is $C(O)C(R^8)(H)(NR^{10}R^{11})$; $R^8$ is a nonpolar amino acid side chain and BASE is cytosine, protected cytosine or thymine.

Nonlimiting examples of subembodiments can be defined by formula (I) in which:
(1) $R^1$ and/or $R^2$ is C(O)-methyl and BASE is cytosine.
(2) $R^1$ and/or $R^2$ is C(O)-methyl and BASE is protected cytosine.
(3) $R^1$ and/or $R^2$ is C(O)-methyl and BASE is thymine.
(4) $R^1$ and/or $R^2$ is $C(O)C(R^8)(H)(NH_2)$; $R^8$ is isopropyl and BASE is cytosine.
(5) $R^1$ and/or $R^2$ is $C(O)C(R^8)(H)(NH_2)$; $R^8$ is isopropyl and BASE is protected cytosine.
(6) $R^1$ and/or $R^2$ is $C(O)C(R^8)(H)(NH_2)$; $R^8$ is isopropyl and BASE is thymine.

In a eighth subembodiment X is O, $R^1$ and/or $R^2$ is C(O)-alkyl (including lower alkyl) or aryl, and BASE is cytosine, protected cytosine, or thymine.

In a ninth subembodiment X is O, $R^1$ and/or $R^2$ is C(O)-lower alkyl and BASE is cytosine, protected cytosine or thymine.

In a tenth subembodiment X is O, $R^1$ and/or $R^2$ is C(O)-methyl and BASE is cytosine, protected cytosine or thymine.

In an eleventh subembodiment X is O, $R^1$ and/or $R^2$ is $C(O)C(R^8)(H)(NR^{10}R^{11})$, and BASE is cytosine, protected cytosine or thymine.

In a twelfth subembodiment X is O, $R^1$ and/or $R^2$ is $C(O)C(R^8)(H)(NR^{10}R^{11})$, $R^8$ is isopropyl, at least one of $R^{10}$ and $R^{11}$ is hydrogen, and BASE is cytosine, protected cytosine or thymine.

In a thirteenth subembodiment X is O, $R^1$ and/or $R^2$ is $C(O)C(R^8)(H)(NR^{10}R^{11})$, $R^8$ is an amino acid side chain, and BASE is cytosine, protected cytosine, or thymine.

In a fourteenth subembodiment X is O, $R^1$ and/or $R^2$ is $C(O)C(R^8)(H)(NR^{10}R^{11})$; $R^8$ is a nonpolar amino acid side chain; at least one of $R^5$ and $R^6$ is hydrogen and B is cytosine, protected cytosine or thymine.

Nonlimiting examples of subembodiments can be defined by formula (I) in which:
(1) X is O, $R^1$ and/or $R^2$ is C(O)-methyl and BASE is cytosine.
(2) X is O, $R^1$ and/or $R^2$ is C(O)-methyl and BASE is protected cytosine.
(3) X is O, $R^1$ and/or $R^2$ is C(O)-methyl and BASE is thymine.
(4) X is O, $R^1$ and/or $R^2$ is $C(O)C(R^8)(H)(NH_2)$; $R^8$ is isopropyl and BASE is cytosine.
(5) X is O, $R^1$ and/or $R^2$ is $C(O)C(R^8)(H)(NH_2)$; $R^8$ is isopropyl and BASE is protected cytosine.
(6) X is O, $R^1$ and/or $R^2$ is $C(O)C(R^8)(H)(NH_2)$; $R^8$ is isopropyl and BASE is thymine.

In a fifteenth subembodiment X is O, R¹ is hydrogen, R² is C(O)-alkyl (including lower alkyl) or aryl, and BASE is cytosine, protected cytosine, or thymine.

In a sixteenth subembodiment X is O, R¹ is hydrogen, R² is C(O)-lower alkyl and BASE is cytosine, protected cytosine or thymine.

In a seventeenth subembodiment X is O, R¹ is hydrogen, R² is C(O)-methyl and BASE is cytosine, protected cytosine or thymine.

In a eighteenth subembodiment X is O, R¹ is hydrogen, R² is C(O)C(R⁸)(H)(NR¹⁰R¹¹), and BASE is cytosine, protected cytosine or thymine.

In a nineteenth subembodiment X is O, R¹ is hydrogen, R² is C(O)C(R⁸)(H)(NR¹⁰R¹¹), R⁸ is isopropyl, at least one of R¹⁰ and R¹¹ is hydrogen, and BASE is cytosine, protected cytosine or thymine.

In a twentieth subembodiment X is O, R¹ is hydrogen, R² is C(O)C(R⁸)(H)(NR¹⁰R¹¹), R⁸ is an amino acid side chain, and BASE is cytosine, protected cytosine, or thymine.

In a twenty-first subembodiment X is O, R¹ is hydrogen, R² is C(O)C(R⁸)(H)(NR¹⁰R¹¹); R⁸ is a nonpolar amino acid side chain; at least one of R⁵ and R⁶ is hydrogen and B is cytosine, protected cytosine or thymine.

Nonlimiting examples of subembodiments can be defined by formula (I) in which:
(1) X is O, R¹ is hydrogen, R² is C(O)-methyl and BASE is cytosine.
(2) X is O, R¹ is hydrogen, R² is C(O)-methyl and BASE is protected cytosine.
(3) X is O, R¹ is hydrogen, R² is C(O)-methyl and BASE is thymine.
(4) X is O, R¹ is hydrogen, R² is C(O)C(R⁸)(H)(NH₂); R⁸ is isopropyl and BASE is cytosine.
(5) X is O, R¹ is hydrogen, R² is C(O)C(R⁸)(H)(NH₂); R⁸ is isopropyl and BASE is protected cytosine.
(6) X is O, R¹ is hydrogen, R² is C(O)C(R⁸)(H)(NH₂); R⁸ is isopropyl and BASE is thymine.

In a twenty-second subembodiment X is O, R¹ and R² are independently C(O)-alkyl (including lower alkyl) or aryl, and BASE is cytosine, protected cytosine, or thymine.

In a twenty-third subembodiment X is O, R¹ and R² are independently C(O)-lower alkyl and BASE is cytosine, protected cytosine or thymine.

In a twenty-fourth subembodiment X is O, R¹ and R² are independently C(O)-methyl and BASE is cytosine, protected cytosine or thymine.

In a twenty-fifth subembodiment X is O, R¹ and R² are independently C(O)C(R⁸)(H)(NR¹⁰R¹¹), and BASE is cytosine, protected cytosine or thymine.

In a twenty-sixth subembodiment X is O, R¹ and R² are independently C(O)C(R⁸)(H)(NR¹⁰R¹¹), R⁸ is isopropyl, at least one of R¹⁰ and R¹¹ is hydrogen, and BASE is cytosine, protected cytosine or thymine.

In a twenty-seventh subembodiment X is O, R¹ and R² are independently C(O)C(R⁸)(H)(NR¹⁰R¹¹), R⁸ is an amino acid side chain, and BASE is cytosine, protected cytosine, or thymine.

In a twenty-eighth subembodiment X is O, R¹ and R² are independently C(O)C(R⁸)(H)(NR¹⁰R¹¹); R⁸ is a nonpolar amino acid side chain; at least one of R⁵ and R⁶ is hydrogen and B is cytosine, protected cytosine or thymine.

Nonlimiting examples of subembodiments can be defined by formula (I) in which:
(1) X is O, R¹ and R² are independently C(O)-methyl and BASE is cytosine.
(2) X is O, R¹ and R² are independently C(O)-methyl and BASE is protected cytosine.
(3) X is O, R¹ and R² are independently C(O)-methyl and BASE is thymine.
(4) X is O, R¹ and R² are independently C(O)C(R⁸)(H)(NH₂); R⁸ is isopropyl and BASE is cytosine.
(5) X is O, R¹ and R² are independently C(O)C(R⁸)(H)(NH₂); R⁸ is isopropyl and BASE is protected cytosine.
(6) X is O, R¹ and R² are independently C(O)C(R⁸)(H)(NH₂); R⁸ is isopropyl and BASE is thymine.

In another embodiment, the invention provides the use of a β-L-2'-deoxypurine of the formula:

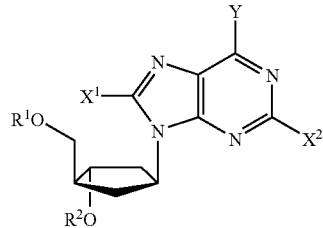

or its pharmaceutically acceptable salt, ester or prodrug thereof, wherein
R¹ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;
R² is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;
Y is OR³, NR³R⁴ or SR³; and
X¹ and X² are independently selected from the group consisting of H, straight chained, branched or cyclic alkyl, acyl, acetyl, butyryl, CO-alkyl, CO-aryl, CO-alkoxyalkyl, halogen, OR⁵, NR⁵R⁶ or SR⁵; and
R³, R⁴, R⁵ and R⁶ are independently H, straight chained, branched or cyclic alkyl (especially cyclopropyl), dialkylaminoalkylene (in particular, dimethylaminomethylene), acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;
and all tautomeric and stereoisomeric forms thereof.

In one embodiment, the amino acid residue is of the formula C(O)C(R⁸)(R⁹)(NR¹⁰R¹¹), wherein
R⁸ is the side chain of an amino acid and wherein, as in proline, R⁸ can optionally be attached to R¹⁰ to form a ring structure; or alternatively, R⁸ is an alkyl, aryl, heteroaryl or heterocyclic moiety;
R⁹ is hydrogen, alkyl (including lower alkyl) or aryl; and
R¹⁰ and R¹¹ are independently hydrogen, acyl (including an acyl derivative attached to R⁸) or alkyl (including but not limited to methyl, ethyl, propyl, and cyclopropyl);
and all tautomeric and stereoisomeric forms thereof.

In another preferred embodiment, R¹ and/or R² is an amino acid residue, and in particular L-valinyl.

In one embodiment, R³ is hydrogen, and R⁴ is dimethylaminomethylene.

In another embodiment, R³ is hydrogen, and R⁴ is acetyl.

In another embodiment, R³ is hydrogen, and R⁴ is L-valinyl.

In another embodiment, the invention provides the use of a β-L-2'-deoxypyrimidine of the formula:

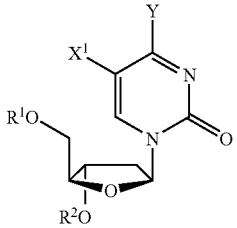

or its pharmaceutically acceptable salt, ester or prodrug thereof, wherein $R^1$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

Y is $OR^3$, $NR^3R^4$ or $SR^3$;

$X^1$ is selected from the group consisting of H, straight chained, branched or cyclic alkyl, acyl, acetyl, butyryl, CO-alkyl, CO-aryl, CO-alkoxyalkyl, halogen, $OR^5$, $NR^5R^6$ or $SR^5$; and $R^3$, $R^4$, $R^5$ and $R^6$ are independently H, straight chained, branched or cyclic alkyl (especially cyclopropyl), dialkylaminoalkylene (in particular, dimethylaminomethylene), acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and all tautomeric and stereoisomeric forms thereof.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl);

and all tautomeric and stereoisomeric forms thereof.

In one particular embodiment, the β-L-2'-deoxypyrimidine is β-L-2'-deoxycytidine of the formula:

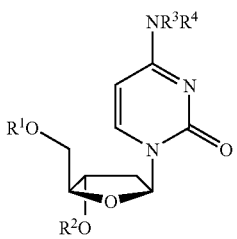

or its pharmaceutically acceptable salt, ester or prodrug thereof, wherein $R^1$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^3$ and $R^4$ are independently H, straight chained, branched or cyclic alkyl (especially cyclopropyl), dialkylaminoalkylene (in particular, dimethylaminomethylene), acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

and all tautomeric and stereoisomeric forms thereof.

In a preferred embodiment, $R^1$ and/or $R^2$ is H.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl);

and all tautomeric and stereoisomeric forms thereof.

In another preferred embodiment, $R^1$ and/or $R^2$ is an amino acid residue, and in particular L-valinyl.

In one embodiment, $R^3$ is hydrogen, and $R^4$ is dimethylaminomethylene.

In another embodiment, $R^3$ is hydrogen, and $R^4$ is acetyl.

In another embodiment, $R^3$ is hydrogen, and $R^4$ is L-valinyl.

In one particular embodiment, the β-L-2'-deoxycytidine is of the formula:

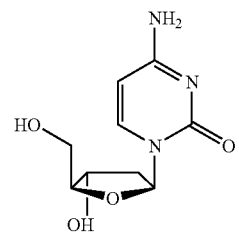

or a pharmaceutically acceptable salt, ester or prodrug thereof.

In another particular embodiment, the β-L-2'-deoxycytidine is of the formula:

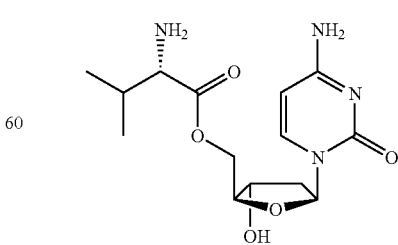

or a pharmaceutically acceptable salt thereof.

In another particular embodiment, the β-L-2'-deoxycytidine is of the formula:

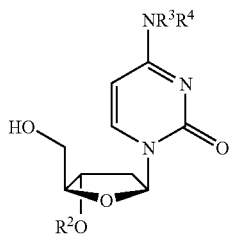

or a pharmaceutically acceptable salt, ester or prodrug thereof, wherein $R^2$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate prodrug; and $R^3$ and $R^4$ are independently H, straight chained, branched or cyclic alkyl, dialkylaminoalkylene, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate prodrug.

In yet another particular embodiment, the β-L-2'-deoxycytidine is of the formula:

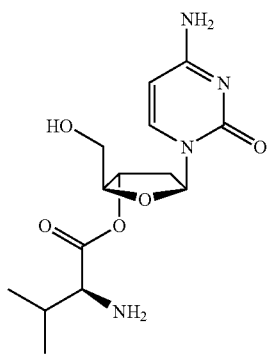

or a pharmaceutically acceptable salt thereof.

In yet another particular embodiment, the β-L-2'-deoxycytidine is of the formula:

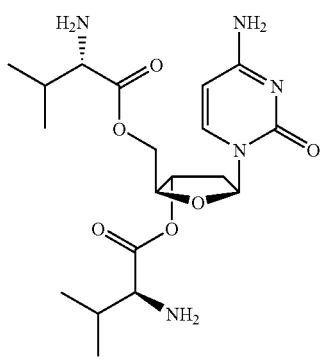

or a pharmaceutically acceptable salt thereof.

In another embodiment, the β-L 2'-deoxynucleoside is β-L-2'-deoxythymidine of the formula:

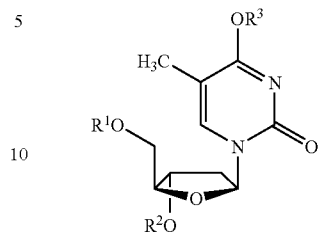

or its pharmaceutically acceptable salt, ester or prodrug thereof, wherein $R^1$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^2$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^3$ is hydrogen, straight chained, branched or cyclic alkyl (especially cyclopropyl), dialkylaminoalkylene (in particular, dimethylaminomethylene), acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

and all tautomeric and stereoisomeric forms thereof.

In a preferred embodiment, $R^1$ and/or $R^2$ is H.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl);

and all tautomeric and stereoisomeric forms thereof.

In another preferred embodiment, $R^1$ and/or $R^2$ is an amino acid residue, and in particular L-valinyl.

In one particular embodiment, the β-L-2'-deoxythymidine is of the formula:

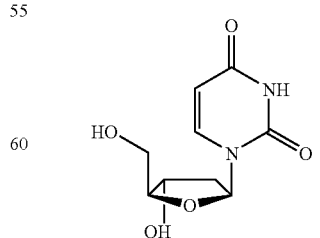

or a pharmaceutically acceptable salt, ester or prodrug thereof; and all tautomeric forms thereof.

In another particular embodiment, the β-L-2'-deoxythymidine is of the formula:

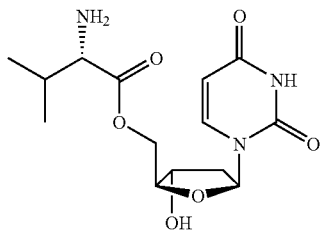

or a pharmaceutically acceptable salt thereof.

In another particular embodiment, the β-L-2'-deoxythymidine is of the formula:

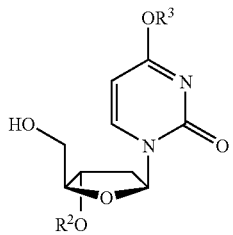

or a pharmaceutically acceptable salt thereof, wherein $R^2$ is hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate prodrug; and $R^3$ is hydrogen, straight chained, branched or cyclic alkyl, dialkylaminoalkylene, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate prodrug;

and all tautomeric and stereoisomeric forms thereof.

In yet another particular embodiment, the β-L-2'-deoxythymidine is of the formula:

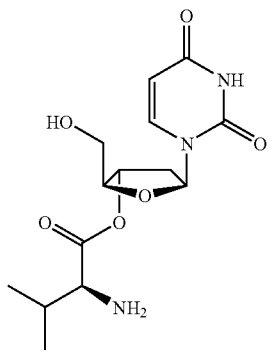

or a pharmaceutically acceptable salt thereof.

In yet another particular embodiment, the β-L-2'-deoxythymidine is of the formula:

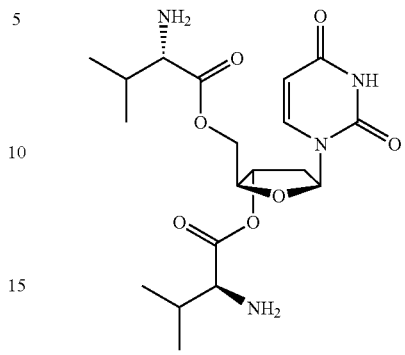

or a pharmaceutically acceptable salt thereof.

II. Definitions

As used herein, the term "resistant virus" refers to a virus that exhibits a three, and more typically, five or greater fold increase in $EC_{50}$ compared to native virus in a constant cell line, including, but not limited to peripheral blood mononuclear cells (PBMCs), or MT2 or MT4 cells.

As used herein, the term hepatitis B and related conditions refers to hepatitis B and related conditions such as anti-HBV antibody positive and HBV-positive conditions, chronic liver inflammation caused by HBV, cirrhosis, acute hepatitis, fulminant hepatitis, chronic persistent hepatitis, and fatigue. The method of the present invention includes the use of 2'-deoxy-β-L-erythro-pentofuranonucleoside derivatives prophylactically to prevent or retard the progression of clinical illness in individuals who are anti-HBV antibody or HBV-antigen positive or who have been exposed to HBV.

The term biologically active nucleoside, as used herein, refers to a nucleoside that exhibits an $EC_{50}$ of 15 micromolar or less when tested in 2.2.15 cells transfected with the hepatitis virion.

As used herein, the term "substantially pure" or "substantially in the form of one optical isomer" refers to a nucleoside composition that includes at least 95% to 98%, or more, preferably 99% to 100%, of a single enantiomer of that nucleoside. In a preferred embodiment, the β-L-2'-deoxynucleoside is administered in substantially pure form for any of the disclosed indications.

Similarly, the term "isolated" refers to a compound that includes at least 85 or 90% by weight, preferably 95% to 98% by weight, and even more preferably 99% to 100% by weight, of the nucleoside, the remainder comprising other chemical species or enantiomers.

The term "substantially pure form" is used throughout the specification to describe a compound which includes approximately 90% or greater, alternatively at least 95%, 96%, 97%, 98%, or 99% or more of a single enantiomer of that compound. When a nucleoside of a particular configuration (D or L) is referred to in this specification, it is presumed that the nucleoside is administered in substantially pure form.

The term "independently" is used herein to indicate that the variable that is independently applied varies independently from application to application. Thus, in a compound such as R"XYR", wherein R" is "independently carbon or nitrogen," both R" can be carbon, both R" can be nitrogen, or one R" can be carbon and the other R" nitrogen.

The term "alkyl", as used herein, unless otherwise specified, refers to a saturated straight, branched, or cyclic, primary, secondary or tertiary hydrocarbon of typically $C_1$ to $C_{18}$, such as $C_1$ to $C_{10}$, preferably $C_1$ to $C_6$, and specifically includes methyl, trifluoromethyl, $CCl_3$, $CFCl_2$, $CF_2Cl$, ethyl, $CH_2CF_3$, $CF_2CF_3$, propyl, isopropyl, cyclopropyl, butyl, isobutyl, sec-butyl, t-butyl, pentyl, cyclopentyl, isopentyl, t-pentyl, neopentyl, amyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Moieties with which the alkyl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "lower alkyl", as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term "aryl", as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term "acyl" refers to a carboxylic acid ester of the formula —C(O)R' in which the non-carbonyl moiety of the ester group (i.e., R') is selected from straight, branched, or cyclic alkyl or lower alkyl, alkoxyalkyl including methoxymethyl, alkaryl, aralkyl or arylalkyl (including benzyl or substituted benzyl), aryloxyalkyl such as phenoxymethyl, aryl including phenyl optionally substituted with halogen (e.g., F, Cl, Br or I), $C_1$ to $C_4$ alkyl or $C_1$ to $C_4$ alkoxy, amino acid residue or heteroaromatic. Aryl groups in the esters optimally comprise a phenyl group. The term acyl specifically includes but is not limited to acetyl, propionyl, butyryl, pentanoyl, 3-methylbutyryl, hydrogen succinyl, 3-chlorobenzoyl, benzoyl, acetyl, pivaloyl, mesylate, propionyl, valeryl, caproic, caprylic, capric, lauric, myristic, palmitic, stearic, and oleic. Alternatively, sulfonate esters such as alkyl or aralkyl sulphonyl including methanesulfonyl, the mono, di or triphosphate ester, trityl or monomethoxytrityl, trialkylsilyl (e.g. dimethyl-t-butylsilyl) or diphenylmethylsilyl are also included. The term "lower acyl" refers to an acyl group in which the non-carbonyl moiety is lower alkyl.

As used herein, the term "purine" or "pyrimidine base", includes, but is not limited to, 6-alkylpurine and $N^6$-alkylpurines, $N^6$-acylpurines, $N^6$-benzylpurine, 6-halopurine, $N^6$-vinylpurine, $N^6$-acetylenicpurine, $N^6$-acylpurine, $N^6$-hydroxyalkyl purine, $N^6$-thioalkyl purine, $N^2$-alkylpurines, $N^4$-alkylpyrimidines, $N^4$-acylpyrimidines, 4-benzylpyrimidine, $N^4$-halopyrimidines, $N^4$-acetylenic pyrimidines, 4-acyl and $N^4$-acyl pyrimidines, 4-hydroxyalkyl pyrimidines, 4-thioalkyl pyrimidines, thymine, cytosine, 6-azapyrimidine, including 6-azacytosine, 2- and/or 4-mercaptopyrimidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytosine, 5-azauracil, triazolopyridine, imidazolopyridine, pyrrolopyrimidine, and pyrazolopyrimidine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl.

Preferred bases include cytosine, 5-fluorocytosine, 5-bromocytosine, 5-iodocytosine, uracil, 5-fluorouracil, 5-bromouracil, 5-iodouracil, 5-methyluracil, thymine, adenine, guanine, inosine, xanthine, 2,6-diaminopurine, 6-aminopurine, 6-chloropurine and 2,6-dichloropurine, 6-bromopurine, 2,6-dibromopurine, 6-iodopurine, 2,6-di-iodopurine, 5-bromovinylcytosine, 5-bromovinyluracil, 5-bromoethenylcytosine, 5-bromoethenyluracil, 5-trifluoromethylcytosine, 5-trifluoromethyluracil.

As used herein, the term "amino acid residue" includes but is not limited to the L or D enantiomers or any mixture thereof, including a racemic mixture, all tautomeric and stereochemical configurations of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

Preferred amino acids are in the L-stereoconfiguration, and a preferred amino acid moiety is L-valinyl.

The abbreviations of amino acids used herein are described in Table 1.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic Acid | Asp | D | GAC | GAU | GAC | GAU |
| Glutamic Acid | Glu | E | GAA | GAG | | |
| Phenylalanine | Phe | F | UUC | UUU | | |
| Glycine | Gly | G | GGA | GCG | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | GUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

The term "immunomodulator" or "modulating an immune response", as used herein, refers to a chemokine or cytokine that regulates either directly or indirectly an immune response, which includes immunostimulatory as well as immunosuppressive effects. Immunomodulation is primarily a qualitative alteration in an overall immune response, although quantitative changes may also occur in conjunction with immunomodulation. Immunomodulation may involve an immune response that is shifted towards a "Th1-type"

immune response, as opposed to a "Th2-type" immune response. Th1-type responses are typically considered cellular immune system (e.g., cytotoxic lymphocytes) responses, while Th2-type responses are generally "humoral", or antibody-based. Th1-type immune responses are normally characterized by "delayed-type hypersensitivity" reactions to an antigen, and can be detected at the biochemical level by increased levels of Th1-associated cytokines such as IFN-gamma, IL-2, IL-12, and TNF-beta, as well as IFN-alpha and IL-6, although IL-6 may also be associated with Th2-type responses as well. Th1-type immune responses are generally associated with the production of cytotoxic lymphocytes (CTLs) and low levels or transient production of antibody. Th2-type immune responses are generally associated with higher levels of antibody production, including IgE production, an absence of or minimal CTL production, as well as expression of Th2-associated cytokines such as IL-4. Accordingly, immunomodulation in one embodiment can be recognized by, for example, an increase in IFN-gamma and/or a decrease in IgE production in an individual treated in accordance with the methods of the invention as compared to the absence of treatment.

Immunomodulatory agents include, but are not limited to, a molecule such as a chemokine or cytokine that affects either directly or indirectly an immune response. Non-limiting examples of immunomodulators include TH1 cytokines, and in particular, interferon, interferon-α, purified interferon-α, interferon-α2a, interferon-α2b, interferon-β, interferon-γ, consensus interferon, pegylated interferon, pegylated interferon-α, granulocyte macrophage colony-stimulating factor, interleukin, interleukin-2, and interleukin-12. In one embodiment, the immunomodulator is interferon, e.g., interferon-γ.

The abbreviations as used herein are meant to refer to the following:

| | |
|---|---|
| Ad IFN | Adenovirus vector expressing woodchuck interferon gamma |
| Ad RFP | Adenovirus vector without woodchuck interferon gamma gene |
| CCC DNA | Covalently closed circular viral form of DNA |
| DNA | Deoxyribonucleic acid |
| FTC | (-)-β-2', 3'-dideoxy-5-fluoro-3'-thiacytidine |
| GFP | Green fluorescent protein |
| HBV | Hepatitis B Virus |
| IFN | Interferon |
| L-FMAU | 1-(2-fluoro-5-methyl-β, L-arabinofuranosyl)thymine |
| M1, M2 | Month 1 or 2, respectively, after the beginning of the treatment |
| PCNA | Proliferating Cell Nuclear Antigen |
| PCR | Polymerase chain reaction |
| Pfu | Plaque forming unit |
| RFP | Red fluorescent protein |
| RI | Replication intermediates |
| RT | Reverse Transcription |
| TUNEL | terminal deoxynucleotidyltransferase (TdT)-mediated dUTP nick-end labeling assay |
| WHV | Woodchuck Hepatitis B Virus |

As used herein, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term host, as used herein, refers to an unicellular or multicellular organism in which the virus can replicate, including cell lines and animals, and preferably a human. Alternatively, the host can be carrying a part of the hepatitis B viral genome, whose replication or function can be altered by the compounds of the present invention. The term host specifically refers to infected cells, cells transfected with all or part of the HBV genome and animals, in particular, primates (including chimpanzees) and humans. In most animal applications of the present invention, the host is a human patient. Veterinary applications in certain indications, however, are clearly anticipated by the present invention (such as chimpanzees).

III. Nucleotide Salt or Prodrug Formulations

The term "pharmaceutically acceptable salt, ester or prodrug" is used throughout the specification to describe any pharmaceutically acceptable form (such as an ester, phosphate ester, salt of an ester or a related group) of a nucleoside compound which, upon administration to a patient, provides directly or indirectly, the β-L-2'-deoxynucleoside, or exhibits activity themselves. Pharmaceutically acceptable salts include those derived from pharmaceutically acceptable inorganic or organic bases and acids. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against HBV, and in particular lamivudine-resistant HBV (M552V), or are metabolized to a compound that exhibits such activity.

As used herein, the term "pharmaceutically acceptable salt or complex" refers to a salt or complex of the β-L-2'-deoxynucleoside that retains the desired biological activity of the parent compound and exhibits minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, bicarbonic acid, carbonic acid and the like), and salts formed with organic acids such as acetic acid, oxalic acid, formic acid, fumaric acid, propionic acid, glycolic acid, lactic acid, pyruvic acid, maleic acid, salicylic acid, tartaric acid, succinic acid, malic acid, ascorbic acid, benzoic acid, tannic acid, palmoic acid, alginic acid, polyglutamic acid, tosic acid, methanesulphonic acid, citric acid, malonic acid, α-ketoglutaric acid, α-glycerophosphonic acid, naphthalenesulfonic acids, naphthalene-disulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzyl-ethylenediamine, ammonium, or ethylenediamine; or (c) combinations of (a) and (b), e.g., a zinc tannate salt or the like.

Any of the nucleosides described herein and/or the compounds that are described herein for use in combination or alternation therapy can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 1995, 27, 1-17. Any of these can be used in combination with the disclosed nucleosides to achieve a desired effect.

In one embodiment, 5' and/or 3'-O positions and/or the $N^4$ position of the β-L-2'-deoxynucleoside is acylated, alkylated or phosphorylated (including mono, di, and triphosphate esters as well as stabilized phosphates and phospholipid). In one embodiment, the acyl group is a carboxylic acid ester in which the non-carbonyl moiety of the ester group is selected from straight, branched, or cyclic alkyl, alkoxyalkyl including methoxymethyl, aralkyl including benzyl, aryloxyalkyl including phenoxymethyl, aryl including phenyl optionally substituted by halogen, alkyl, alkyl or alkoxy, sulfonate esters such as alkyl or aralkyl sulphonyl including methanesulfonyl, trityl or monomethoxytrityl, substituted benzyl, trialkylsilyl, or diphenylmethylsilyl. Aryl groups in the esters optimally comprise a phenyl group. The alkyl group can be straight, branched or cyclic and is preferably $C_1$ to $C_{18}$.

The β-L-2'-deoxynucleoside can be converted into a pharmaceutically acceptable ester by reaction with an appropriate esterifying agent, for example, an acid halide or anhydride. The nucleoside or its pharmaceutically acceptable prodrug can be converted into a pharmaceutically acceptable salt thereof in a conventional manner, for example, by treatment with an appropriate base or acid. The ester or salt can be converted into the parent nucleoside, for example, by hydrolysis. Modifications of the active compounds, specifically at the 5' and/or 3'-O positions and/or the $N^4$ position, can affect the bioavailability and rate of metabolism of the active species, thus providing control over the delivery of the active species. A preferred modification is a 3' and/or 5'-aminoacid ester, including the L-valinyl ester.

The active nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi "Novel membrane-interactive ether lipid analogs that inhibit infectious HIV-1 production and induce defective virus formation." *AIDS Res. Hum. Retro Viruses*, 1990. 6, 491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest "Synthesis and evaluation of novel ether lipid nucleoside conjugates for anti-HIV activity." *J. Med. Chem.* 1991, 34, 1408.1414; Hosteller, K. Y., D. D. Richman, D. A. Carson, L. M. Stuhmiller, G. M. T. van Wijk, and H. van den Bosch "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine." *Antimicrob. Agents Chemother.* 1992, 36, 2025.2029; Hosetler, K. Y., L. M. Stuhmiller, H. B. Lenting, H. van den Bosch, and D. D. Richman, "Synthesis and antiretroviral activity of phospholipid analogs of azidothymidine and other antiviral nucleosides." *J. Biol. Chem.* 1990, 265, 61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. Nos. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Nonlimiting examples of nucleotide prodrugs are described in the following references: Ho, D. H. W. "Distribution of Kinase and deaminase of 1β-D-arabinofuranosylcytosine in tissues of man and muse." *Cancer Res.* 1973, 33, 2816-2820; Holy, A. "Isopolar phosphorous-modified nucleotide analogues," In: De Clercq (Ed.), JAI Press, *Advances in Antiviral Drug Design*, 1992, Vol. I, 179-231; Hong, C. I., Nechaev, A., and West, C. R. "Synthesis and antitumor activity of 1β-D-arabino-furanosylcytosine conjugates of cortisol and cortisone." *Biochem. Biophys. Rs. Commun.* 1979a, 88, 1223-1229; Hong, C. I., Nechaev, A., Kirisits, A. J. Buchheit, D. J. and West, C. R. "Nucleoside conjugates as potential antitumor agents. 3. Synthesis and antitumor activity of 1-(β-D-arabinofuranosyl) cytosine conjugates of corticosteroids and selected lipophilic alcohols." *J. Med. Chem.* 1980, 28, 171-177; Hosteller, K. Y., Stuhmiller, L. M., Lenting, H. B. M. van den Bosch, H. and Richman *J. Biol. Chem.* 265, 6112-6117; Hostetler, K. Y., Carson, D. A. and Richman, D. D. "Phosphatidylazidothymidine: mechanism of antiretroviral action in CEM cells." *J. Biol Chem.* 1991, 266, 11714-11717; Hosteller, K. Y., Korba, B. Sridhar, C., Gardener, M. "Antiviral activity of phosphatidyl-dideoxycytidine in hepatitis B-infected cells and enhanced hepatic uptake in mice." *Antiviral Res.* 1994a, 24, 59-67; Hosteller, K. Y., Richman, D. D., Sridhar. C. N. Felgner, P. L. Felgner, J., Ricci, J., Gardener, M. F. Selleseth, D. W. and Ellis, M. N. "Phosphatidylazidothymidine and phosphatidyl-ddC: Assessment of uptake in mouse lymphoid tissues and antiviral activities in human immunodeficiency virus-infected cells and in rauscher leukemia virus-infected mice." *Antimicrobial Agents Chemother.* 1994b, 38, 2792-2797; Hunston, R. N., Jones, A. A. McGuigan, C., Walker, R. T., Balzarini, J., and DeClercq, E. "Synthesis and biological properties of some cyclic phosphotriesters derived from 2'-deoxy-5-fluorouridine." *J. Med. Chem.* 1984, 27, 440-444; Ji, Y. H., Moog, C., Schmitt, G., Bischoff, P. and Luu, B. "Monophosphoric acid esters of 7-β-hydroxycholesterol and of pyrimidine nucleoside as potential antitumor agents: synthesis and preliminary evaluation of antitumor activity." *J. Med. Chem.* 1990, 33, 2264-2270; Jones, A. S., McGuigan, C., Walker, R. T., Balzarini, J. and DeClercq, E. "Synthesis, properties, and biological activity of some nucleoside cyclic phosphoramidates." *J. Chem. Soc. Perkin Trans. I*, 1984, 1471-1474; Juodka, B. A. and Smart, J. "Synthesis of diribonucleoside phosph (P→N) amino acid derivatives." *Coll. Czech. Chem. Comm.* 1974, 39, 363-968; Kataoka, S., Imai, J., Yamaji, N., Kato, M., Saito, M., Kawada, T. and Imai, S. "Alkylated cAMP derivatives; selective synthesis and biological activities." *Nucleic Acids Res. Sym. Ser.* 1989, 21, 1-2; Kataoka, S., Uchida, "(cAMP) benzyl and methyl triesters." *Heterocycles* 32, 1351-1356; Kinchington, D., Harvey, J. J., O'Connor, T. J., Jones, B. C. N. M., Devine, K. G., Taylor-Robinson D., Jeffries, D. J. and McGuigan, C. "Comparison of antiviral effects of zidovudine phosphoramidate and phosphorodiamidate derivatives against HIV and ULV in vitro." *Antiviral Chem. Chemother.* 1992, 3, 107-112; Kodama, K., Morozumi, M., Saithoh, K. I., Kuninaka, H., Yosino, H. and Saneyoshi, M. "Antitumor activity and pharmacology of 1-β-D-arabinofuranosylcytosine-5'-stearylphosphate; an orally active derivative of 1-β-D-arabinofuranosylcytosine." *Jpn. J. Cancer Res.* 1989, 80, 679-685; Korty, M. and Engels, J. "The effects of adenosine- and guanosine 3',5' phosphoric and acid benzyl esters on guinea-pig ventricular myocardium." *Naunyn-Schmiedeberg's Arch. Pharmacol.* 1979, 310, 103-111; Kumar, A., Goe, P. L., Jones, A. S. Walker, R. T. Balzarini, J. and DeClercq, E. "Synthesis and biological evaluation of some cyclic phosphoramidate nucleoside derivatives." *J. Med. Chem,* 1990, 33, 2368-2375; LeBec, C., and Huynh-Dinh, T. "Synthesis of lipophilic phosphate triester derivatives of 5-fluorouridine an arabinocytidine as anticancer prodrugs." *Tetrahedron Lett.* 1991, 32, 6553-6556; Lichtenstein, J., Barner, H. D. and Cohen, S. S. "The metabolism of exogenously supplied nucleotides by *Escherichia coli.,*" *J. Biol. Chem.* 1960, 235, 457-465; Lucthy, J., Von Daeniken, A., Friederich, J. Manthey, B., Zweifel, J., Schlatter, C. and Benn, M. H. "Synthesis and toxicological properties of three naturally occurring cyanoepithioalkanes". *Mitt. Geg. Lebensmittelunters. Hyg.* 1981, 72, 131-133 (*Chem. Abstr.* 95, 127093); McGigan, C. Tollerfield, S. M. and Riley, P.a. "Synthesis and biological evaluation of some phosphate triester derivatives of the anti-viral drug Ara." *Nucleic Acids Res.* 1989, 17, 6065-6075; McGuigan, C., Devine, K. G., O'Connor, T. J., Galpin, S. A., Jeffries, D. J. and Kinchington, D. "Synthesis and evaluation of some novel phosphoramidate derivatives of 3'-azido-3'-deoxythymidine (AZT) as anti-HIV compounds." *Antiviral Chem. Chemother.* 1990a, 1, 107-113; McGuigan, C., O'Connor, T. J., Nicholls, S. R. Nickson, C. and Kinchington, D. "Synthesis and anti-HIV activity of some novel substituted dialkyl phosphate derivatives of AZT and ddCyd." *Antiviral Chem. Chemother.* 1990b, 1, 355-360; McGuigan, C., Nicholls, S. R., O'Connor, T. J., and Kinchington, D. "Synthesis of some novel dialkyl phosphate derivative of 3'-modified nucleosides as potential anti-AIDS drugs." *Antiviral Chem. Chemother.* 1990c, 1, 25-33; McGuigan, C., Devin, K. G., O'Connor, T. J., and Kinchington, D. "Synthesis and anti-HIV activity of some haloalkyl phosphoramidate derivatives of 3'-azido-3'deoxythylmidine (AZT); potent activity of the trichloroethyl methoxyalaninyl compound." *Antiviral Res.* 1991, 15, 255-263; McGuigan, C., Pathirana, R. N., Mahmood, N., Devine, K. G. and Hay, A. J. Aryl phosphate derivatives of AZT retain activity against HIV-1 in cell lines which are resistant to the action of AZT. *Antiviral Res.* 1992, 17, 311-321; McGuigan, C., Pathirana, R. N., Choi, S. M., Kinchington, D. and O'Connor, T. J. Phosphoramidate derivatives of AZT as inhibitors of HIV; studies on the carboxyl terminus. *Antiviral Chem. Chemother.* 1993a, 4, 97-101; McGuigan, C., Pathirana, R. N., Balzarini, J. and DeClercq, E. "Intracellular delivery of bioactive AZT nucleotides by aryl phosphate derivatives of AZT." *J. Med. Chem.* 1993b, 36, 1048-1052.

Alkyl hydrogen phosphate derivatives of the anti-HIV agent AZT may be less toxic than the parent nucleoside analogue. *Antiviral Chem. Chemother.* 5, 271-277; Meyer, R. B., Jr., Shuman, D. A. and Robins, R. K. "Synthesis of purine nucleoside 3',5'-cyclic phosphoramidates." *Tetrahedron Lett.* 1973, 269-272; Nagyvary, J. Gohil, R. N., Kirchner, C. R. and Stevens, J. D. "Studies on neutral esters of cyclic AMP," *Biochem. Biophys. Res. Commun.* 1973, 55, 1072-1077; Namane, A. Gouyette, C., Fillion, M. P., Fillion, G. and Huynh-Dinh, T. "Improved brain delivery of AZT using a glycosyl phosphotriester prodrug." *J. Med. Chem.* 1992, 35, 3039-3044; Nargeot, J. Nerbonne, J. M. Engels, J. and Leser, H. A. *Natl. Acad. Sci. U.S.A.* 1983, 80, 2395-2399; Nelson, K. A., Bentrude, W. G. Stser, W. N. and Hutchinson, J. P. "The question of chair-twist equilibria for the phosphate rings of nucleoside cyclic 3',5' monophosphates. $^1$HNMR and x-ray crystallographic study of the diastereomers of thymidine phenyl cyclic 3',5'-monophosphate." *J. Am. Chem. Soc.* 1987, 109, 4058-4064; Nerbonne, J. M., Richard, S., Nargeot, J. and Lester, H. A. "New photoactivatable cyclic nucleotides produce intracellular jumps in cyclic AMP and cyclic GMP concentrations." *Nature* 1984, 301, 74-76; Neumann, J. M., Herv_, M., Debouzy, J. C., Guerra, F. I., Gouyette, C., Dupraz, B. and Huyny-Dinh, T. "Synthesis and transmembrane transport studies by NMR of a glucosyl phospholipid of thymidine." *J. Am. Chem. Soc.* 1989, 111, 4270-4277; Ohno, R., Tatsumi, N., Hirano, M., Imai, K. Mizoguchi, H., Nakamura, T., Kosaka, M., Takatuski, K., Yamaya, T., Toyama K., Yoshida, T., Masaoka, T., Hashimoto, S., Ohshima, T., Kimura, I., Yamada, K. and Kimura, J. "Treatment of myelodysplastic syndromes with orally administered 1-β-D-arabinouranosylcytosine -5'stearylphosphate." *Oncology* 1991, 48, 451-455. Palomino, E., Kessle, D. and Horwitz, J. P. "A dihydropyridine carrier system for sustained delivery of 2',3'dideoxynucleosides to the brain." *J. Med. Chem.* 1989, 32, 22-625; Perkins, R. M., Barney, S. Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. "Activity of BRL47923 and its oral prodrug, SB203657A against a rauscher murine leukemia virus infection in mice." *Antiviral Res.* 1993, 20 (Suppl. I), 84; Piantadosi, C., Marasco, C. J., Jr., Norris-Natschke, S. L., Meyer, K. L., Gumus, F., Surles, J. R., Ishaq, K. S., Kucera, L. S. Iyer, N., Wallen, C. A., Piantadosi, S. and Modest, E. J. "Synthesis and evaluation of novel ether lipid nucleoside conjugates for anti-HIV-1 activity." *J. Med. Chem.* 1991, 34, 1408-1414; Pompon, A., Lefebvre, I., Imbach, J. L., Kahn, S. and Farquhar, D. "Decomposition pathways of the mono- and bis(pivaloyloxymethyl)esters of azidothymidine-5'-monophosphate in cell extract and in tissue culture medium; an application of the "on-line ISRP-cleaning HPLC technique." *Antiviral Chem Chemother.* 1994, 5, 91-98; Postemark, T. "Cyclic AMP and cyclic GMP." *Annu. Rev. Pharmacol.* 1974, 14, 23-33; Prisbe, E. J., Martin, J. C. M., McGhee, D. P. C., Barker, M. F., Smee, D. F. Duke, A. E., Matthews, T. R. and Verheyden, J. P. J. "Synthesis and antiherpes virus activity of phosphate an phosphonate derivatives of 9-[(1,3-dihydroxy-2-propoxy)methyl]guanine." *J. Med. Chem.* 1986, 29, 671-675; Pucch, F., Gosselin, G., Lefebvre, I., Pompon, a., Aubertin, A. M. Dim, and Imbach, J. L. "Intracellular delivery of nucleoside monophosphate through a reductase-mediated activation process." *Antiviral Res.* 1993, 22, 155-174; Pugaeva, V. P., Klochkeva, S. I., Mashbits, F. D. and Eizengart, R. S. "Toxicological assessment and health standard ratings for ethylene sulfide in the industrial atmosphere." *Gig. Trf Prof Zabol.* 1969, 14, 47-48 (*Chem. Abstr.* 72, 212); Robins, R. K. "The potential of nucleotide analogs as inhibitors of Retro viruses and tumors." *Pharm. Res.* 1984, 11-18; Rosowsky, A., Kim. S. H., Ross and J. Wick, M. M. "Lipophilic 5'-(alkylphosphate) esters of 1-β-D-arabinofuranosylcytosine and its $N^4$-acyl and 2.2'-anhydro-3'-O-acyl derivatives as potential prodrugs." *J. Med. Chem.* 1982, 25, 171-178; Ross, W. "Increased sensitivity of the walker turnout towards aromatic nitrogen mustards carrying basic side chains following glucose pretreatment." *Biochem. Pharm.* 1961, 8, 235-240; Ryu, E. K., Ross, R. J. Matsushita, T., MacCoss, M., Hong, C. I. and West, C. R. "Phospholipid-nucleoside conjugates. 3. Synthesis and preliminary biological evaluation of 1-β-D-arabinofuranosylcytosine 5' diphosphate [-], 2-diacylglycerols." *J. Med. Chem.* 1982, 25, 1322-1329; Saffhill, R. and Hume, W. J. "The degradation of 5-iododeoxyuridine and 5-bromoethoxyuridine by serum from different sources and its consequences for the use of these compounds for incorporation into DNA." *Chem. Biol. Interact.* 1986, 57, 347-355; Saneyoshi, M., Morozumi, M., Kodama, K., Machida, J., Kuninaka, A. and Yoshino, H. "Synthetic nucleosides and nucleotides. XVI. Synthesis and biological evaluations of a series of 1-β-D-arabinofuranosylcytosine 5'-alky or arylphosphates." *Chem Pharm. Bull.* 1980, 28, 2915-2923; Sastry, J. K., Nehete, P. N., Khan, S., Nowak, B. J., Plunkett, W., Arlinghaus, R. B. and Farquhar, D. "Membrane-permeable dideoxyuridine 5'-monophosphate analogue inhibits human immunodeficiency virus infection." *Mol. Pharmacol.* 1992, 41, 441-445; Shaw, J. P., Jones, R. J. Arimilli, M. N., Louie, M. S., Lee, W. A. and Cundy, K. C. "Oral bioavailability of PMEA from PMEA prodrugs in male Sprague-Dawley rats." *9th Annual AAPS Meeting* 1994 San Diego, Calif. (Abstract). Shuto, S., Ueda, S., Imamura, S., Fukukawa, K. Matsuda, A. and Ueda, T. "A facile one-step synthesis of 5' phosphatidiylnucleosides by an enzymatic two-phase reaction." *Tetrahedron Lett.* 1987, 28, 199-202; Shuto, S. Itoh, H., Ueda, S., Imamura, S., Kukukawa, K., Tsujino, M., Matsuda, A. and Ueda, T. *Pharm. Bull.* 1988, 36, 209-217. An example of a useful phosphate prodrug group is the S-acyl-2-thioethyl group, also referred to as "SATE."

IV. Combination or Alternation Therapy

It has been recognized that drug-resistant variants of HBV can emerge after prolonged treatment with an antiviral agent. Drug resistance most typically occurs by mutation of a gene that encodes for an enzyme used in the viral life cycle, and most typically in the case of HBV, DNA polymerase. Recently, it has been demonstrated that the efficacy of a drug against HBV infection can be prolonged, augmented, or restored by administering the compound in combination or alternation with a second, third, fourth, etc., antiviral compound that induces a different mutation from that caused by the principle drug. Alternatively, the pharmacokinetics, biodistribution or other parameter of the drug can be altered by such combination or alternation therapy. The dosages will depend on such factors as absorption, biodistribution, metabolism and excretion rates for each drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. Examples of suitable dosage ranges for anti-HBV compounds can be found in the scientific literature and in the Physicians Desk Reference. Many examples of suitable dosage ranges for other compounds described herein are also found in public literature or can be identified using known procedures. These dosage ranges can be modified as desired to achieve a desired result.

In general, during combination therapy, effective dosages of two or more agents are administered together, whereas in alternation therapy, an effective dosage of each agent is administered serially. In alternation therapy, for example, one or more first agents can be administered in an effective amount for an effective time period to treat the viral infection, and then one or more second agents substituted for those first agents in the therapy routine and likewise given in an effective amount for an effective time period. In general, combination therapy is typically preferred over alternation therapy because it induces multiple simultaneous stresses on the virus.

In any of the embodiments described herein, if the β-L-2'-nucleoside of the present invention is administered in combination or alternation with a second nucleoside or non-nucleoside reverse transcriptase inhibitor that is phosphorylated to an active form, it is preferred that a second compound be phosphorylated by an enzyme that is different from that which phosphorylates the selected β-L-2'-deoxynucleoside of the present invention in vivo. Examples of kinase enzymes are thymidine kinase, cytosine kinase, guanosine kinase, adenosine kinase, deoxycytidine kinase, 5'-nucleotidase and deoxyguanosine kinase.

The anti-hepatitis B viral activity, against either wild-type or a resistant strain of HBV, of the β-L-2'-deoxynucleosides provided herein, and in particular β-L-2'-dC or β-L-2'-dT, or the pharmaceutically acceptable salts, esters, phosphates or prodrugs of these compounds, can be enhanced by administering two or more of these nucleosides in combination or alternation. Alternatively, for example, one or more of the β-L-2'-deoxynucleosides provided herein, and in particular β-L-2'-dC or β-L-2'-dT, can be administered in combination and/or alternation with one or more other compounds that exhibit activity against hepatitis B virus. Non-limiting examples include FTC, L-FMAU, DAPD, DXG, famciclovir, penciclovir, BMS-200475, bis pom PMEA (adefovir, dipivoxil), lobucavir, ganciclovir, tenofovir, Lfd4C, foscamet (trisodium phosphonoformate), isoprinosine, levamizole, N-acetylcystine (NAC), interferon, pegylated interferon, ribavirin, PC1323 or polyadencyclic polyuridylic acid. In one embodiment, the β-L-2'-deoxynucleosides provided herein, and in particular β-L-2'-dC or β-L-2'-dT, can be administered in combination and/or alternation with 3TC.

Examples of agents that have been identified as active against the hepatitis B virus, and thus can be used in combination and/or alternation with the composition of the present invention include:

| Drug Name | Drug Class | Company | FDA Status |
| --- | --- | --- | --- |
| Intron A (interferon α-2b) | interferon | Schering-Plough | FDA-approved |
| Epivir-HBV (lamivudine; 3TC) | nucleoside analogue | GlaxoSmithKline | FDA-approved |
| Adefovir dipivoxil | nucleotide analogue | Gilead Sciences | FDA approved |
| Coviracil (emtricitabine; FTC) | nucleoside analogue | Gilead Sciences | Phase III |
| Entecavir | nucleoside analogue | Bristol-Myers Squibb | Phase III |
| Clevudine (L-FMAU) | nucleoside analogue | Gilead Sciences | Phase II |

-continued

| Drug Name | Drug Class | Company | FDA Status |
|---|---|---|---|
| ACH 126, 443 (L-Fd4C) | nucleoside analogue | Achillion Pharmaceuticals | Phase II |
| AM 365 | nucleoside analogue | Amrad | Phase II (Asia and Australia) |
| DAPD | nucleoside analogue | Gilead Sciences | Phase II |
| LdT (telbavudine) | nucleoside analogue | Idenix | Phase III |
| XTL 001 | monoclonal antibody | XTL Biopharm | Phase II (Israel) |
| Theradigm | Immune stimulant | Epimmune | Phase II |
| Zadaxin** (thymosin) | Immune stimulant | SciClone | Phase II with Epivir-HBV |
| EHT 899 | viral protein | Enzo Biochem | Phase II (Israel) |
| HBV DNA vaccine | Immune stimulant | PowderJect (UK) | Phase I |
| MCC 478 | nucleoside analogue | Eli Lilly | Phase I (Germany) |
| valLdC (valtorcitabine) | nucleoside analogue | Idenix | Phase II |
| ICN 2001 | nucleoside analogue | ICN | Preclinical |
| Fluoro L and D nucleosides | nucleoside analogue | Pharmasset | Preclinical |
| Racivir | nucleoside analogue | Pharmasset | Preclinical |
| Robustaflavone | nucleoside analogue | Advanced Life Sciences | Preclinical |
| Post Exposure and/or Post Liver Transplant Therapies | | | |
| BayHepB | HBV immuneglobulin | Bayer (US) | FDA-approved |
| anti-hepatitis B | HBV immuneglobulin | Cangene (Canada) | NDA submitted 2001 |
| Nabi-HB | HBV immuneglobulin | Nabi | FDA-approved |

**Zadaxin: orphan drug approval in US

Sources:

Hepatitis B Foundation Drug Watch. Compounds in Development for Hepatitis B. www.hepb.org, Pharmaceutical Research and Manufacturers of America. Mark Nelson, MD. Selected Highlights from Drug Development for Antiretroviral Therapies 2001 (Hep DART 2001) Dec. 16-20, 2001, Maui, Hi.; Selected Highlights from American Association for the Study of Liver Diseases 52nd Annual Meeting (52nd AASLD). Nov. 9-13, 2001. Dallas, Tex.; Report on Hepatitis B from Digestive Disease Week 2001; May 20-23, 2001, Atlanta, Ga.

In one embodiment, the 2'-deoxy-β-L-erythro-pentofuranonucleoside is administered in alternation or combination with one or more such as immunostimulatory agent and/or immunomodulator, such as a TH1 cytokine, and in particular an interferon, preferably interferon gamma for the treatment of wild-type or a resistant strain of HBV, and/or for the suppression or prevention of expression of a resistant strain of HBV. For example, immunostimulatory sequences may be used, such as those described herein above, as well as in: Krieg et al. (1989) *J. Immunol.* 143:24482451; Tokunaga et al. (1992) *Microbiol. Immunol.* 36:55-66; Kataoka et al. (1992) *Jpn'. J Cancer Res.* 83:244-247; Yamamoto et al. (1992) *J. Immunol.* 148:4072-4076; Mojcik et al. (1993) *Clin. Immuno. and Immunopathol.* 67:13 0-13 6; Branda, et al. (1993) *Biochem. Pharmacol.* 45:2037-2043; Pisetsky et al. (1994) *Life Sci.* 54(2):101-107; Yamamoto et al. (1994a) *Antisense Research and Development.* 4:119-122; Yamamoto et al. (1994b) *Jpn. J Cancer Res.* 85:775-779; Raz et al. (1994) *Proc. Natl. Acad. Sci. USA* 91:9519-9523; Kimura et al. (1994) *J. Biochem. (Tokyo)* 116:991-994; Krieg et al. (1995) *Nature* 374:546549; Pisetsky et al. (1995) *Ann. N.Y Acad. Sci.* 772:152-163; Pisetsky (1996a) *J Immunol.* 156:421-423; Pisetsky (1996b) *Immunity* 5:303-310; Zhao et al. (1996) *Biochem. Pharmacol.* 51:173-182; Yi et al. (1996) *J. Immunol.* 156:558-564; Krieg (1996) *Trends Microbiol.* 4(2):73-76; Krieg et al.(1996) *Antisense Nucleic Acid Drug Dev.* 6:133-139; Klimnan et al. (1996) *Proc. Nad. Acad. Sci. USA.* 93:2879-2883; Raz et al. (1996); Sato et al. (1996) *Science* 273:3 52-3 54; Stacey et al. (1996) *J Immunol.* 157:2116-2122; Ballas et al. (1996) *J Immunol.* 157:1840-1845; Branda et al. (1996) *J Lab. Clin. Med* 128:329338; Sonehara et al. (1996) *J Interferon and Cytokine Res.* 16:799-803; Klimnan et al. (1997) *J Immunol.* 158:3635-3639; Sparwasser et al. (1997) *Eur. J Immunol.* 27:16711679; Roman et al. (1997); Carson et al. (1997) *J Exp. Med* 186:1621-1622; Chace et al. (1997) *Clin. Immunol. and Immunopathol,* 84:185-193; Chu et al. (1997) *J Exp. Med* 186:1623-1631; Lipford et al. (1997a) *Eur. J Immunol.* 27:2340-2344; Lipford et al. (1997b) *Eur. J Immunol.* 27:3420-3426; Weiner et al. (1997) *Proc. Natl. Acad Sci.* USA 94:10833-10837; Macfarlane et al. (1997) *Immunology* 91:586-593; Schwartz et al. (1997) *J Clin. Invest.* 100:68-73; Stein et al. (1997), *Antisense Technology,* Ch. 11 pp. 241-264, C. Lichtenstein and W. Nellen, Eds., IRL Press; Wooldridge et al. (1997) *Blood* 89:29942998; Leclerc et al. (1997) *Cell. Immunol.* 179:97-106; Kline et al. (1997) *J Invest. Med* 45(3):282A; Yi et al. (1998a) *J Immunol.* 160:1240-1245; Yi et al. (1998b) *J Immunol.* 160:4755-4761; Yi et al. (1998c) *J Immunol.* 160:5898-5906; Yi et al. (1998d) *J Immunol.* 161:4493-4497; Krieg (1998) *Applied Antisense Oligonucleotide Technology* Ch. 24, pp. 431-448, C. A. Stein and A. M. Krieg, Eds., Wiley-Liss, Inc.; Krieg et al. (1998a) *Trends Microbiol.* 6:23-27; Krieg et al. (1998b) *J Immunol.* 161:2428-2434; Krieg et al. (1998c) *Proc. Nad. Acad. Sci. USA* 95:12631-12636; Spiegelberg et al. (1998) Allergy 53(45S):9397; Homer et al. (1998) *Cell Immunol.* 190:77-82; Jakob et al. (1998) *J Immunol.* 161:3042-3049; Redford et al. (1998) *J Immunol.* 161: 3930-3935; Weeratna et al. (1998) *Antisense & Nucleic Acid Drug Development* 8:351-356; McCluskie et al. (1998) *J Immunol.* 161(9):4463-4466; Grarnzinski et al. (1998) *Mol. Med* 4:109-118; Liu et al. (1998) *Blood* 92:3730-3736; Moldoveanu et al. (1998) *Vaccine* 16: 1216-1224; Brazolot Milan et al. (1998) *Proc. Natl. Acad. Sci. USA* 95:15553-15558; Briode et al. (1998) *J Immunol.* 161:7054-7062; Briode et al. (1999) *Int. Arch. Allergy Immunol.* 118:453-456; Kovarik et al. (1999) *J Immunol.* 162:1611-1617; Spiegelberg et al. (1999) *Pediatr. Pulmonol. Suppl.* 18:118-121; Martin-Orozco et al. (1999) *Int. Immunol.* 11:1111-1118; EP 468, 520; WO 96/02555; WO 97/28259; WO 98/16247; WO 98/18810; WO 98/37919; WO 01/68116 PCT/US01/07839; WO99/33488; WO 99/51259 and WO 99/62923. See also Zimmermann et al. (1998) *J. Immunol.* 160:3627-3630; Krieg (1999) *Trends Microbiol* 7:64-65; U.S. Pat. Nos. 5,663,153; 5,723,335; 5,849,719; and 6,174,872. See also WO 99/56755, WO 00/06588, WO 00/16804; WO 00/21556; WO 00/67023 and WO 01/12223.

It was shown in the woodchuck model and in transgenic mice, that the intrahepatic expression of TH1 cytokines including IFN gamma, TNF alpha, and Interleukine 12 can induce an inhibition of viral replication via a non-cytolytic pathyway. (Guidotti, L. G., P. Borrow, A. Brown, H. McClary, R. Koch, and F. V. Chisari "Noncytopathic clearance of lymphocytic choriomeningitis virus from the hepatocyte" *J Exp Med.* 1999, 189, 1555-1564; Guo, J. T., H. Zhou, C. Liu, C. Aldrich, J. Saputelli, T. Whitaker, M. I. Barrasa, W. S. Mason, and C. Seeger "Apoptosis and regeneration of hepatocytes during recover from transient hepadnavirus infections" *J Virol.* 2000, 74, 1495-1505.

In another embodiment, the β-L-2'-deoxynucleosides provided herein, and in particular β-L-2'-dC or β-L-2'-dT, can be administered in combination and/or alternation with an interferon, such as interferon alpha or interferon gamma provides superior therapy in humans against hepatitis B virus, either wild-type or a resistant strain, and/or for the prevention or suppression of expression of resistant HBV. In one embodiment, the interferon is administered in the form of a protein, for examples directly into the vein or artery. In an alternate embodiment of the invention, the interferon is administered in the form of a nucleic acid, gene or gene fragment thereof that is expressed by the host. The interferon nucleic acid can be delivered to the host "naked", i.e., without a vector, or alternatively, can be delivered via a vector, including but not limited to a viral vector such as an adenovirus vector. In one particular embodiment of the present invention, the immunomodulator is delivered in the form of a gene or gene fragment thereof, and the delivery is mediated by an adenovirus. In one particular embodiment of the invention, the immunomodulator is interferon (such as interferon gamma), and its delivery is in the form of a gene or gene fragment that is mediated by an adenovirus.

In one embodiment, the interferon is interferon alpha, optionally, pegylated interferon alpha. In another embodiment, the interferon is selected from the group, including, but not limited to: interferon alpha-2a, interferon alpha-2b, pegylated interferon alpha-2a, pegylated interferon alpha-2b ROFERON®-A (interferon alpha-2a, Roche), PEGASYS® (pegylated interferon alpha-2a, Roche), INTRON® A (Interferon alpha-2b, Schering Corporation), PEG-INTRON® (pegylated Interferon alpha-2b, Schering Corporation), consensus interferon, INFERGEN (interferon alphacon-1) by InterMune, OMNIFERON (natural interferon) by Viragen, ALBUFERON by Human Genome Sciences, Oral Interferon Alpha by Amarillo Biosciences, and SuperFeron (natural human multi-subtype IFN-alpha, Genetrol, Inc.). In an alternate embodiment, the interferon is interferon gamma. In yet another embodiment, the interferon is interferon beta, interferon omega or interferon tau. In another embodiment, the interferon is selected from the group, including, but not limited to: REBIF (interferon beta-1a) by Ares-Serono, Omega Interferon by BioMedicine, interferon gamma-1b by InterMune, and HuFeron (human IFN-beta, Genetrol, Inc.).

Immunostimulatory Sequences

The term "ISS" or "immunostimulatory sequence" as used herein refers to polynucleotide sequences, alone and/or complexed with MC, that effect a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, CD4+T lymphocytes, CD8+T lymphocytes, B lymphocytes, and the like. Preferably, the ISS sequences preferentially activate a Th1-type response. A polynucleotide for use in the invention contains at least one ISS. As used herein, "ISS" is also a shorthand term for an ISS-containing polynucleotide.

A polynucleotide comprising an ISS (or a composition comprising such a polynucleotide) may be used in the methods and compositions disclosed herein. The immunomodulatory polynucleotide can contain at least one ISS or multiple ISSs. The ISSs can be adjacent within the polynucleotide, or they can be separated by additional nucleotide bases within the polynucleotide. Alternately, multiple ISSs may be delivered as individual polynucleotides.

ISS have been described in the art and may be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995); Yamamoto et al. (1992); Ballas et al. (1996); Klinman et al. (1997); Sato et al. (1996); Pisetsky (1996a); Shimada et al. (1986); *Jpn. Cancer Res.* 77:808-816; Cowdery et al. (1996) *J Immunol.* 156:4570-4575; Roman et al. (1997); and Lipford et al. (1997a).

The ISS can be of any length greater than 6 bases or base pairs and generally comprises the sequence 5'-cytosine, guanine-3', preferably greater than 15 bases or base pairs, more preferably greater than 20 bases or base pairs in length. As is well-known in the art, the cytosine of the 5'-cytosine, guanine-3' sequence is unmethylated. An ISS may also comprise the sequence 5'-purine, purine, C, G, pyrimidine, pyrimidine, C, G-3'. An ISS may also comprise the sequence 5'-purine, purine, C, G, pyrimidine, pyrimidine, C, C3'. As indicated in polynucleotide sequences below, an ISS may comprise (i.e., contain one or more of) the sequence 5'-T, C, G-3'. In some embodiments, an ISS may comprise the sequence 5'-C, G, pyrimidine, pyrimidine, C, G-3' (such as 5'-CGTTCG-3'). In some embodiments, an ISS may comprise the sequence 5'-C, G, pyrimidine, pyrimidine, C, G, purine, purine-3'. In some embodiments, an ISS comprises the sequence 5'-purine, purine, C, G, pyrimidine, pyrimidine-3' (such as 5'-AACGTT-3').

In some embodiments, an ISS may comprise the sequence 5'-purine, T, C, G, pyrimidine, pyrimidine-3'.

In some embodiments, an ISS-containing polynucleotide is less than about any of the following lengths (in bases or base pairs): 10,000; 5,000; 2500; 2000; 1500; 1250; 1000; 750; 500; 300; 250; 200; 175; 150; 125; 100; 75; 50; 25; 10. In some embodiments, an ISS-containing polynucleotide is greater than about any of the following lengths (in bases or base pairs): 8; 10; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the ISS can be any of a range of sizes having an upper limit of 10,000; 5,000; 2500; 2000; 1500; 1250; 1000; 750; 500; 300; 250; 200; 175; 150; 125; 100; 75; 50; 25; or 10 and an independently selected lower limit of 8; 10; 15; 20; 25; 30; 40; 50; 60; 75; 100; 125; 150; 175; 200; 250; 300; 350; 400; 500; 750; 1000; 2000; 5000; 7500, wherein the lower limit is less than the upper limit.

In some embodiments, the ISS includes any of the following sequences:

```
GACGCTCC;  GACGTCCC;  GACGTTCC;  GACGCCCC;
AGCGTTCC;  AGCGCTCC;  AGCGTCCC;  AGCGCCCC;
AACGTCCC;  AACGCCCC;  AACGTTCC;  AACGCTCC;
GGCGTTCC;  GGCGCTCC;  GGCGTCCC;  GGCGCCCC;
GACGCTCG;  GACGTCCG;  GACGCCCG;  GACGTTCG;
AGCGCTCG;  AGCGTTCG;  AGCGTCCG;  GCGCCCG;
AACGTCCG;  AACGCCCG;  AACGTTCG;  AACGCTCG;
GGCGTTCG;  GGCGCTCG;  GGCGTCCG;  GGCGCCCG.
```

In some embodiments, the immunomodulatory polynucleotide includes the sequence

```
5'-TGACTGTGAACGTTCGAGATGA-Y (SEQ ID NO: 1).
```

In some embodiments, the ISS includes any of the following sequences:

```
GACGCU;  GACGUC;  GACGUU;  GACGUT;  GACGTU;  AGCGUU;
AGCGCU;  AGCGUC;  AGCGUT;  AGCGTU;  AACGUC;  AACGUU;
AACGCU;  AACGUT;  AACGTU;  GGCGUU;  GGCGCU;  GGCGUC;
GGCGUT;  GGCGTU.
```

In some embodiments, the ISS includes any of the following sequences.

```
GABGCTCC;  GABGTCCC;  GABGTTCC;  GABGCCCC;
AGBGTTCC;  AGBGCTCC;  AGBGTCCC;  AGBGCCCC;
AABGTCCC;  AABGCCCC;  AABGTTCC;  AABGCTCC;
GGBGTTCC;  GGBGCTCC;  GGBGTCCC;  GGBGCCCC;
GABGCTCG;  GABGTCCG;  GABGCCCG;  GABGTTCG;
AGBGCTCG;  AGBGTTCG;  AGBGTCCG;  GBGCCCG;
AABGTCCG;  AABGCCCG;  AABGTTCG;  AABGCTCG;
GGBGTTCG;  GBGCTCG;   GGBGTCCG;  GGBGCCCG;
GABGCTBG;  GABGTCBG;  GABGCCBG;  GABGTTBG;
AGBGCTBG;  AGBGTTBG;  AGBGTCBG;  AGBGCCBG;
AABGTCBG;  AABGCCBG;  AABGTTBG;  AABGCTBG;
GGBGTTBG;  GGBGCTBG;  GGBGTCBG;  GGBGCCBG,
``` where B is 5-bromocytosine.

In some embodiments, the ISS includes any of the following sequences:

```
GABGCUCC;  GABGUCCC;  GABGUTCC;  GABGTUCC;
GABGUUCC;  GBGUUCC;   AGBGTUCC;  AGBGUTCC;
AGBGCUCC;  AGBGUCCC;  AABGUCCC;  ABGUUCC;
AABGUTCC;  AABGTUCC;  AABGCUCC;  GGBGUUCC;
GGBGUTCC;  GBGTUCC;   GGBGCUCC;  GGBGUCCC;
GABGCUCG;  GABGUCCG;  GABGUUCG;  ABGUTCG;
GABGTUCG;  AGBGCUCG;  AGBGUUCG;  AGBGUTCG;
AGBGTUCG;  AGBGUCCG;  AABGUCCG;  AABGUUCG;
AABGUTCG;  AABGTUCG;  AABGCUCG;  GGBGUUCG;
GGBGUTCG;  GGBGTUCG;  GGBGCUCG;  GGBGUCCG;
GABGCUBG;  GABGUCBG;  GABGUUBG;  GABGUTBG;
GABGTUBG;  AGBGCUBG;  AGBGUUBG;  AGBGUCBG;
AGBGUTBG;  AGBGTUBG;  AABGUCBG;  AABGUUBG;
AABGUTBG;  AABGTUBG;  AABGCUBG;  GGBGUUBG;
GGBGUTBG;  GGBGTUBG;  GGBGCUBG;  GGBGUCBG,
``` where B is 5-bromocytosine.

In other embodiments, the ISS comprises any of the sequences:

```
5'-TGACCGTGAACGTTCGAGATGA-3';

5'-TCATCTCGAACGTTCCACAGTCA-3';

5'-TGACTGTGAACGTTCCAGATGA-3';

5'-TCCATAACGTTCGCCTAACGTTCGTC-3';

5'-TGACTGTGAABGTTCCAGATGA-3',
where B is 5-bromocytosine;

5'-TGACTGTGAABGTTCGAGATGA-3',
where B is 5-bromocytosine, and

5'-TGACTGTGAABGTTBGAGATGA-3',
where B is 5-bromocytosine.
```

An ISS and/or ISS-containing polynucleotide may contain modifications. Modifications of ISS include any known in the art, but are not limited to, modifications of the 3'-OH or 5'-OH group, modifications of the nucleotide base, modifications of the sugar component, and modifications of the phosphate group. Examples of such modifications are described below.

An ISS may be single stranded or double stranded DNA, as well as single or double-stranded RNA or other modified polynucleotides. An ISS may or may not include one or more palindromic regions, which may be present in the motifs described above or may extend beyond the motif. An ISS may comprise additional flanking sequences, some of which are described herein. An ISS may contain naturally-occurring or modified, non-naturally occurring bases, and may contain modified sugar, phosphate, and/or termini. For example, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. The oligonucleotides may comprise phosphorothioate backbones. Sugar modifications known in the field, such as 2'-alkoxy-RNA analogs, 2'-amino-RNA analogs and 2'-alkoxy- or amino-RNA/DNA chimeras and others described herein, may also be made and combined with any phosphate modification. Examples of base modifications include, but are not limited to, addition of an electron-withdrawing moiety to C-5 and/or C-6 of a cytosine of the ISS (e.g., 5-bromocytosine, 5-chlorocytosine, 5-fluorocytosine, 5-iodocytosine).

The ISS can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

The ISS can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular ISS can be isolated, synthesized through recombinant methods, or chemically synthesized. Where the circular ISS is obtained through isolation or through recombinant methods, the ISS will preferably be a plasmid. The chemical synthesis of smaller circular oligonucleotides can be performed using any method described in the literature. See, for instance, Gao et al. (1995) *Nucleic Acids Res.* 23:2025-2029; and Wang et al. (1994) *Nucleic Acids Res.* 22:2326-2333.

The techniques for making oligonucleotides and modified oligonucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in *Protocols for Oligonucleotides and Analogs, Synthesis and Properties* (Agrawal, ed.) Humana Press, Totowa, N.J.; Warner et al. (1984) *DNA* 3:401 and U.S. Pat. No. 4,458,066.

The ISS can also contain phosphate-modified oligonucleotides. Synthesis of polynucleotides containing modified phosphate linkages or non-phosphate linkages is also know in the art. For a review, see Matteucci (1997) "Oligonucleotide Analogs: an Overview" in *Oligonucleotides as TherapeuticAgents*, (D. J. Chadwick and G. Cardew, ed.) John Wiley and Sons, New York, N.Y. The phosphorous derivative (or modified phosphate group) which can be attached to the sugar or sugar analog moiety in the oligonucleotides of the present invention can be a monophosphate, diphosphate, triphosphate, alkylphosphonate, phosphorothioate, phosphorodithioate or the like. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841-1848; Chaturvedi et al. (1996) *Nucleic Acids Res.* 24:2318-2323; and Schultz et al. (1996) *Nucleic Acids Res.* 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in *Protocols for Oligonucleotides and Analogs, Synthesis and Properties* (Agrawal, ed.) Humana Press, pp. 165-190). Similarly the synthesis of other phosphate analogs, such as phosphotriester (Miller et al. (1971) *JACS* 93:6657-6665), non-bridging phosphoramidates (Jager et al. (1988) *Biochem.* 27:7247-7246), N3' to P5' phosphoramidates (Nelson et al. (1997) *JOC* 62:7278-7287) and phosphorodithioates (U.S. Pat. No. 5,453,496) has also been described. Other non-phosphorous based modified oligonucleotides can also be used (Stirchak et al. (1989) *Nucleic Acids Res.* 17:6129-6141). Oligonucleotides with phosphorothioate backbones can be more immunogenic than those with phosphodiester, backbones and appear to be more resistant to degradation after injection into the host. Braun et al. (1988) *J Immunol.* 141: 2084-2089; and Latimer et al. (1995) *Mol. Immunol.* 32:1057-1064.

ISS-containing polynucleotides used in the invention can comprise ribonucleotides (containing ribose as the only or principal sugar component), deoxyribonucleotides (containing deoxyribose as the principal sugar component), or, as is known in the art, modified sugars or sugar analogs can be incorporated in the ISS. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the ISS, the sugar moiety is preferably the furanoside of ribose, deoxyribose, arabinose or 2'-O-alkylribose, and the sugar can be attached to the respective heterocyclic bases either in a α or β anomeric configuration. Sugar modifications include, but are not limited to, 2'-alkoxy-RNA analogs, 2'-amino-RNA analogs and 2'-alkoxy- or amino-RNA/DNA chimeras. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an ISS.

The heterocyclic bases, or nucleic acid bases, which are incorporated in the ISS can be the naturally-occurring principal purine and pyrimidine bases, (namely uracil or thymine, cytosine, adenine and guanine, as mentioned above), as well as naturally occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the ISS can include one or several heterocyclic bases other than the principal five base components of naturally-occurring nucleic acids. Preferably, however, the heterocyclic base in the ISS includes, but is not limited to, uracil-5-yl, cytosine-5-yl, adenine-7-yl, adenine-8-yl, guanine-7-yl, guanine-8-yl, 4-aminopyrrolo[2.3-d]pyrimidin-5-yl, 2-amino-4-oxopyrolo [2,3-d]pyrimidin-5-yl, 2-amino-4-oxopyrrolo [2.3-d]pyrimidin-3-yl groups, where the purines are attached to the sugar moiety of the ISS via the 9-position, the pyrimidines via the 1-position, the pyrrolopyrimidines via the 7-position and the pyrazolopyrimidines via the 1-position.

The ISS and/or IMP may comprise at least one modified base as described, for example, in the commonly owned international application WO 99/62923. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the ISS. Preferably, the electron-withdrawing moiety is a halogen. Modified cytosines can include, but are not limited to, azacytosine, 5-bromocytosine, 5-chlorocytosine, chlorinated cytosine, cyclocytosine, cytosine arabinoside, 5-fluorocytosine, fluoropyrimidine, 5,6-dihydrocytosine, 5-iodocytosine, 5-nitrocytosine, 5-hydroxy-cytosine, and any other pyrimidine analog or modified pyrimidine. Preferred modified uracils are modified at C-5 and/or C-6, preferably with a halogen, and include, but are not limited to, bromouracil such as 5-bromouracil, chlorouracil such as 5-chlorouracil, fluorouracil such as 5-fluorouracil, iodouracil such as 5-iodouracil and hydroxyuracil. Also see, Kandimalla et al., 2001, *Bioorg. Med. Chem.* 9:807-813. See, for example, International Patent Application No. WO 99/62923. Other examples of base modifications include the addition of one or more thiol groups to the base including, but not limited to, 6-thio-guanine, 4-thio-thymine and 4-thiouracil. Additionally, some IMPs may comprise modified bases such as 7-deazaguanosine in place of any guanosine residue, or a modified cytosine selected from N4-ethylcytosine or N4-methylcytosine in place of any cytosine residue, including the cytosine of the 5'-CG-3'.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513; 5,015,733; 5,118,800; 5,118,802) and can be used similarly.

The ISS used in the methods of the invention may be produced as ISS-microcarrier complexes. ISS-microcarrier complexes comprise an ISS-containing polynucleotide bound to a microcarrier (MC). ISS-MC complexes comprise an ISS bound to the surface of a microcarrier (i.e., the ISS is not encapsulated in the MC), adsorbed within a microcarrier (e.g., adsorbed to PLGA beads), or encapsulated within a MC (e.g., incorporated within liposomes).

ISS-containing oligonucleotides bound to microparticles (SEPHAROSE®) beads) have previously been shown to have immunostimulatory activity in vitro (Liang et al., (1996), *J Clin. Invest.* 98:1119-1129). However, recent results show that ISS-containing oligonucleotides bound to gold, latex and magnetic particles are not active in stimulating proliferation of 7TD1 cells, which proliferate in response to ISS-containing oligonucleotides (Manzel et al., (1999). *Antisense Nucl. Acid Drug Dev.* 9:459-464).

Microcarriers are not soluble in pure water, and are less than about 50-60 μm in size, preferably less than about 10 μm in size, more preferably from about 10 μm to about 10 μm, 25 nm to about 5 μm, 50 nm to about 4.5 μm or 1.0 μn to about 2.0 μm in size. Microcarriers may be any shape, such as spherical, ellipsoidal, rod-shaped, and the like, although spherical microcarriers are normally preferred. Preferred microcarriers have sizes of or about 50 nm, 200 μm, 1 μm, 1.2 μm, 1.4 μm, 1.5 μm, 1.6 μm, 1.8 μm, 2.0 μm, 2.5 μm or 4.5 μm. The "size" of a microcarrier is generally the "design size" or intended size of the particles stated by the manufacturer. Size may be a directly measured dimension, such as average or maximum diameter, or may be determined by an indirect assay such as a filtration screening assay. Direct measurement of microcarrier size is typically carried out by microscopy, generally light microscopy or scanning electron microscopy (SEM), in comparison with particles of known size or by reference to a micrometer. As minor variations in size arise during the manufacturing process, microcarriers are considered to be of a stated size if measurements show the microcarriers are ± about 5-10% of the stated measurement. Size characteristics may also be determined by dynamic light scattering. Alternately, microcarrier size may be determined by filtration screening assays. A microcarrier is less than a stated size if at least 97% of the particles pass through a "screentype" filter (i.e., a filter in which retained particles are on the surface of the filter, such as polycarbonate or polyethersulfone filters, as opposed to a "depth filter" in which retained particles lodge within the filter) of the stated size. A microcarrier is larger than a stated size if at least about 97% of the microcarrier particles are retained by a screen-type filter of the stated size. Thus, at least about 97% microcarriers of about 1 0 tim to about I 0 nm in size pass through a 10 μn pore screen filter and are retained by a 10 nm screen filter.

As above discussion indicates, reference to a size or size range for a microcarrier implicitly includes approximate variations and approximations of the stated size and/or size range. This is reflected by use of the term "about" when referring to a size and/or size range, and reference to a size or size range without reference to "about" does not mean that I 0 the size and/or size range is exact.

Microcarriers may be solid phase (e.g., polystyrene beads) or liquid phase (e.g., liposomes, micelles, or oil droplets in an oil and water emulsion). Liquid phase microcarriers include-liposomes, micelles, oil droplets and other lipid or oil-based particles. One preferred liquid phase microcarrier is oil droplets within an oil-in-water emulsion. Preferably, oil-in-water emulsions used as microcarriers comprise biocompatible substituents such as squalene. Liquid phase microcarriers are normally considered nonbiodegradable, but may be biodegradable liquid phase microcarriers may be produced by incorporation of one or more biodegradable polymers in the liquid microcarrier formulation. In one preferred embodiment, the microcarrier is oil droplets in an oil-in water emulsion prepared by emulsification of squalene, sorbitan trioleate, TWEEN 80® in an aqueous pH buffer.

Solid phase microcarriers for use in ISS-microcarrier complexes may be made from biodegradable materials or nonbiodegradable materials, and may include or exclude agarose or modified agarose microcarriers. Useful solid phase biodegradable microcarriers include, but are not limited to: biodegradable polyesters, such as poly(lactic acid), poly(glycolic acid), and copolymers (including block copolymers) thereof, as well as block copolymers of poly(lactic acid) and poly(ethylene glycol); polyorthoesters such as polymers based on 3,9-diethylidene-2,4,8,10-tetraoxaspiro[5.5]undecane (DETOSU); polyanhydrides such as poly(anhydride) polymers based on sebacic acid, p-(carboxyphenoxy)propane, or p-(carboxy-phenoxy)hexane; polyanhydride imides, such as polyanhydride polymers based on sebacic acid-derived monomers incorporating amino acids (i.e., linked to sebacic acid by imide bonds through the amino-terminal nitrogen) such as glycine or alanine; polyanhydride esters; polyphosphazenes, especially poly(phosphazenes) which contain hydrolysis-sensitive ester groups which can catalyze degradation of the polymer backbone through generation of carboxylic acid groups (Schacht et al. (1996) *Biotechnol. Bioeng.* 1996:102); and polyamides such as poly(lactic acid-co-lysine). A wide variety of nonbiodegradable materials suitable for manufacturing microcarriers are also known, including, but not limited to polystyrene, polyethylene, latex, gold, and ferromagnetic or paramagnetic materials. Solid phase microcarriers may be covalently modified to incorporate one or more moieties for use in linking the ISS, for example by addition of amine groups for covalent linking using amine-reactive crosslinkers.

The ISS-microcarrier complexes may be covalently or noncovalently linked. Covalently linked ISS-MC complexes may be directly linked or be linked by a crosslinking moiety of one or more atoms (typically the residue of a crosslinking agent). The ISS may be modified to allow or augment binding to the MC (e.g., by incorporation of a free sulfhydryl for covalent crosslinking or addition of a hydrophobic moieties such as lipids, steroids, sterols such as cholesterol, and terpenes, for hydrophobic bonding), although unmodified ISS may be used for formation of noncovalent ISS-MC complex formation by electrostatic interaction or by base pairing (e.g., by base pairing at least one portion of the ISS with a complementary oligonucleotide bound to the microcarrier). ISS-containing polynucleotides may be linked to solid phase microcarriers or other chemical moieties to facilitate ISS-MC complex formation using conventional technology known in the art such as use of available heterobifunctional crosslinkers (e.g., succinimidyl 4-(N-maleimidomethyl)cyclohexane-1-carboxylate or its sulfo-derivatives for covalently linking an amine-derivatized microcarrier and an ISS modified to contain a free sulfhydryl) or by addition of compounds such as cholesterol (e.g., by the method of Godard et al. (1995) *Eur. J Biochem.* 232:404-410) to facilitate binding to hydrophobic microcarriers such as oil droplets in oil-in-water emulsions. Alternatively, modified nucleosides or nucleotides, such as are known in the art, can be incorporated at either terminus, or at internal positions in the ISS. These can contain blocked functional groups which, when deblocked, are reactive with a variety of functional groups which can be present on, or attached to, the microcarrier or a moiety which would facilitate binding to a microcarrier. Certain embodiments of non-covalently linked Iss-Mc complexes utilize a binding pair (e.g., an antibody and its cognate antigen or biotin and streptavidin or avidin), where one member of the binding pair is bound to the ISS and the microcarrier is derivatized with the other member of the binding pair (e.g., a biotinylated ISS and a streptavidin-derivatized microcarrier may be combined to form a noncovalently linked ISS-MC complex).

Non-covalent ISS-MC complexes bound by electrostatic binding typically exploit the highly negative charge of the polynucleotide backbone. Accordingly, microcarriers for use in non-covalently bound ISS-MC complexes are generally positively charged at physiological pH (e.g., about pH 6.8-7.4). The microcarrier may intrinsically possess a positive charge, but microcarriers made from compounds not normally possessing a positive charge may be derivatized or otherwise modified to become positively charged. For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles.

Solid phase microspheres are prepared using techniques known in the art. For example, they can be prepared by emulsion-solvent extraction/evaporation technique. Generally, in this technique, biodegradable polymers such as polyanhydrates, poly(alkyl-α-cyanoacrylates) and poly(α-hydroxy esters), for example, poly(lactic acid), poly(glycolic acid), poly(D,L-lactic-co-glycolic acid) and poly (caprolactone), are dissolved in a suitable organic solvent, such as methylene chloride, to constitute the dispersed phase (DP) of emulsion. DP is emulsified by high-speed homogenization into excess volume of aqueous continuous phase (CP) that contains a dissolved surfactant, for example, polyvinylalcohol (PVA) or polyvinylpirrolidone (PVP). Surfactant in CP is to ensure the formation of discrete and suitably-sized emulsion droplet. The organic solvent is then extracted into the CP and subsequently evaporated by raising the system temperature. The solid, microparticles are then separated by centrifugation or filtration, and dried, for example, by lyophilization or application of vacuum, before storing at 4° C.

Generally, to prepare cationic microspheres, cationic lipids or polymers, for example, 1,2-dioleoyl-1,2,3-trimethylammonlopropane (DOTAP), cetyltrimethyl-ammonium bromide (CTAB) or polylysine, are added either to DP or CP, as per their solubility in these phases.

Physico-chemical characteristics such as mean size, size distribution and surface charge of dried microspheres may be determined. Size characteristics are determine, for example, by dynamic light scattering technique and the surface charge was determined by measuring the zeta potential.

Generally, ISS-containing polynucleotides can be adsorbed onto the cationic microspheres by overnight aqueous incubation of ISS and the particles at 4° C. Microspheres are characterized for size and surface charge before and after ISS association. Selected batches may then evaluated for activity as described herein.

An ISS-containing polynucleotide may be administered before, during and/or after exposure to a virus. An ISS polynucleotide may also be administered before, during and/or after infection by a virus. An ISS polynucleotide may also be administered before or after onset of symptoms of virus infection. Accordingly, administration of ISS-containing polynucleotide may be at various times with respect to exposure to, infection by and/or onset of symptoms by infection by virus. Further, there may be one or more administrations. If the ISS-containing polynucleotide is administered on multiple occasions, the ISS may be administered on any schedule selected by the clinician, such as daily, every other day, every three days, every four days, every five days, every six days, weekly, biweekly, monthly or at ever longer intervals (which may or may not remain the same during the course of treatment). Where multiple administrations are given, the IS S-containing polynucleotide may be given in 2, 3, 4, 5, 6, 7, 8, 9, 10 or more separate administrations. Generally, but not necessarily, an interval of at least about three days is necessary to allow effect of ISS-containing polynucleotides.

When ISS-containing polynucleotide is administered to an individual at risk of exposure to virus (i.e., before infection), ISS-containing polynucleotide is preferably administered less than about 14 days before exposure to virus, preferably less than about 10 days before exposure to virus, more preferably less than about 7 days before exposure to virus, even more preferably less than about 5 days before exposure to virus. In some embodiments, ISS-containing polynucleotide is administered about 3 days before exposure to virus.

In a further embodiment, the ISS-containing polynucleotide is administered after exposure to a virus, but prior to appearance of symptoms. Preferably, the ISS containing polynucleotide is administered less than about three days after exposure, more preferably less than about one day, 12 hours, six hours or two hours after exposure, if the time of exposure is known or suspected.

In another embodiment, the ISS-containing polynucleotide is administered after appearance of at least one symptom of virus infection. For example, ISS containing polynucleotide is administered within about 28, 21, 14, 7, 5 or 3 days following appearance of a symptom of virus infection. However, some infected 10 individuals exhibiting symptoms will already have undertaken one or more courses of treatment with another therapy. In such individuals, or in individuals who failed to appreciate the import of their symptoms, the ISS-containing polynucleotide may be administered at any point following infection.

Additionally, treatments employing an ISS-containing polynucleotide may also be employed in conjunction with other treatments or as 'second line' treatments employed after failure of a 'first line' treatment.

ISS polynucleotides may be formulated in any form known in the art, such as dry powder, semi-solid or liquid formulations. For parenteral administration ISS polynucleotides preferably administered in a liquid formulation, although solid or semisolid formulations may also be acceptable, particularly where the ISS polynucleotide is formulated in a slow release depot form. ISS polynucleotides are generally formulated in liquid or dry powder form for topical administration, although semi-solid formulations may occasionally be useful.

ISS polynucleotide formulations may contain additional components such as salts, buffers, bulking agents, osmolytes, antioxidants, detergents, surfactants and other pharmaceutically-acceptable excipients as are known in the art. Generally, liquid ISS polynucleotide formulations made in USP water for injection and are sterile, isotonic and pH buffered to a physiologically-acceptable pH, such as about pH 6.8 to 7.5.

ISS-containing polynucleotides may be formulated in delivery vehicles such as liposomes, oil/water emulsion or slow release depot formulations. Methods of formulating polynucleotides in such forms are well known in the art.

ISS-containing polynucleotide formulations may also include or exclude immunomodulatory agents such as adjuvants and immunostimulatory cytokines, which are well known in the art.

A suitable dosage range or effective amount is one that provides the desired reduction of symptoms and/or suppression of viral infection and depends on a number of factors, including the particular respiratory virus, ISS sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for an ISS-containing polynucleotide of about 20 bases, a dosage range may be selected from, for example, an independently selected lower limit such as about 0.1, 0.25, 0.5, 1, 2, 5, 10, 20, 30, 40, 50, 60, 80, 100, 200, 300, 400 or 500 µm/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 µm/kg. For example, a dose may be about any of the following: 0.1 to 100 µm/kg, 0.1 to 50 µm/kg, 0.1 to 25 µm/kg, 0.1 to 10 µm/kg, 1 to 500 µm/kg, 100 to 400 µm/kg, 200 to 300 µm/kg, 1 to 100 µm/kg, 100 to 200 µm/kg, 300 to 400 µm/kg, 400 to 500 µm/kg, 500 to 1000 µm/kg, 500 to 5000 µm/kg, or 500 to 10,000 µm/kg. Generally, parenteral routes of administration may require higher doses of ISS compared to more direct application to infected tissue, as do ISS-containing polynucleotides of increasing length.

Polynucleotides comprising an ISS may be administered by systemic (e.g., parenteral) or local (e.g., topical) administration.

In one embodiment, the ISS-containing polynucleotide(s) is topically administered, such as respiratory mucosa (such as nasal passages or lung). Nasopharyngeal and pulmonary routes of administration include, but are not limited to, intranasal, inhalation, transbronchial and transalveolar routes. The ISS-containing polynucleotide may thus be administered by inhalation of aerosols, atomized liquids or powders. Devices suitable for administration by inhalation of ISS-containing compositions include, but are not limited to, nebulizers, atomizers, vaporizers, and metered-dose inhalers. Nebulizers, atomizers, vaporizers and metered-dose inhalers filled with or employing reservoirs containing formulations comprising the ISS-containing polynucleotide(s) are among a variety of devices suitable for use in inhalation delivery of the ISS-containing polynucleotide(s). Other methods of delivering to respiratory inucosa include delivery of liquid formulations, such as by nose drops.

In other embodiments, the ISS-containing polynucleotide is administered parenterally. Parenteral routes of administration include, but are not limited to, transdermal, transmucosal and direct injection. Parenteral administration by injection may be by any parenteral injection route, including, but not limited to, intravenous (IV), intraperitoneal (IP), intramuscular (IM), subcutaneous (SC) and intradermal (ID) routes.

Transdermal and transmucosal administration may be accomplished by, for example, inclusion of a carrier (e.g., dimethylsulfoxide, DMSO), by application of electrical impulses (e.g., iontophoresis) or a combination thereof. A variety of devices are available for transdermal administration which may be used in accordance with the invention, Because respiratory viruses infect cells of the respiratory tract, routes which deliver ISS polynucleotides to, the respiratory tract, such as inhalation and intranasal delivery (discussed above), are considered local routes of administration rather than systemic routes of administration, even though delivery through such routes are normally considered parenteral, systemic routes of administration.

IV, IP, IM and ID administration may be by bolus or infusion administration. For SC administration, administration may be by bolus, infusion or by implantable device, such as an implantable minipump (e.g., osmotic or mechanical minipump) or slow release implant. The ISS polynucleotide(s) may also be delivered in a slow release formulation adapted for IV, IP, IM, ID or SC administration. Administration by inhalation is preferably accomplished in discrete doses (e.g., via a metered dose inhaler), although delivery similar to an infusion may be accomplished through use of a nebulizer. Administration via the transdermal and transmucosal routes may be continuous or pulsatile.

Other Agents

Other therapeutic agents that can be used in the method and compositions disclosed herein include Ribavirin (Ribapharm, Inc.), hepatitis B immune globulin (Nabi-HB intravenous, Nabi Pharmaceuticals), ZADAXIN™ (thymosin alpha 1, SCV-07 (SciClone Pharmaceuticals), Theradigm (Epimmune), anti-hepatitis B hyperimmune product (Cangene Corp), RC-529 (Corixa/Rhein Biochem), HYB2055 (Hybridon), ViroKine (human antiviral proteins, Genetrol, Inc.), Levovirin (Ribapharm, Inc.), interleukin-2 (IL-2), tumor necrosis factor-alpha, interleukin 1-beta, interleukin-12 (IL-12), Granulocyte-macrophage colony-stimulating factor (GM-CSF), polyadenylic-polyuridylic acid, thymosin alpha, Ampligen® (Hemispherx BioPharma), Polyadenur™ (Poly A:Poly U RNA, Hemispherx BioPharms), Oragen™ (Hemispherx BioPharms), Hepatitis B Virus (HBV)-specific Cytotoxic T Lymphocytes (CTL) (CellExSys, Inc.), therapeutic hepatitis b vaccine (Epimmune), P J Hep B DNA prophylactic vaccine (Powderject Pharmaceuticals), interleukin 4, interleukin 6, interleukin 7, granulocyte colony stimulating factor Hepatitis B virus surface antigen vaccines also may be used in the methods and compositions disclosed herein. In one embodiment, FTC and a hepatitis B virus antigen vaccine, such as a surface antigen vaccine, is administered in combination or in alternation to a host in an effective amount for the treatment or prophylaxis of a hepatitis B virus infection, optionally incombination with another therapeutic agent, such as interferon.

Other vaccines that can be administered include Engerix-B® (GlaxoSmithKline), Recombivax HB® (Merck), Hepatitis B Vaccine (Recombinant), P J Hep B DNA therapeutic vaccine (Powderject Pharmaceuticals), Hepavax-Gene® (DNA recombinant hepatitis B vaccine , Berna Biotech group), Gen H-B Vax™ (Chiron Corporation), Hepatavax-B® (Merck & Co.), Hevac B® (Pasteur), KGC® (Korea Green Cross), TGP 943™ (Takeda Chem, Japan), Gen Hevac B® (Pasteur, France), Bio-Hep-B™/Sci-B-Vac™ (Bio-Technology General, Israel), AG-3™, Hepagene™, Hepacare™, (Medeva, UK, Evans UK).

V. Gene Therapy

Another aspect of the present invention is using in vivo gene therapy methods to deliver immunomodulators in combination and/or alternation with the β-L-2'-deoxynucleoside of the present invention, with different methods of action and/or synergistic effects, to treat HBV. Gene therapy methods relate to the introduction of nucleic acid (DNA, RNA, and antisense DNA or RNA) sequences into a host, such as an animal, and in particular a human, to increase the expression of the immunomodulator which may be operatively linked to a promoter and/or any other genetic elements necessary for its expression by the target tissue. Such gene therapy and delivery techniques and methods are known in the art, see, for example, WO 90/11092, WO 98/11779; U.S. Pat. Nos. 5,693, 622, 5,705,151, 5,580,859; Tabata H. et al. (1997) *Cardiovasc. Res.* 35(3):470-479, Chao J et al. (1997) *Pharmacol. Res.* 35(6):517-522, Wolff J. A. (1997) *Neuromuscul. Disord.* 7(5):314-318, Schwartz B. et al. (1996) *Gene Ther.* 3(5):405-411, Tsurumi Y. et al. (1996) *Circulation* 94(12):3281-3290.

The polypeptide vector constructs used in the gene therapy method are preferably constructs that will not integrate into the host genome nor will they contain sequences that allow for replication. Any strong promoter known to those skilled in the art can be used for driving the expression of DNA.

The polypeptide constructs may be delivered by any method that delivers injectable materials to the cells of an animal, such as, injection into the interstitial space of tissues (heart, muscle, skin, lung, liver, intestine and the like). The polypeptide constructs can be delivered in a pharmaceutically acceptable liquid or aqueous carrier.

The polypeptide construct can be delivered to the interstitial space of tissues within an animal, including the muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts.

In a further embodiment of the invention, cells that are genetically engineered to express the immunomodulator are administered to a patient in vivo. Such cells may be obtained from the patient or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the immunomodulator, or alternatively, by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the immunomodulator can be placed under the control of a strong constitutive or inducible promoter or promoter/enhancer to achieve immunomodulator expression, and preferably secretion. The engineered cells which express and preferably secrete the immunomodulator can be introduced into the patient systemically, e.g., in the circulation, or intraperitoneally.

Alternatively, the cells can be incorporated into a matrix and implanted in the body, e.g., genetically engineered endothelial cells can be implanted as part of a lymphatic or vascular graft. (See, for example, Anderson et al. U.S. Pat. No. 5,399, 349; and Mulligan & Wilson, U.S. Pat. No. 5,460,959).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Eukaryotic cells that may be transduced with the infectious viral particles containing a nucleic acid, gene or gene fragment thereof for the expression of an immunomodulator include, but are not limited to, primary cells, such as primary nucleated blood cells, such as leukocytes, granulocytes, monocytes, macrophages, lymphocytes (including T-lymphocytes and B-lmphocytes), totipotent stem cells, and tumor infiltrating lymphocytes (TIL cells); bone marrow cells; endothelial cells; epithelial cells; keratinocytes; stem cells; hepatocytes, including hepatocyte precursor cells; hepatocytes, including hepatocyte precursor cells; fibroblasts; mesenchymal cells; mesothelial cells; and parenchymal cells.

In one embodiment, the cells may be targeted to a specific site, whereby the cells function as a therapeutic at such site. Alternatively, the cells may be cells that are not targeted to a specific site, and such cells function as a systemic therapeutic.

Transduced cells may be used, for example, in the treatment of HBV by introducing to host cells, such as blood cells that have been removed from a patient and expanded in culture, infectious viral particles in accordance with the present invention which contain genes that encode an immunomodulator. The cells can be expanded in number before or after transduction with the infectious viral particles containing the desired genes. Thus, the procedure is performed in such a manner that upon injection into the patient, the transformed cells will produce an immunomodulator in the patient's body.

The gene or nucleic acid carried by the transduced cells specifically comprises the sequence for an immunomodulator, but can be also comprise any sequence that directly or indirectly enhances the therapeutic effects of the cells. The gene carried by the transduced cells can also include sequences that allow the transduced cells to exert a therapeutic effect that it would not ordinarily have, such as a gene encoding a clotting factor useful in the treatment of hemophilia. The gene can encode one or more products having therapeutic effects. Examples of suitable genes or nucleic acids include those that encode cytokines such as TNF, interleukins (interleukins 1-14), interferons (.alpha., beta, .gamma.-interferons), T-cell receptor proteins and Fc receptors for antigen-binding domains of antibodies, such as immunoglobulins. Additional examples of suitable genes include genes that modify cells to "target" to a site in the body to which the cells would not ordinarily "target," thereby making possible the use of the cell's therapeutic properties at that site. For example, blood cells such as TIL cells can be modified, for example, by introducing a Fab portion of a monoclonal antibody into the cells, thereby enabling the cells to recognize a chosen antigen.

It is typical but not required to deliver the nucleic acid to the cell using a carrier known as a "vector." The most common types of vectors used in gene therapy are viruses. Scientists use viruses because they have a unique ability to enter a cell's DNA. Viruses used as vectors in gene therapy are genetically disabled; they are unable to reproduce themselves. Most gene therapy clinical trials rely on mouse retroviruses to deliver the desired gene. Other viruses used as vectors include adenoviruses, adeno-associated viruses, poxviruses and the herpes virus.

For example, cells from the patient are removed and grown in the laboratory. The cells are exposed to the virus that is carrying the desired gene. The virus enters the cells, and the desired gene becomes part of the cells' DNA. The cells grow in the laboratory and are then returned to the patient. This type of gene therapy is called ex vivo, which means "outside the body." The gene is transferred into the patient's cells while the cells are outside the patient's body. In other studies, vectors or liposomes (fatty particles) are used to deliver the desired gene to cells in the patient's body. This form of gene therapy is called in vivo, because the gene is transferred to cells inside the patient's body.

When viral vectors are used to carry genes into the body, they might alter more than the intended cells. Another danger is that the new gene might be inserted in the wrong location in the DNA, possibly causing cancer or other damage. In addition, when DNA is injected directly, or when a liposome delivery system is used, there is a chance that the DNA could be introduced into reproductive cells, producing inheritable changes.

Other concerns include the possibility that transferred genes could be "overexpressed," producing so much of the missing protein as to be harmful; that the viral vector could cause inflammation or an immune reaction; and that the virus could be transmitted from the patient to other individuals or into the environment.

There are many vectors known in the art. Any known vector can be used in the present invention. In a preferred embodiment of the present invention, the vector can target a specific cell type for specific gene delivery.

Adenoviral Vectors

Any of the adenoviral vectors can be used to transfect cells and/or cell lines to express and/or secrete an immunomodulator. Adenoviruses are non-enveloped viruses containing a linear double stranded DNA genome. While there are over 40 serotype strains of adenovirus, most of which cause benign respiratory tract infections in humans, subgroup C serotypes 2 or 5 are predominantly used as vectors. The life cycle does not normally involve integration into the host genome, rather they replicate as episomal elements in the nucleus of the host cell and consequently there is no risk of insertional mutagenesis. The wild type adenovirus genome is approximately 35 kb of which up to 30 kb can be replaced with foreign DNA (Smith, 1995, Verma and Somia, 1997). There are four early transcriptional units (E1, E2, E3 and E4) that have regulatory functions, and a late transcript, which codes for structural proteins. Progenitor vectors have either the E1 or E3 gene inactivated, with the missing gene being supplied in trans either by a helper virus, plasmid or integrated into a helper cell genome (human fetal kidney cells, line 293, Graham, F. L., Smiley, J., Russell, W. L. and Naim, R. (1997). *General Virology* 36: 59-72.). Second generation vectors additionally use an E2a temperature sensitive mutant (Engelhardt, J. F., Litsky, L., and Wilson, J. M. (1994). *Human Gene Therapy* 5: 1217-1229.) or an E4 deletion (Armentano, D., Zabner, J., et al. (1997). *Journal of Virology* 71: 2408-2416.). The most recent "gutless" vectors contain only the inverted terminal repeats (ITRs) and a packaging sequence around the transgene, all the necessary viral genes being provided in trans by a helper virus (Chen, H., Mack, L. M., Kelly, R., et al. (1997). *Proceedings of the National Academy of Sciences of the U.S.A.* 94: 1645-1650.).

Adenoviral vectors are very efficient at transducing target cells in vitro and vivo, and can be produced at high titres ($>10^{11}$/mL). With the exception of Geddes, B. J., Harding, T. C., Lightman, S. L. and Uney, J. B. (1997). *Nature Medicine* 3: 1402-1404.), who showed prolonged transgene expression in rat brains using an E1 deletion vector, transgene expression in vivo from progenitor vectors tends to be transient (Verma, I. M. and Somia, N. (1997). Gene therapy—promises, problems and prospects. Nature 389: 239-242.). Following intravenous injection, 90% of the administered vector is degraded in the liver by a non-immune mediated mechanism (Worgall, S., Wolff, G., Falck-Pedersen, E. and Crystal R. G. (1997). *Human Gene Therapy* 8: 37-44.). Thereafter, an MHC class I restricted immune response occurs, using CD8+ CTLs to eliminate virus infected cells and CD4+ cells to secrete IFN-alpha which results in anti-adenoviral antibody (Yang, Y. and Wilson, J. M. (1995). *Journal of Immmunology* 155: 2564-2569.). Alteration of the adenoviral vector can remove some CTL epitopes, however the epitopes recognized differ with the host MHC haplotype (Sparer, T. E., Wynn, S. G., Clarket al. (1997). *Journal of Virology* 71: 2277-2284. Jooss, K., Ertl, H. C. J. and Wilson, J. M. (1998). *Journal of Virology* 72: 2945-2954.). The remaining vectors, in those cells that are not destroyed, have their promoter inactivated (Armentano, D., Zabner, J., et al. (1997). *Journal of Virology* 71: 2408-2416.) and persisting antibody prevents subsequent administration of the vector.

Approaches to avoid the immune response involving transient immunosupressive therapies have been successful in prolonging transgene expression and achieving secondary gene transfer (Jooss, K., Yang, Y. and Wilson, J. M. (1996). *Human Gene Therapy* 7: 1555-1566. Kay, M. A., Meuse, L., et al. (1997). *Proceedings of the National Academy of Sciences of the U.S.A.* 94: 4686-4691). A less interventionist method has been to induce oral tolerance by feeding the host UV inactivated vector (Kagami, H., Atkinson, J. C., et al. (1998). *Human Gene Therapy* 9: 305-313.). However, it is desirable to manipulate the vector rather than the host. Although only replication deficient vectors are used, viral proteins are expressed at a very low level which are presented to the immune system. The development of vectors containing fewer genes, culminating in the "gutless" vectors which contain no viral coding sequences, has resulted in prolonged in vivo transgene expression in liver tissue (Schiedner, G., Morral, N., et al. (1998). *Nature Genetics* 18: 180-183.). The initial delivery of large amounts of DNA packaged within adenovirus proteins, the majority of which will be degraded and presented to the immune system may still cause problems for clinical trials. Moreover the human population is heterogeneous with respect to MHC haplotype and a proportion of the population will have been already exposed to the adenoviral strain (Gahry-Sdard, H., Molinier-Frenkel, V., et al. (1997). *Journal of Clinical Investigation* 100: 2218-2226.)

Until recently, the mechanism by which the adenovirus targeted the host cell was poorly understood. Tissue specific expression was therefore only possible by using cellular promoter/enhancers e.g. the myosin light chain 1 promoter (Shi, Q., Wang, Y. and Worton, R. (1997). *Human Gene Therapy* 8: 403-410.) and the smooth muscle cell SM22a promoter (Kim, S., Lin, H., et al. (1997). *Journal of Clinical Investigation* 100: 1006-1014.), or by direct delivery to a local area (Rome, J. J., Shayani, V., et al. (1994). *Human Gene Therapy* 5: 1249-1258.). Uptake of the adenovirus particle has been shown to be a two stage process involving an initial interaction of a fibre coat protein in the adenovirus with a cellular receptor or receptors, which include the MHC class I molecule (Hong, S. S., Karayan, L., et al. (1997). *EMBO Journal* 16: 2294-2306.) and the coxsackievirus-adenovirus receptor (Bergelson, J. M., Cunningham J. A., et al. (1997). *Science* 275: 1320-1323.). The penton base protein of the adenovirus particle then binds to the integrin family of cell surface heterodimers (Wickham, T. J., Mathias, P., et al. (1993). *Cell* 73: 309-319.) allowing internalisation via receptor mediated endocytosis. Most cells express primary receptors for the adenovirus fibre coat protein, however internalisation is more selective (Harris, J. D. and Lemoine, N. R. (1996). *Trends in Genetics* 12: 400-404.). Methods of increasing viral uptake include stimulating the target cells to express an appropriate integrin (Davison, E., Diaz, R. M., et al. (1997). *Journal of Virology* 71: 6204-6207.) and conjugating an antibody with specificity for the target cell type to the adenovirus (Wickham, T. J., Lee, G. M, et al. (1997b). *Journal of Virology* 71: 7663-7669. Goldman, C. K., Rogers, B. E., et al. (1997). *Cancer Research* 57: 1447-1451.). The use of antibodies though increases the production difficulties of the vector and the potential risk of activating the complement system. By incorporating receptor binding motifs into the fibre coat protein, Wickham et al. (Wickham, T. J., Tzeng, E., et al. (1997a). *Journal of Virology* 71: 8221-8229.) were able to redirect the virus to bind the integrin expressed by damaged endothelial or smooth muscle cells, or heparin sulphate receptors which is expressed by numerous cells types.

Any of the adeno-associated viral vectors can be used to transfect cells and/or cell lines to express and/or secrete an immunomodulator. Adeno-associated viruses (AAV) are non-pathogenic human parvoviruses, dependant on a helper virus, usually adenovirus, to proliferate. They are capable of infecting both dividing and non dividing cells, and in the absence of a helper virus integrate into a specific point of the host genome (19q 13-qter) at a high frequency (Kotin, R. M., Siniscalco, M., et al. (1990). *Proceedings of the National Academy of Sciences of the U.S.A.* 87: 2211-2215.). The wild type genome is a single stranded DNA molecule, consisting of two genes; rep, coding for proteins which control viral replication, structural gene expression and integration into the host genome, and cap, which codes for capsid structural proteins. At either end of the genome is a 145 bp terminal repeat (TR), containing a promoter.

When used as a vector, the rep and cap genes are replaced by the transgene and its associated regulatory sequences. The total length of the insert cannot greatly exceed 4.7 kb, the length of the wild type genome (Smith, A. E. (1995). *Annual Review of Microbiology* 49: 807-838.). Production of the recombinant vector requires that rep and cap are provided in trans, along with helper virus gene products (E1a, E1b, E2a, E4 and VA RNA from the adenovirus genome). The conventional method is to cotransfect two plasmids, one for the vector and another for rep and cap, into 293 cells infected with adenovirus (Samulski, R. J., Chang, L., and Shenk, T. (1989). *Journal of Virology* 63: 3822-3828.). This method, however, is cumbersome, low yielding (<$10^4$ particles/ml) and prone to contamination with adenovirus and wild type AAV. One of the reasons for the low yield is the inhibitory effect of the rep gene product on adenovirus replication (Vincent, K. A, Piraino, S. T. and Wadsworth, S. C. (1997). *Journal of Virology* 71: 1897-1905.). More recent protocols remove all adenoviral structural genes and use rep resistant plasmids (Xiao, X., Li, J. and Samulski, R. J. (1998) *Journal of Virology* 72: 2224-2232.) or conjugate a rep expression plasmid to the mature virus prior to infection (Fisher, K. J., Kelley, W. M, Burda, J. F. and Wilson, J. M. (1996) *Human Gene Therapy* 7: 2079-2087.).

In the absence of rep, the AAV vector will only integrate at random, as a single provirus or head to tail concatamers, once the terminal repeats have been slightly degraded (Rutledge, E. A. and Russell, D. W. (1997). *Journal of Virology* 71: 8429-8436.). Interest in AAV vectors has been due to their integration into the host genome allowing prolonged transgene expression. Gene transfer into vascular epithelial cells (Maeda, Y., Ikeda, U., et al. (1997). *Cardiovascular Research* 35: 514-521.), striated muscle (Fisher, K. J., Jooss, K., et al. (1997). *Nature Medicine* 3: 306-316. Herzog, R. W., et al. (1997). *Proceedings of the National Academy of Sciences of the U.S.A.* 94: 5804-5809.) and hepatic cells (Snyder, R. O., Miao, C. H., et al. (1997). *Nature Genetics* 16: 270-275.) has been reported, with prolonged expression when the transgene is not derived from a different species. Neutralising antibody to the AAV capsid may be detectable, but does not prevent readministration of the vector or shut down promoter activity. It is possibly due to the simplicity of the viral capsid, that the immune response is so muted. As AAV antibodies will be present in the human population this will require further investigation. There has been no attempt to target particular cell types other than by localised vector delivery.

In particular, the adeno-associated vectors disclosed in U.S. Pat. No. 5,693,531, which is hereby incorporated by reference, can be used, including AAVp5neo; pSV-β-Galactosidase; TRF169; LZ11; pSP72; pSP72nLacZ; pAdRSV4; pAdRSVnLacZ; AAVmLac; SV40; pBluescriptSK; pSV40 ori AAV1; and pKMT11.

Retroviral Vectors

Any of the retroviral vectors can be used to transfect cells and/or cell lines to express and/or secrete an immunomodulator. Retroviruses are a class of enveloped viruses containing a single stranded RNA molecule as the genome. Following infection, the viral genome is reverse transcribed into double stranded DNA, which integrates into the host genome and is expressed as proteins. The viral genome is approximately 10 kb, containing at least three genes: gag (coding for core proteins), pol (coding for reverse transcriptase) and env (coding for the viral envelope protein). At each end of the genome are long terminal repeats (LTRs) which include promoter/enhancer regions and sequences involved with integration. In addition there are sequences required for packaging the viral DNA (psi) and RNA splice sites in the env gene. Some retroviruses contain protooncogenes, which when mutated can cause cancers, however, in the production of vectors these are removed. Retroviruses can also transform cells by integrating near to a cellular protooncogene and driving inappropriate expression from the LTR, or by disrupting a tumor suppresser gene. This event, termed insertional mutagenesis, though extremely rare could still occur when retroviruses are used as vectors.

Retroviral vectors are most frequently based upon the Moloney murine leukemia virus (Mo-MLV), which is an amphotrophic virus, capable of infecting both mouse cells, enabling vector development in mouse models, and human cells, enabling human treatment. The viral genes (gag, pol and env) are replaced with the transgene of interest and expressed on plasmids in the packaging cell line. Because the non-essential genes lack the packaging sequence (psi) they are not included in the virion particle. To prevent recombination resulting in replication competent retroviruses, all regions of homology with the vector backbone should be removed and the non-essential genes should be expressed by at least two transcriptional units (Markowitz, D., Goff, S. and Bank, A. (1988). A safe packaging line for gene transfer: separating viral genes on two different plasmids. Journal of Virology 62: 1120-1124.). Even so, replication competent retroviruses do occur at a low frequency.

The essential regions include the 5' and 3' LTRs, and the packaging sequence lying downstream of the 5' LTR. Transgene expression can either be driven by the promoter/enhancer region in the 5' LTR, or by alternative viral (e.g. cytomegalovirus, Rous sarcoma virus) or cellular (e.g. beta actin, tyrosine) promoters. Mutational analysis has shown that up to the entire gag coding sequence and the immediate upstream region can be removed without effecting viral packaging or transgene expression (Kim, S. H., Yu, S. S., et al. (1998). *Journal of Virology* 72: 994-1004.). However the exact positioning of the transgene start codon and small alterations of the 5' LTR influence transgene expression (Rivire, I., Brose, K. and Mulligan, R. C. (1995). *Proceedings of the National Academy of Sciences of the U.S.A.* 92: 6733-6737.). To aid identification of transformed cells selectable markers, such as neomycin and beta galactosidase, can be included and transgenes expression can be improved with the addition of internal ribosome sites (Saleh, M. (1997). *Human Gene Therapy* 8: 979-983.). The available carrying capacity for retroviral vectors is approximately 7.5 kb (Verma, I. M. and Somia, N. (1997). *Nature* 389: 239-242.), which is too small for some genes even if the cDNA is used.

The retroviral envelope interacts with a specific cellular protein to determine the target cell range. Altering the env gene or its product has proved a successful means of manipulating the cell range. Approaches have included direct modifications of the binding site between the envelope protein and the cellular receptor, however these approaches tend to interfere with subsequent internalisation of the viral particle (Harris, J. D. and Lemoine, N. R. (1996). *Trends in Genetics* 12: 400-404.). By replacing a portion of the env gene with 150 codons from the erythropoietin protein (EPO), Kasahara et al. (Kasahara, N., Dozy, A. M. and Kan, Y. W. (1994). *Science* 266: 1374-1376.) were able to target EPO receptor bearing cells with high affinity. Coupling an antibody to the viral particle with affinity for a second cell specific antibody via a streptovadin bridge, improves viral uptake, but internalisation tends to lead to viral degradation (Roux, P., Jeanteur, P., and Piechaczyk, M. (1989). *Proceedings of the National Academy of Sciences USA* 86: 9079-9083.). Neda et al (Neda, H., Wu, C. H., and Wu. G. Y. (1991) *The Journal of Biological Chemistry* 266: 14143-14146.) treated viral particles with lactose which resulted in uptake by cells, principally hepatocytes, expressing asiaglycoprotein receptors. Subsequently there was efficient viral transgene expression, possibly due to acidification of the endosome allowing fusion of the viral envelope with the endosome membrane.

Viruses differ with respect to their tropisms, therefore by replacing the env gene with that of another virus, the host range can be extended, in a technique known as pseudotyping. Vesicular stomatitis virus G protein has been included in Mo-MLV derived vectors (Burns, J. C., Matsubara, T., et al. (1994). *Developmental Biology* 165: 285-289.), which are also more stable when purified by ultracentrifugation. Recently, Qing (Qing, K., Bachelot, T., Mukherjee, P., et al. (1997). *Journal of Virology* 71: 5663-5667.) improved transduction into numerous cell lines by first treating the recipient cells with an adeno-associated vector (discussed below) expressing the cellular receptor for retroviral envelope protein.

A requirement for retroviral integration and expression of viral genes is that the target cells should be dividing. This limits gene therapy to proliferating cells in vivo or ex vivo, whereby cells are removed from the body, treated to stimulate replication and then transduced with the retroviral vector, before being returned to the patient. Ex vivo cells can be more efficiently transduced, due to exposure to higher virus titres and growth factors (Glimm, H., Kiem, H. P., et al. (1997). *Human Gene Therapy* 8: 2079-2086.). Furthermore ex vivo treated tumor cells will associate with the tumor mass and can direct tumoricidal effects (Oldfield, E. H. and Ram, Z. (1995). *Human Gene Therapy* 6: 55-85; Abdel-Wahab, Z., Weltz, C., et al. (1997). *Cancer* 80: 401-412.).

Lentiviruses are a subclass of retroviruses that are able to infect both proliferating and non-proliferating cells. They are considerably more complicated than simple retroviruses, containing an additional six proteins, tat, rev, vpr, vpu, nef and vif. Current packaging cell lines have separate plasmids for a pseudotype env gene, a transgene construct, and a packaging construct supplying the structural and regulatory genes in trans (Naldini, L., Blmer, U., et al. (1996). *Science* 272: 263-267.). Early results using marker genes have been promising, showing prolonged in vivo expression in muscle, liver and neuronal tissue (Blmer, U., Naldini, L., et al. (1997). *Journal of Virology* 71: 6641-6649. ; Miyoshi, H., Takahashi, M., Gage, F. H. and Verma, I. M. (1997). *Proceedings of the National Academy of Sciences of the U.S.A.* 94: 10319-10323.; Kafri, T., Blmer, U., et al. (1997). *Nature Genetics* 17: 314-317). Interestingly the transgenes are driven by an internally engineered cytomegalovirus promoter, which unlike when in MoMLV vectors, is not inactivated. This may be due to the limited inflammatory response to the vector injection, which was equal in magnitude to the saline control (Blmer, U., Naldini, L., Kafri, T., Trono, D., Verma, I. M. and Gage, F. H. (1997). *Journal of Virology* 71: 6641-6649).

The lentiviral vectors used are derived from the human immunodeficiency virus (HIV) and are being evaluated for safety, with a view to removing some of the non-essential regulatory genes. Mutants of vpr and vif are able to infect neurones with reduced efficiency, but not muscle or liver cells (Blmer, U., Naldini, L., Kafri, T., Trono, D., Verma, I. M. and Gage, F. H. (1997). *Journal of Virology* 71: 6641-6649; Kafri, T., Blmer, U., et al. (1997). *Nature Genetics* 17: 314-317.).

In a particular embodiment, the retroviral vectors pLXIN, pSIR, pLXSH, pLNCX, pLAPSN, pFB and pFB-Neo are used.

Herpes Simplex Viral Vectors

Any of the herpes simplex viral vectors can be used to transfect cells and/or cell lines to express and/or secrete an immunomodulator. Herpes simplex virus type 1 (HSV-1) is a human neurotropic virus, consequently interest has largely focused on using HSV-1 as a vector for gene transfer to the nervous system. The wild type HSV-1 virus is able to infect neurones and either proceed into a lytic life cycle or persist as an intranuclear episome in a latent state. Latently infected neurones function normally and are not rejected by the immune system. Though the latent virus is transcriptionally almost silent, it does possess neurone specific promoters that are capable of functioning during latency. Antibodies to HSV-1 are common in the human population, however complications due to herpes infection, such as encephalitis, are very rare.

The viral genome is a linear double stranded DNA molecule of 152 kb. There are two unique regions, long and short (termed UL and US) which are linked in either orientation by internal repeat sequences (IRL and IRS). At the non-linker end of the unique regions are terminal repeats (TRL and TRS). There are up to 81 genes (Marconi, P., Krisky, D., et al. (1996). *Proceedings of the National Academy of Sciences USA* 93:11319-11320.), of which about half are not essential for growth in cell culture. Once these non essential genes have been deleted, 40-50 kb of foreign DNA can be accommodated within the virus (Glorioso, J. C., DeLuca, N. A. and Fink, D. J (1995). *Annual Review of Microbiology* 49: 675-710.). Three main classes of HSV-1 genes have been identified, namely the immediate-early (IE or alpha) genes, early (E or beta) genes and late (L or gamma) genes.

Following infection in susceptible cells, lytic replication is regulated by a temporally co-ordinated sequence of gene transcription. Vmw65 (a tegument structural protein) activates the immediate early genes (IP0, ICP4, ICP22, ICP27 and ICP477) that are transactivating factors allowing the production of early genes. The early genes encode genes for nucleotide metabolism and DNA replication. Late genes are activated by the early genes and code for structural proteins. The entire cycle takes less than 10 h and invariably results in cell death.

The molecular events leading to the establishment of latency have not been fully determined. Gene expression during latency is driven by the latency associated transcripts (LATs) located in the IRL region of the genome. Two LATs (2.0 and 1.5 kb) are transcribed in the opposite direction to the IE gene ICP0. LATs have a role in HSV-1 reactivation from latency (Steiner, I., Spivack, J. G., et al. (1989). *EMBO Journal* 8: 505-511.) and the establishment of latency (Sawtell, N. M. and Thompson, R. L. (1992). *Journal of Virology* 66: 2157-2169.). Two latency active promoters that drive expression of the LATs have been identified (Marconi, P., Krisky, D., et al. (1996). *Proceedings of the National Academy of Sciences USA* 93: 11319-11320.) and may prove useful for vector transgene expression.

Two basic approaches have been used for production of HSV-1 vectors, namely amplicons and recombinant HSV-1 viruses. Amplicons are bacterially produced plasmids containing col E1 ori (an *Escherishia coli* origin of replication), OriS (the HSV-1 origin of replication), HSV-1 packaging sequence, the transgene under control of an immediate-early promoter and a selectable marker (Federoff, H. J., Geschwind, M. D., Geller, A. I. and Kessler, J. A. (1992). *Proceedings of the National Academy of Sciences USA* 89: 1636-1640.). The amplicon is transfected into a cell line containing a helper virus (a temperature sensitive mutant) which provides all the missing structural and regulatory genes in trans. Both the helper and amplicon containing viral particles are delivered to the recipient. More recent amplicons include an Epstein-Barr virus derived sequence for plasmid episomal maintenance (Wang, S. and Vos, J. (1996). *Journal of Virology* 70: 8422-8430.).

Recombinant viruses are made replication deficient by deletion of one the immediate-early genes e.g. ICP4, which is provided in trans. Though they are less pathogenic and can direct transgene expression in brain tissue, they are toxic to neurones in culture (Marconi, P., Krisky, D., et al. (1996). *Proceedings of the National Academy of Sciences USA* 93: 11319-11320.). Deletion of a number of immediate-early genes substantially reduces cytotoxicity and also allows expression from promoters that would be silenced in the wild type latent virus. These promoters may be of use in directing long term gene expression.

Replication-conditional mutants are only able to replicate in certain cell lines. Permissive cell lines are all proliferating and supply a cellular enzyme to complement for a viral deficiency. Mutants include thymidine kinase (During, M. J., Naegele, J. R., OMalley, K. L. and Geller, A. I. (1994). *Science* 266: 1399-1403.), ribonuclease reductase (Kramm, C. M., Chase, M., et al. (1997). *Human Gene Therapy* 8: 2057-2068.), UTPase, or the neurovirulence factor g34.5 (Kesari, S., Randazzo, B. P., et al. (1995). *Laboratory Investigation* 73: 636-648.).

Non-Viral Vectors

Viral vectors all induce an immunological response to some degree and may have safety risks (such as insertional mutagenesis and toxicity problems). Further, their capacity is limited and large scale production may be difficult to achieve. Therefore, in one embodiment of the invention, non-viral methods of gene transfer are used, which may require only a small number of proteins, have a virtually infinite capacity, have no infectious or mutagenic capability and large scale production is possible using pharmaceutical techniques. There are three methods of non-viral DNA transfer, namely: naked DNA, liposomes and molecular conjugates.

Naked Nucleic Acids

Naked DNA or nucleic acids can be used to deliver the immunomodulator to the host. It can be delivered, for example, in the form of a plasmid can be directly injected into muscle cells (Wolff, J. A., Malone, R. W., Williams, P., Chong, W., Acsadi, G., Jani, A. and Felgner P. L. (1990). *Science* 247: 1465-1468.) or attached to gold particles that are bombarded into the tissue (Cheng, L., Ziegelhoffer, P. R. and Yang, N. S. (1993). *Proceedings of the National Academy of Sciences of the U.S.A.* 90: 4455-4459.). The terms "naked" nucleic acid, DNA or RNA refer to sequences that are free from any delivery vehicle that act to assist, promote, or facilitate entry into the cell, including viral sequences, viral particles, liposome formulations, lipofectin or precipitating agents and the like. Though not very efficient, this can result in prolonged low level expression in vivo. Unlike other gene therapies techniques, one major advantage of introducing naked nucleic acid sequences into target cells is the transitory nature of the immunomodulator synthesis in the cells. Studies have shown that non-replicating DNA sequences can be introduced into cells to provide production of the desired immunomodulator for periods of up to six months. The simplicity of this method, and sustained expression has led to the development of DNA vaccines. Compared to conventional attenuated and protein based vaccines, they are unaffected by pre-existing immunity e.g. due to maternal antibodies, relatively cheap, and can deliver a number of pathogen antigens on a single plasmid (Manickan, E., Karem, K. L., and Rouse, B. T. (1997). *Critical Reviews in Immunology* 17: 139-154.). DNA vaccines are being developed for those pathogens where there is no existing vaccine e.g. HIV (Lekutis, C., Shiver, J. W., Liu, M. A., and Letvin, L. N. (1997). *The Journal of Immunology* 158: 4471-4477.) or the current vaccine not fully effective e.g. influenza (Macklin, M. D., McCabe, D., et al. (1998).

*Journal of Virology* 72: 1491-1496.). By using a highly conserved gene Ulmer et al. (Ulmer, J. B., Donnelly, J. J., et al. (1993). *Science* 254: 1745-1749.) were able to immunize mice against two serologically distinct influenza virus strains. In most cases however, DNA vaccines have not been shown to be better than the existing vaccines (Macklin, M. D., McCabe, D., et al. (1998). *Journal of Virology* 72: 1491-1496.). The actual type of immune response can be controlled by cotransformation of a gene coding for the appropriate cytokine (Xiang, Z. and Ertl, H. C. (1995). *Immunity* 2: 129-135.) and this method may prove useful in redirecting inappropriate immune responses (Manickan, E., Karem, K. L., and Rouse, B. T. (1997). *Critical Reviews in Immunology* 17: 139-154.). Other uses for naked DNA include cancer immunopotentiation (discussed below, Corr. M., Tighe, H., Lee. D., Dudler, J., et al. (1997). *The Journal of Laboratory Investigation* 159: 4999-5004.), repair of pancreatic insulin function (Goldfine. I. D., German, M. S., Tseng, H., et al. (1997). *Nature Biotechnology* 15: 1378-1382.), and stimulation of collateral blood vessel development (Takeshita, S., Tsurumi, Y., et al. (1996). *Laboratory Investigation* 75: 487-501.). Expression of the gene product in muscle tissue can be improved by the coadministration of collagenase, papaverine and ischaemic conditions (Budker, V., Zhang, G., Danko, I., Williams, P. and Wolff, J. (1998). *Gene Therapy* 5: 272-276.). The use of a muscle specific promoter (Skarli, M., Kiri, A., et al. (1998). *Gene Therapy* 5: 514-520.) and other intragene regulatory sequences, such as the poly A and transcription termination sequence (Hartikka, J., Sawdey, M., et al. (1996). *Human Gene Therapy* 7: 1205-1217.) will also improve transgene expression.

For the naked polypeptide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The route of administration is by the parenteral route of injection into the interstitial space of tissues, or other parenteral routes may also be used, such as, inhalation of an aerosol formulation particularly for delivery to lungs or bronchial tissues, throat or mucous membranes of the nose. In addition, naked polypeptide constructs can be delivered to arteries during angioplasty by the catheter used in the procedure.

The immunomodulator may also be delivered in liposome formulations (such as those taught in Felgner P. L. et al. (1995) *Ann. NY Acad. Sci.* 772:126-139 and Abdallah B. et al. (1995) *Biol. Cell* 85(1):1-7) which can be prepared by methods well known to those skilled in the art. Liposomes are lipid bilayers entrapping a fraction of aqueous fluid. DNA will spontaneously associate to the external surface of cationic liposomes (by virtue of its charge) and these liposomes will interact with the cell membrane (Feigner, J. H., Kumar, R., et al. (1994). *Journal of Biological Chemistry* 269: 2550-2561.). In vitro up to 90% of certain cell lines may be transfected. By including a small amount of an anionic lipid in an otherwise cationic liposome the DNA can be incorporated into the internal surface of the liposome, thus protecting it from enzymatic degradation. (Crespo et al, 1996, cited in Alio, S. F. (1997). *Biochemical Pharmacology* 54: 9-13.). To facilitate uptake into the cell as endosomes, targeting proteins have been included in liposomes, e.g. anti-MHC antibody (Wang, C., and Huang, L. (1987). *Proceedings of the National Academy of Sciences USA* 84: 7851-7855.) transferrin (Stavridis, J. C., Deliconstantinos, G., et al. (1986). *Experimental Cell Research* 164: 568-572.), and the Sendai virus or its F protein (Dzau, J. V., Mann, M. J, Morishita, R. and Kaneda, Y. (1996). *Proceedings of the National Academy of Sciences USA* 93: 11421-11425.). The Sendai virus additionally allows the plasmid DNA to escape from the endosome into the cytoplasm, thus avoiding degradation. The inclusion of a DNA binding protein (28 kDa high mobility group 1 protein) enhances transcription by bringing the plasmid into the nucleus (Dzau et al, 1997 *Am J Cardiol*. Nov. 6, 1997;80 (9A):33I-39I).

Molecular conjugates consist of protein or synthetic ligands to which a DNA binding agent has been attached. Delivery to the cell can be improved by using similar techniques to those for liposomes. Targeting proteins include asialoglycoprotein (Wagner, E., Cotten, M., Foisner, R. and Birnstiel, M. L. (1991). *Proceedings of the National Academy of Sciences USA* 88: 4255-4259.), transferrin (Wu, C. H., Wilson, J. M. and Wu., G. Y. (1989). *Journal of Biological Chemistry*. 264: 16985-16987.), polymeric IgA (Ferkol, T., Kaetzel, C. S. and Davis, P. B. (1993). *Journal of Clinical Investigation* 92: 2394-2400.) and adenovirus (Madon, J. and Blum, H. E. (1996). *Hepatology* 24: 474-481.). Transgene expression tends to be transient and is limited by endosome/lysosomal degradation.

VI. Pharmaceutical Compositions

Humans suffering from any of the disorders described herein, including hepatitis B, can be treated by administering to the patient an effective amount of a β-2'-deoxy-β-L-erythro-pentofuranonucleoside, for example, β-L-2'-deoxyadenosine, β-L-2'-deoxycytidine, β-L-2'-deoxyuridine, β-L-2'-deoxyguanosine or β-L-2'-deoxythymidine or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount of compound to inhibit viral replication in vivo, without causing serious toxic effects in the patient treated. By "inhibitory amount" is meant an amount of active ingredient sufficient to exert an inhibitory effect as measured by, for example, an assay such as the ones described herein.

A preferred dose of the compound for all of the abovementioned conditions will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable prodrug can be calculated based on the weight of the parent nucleoside to be delivered. If the prodrug exhibits activity in itself, the effective dosage can be estimated as above using the weight of the prodrug, or by other means known to those skilled in the art.

The compound is conveniently administered in unit any suitable dosage form, including but not limited to one containing 7 to 3000 mg, preferably 70 to 1400 mg of active ingredient per unit dosage form. A oral dosage of 50-1000 mg is usually convenient.

Ideally the active ingredient should be administered to achieve peak plasma concentrations of the active compound of from about 0.2 to 70 μM, preferably about 1.0 to 10 μM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable derivative or salts thereof can also be mixed with other active materials that do not impair the desired action, or with materials that supplement the desired action, such as antibiotics, antifungals, antiinflammatories, protease inhibitors, or other nucleoside or nonnucleoside antiviral agents. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

VII. Controlled Release Formulations

All of the U.S. patents cited in this section on controlled release formulations are incorporated by reference in their entirety.

The field of biodegradable polymers has developed rapidly since the synthesis and biodegradability of polylactic acid was reported by Kulkarni et al. ("Polylactic acid for surgical implants," Arch. Surg, 1966, 93, 839). Examples of other polymers which have been reported as useful as a matrix material for delivery devices include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, for example, U.S. Pat. Nos. 4,891,225 and 4,906,474 to Langer (polyanhydrides), U.S. Pat. No. 4,767,628 to Hutchinson (polylactide, polylactide-co-glycolide acid), and U.S. Pat. No. 4,530,840 to Tice, et al. (polylactide, polyglycolide, and copolymers). See also U.S. Pat. No. 5,626,863 to Hubbell, et al which describes photopolymerizable biodegradable hydrogels as tissue contacting materials and controlled release carriers (hydrogels of polymerized and crosslinked macromers comprising hydrophilic oligomers having biodegradable monomeric or oligomeric extensions, which are end capped monomers or oligomers capable of polymerization and crosslinking); and PCT WO 97/05185 filed by Focal, Inc. directed to multiblock biodegradable hydrogels for use as controlled release agents for drug delivery and tissue treatment agents.

Degradable materials of biological origin are well known, for example, crosslinked gelatin. Hyaluronic acid has been crosslinked and used as a degradable swelling polymer for biomedical applications (U.S. Pat. No. 4,957,744 to Della Valle et. al.; "Surface modification of polymeric biomaterials for reduced thrombogenicity," Polym. Mater. Sci. Eng., 1991, 62, 731-735]).

Many dispersion systems are currently in use as, or being explored for use as, carriers of substances, particularly biologically active compounds. Dispersion systems used for pharmaceutical and cosmetic formulations can be categorized as either suspensions or emulsions. Suspensions are defined as solid particles ranging in size from a few manometers up to hundreds of microns, dispersed in a liquid medium using suspending agents. Solid particles include microspheres, microcapsules, and nanospheres. Emulsions are defined as dispersions of one liquid in another, stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, as defined in U.S. Pat. Nos. 4,622,219 and 4,725,442 issued to Haynes. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

U.S. Pat. No. 4,938,763 to Dunn, et al., discloses a method for forming an implant in situ by dissolving a nonreactive, water insoluble thermoplastic polymer in a biocompatible, water soluble solvent to form a liquid, placing the liquid within the body, and allowing the solvent to dissipate to produce a solid implant. The polymer solution can be placed in the body via syringe. The implant can assume the shape of its surrounding cavity. In an alternative embodiment, the implant is formed from reactive, liquid oligomeric polymers which contain no solvent and which cure in place to form solids, usually with the addition of a curing catalyst.

A number of patents disclose drug delivery systems that can be used to administer a β-L-2'-deoxynucleoside or a nucleotide or other defined prodrug thereof. U.S. Pat. No. 5,749,847 discloses a method for the delivery of nucleotides into organisms by electrophoration. U.S. Pat. No. 5,718,921 discloses microspheres comprising polymer and drug dispersed there within. U.S. Pat. No. 5,629,009 discloses a delivery system for the controlled release of bioactive factors. U.S. Pat. No. 5,578,325 discloses nanoparticles and microparticles of non-linear hydrophilic hydrophobic multiblock copolymers. U.S. Pat. No. 5,545,409 discloses a delivery system for the controlled release of bioactive factors. U.S. Pat. No. 5,494,682 discloses ionically cross-linked polymeric microcapsules.

U.S. Pat. No. 5,728,402 to Andrx Pharmaceuticals, Inc. describes a controlled release formulation that includes an internal phase which comprises the active drug, its salt, ester or prodrug, in admixture with a hydrogel forming agent, and an external phase which comprises a coating which resists dissolution in the stomach. U.S. Pat. Nos. 5,736,159 and 5,558,879 to Andrx Pharmaceuticals, Inc. discloses a controlled release formulation for drugs with little water solubility in which a passageway is formed in situ. U.S. Pat. No. 5,567,441 to Andrx Pharmaceuticals, Inc. discloses a once-a-day controlled release formulation. U.S. Pat. No. 5,508,040 discloses a multiparticulate pulsatile drug delivery system. U.S. Pat. No. 5,472,708 discloses a pulsatile particle based drug delivery system. U.S. Pat. No. 5,458,888 describes a controlled release tablet formulation which can be made using a blend having an internal drug containing phase and an external phase which comprises a polyethylene glycol polymer which has a weight average molecular weight of from 3,000 to 10,000. U.S. Pat. No. 5,419,917 discloses methods for the modification of the rate of release of a drug form a hydrogel which is based on the use of an effective amount of a pharmaceutically acceptable ionizable compound that is capable of providing a substantially zero-order release rate of drug from the hydrogel. U.S. Pat. No. 5,458,888 discloses a controlled release tablet formulation.

U.S. Pat. No. 5,641,745 to Elan Corporation, plc discloses a controlled release pharmaceutical formulation which comprises the active drug in a biodegradable polymer to form microspheres or nanospheres. The biodegradable polymer is suitably poly-D,L-lactide or a blend of poly-D,L-lactide and poly-D,L-lactide-co-glycolide. U.S. Pat. No. 5,616,345 to Elan Corporation plc describes a controlled absorption formulation for once a day administration that includes the active compound in association with an organic acid, and a multi-layer membrane surrounding the core and containing a major proportion of a pharmaceutically acceptable film-forming, water insoluble synthetic polymer and a minor proportion of a pharmaceutically acceptable film-forming water soluble synthetic polymer. U.S. Pat. No. 5,641,515 discloses a controlled release formulation based on biodegradable nanoparticles. U.S. Pat. No. 5,637,320 discloses a controlled absorption formulation for once a day administration. U.S. Pat. Nos. 5,580,580 and 5,540,938 are directed to formulations and their use in the treatment of neurological diseases. U.S. Pat. No. 5,533,995 is directed to a passive transdermal device with controlled drug delivery. U.S. Pat. No. 5,505,962 describes a controlled release pharmaceutical formulation.

VIII. Preparation of the Active Compounds

The β-L-2'-deoxynucleosides of the present invention are known in the art and can be prepared according to the method disclosed by Holy, *Collect. Czech. Chem. Commun.* 1972, 37 (12), 4072-87 and *Mol. Phys.* 1967, 3 (4), 386-95.

A general process for obtaining β-L-2'-deoxynucleosides (β-L-dN) is shown in FIG. 1, using L-ribose or L-xylose as a starting material.

Mono, di and triphosphate derivatives of the active nucleosides can be prepared as described according to published methods. The monophosphate can be prepared according to the procedure of Imai et al., *J. Org. Chem.*, June 1969, 34 (6), 1547-1550. The diphosphate can be prepared according to the procedure of Davisson et al., *J. Org. Chem.,* 1987, 52 (9), 1794-1801. The triphosphate can be prepared according to the procedure of Hoard et al., *J. Am. Chem. Soc.,* 1965, 87 (8), 1785-1788.

Method for the Preparation of β-L-5'-derivatives of β-L-nucleosides

β-L-5'-derivatives of a β-L-nucleoside can be made by any means known in the art, particularly by known methods to protect primary alcohols with acyl moieties, i.e., via an anhydride or with the aid of a coupling agent. As a non-limiting example, the β-L-5'-derivatives can be prepared according to the following reaction sequence:

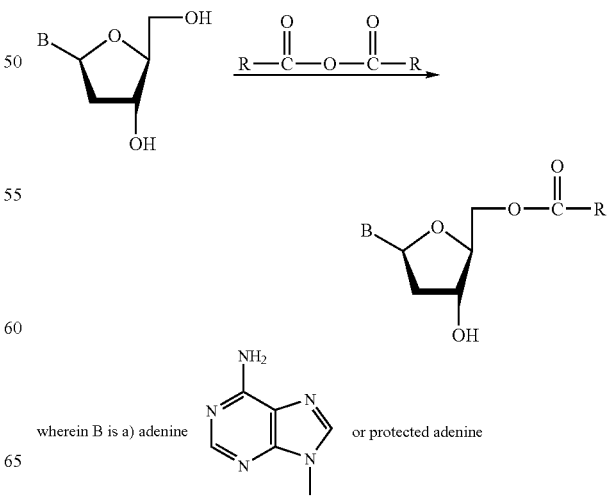

wherein B is a) adenine or protected adenine

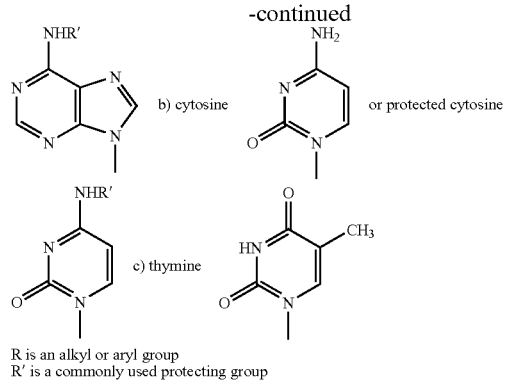

R is an alkyl or aryl group
R' is a commonly used protecting group

In a preferred embodiment, the 5'-derivative is derived from an aminoacyl moiety. The key starting material for this process is an appropriately substituted β-L-nucleoside. The β-L-nucleoside can be purchased or can be prepared by any known means including standard coupling reactions with an L-sugar moiety, such as deoxyribose. The aminoacyl derivatives can be made by selectively coupling an amino acid to a β-L-nucleoside, preferably without any additional protection of the nucleoside. The coupling reaction can be achieved using appropriate coupling reagents that promote the coupling. Some non-limiting examples of coupling reagents are Mitsunobu-type reagents (e.g. dialkyl azodicarboxylates such as diisopropyl azodicarboxylate and diethyl azodicarboxylate) with triphenyl phosphine or various types of carbodiimides.

The coupling reaction can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

Scheme 1 is a non-limiting example of the preparation of a β-L-5'-aminoacyl-nucleoside derived from L-deoxyribonucleoside.

Method for the Preparation of β-L-3'-derivatives of β-L-nucleosides

β-L-3'-derivatives of a 2'-deoxy-nucleoside can be made by any means known in the art, particularly by known methods to protect secondary alcohols with acyl moieties, i.e., via an anhydride or with the aid of a coupling agent. As a non-limiting example, the 3'-derivatives can be prepared according to the following reaction sequence:

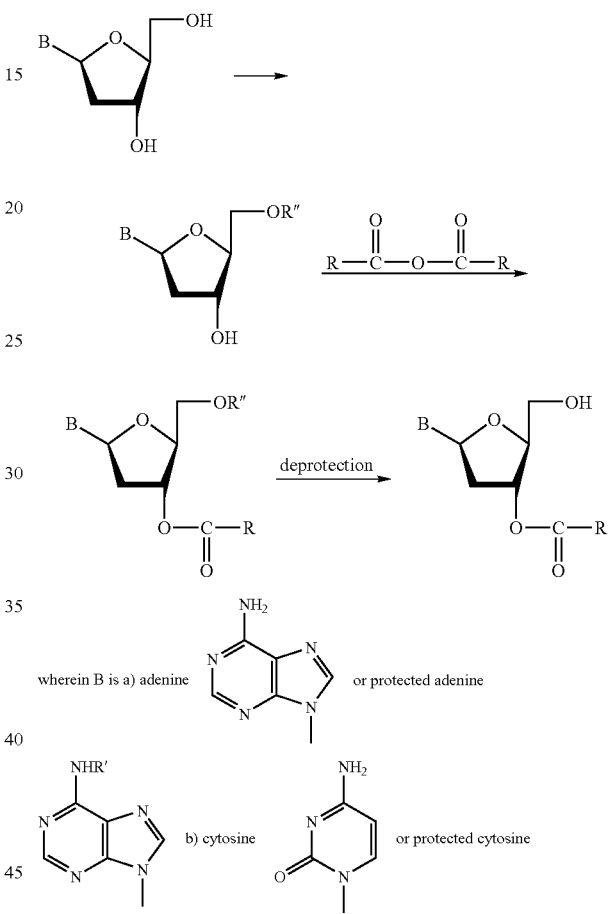

Scheme 1

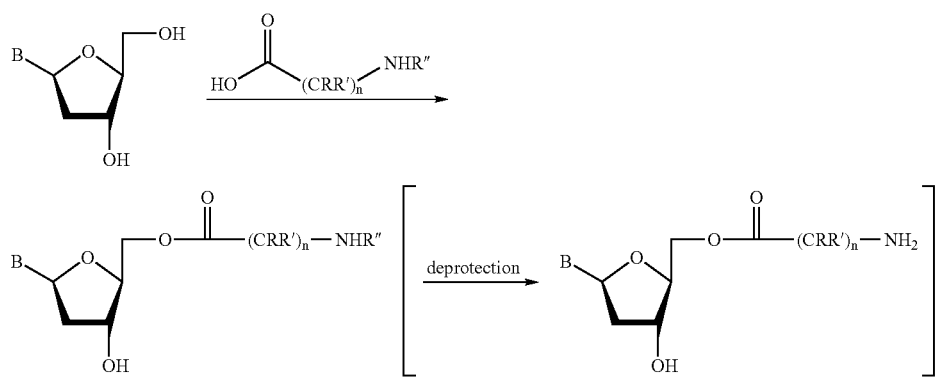

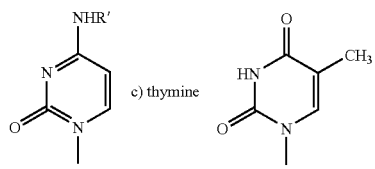

R is an alkyl or aryl group
R' and R" are commonly used protecting group

Alternatively, the 3'-derivative is derived from an aminoacyl moiety. The key starting material for this process is also an appropriately substituted β-L nucleoside. The β-L nucleoside can be purchased or can be prepared by any known means including standard coupling reactions with an L-sugar moiety.

These aminoacyl derivatives can be made by first selectively protecting the 5'-hydroxyl with a suitable oxygen protecting group, such as an acyl or silyl protecting group, and optionally protecting any free amine in the heterocyclic or heteroaromatic base. Subsequently, the free 3'-hydroxyl can be coupled to an N-protected α or β amino acid.

Subsequently, the β-L-nucleoside is coupled to the aminoacyl using standard coupling reagents that promote the coupling. Some non-limiting examples of coupling reagents are Mitsunobu-type reagents (e.g. dialkyl azodicarboxylates such as diisopropyl azodicarboxylate and diethyl azodicarboxylate) with triphenyl phosphine or various types of carbodiimides.

The coupling reaction can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

Scheme 2 is a non-limiting example of the preparation of a β-L-3'-aminoacyl-nucleoside derived from L-deoxyribonucleoside.

Method for the Preparation of β-L-3',5'-bis-O-derivatives of β-L-nucleosides

β-L-3',5'-bis-O-derivatives of a β-L-nucleoside can be made by any means known in the art, particularly by known methods to protect primary and secondary alcohols with acyl moieties, i.e., via an anhydride or with the aid of a coupling agent. As a non-limiting example, the 3',5'-bis-O-derivatives can be prepared according to the following reaction sequence:

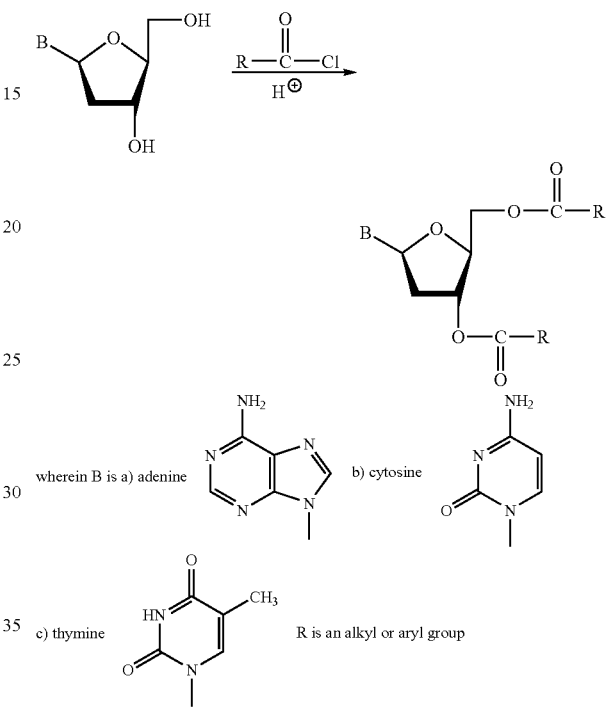

In a preferred embodiment, the 3',5'-bis-O-derivative is derived from an aminoacyl moiety. The key starting material for this process is also an appropriately substituted β-L-nucleoside. The 3',5'-bis-O-derivatives of the β-L-nucleosides can be purchased or can be prepared by any known means including standard coupling reactions with an L-sugar moiety, such as deoxyribose. Subsequently, the free 3'- and 5'-hydroxyl can be coupled to a N-protected α or β amino acid. The coupling reaction can be achieved using appropriate coupling reagents that promote the coupling. Some non-lim- Scheme 2

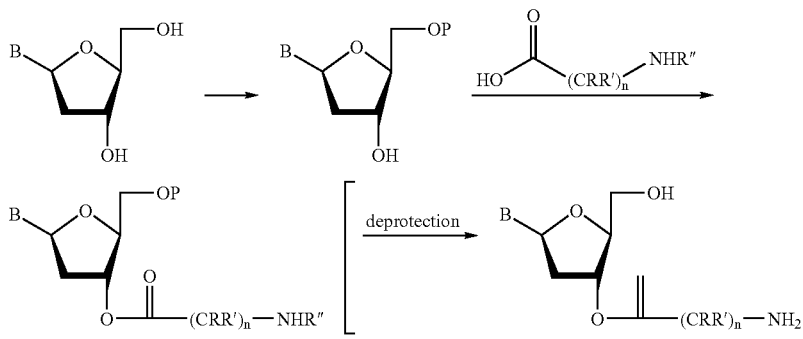

iting examples of coupling reagents are Mitsunobu-type reagents (e.g. dialkyl azodicarboxylates such as diisopropyl azodicarboxylate and diethyl azodicarboxylate) with triphenyl phosphine or various types of carbodiimides.

The coupling reaction can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

Scheme 3 is a non-limiting example of the preparation of a β-L-3',5'-di-aminoacyl-nucleoside derived from L-deoxyribonucleoside.

Optional Method for Derivatization of the Heteroaromatic or Heterocyclic Base

The title compounds can be made by optionally protecting any free amino in the heterocyclic or heteroaromatic base, for example $N^4$-cytosine, $N^6$-adenine or $N^2$-guanine. For example, the amine can be protected by an acyl moiety or a dialkylaminomethylene moiety by the following general protocol.

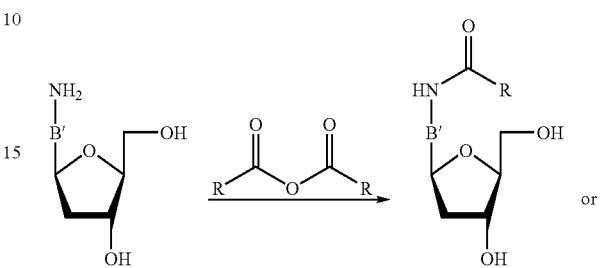

Scheme 3

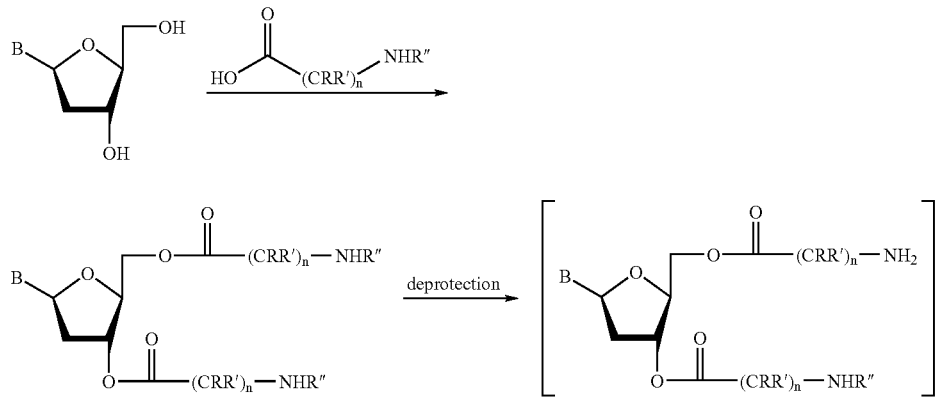

Optional Method for the Extension of the Aminoacyl Moiety

The title compounds can be made by reacting the 3' and 5'-hydroxyl with a suitable derivative, such as an acyl, and in particular an aminoacyl group. If the nucleoside is derivatized with an aminoacyl moiety, it may be desirable to further couple the free amine to a N-protected α or β amino acid. The coupling reaction can be achieved using appropriate coupling reagents that promote the coupling. Some non-limiting examples of coupling reagents are Mitsunobu-type reagents (e.g. dialkyl azodicarboxylates such as diisopropyl azodicarboxylate and diethyl azodicarboxylate) with triphenyl phosphine or various types of carbodiimides.

The coupling reaction can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

-continued

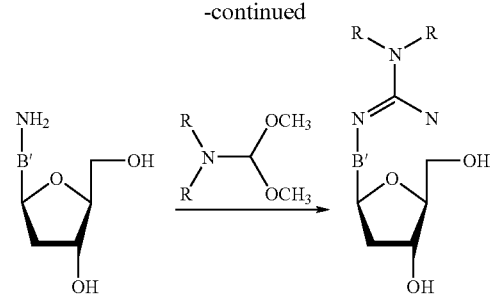

The protection can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

Subsequently, the free 3'-hydroxyl can be coupled to a N-protected α or β amino acid. The coupling reaction can be achieved using appropriate coupling reagents that promote the coupling. Some non-limiting examples of coupling reagents are Mitsunobu-type reagents (e.g. dialkyl azodicarboxylates such as diisopropyl azodicarboxylate and diethyl azodicarboxylate) with triphenyl phosphine or various types of carbodiimides.

The coupling reaction can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

In an alternate embodiment, the $N^4$- or $N^6$-acyl derivative is derived from an aminoacyl moiety, and can be prepared according to the following reaction sequence, by optionally protecting the free hydroxyls, followed by a condensation reaction with the appropriately protected amino ester, and the removal of the hydroxyl protecting groups, if necessary.

EXAMPLES

Melting points were determined in open capillary tubes on a Gallenkamp MFB-595-010 M apparatus and are uncorrected. The UV absorption spectra were recorded on an Uvikon 931 (KONTRON) spectrophotometer in ethanol. $^1$H—NMR spectra were run at room temperature in DMSO-$d_6$ with a Bruker AC 250 or 400 spectrometer. Chemical shifts are given in ppm, DMSO-$d_5$ being set at 2.49 ppm as reference. Deuterium exchange, decoupling experiments or 2D-COSY were performed in order to confirm proton assignments. Signal multiplicities are represented by s (singlet), d (doublet), dd (doublet of doublets), t (triplet), q (quadruplet), br (broad), m (multiplet). All J-values are in Hz. FAB mass spectra were recorded in the positive-(FAB>0) or negative-(FAB<0) ion mode on a JEOL DX 300 mass spectrometer The matrix was 3-nitrobenzyl alcohol (NBA) or a mixture (50:50, v/v) of glycerol and thioglycerol (GT). Specific rotations were measured on a Perkin-Elmer 241 spectropolarimeter (path length 1 cm) and are given in units of $10^{-1}$ deg cm$^2$ g$^{-1}$. Elemental analysis were carried out by the "Service de Microanalyses du CNRS, Division de Vernaison" (France). Analyses indicated by the symbols of the elements or functions were within ±0.4% of theoretical values. Thin layer chromatography was performed on precoated aluminium sheets of Silica Gel 60 $F_{254}$ (Merck, Art. 5554), visualisation of products being accomplished by UV absorbency followed by charring with 10% ethanolic sulfuric acid and heating. Column chromatography was carried out on Silica Gel 60 (Merck, Art. 9385) at atmospheric pressure.

Example 1

Stereospecific Synthesis of 2'-Deoxy-β-L-Cytidine

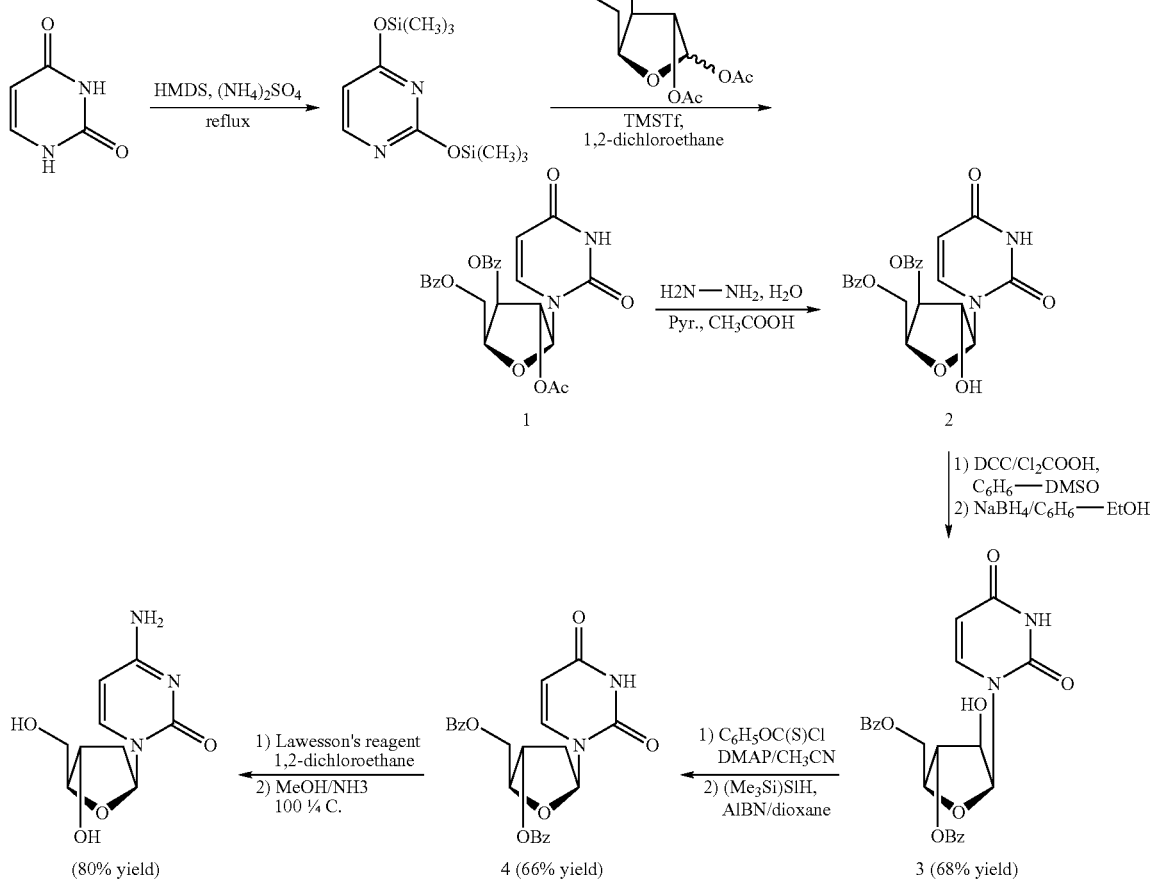

1-(3,5-Di-O-benzoyl-β-L-xylofuranosyl)uracil (2)

Hydrazine hydrate (1.4 mL, 28.7 mmol) was added to a solution of 1-(2-O-acetyl-3,5-di-O-benzoyl-β-L-xylofuranosyl)uracil 1 [Ref.: Gosselin, G.; Bergogne, M.-C.; Imbach, J.-L., "Synthesis and Antiviral Evaluation of β-L-Xylofuranosyl Nucleosides of the Five Naturally Occurring Nucleic Acid Bases", *Journal of Heterocyclic Chemistry*, Oct.-Nov. 30, 1993, 1229-1233] (4.79 g, 9.68 mmol) in pyridine (60 mL) and acetic acid (15 mL). The solution was stirred overnight at room temperature. Acetone was added (35 mL) and the mixture was stirred for 30 minutes. The reaction mixture was evaporated under reduced pressure. The resulting residue was purified by silica gel column chromatography [eluent: stepwise gradient of methanol (0-4%) in dichloromethane to give 2 (3.0 g, 68%) which was crystallized from cyclohexane/dichloromethane: mp=111-114° C.; $^1$H—NMR (DMSO-d$_6$): δ 11.35 (br s, 1H, NH), 7.9-7.4 (m, 11H, 2 C$_6$H$_5$CO, H-6), 6.38 (d, 1H, OH-2', $J_{OH-2'}$=4.2 Hz), 5.77 (d, 1H, H-1', $J_{1'-2'}$=1.9 Hz), 5.55 (d, 1H, H-5, $J_{5-6}$=8 Hz), 5.54 (dd, 1H, H-3', $J_{3'-2'}$=3.9 Hz and $J_{3'-4'}$=1.8 Hz), 4.8 (m, 1H, H-4'), 4.7 (m, 2H, H-5' and H-5"), 4.3 (m, 1H, H-2'); MS: FAB>0 (matrix GT) m/z 453 (M+H)$^+$, 105 (C$_6$H$_5$CO)$^+$; FAB<0 (matrix GT) m/z 451 (M–H)$^-$, 121 (C$_6$H$_5$CO$_2$)$^-$, 111 (B)$^-$; Anal. Calcd for C$_{23}$H$_{20}$N$_2$O$_8$.H$_2$O: C, 58.09; H, 4.76; N, 5.96. Found: C, 57.71; H, 4.42; N, 5.70.

1-(3,5-Di-O-benzoyl-β-L-arabinofuranosyl)uracil (3)

To a solution of 1-(3,5-di-O-benzoyl-β-L-xylofuranosyl)uracil 2 (8 g, 17.7 mL) in an anhydrous benzene-DMSO mixture (265 mL, 6:4, v/v) were added anhydrous pyridine (1.4 mL), dicyclohexylcarbodiimide (10.9 g, 53 mmol) and dichloroacetic acid (0.75 mL). The resulting mixture was stirred at room temperature for 4 hours, then diluted with ethyl acetate (400 mL) and a solution of oxalic acid (4.8 g, 53 mmol) in methanol (14 mL) was added. After being stirred for 1 h, the solution was filtered. The filtrate was washed with a saturated NaCl solution (2×500 mL), 3% NaHCO$_3$ solution (2×500 mL) and water (2×500 mL). The organic phase was dried over Na$_2$SO$_4$, then evaporated under reduced pressure. The resulting residue was then solubilized in an EtOH absolute-benzene mixture (140 mL, 2:1, v/v). To this solution at 0° C. was added NaBH$_4$ (0.96 g, 26.5 mmol). After being stirred for 1 h, the solution was diluted with ethyl acetate (400 mL), then filtered. The filtrate was washed with a saturated NaCl solution (400 mL) and water (400 mL). The organic phase was dried over Na$_2$SO$_4$, then evaporated under reduced pressure. The resulting crude material was purified by silica gel column chromatography [eluent: stepwise gradient of methanol (0-3%) in dichloromethane to give 3 (5.3 g, 66%) which was crystallized from acetonitrile: mp=182-183° C.; $^1$H—NMR (DMSO-d$_6$): δ 11.35 (br s, 1H, NH), 8.0-7.5 (m, 11H, 2 C$_6$H$_5$CO, H-6), 6.23 (br s, 1H, OH-2'), 6.15 (d, 1H, H-1', $J_{1'-2'}$=4 Hz), 5.54 (d, 1H, H-5, $J_{5-6}$=8.1 Hz), 5.37 (t, 1H, H-3', $J_{3'-2'}$=$J_{3'-4'}$=2.6 Hz), 4.7-4.6 (m, 2H, H-5' and H-5"), 4.5 (m, 1H, H-4'), 4.4 (m, 1H, H-2'); MS: FAB>0 (matrix GT) m/z 453 (M+H)$^+$, 341 (S)$^+$, 113 (BH$_2$)$^+$, 105 (C$_6$H$_5$CO)$^+$; FAB<0 (matrix GT) m/z 451 (M–H)$^-$, 121 (C$_6$H$_5$CO$_2$)$^-$, 111 (B)$^-$; Anal. Calcd for C$_{23}$H$_{20}$N$_2$O$_8$: C, 61.06; H, 4.46; N, 6.19. Found: C, 60.83; H, 4.34; N, 6.25.

1-(3,5-Di-O-benzoyl-2-deoxy-β-L-erythro-pentofuranosyl)uracil (4)

To a solution of 1-(3,5-di-O-benzoyl-β-L-arabinofuranosyl)uracil 3 (5.2 g, 11.4 mmoL) in anhydrous 1,2-dichloroethane (120 mL) were added phenoxythiocarbonyl chloride (4.7 mL, 34.3 mL) and 4-(dimethylamino)pyridine (DMAP, 12.5 g, 102.6 mmoL). The resulting solution was stirred at room temperature under argon atmosphere for 1 h and then evaporated under reduced pressure. The residue was dissolved in dichloromethane (300 mL) and the organic solution was successively washed with an ice-cold 0.2 N hydrochloric acid solution (3×200 mL) and water (2×200 mL), dried over Na$_2$SO$_4$ then evaporated under reduced pressure. The crude material was co-evaporated several times with anhydrous dioxane and dissolved in this solvent (110 mL). To the resulting solution were added under argon tris-(trimethylsilyl)silane hydride (4.2 mL, 13.7 mmol) and α,α'-azoisobutyronitrile (AIBN, 0.6 g, 3.76 mmol). The reaction mixture was heated and stirred at 100° C. for 1 hour under argon, then cooled to room temperature and evaporated under reduced pressure. The residue was purified by silica gel column chromatography [eluent: stepwise gradient of methanol (0-5%)] to give 4 (2.78 g, 56%) which was crystallized from EtOH: mp=223-225° C.; H—NMR (DMSO-d$_6$): δ 11.4 (br s, 1H, NH), 8.0-7.5 (m, 11H, 2 C$_6$H$_5$CO, H-6), 6.28 (t, 1H, H-1', J=7 Hz), 5.5 (m, 2H, H-1' and H-5), 4.6-4.4 (m, 3H, H-4', H-5' and H-5"), 2.6 (m, 2H, H-2' and H-2"); MS: FAB>0 (matrix GT) m/z 437 (M+H)$^+$, 3325 (S)$^+$; FAB<0 (matrix GT) mz 435 (M–H)$^-$, 111 (B)$^-$; Anal. Calcd for C$_{23}$H$_{20}$N$_2$O7: C, 63.30; H, 4.62; N, 6.42.
Found: C, 62.98; H, 4.79; N, 6.40.

2'-Deoxy-β-L-cytidine (β-L-dC)

Lawesson's reagent (1.72 g, 4.26 mmol) was added under argon to a solution of 1-(3,5-di-O-benzoyl-2-deoxy-β-L-erythro-pentofuranosyl)uracil 4 (2.66 g, 6.1 mmol) in anhydrous 1,2-dichloroethane (120 mL) and the reaction mixture was stirred under reflux for 2 hours. The solvent was then evaporated under reduced pressure and the residue was purified by silica gel column chromatography [eluent: stepwise gradient of ethyl acetate (0-8%) in dichloromethane] to give the 4-thio intermediate as a yellow foam. A solution of this thio-intermediate (1.5 g, 3.31 mmol) in methanolic ammonia (previously saturated at –10° C. and tightly stopped) (50 mL) was heated at 100° C. in a stainless-steel bomb for 3 h and then cooled to 0° C. The solution was evaporated under reduced pressure. The resulting crude material was purified by silica gel column chromatography [eluent: stepwise gradient of methanol(0-20%) in dichloromethane]. Finally, the appropriate fractions were pooled, filtered through a unit Millex HV-4 (0,45 μm, Millipore) and evaporated under reduced pressure to provide the desired 2'-deoxy-β-L-cytidine (β-L-dC) as a foam (0.6 g, 80%) which was crystallized from absolute EtOH: mp=198-199° C.; $^1$H—NMR (DMSO-d$_6$): δ 7.77 (d, 1H, H-6, $J_{6-5}$=7.4 Hz), 7.10 (br d, 2H, NH-$_2$), 6.13 (t, 1H, H-1', J=6.7 Hz ), 5.69 (d, 1H, H-5,$J_{5-6}$=7.4 Hz), 5.19 (d, 1H, OH-3', $J_{OH-3'}$=4.1 Hz ), 4.96 (t, 1H, OH-5', $J_{OH-5'}$=$J_{OH-5''}$=5.2 Hz ), 4.1 (m, 1H, H-3'), 3.75 (m, 1H, H-4'), 3.5 (m, 2H, H-5' and H-5"), 2.0 (m, 1H, H-2'), 1.9 (m, 1H, H-2"); MS: FAB>0 (matrix GT) m/z 228 (M+H)$^+$, 112 (BH$_2$)$^+$; FAB<0 (matrix GT) m/z 226(M–H)$^-$; [α]$^{20}_D$=–69 (c 0.52, DMSO) [[α]$^{20}_D$=+76 (c 0.55, DMSO) for a commercially available hydrochloride salt of the D-enantiomer]. Anal. Calcd for C$_9$H$_{13}$N$_3$O$_4$: C, 47.57 ; H, 5.77 ; N, 18.49. Found: C, 47.35 ; H, 5.68 ; N, 18.29.

Example 2

Stereoselective Synthesis of 2'-Deoxy-β-L-Cytidine (β-L-dC)

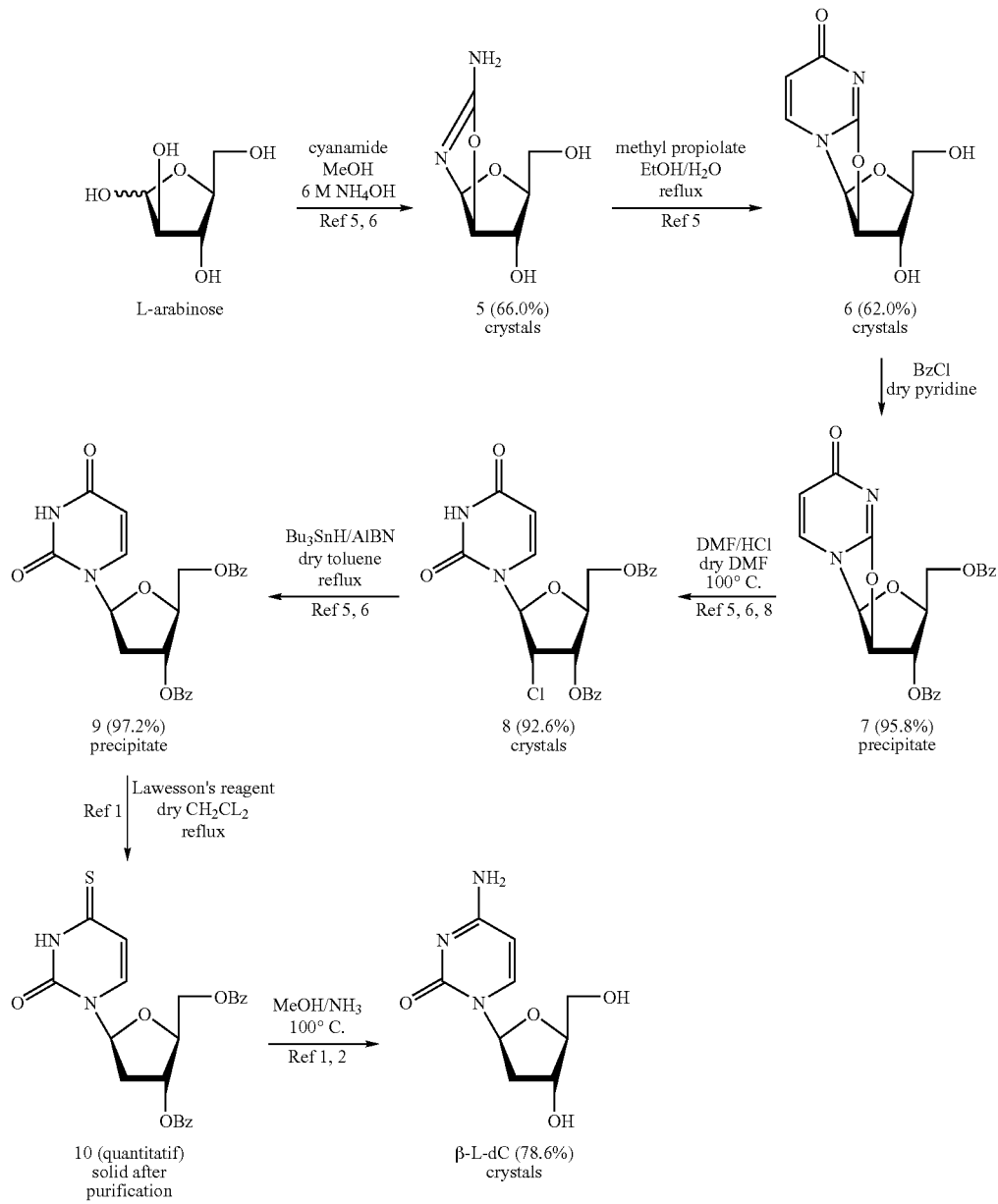

2-Amino-β-L-arabinofurano-[1',2':4,5]-oxazoline (5)

A mixture of L-arabinose (170 g, 1.13 mol: Fluka, >99.5%, ref 10839), cyanamide (100 g, 2.38 mol: Fluka, >98%, ref 28330), methanol (300 mL), and 6M-NH$_4$OH (50 mL) was stirred at room temperature for 3 days and then kept at −10° C. overnight. The product was collected with suction, washed successively with methanol and ether, and dried in vacuo. Yield, 130 g (66.0%) of the analytically pure compound 5, m.p. 170-172° C.; $^1$H NMR (DMSO-d$_6$) δ ppm 6.35 (br s, 2H, NH$_2$), 5.15 (d, 1H, H-1, J=5.6 Hz ), 5.45 (br s, 1H, OH-3), 4.70 (br s, 1H, OH-5), 4.55 (d, 1H, H-2, J=5.6 Hz ), 4.00 (br s, 1H, H-3), 3.65 (m, 1H, H-4), 3.25 (m, 2H, H-5, H-5').

O$^{2,2'}$-anhydro-β-L-uridine (6)

A solution of compound 5 (98.8 g, 0.57 mol) and methyl propiolate (98 mL: Fluka, >97%, ref 81863) in 50% aqueous ethanol (740 mL) was refluxed for 5 hours, then cooled and concentrated under diminished pressure to the half of the original volume. After precipitation with acetone (600 ml), the product was collected with suction, washed with ethanol and ether, and dried. The mother liquor was partially concentrated, the concentrate precipitated with acetone (1000 ml), the solid collected with suction, and washed with acetone and ether to afford another crop of the product. Over-all yield, 80 g (62%) of compound 6, m.p. 236-240° C.; $^1$H NMR (DMSO-d$_6$) δ ppm 7.87 (d, 1H, H-6, J=7.4 Hz ), 6.35 (d, 1H, H-1', J=5.7 Hz), 5.95 (d, 1H, H-5, J=7.4 Hz), 5.90 (d, 1H, OH-3'), 5.20 (d, 1H, H-2', J=5.7 Hz ), 5.00 (m, 1H, OH-3), 4.44 (br s, 1H, H-3'), 4.05 ( m, 1H, H-4'), 3.25 (m, 2H, H-5, H-5').

3',5'-Di-O-benzoyl-O$^{2,2'}$-anhydro-β-L-uridine (7)

To a solution of compound 6 (71.1 g, 0.31 mol) in anhydrous pyridine (1200 ml) was added benzoyl chloride (80.4 mL: Fluka, p.a., ref 12930) at 0° C. and under argon. The reaction mixture was stirred at room temperature for 5 hours under exclusion of atmospheric moisture and stopped by addition of ethanol. The solvents were evaporated under reduced pressure and the resulting residue was coevaporated with toluene and absolute ethanol. The crude mixture was then diluted with ethanol and the precipitate collected with suction, washed successively with ethanol and ether, and dried. Yield, 129 g (95.8%) of compound 7, m.p. 254° C.; $^1$H NMR (DMSO-d$_6$) δ ppm 8.1-7.4 (m, 11H, C$_6$H$_5$CO, H-6), 6.50 (d, 1H, H-1', J=5.7 Hz), 5.90 (d, 1H, H-5, J=7.5 Hz), 5.80 (d, 1H, H-2', J=5.8 Hz), 5.70 (d, 1H, H-3') 4.90 (m, 1H, H-4'), 4.35 (m, 2H, H-5, H-5').

3',5'-Di-O-benzoyl-2'-chloro-2'-deoxy-β,L-uridine (8)

To a solution of compound 7 (60.3 g, 0.139 mol) in dimethylformamide (460 ml) was added at 0° C. a 3.2 N—HCl/DMF solution (208 ml, prepared in situ by adding 47.2 ml of acetyl chloride (Fluka, p.a., ref 00990) at 0° C. to a solution of 27.3 mL of methanol and 133.5 mL of dimethylformamide). The reaction mixture was stirred at 100° C. for 1 hour under exclusion of atmospheric moisture, cooled down, and poured into water (4000 mL). The precipitate of compound 8 was collected with suction, washed with water, and recrystallized from ethanol. The crystals were collected, washed with cold ethanol and ether, and dried under diminished pressure. Yield, 60.6 g (92.6%) of compound 8, m.p. 164-165° C.; $^1$H NMR (DMSO-d$_6$) δ ppm 8.7 (br s, 1H, NH), 8.1-7.3 (m, 11H, C$_6$H$_5$CO, H-6), 6.15 (d, 1H, H-1', J=4.8 Hz), 5.5 (m, 2H, H-5, H-2'), 4.65 (m, 4H, H-3', H-4', H-5', H-5").

3',5'-Di-O-benzoyl-2'-deoxy-β,L-uridine (9)

A mixture of compound 8 (60.28 g, 0.128 mol), tri-n-butyltin hydride (95 mL: Fluka, >98%, ref 90915) and azabisisobutyronitrile (0.568 g: Fluka, >98%, ref 11630) in dry toluene (720 ml) was refluxed under stirring for 5 hours and cooled down. The solid was collected with suction and washed with cold toluene and petroleum ether. The filtrate was concentrated under reduced pressure and diluted with petroleum ether to deposit an additional crop of compound 2. Yield, 54.28 g (97.2%) of compound 2; m.p. 220-221° C.; $^1$H NMR (CDCl$_3$) δ ppm 8.91 (br s, 1H, NH), 8.1-7.5 (m, 11H, C$_6$H$_5$CO and H-6), 6.43 (q, 1H, H-1', J$_{1',2'}$=5.7 Hz and J$_{1',2''}$=8.3 Hz), 5.7-5.6 (m, 2H, H-3' and H-5), 4.8-4.6 (m, 3H, H-5', H-5" and H-4'), 2.8-2.7 (m, 1H, H-2'), 2.4-2.3 (m, 1H, H-2").

3',5'-Di-O-benzoyl-2'-deoxy-β-L-4-thio-uridine (10)

A solution of compound 9 (69 g, 0.158 mol) and Lawesson's reagent (74 g: Fluka, >98%, ref 61750) in anhydrous methylene chloride (3900 ml) was refluxed under argon overnight. After evaporation of the solvent, the crude residue was purified by a silica gel column chromatography [eluant: gradient of methanol (0-2%) in methylene chloride] to afford pure compound 10 (73 g) in quantitative yield; $^1$H NMR (CDCl$_3$) δ ppm 9.5 (br s, 1H, NH), 8.1-7.4 (m, 10H, C$_6$H$_5$CO), 7.32 (d, 1H, H-6, J=7.7 Hz), 6.30 (dd, 1H, H-1', J=5.6 Hz and J=8.2 Hz), 6.22 (d, 1H, H-5, J=7.7 Hz), 5.6 (m, 1H, H-3'), 4.7 (m, 2H, H-5', H-5"), 4.5 (m, 1H, H-4'), 2.8 (m, 1H, H-2'), 2.3 (m, 1H, H-2").

2'-Deoxy-β-L-cytosine

A solution of compound 10 (7.3 g, 0.016 mol) in methanol saturated with ammonia previously saturated at −5° C., tightly stoppered, and kept in a freezer (73 mL) was heated at 100° C. in a stainless steel cylinder for 3 hours. After cooling carefully, the solvent was evaporated under reduced pressure. An aqueous solution of the residue was washed with ethyl acetate and evaporated to dryness. Such a procedure was carried out on 9 other samples (each 7.3 g) of compound 10 (total amount of 10=73 g). The 10 residues were combined, diluted with absolute ethanol and cooled to give 2'-deoxy-β-L-cytosine as crystals. Trace of benzamide were eliminated from the crystals of 2'-deoxy-β-L-cytosine by a solid-liquid extraction procedure (at reflux in ethyl acetate for 1 hour). Yield, 28.75 g (78.6%) of compound 6; m. p. 141-145° C.; $^1$H NMR (DMSO) δ ppm 8.22 and 8.00 (2 br s, 2H, NH$_2$), 7.98 (d, 1H, H-6, J=7.59 Hz), 6.12 (t, 1H, H-1', J=6.5 Hz and J=7.6 Hz), 5.89 (d, 1H, H-5, J=7.59 Hz), 5.3 (br s, 1H, OH-3'), 5.1 (br s, 1H, OH-5'), 4.2 (m, 1H, H-3'), 3.80 (q, 1H, H-4', J=3.6 Hz and J=6.9 Hz), 3.6-3.5 (m, 2H, H-5', H-5"), 2.2-2.0 (m, 2H, H-2', H-2"); FAB<0, (GT) m/e 226 (M−H)$^−$, 110 (B)$^−$; FAB>0 (GT) 228 (M+H)$^+$, 112 (B+2H)$^+$; [α]$_D^{20}$−56.48 (c=1.08 in DMSO); UV (pH 7) λ$_{max}$=270 nm (ε=10000).

Example 3

Stereoselective Synthesis of 2'-Deoxy-β-L-Thymidine (β-L-dT)

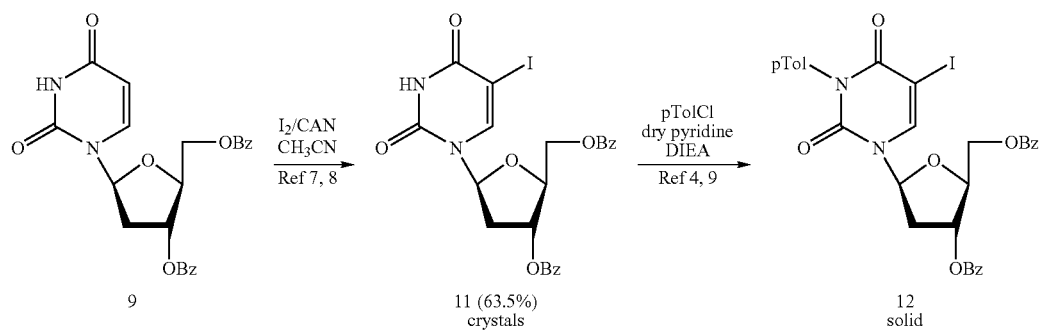

9

11 (63.5%)
crystals 12
solid

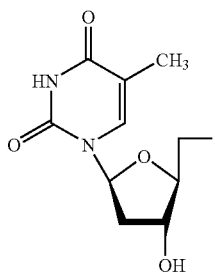

β-L-dT (64.8%)
crystals after purification

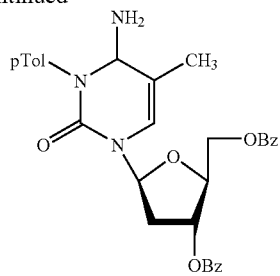

13 (48.3%, 2 steps)
solid after purification

3',5'-Di-O-benzoyl-2'-deoxy-5-iodo-β-L-uridine (11)

3',5'-Di-O-benzoyl-2'-deoxy-5-iodo-β-L-uridine (11)

A mixture of compound 2 (105.8 g, 0.242 mol), iodine (76.8 g: Fluka, 99.8%, ref 57650), cerium ammonium nitrate (CAN) (66.4 g: Aldrich, >98.5%, ref 21,547-3) and acetonitrile (2550 ml) was stirred at 80° C. for 3 h then the reaction mixture was cooled at room temperature leading to crystallization of compound 11 (86.6 g, 63.5%); m. p. 192-194° C.; $^1$H NMR (DMSO) δ ppm 0.8.34 (s, 1H, NH), 8.2-7.2 (m, 11H, 2 C$_6$H$_5$CO, H-6), 6.31 (q, 1H, H-1', J=5.5 Hz and J=8.7 Hz ), 5.5 (m, 1H, H-3'), 4.7 (m, 2H, H-5', H-5"), 4.5 (m, 1H, H-4'), 2.7 (m, 1H, H-2'), 2.3 (m, 1H, H-2"); FAB<0, (GT) m/e 561 (M−H)$^−$, 237 (B)$^−$; FAB>0 (GT) 563 (M+H)$^+$; [α]$_D^{20}$+39.05 (c=1.05 in DMSO); UV (EtOH 95) ν$_{max}$=281 nm (ε=9000), ν$_{min}$=254 nm (ε=4000), ν$_{max}$=229 nm (ε=31000); Anal. Calcd for C$_{23}$H$_{19}$IN$_2$O$_7$: C, 49.13 H, 3.41 N, 4.98 I, 22.57. Found: C, 49.31 H, 3.53 N, 5.05 I, 22.36.

3',5'-Di-O-benzoyl-2'-deoxy-3-N-toluoyl-β-L-thymidine (13)

To a solution of compound 11 (86.6 g, 0.154 mol) in anhydrous pyridine (1530 ml) containing diisopropylethylamine (53.6 ml: Aldrich, >99.5%, ref 38,764-9) was added, portionwise at 0° C., p-toluoyl chloride (40.6 ml: Aldrich, 98%, ref 10,663-1). The reaction mixture was stirred for 2 hours at room temperature, then water was added to stop the reaction and the reaction mixture was extracted with methylene chloride. The organic phase was washed with water, dried over sodium sulfate and evaporated to dryness to give crude 3',5'-di-O-benzoyl-2'-deoxy-3-N-toluoyl-5-iodo-β-L-uridine (12) which can be used for the next step without further purification.

A solution of the crude mixture 12, palladium acetate (3.44 g: Aldrich, >99.98%, ref 37,987-5), triphenylphosphine (8.0 g: Fluka, >97%, ref 93092) in N-methylpyrolidinone (1375 mL: Aldrich, >99%, ref 44,377-8) with triethylamine (4.3 mL) was stirred at room temperature for 45 minutes. Then, tetramethyltin (42.4 mL: Aldrich, >99%, ref 14,647-1) was added dropwise at 0° C. under argon. After stirring at 100-110° C. overnight, the reaction mixture was poured into water and extracted with diethyl ether. The organic solution was dried over sodium sulfate and concentrated under reduced pressure. The residue was purified by a silica gel column chromatography [eluant: stepwise gradient of ethyl acetate (0-10%) in toluene] to give compound 13 as a foam (42.3 g, 48.3% for the 2 steps). $^1$H NMR (DMSO) δ ppm .8.3-7.2 (m, 15H, 2C$_6$H$_5$CO, 1 CH$_3$C$_6$H$_4$CO, H-6), 6.29 (t, 1H, H-1', J=7.0 Hz ), 5.7 (m, 1H, H-3'), 4.7-4.5 (m, 3H, H-5', H-5", H-4'), 2.7-2.6 (m, 2H, H-2', H-2"); FAB<0, (GT) m/e 567 (M−H)$^−$, 449 (M-CH$_3$C$_6$H$_4$CO)$^−$, 243 (B)$^−$, 121 (C$_6$H$_5$COO)$^−$; FAB>0 (GT) 1137 (2M+H)$^+$, 569 (M+H)$^+$, 325 (M−B)$^−$, 245 (B+2H)$^+$, 119 (CH$_3$C$_6$H$_5$CO)$^+$.

2'-Deoxy-β-L-thymidine

A solution of compound 13 (42.3 g, 0.074 mol) in methanol previously saturated with ammonia at −5° C., tightly stoppered, and kept in a freezer (1850 mL) was stirred at room temperature for two days. After evaporation of the solvent, the residue was diluted with water and washed several times with ethyl acetate. The aqueous layer was separated, evaporated under reduced pressure and the residue was purified by a silica gel column chromatography [eluant: stepwise gradient of methanol (0-10%) in methylene chloride] to give pure 2'-deoxy-β-L-thymidine (11.62 g, 64.8%) which was crystalized from ethanol; m.p. 185-188° C.; $^1$H NMR (DMSO) δ ppm 11.3 (s, 1H, NH), 7.70 (s, 1H, H-6), 6.2 (pt, 1H, H-1'), 5.24 (d, 1H, OH-3', J=4.2 Hz), 5.08 (t, 1H, OH-5', J=5.1 Hz ), 4.2 (m, 1H, H-3'), 3.7 (m, 1H, H-4'), 3.5-3.6 (m, 2H, H-5', H-5"), 2.1-2.0 (m, 2H, H-2', H-2"); FAB<0, (GT) m/e 483 (2M−H)$^−$, 349 (M+T−H)$^−$, 241 (M−H)$^−$, 125 (B)$^−$; FAB>0 (GT) 243 (M+H)$^+$, 127 (B+2H)$^+$;)$^+$; [α]$_D^{20}$−13.0 (c=1.0 in DMSO); UV (pH 1) ν$_{max}$=267 nm (ε=9700), ν$_{min}$=234 nm (ε=2000).

Example 4

Chemical Synthesis of β-L-dC 5'-L-Valyl Ester

As an illustrative example of the synthesis of β-L-dC amino esters, β-L-dC 5'-L-valyl ester is synthesized by first protecting the amine group of β-L-dC using (CH$_3$)$_3$SiCl. The protected β-L-dC undergoes esterification by the addition of N-Boc L-valine. The ester is then deprotected to yeild β-L-dC 5'-L-valyl ester. Other methods for synthesizing amino acid esters are disclosed in U.S. Pat. Nos. 5,700,936 and 4,957,924, incorporated herein by reference. The L-valinyl 5'-O-ester of L-dA, L-dC, L-dT, and L-dU are preferred embodiments of this invention.

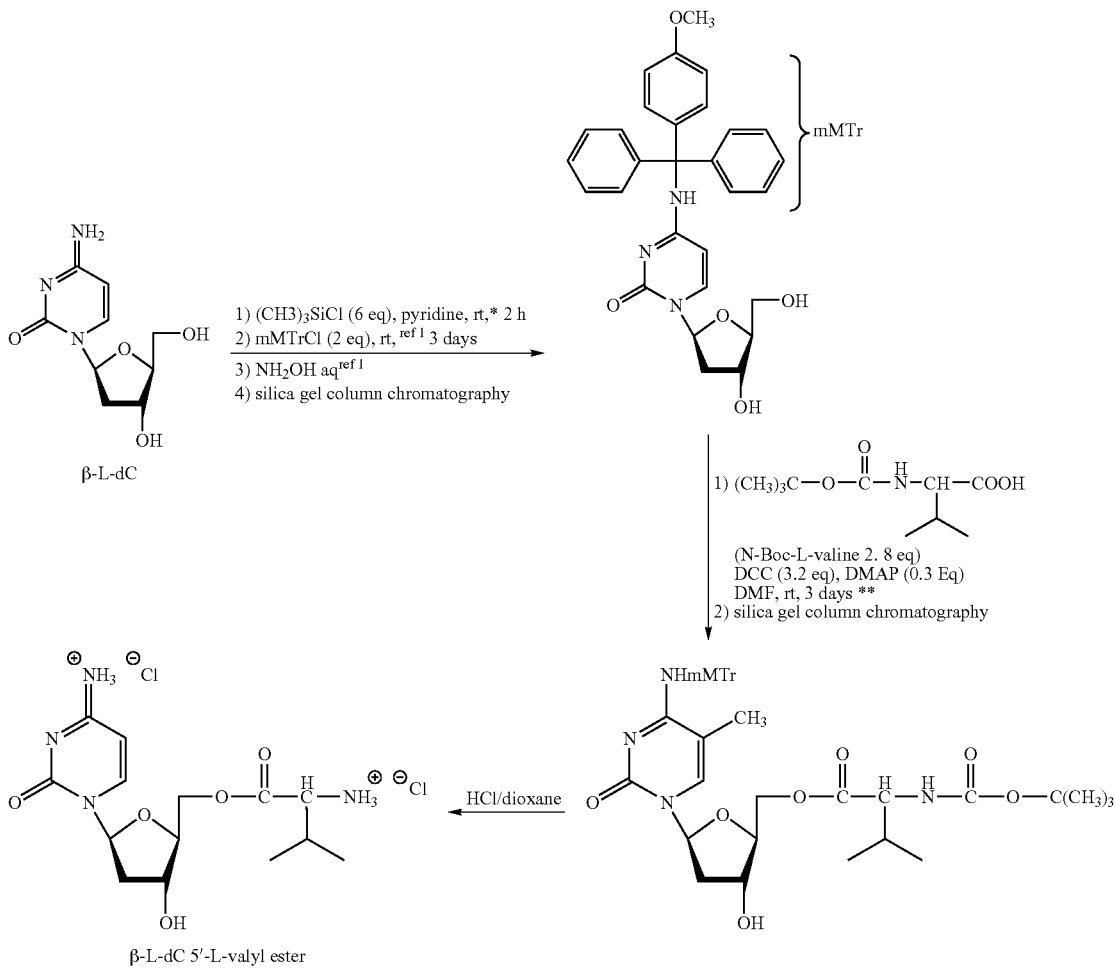

* Ref 1: by modification of a previously described procedure in the D series: Nyilas, A. et al. *Tetrahedron* 1990, 46 (6), 2149-2164.
** Ref 2: by modification of a previously described procedure for the acyclovir L-valyl ester: Beauchamp, L.M.. et al. *Antiviral Chemistry & Chemotherapy* 1992, 3 (3), 157-164.

Example 5

$^4$N-mMTr-2'-deoxy-β-L-cytidine (1, FIG. 1)

β-L-dC (1 g; 4.40 mmol) was taken up in dry pyridine (44 ml). After transient protection with trimethylsilyl group (TM-SCl, 3.34 ml, 26.4 mmol) followed by addition of mMTrCl (3.38 mg, 11 mmol) and 4-dimethylaminopyridine (DMAP, 540 mg, 4.40 mmol) the reaction mixture was stirred for 3 days at room temperature {A. Nyilas; C. Glemarec; J. Chattopadhyaya; *Tetrahedron Lett.* 1990, 46, 2149-2164}. After sodium bicarbonate extraction the organic layer was washed with water, evaporated and taken up in dioxane (40 mL). Aqueous ammonia (8.5 ml) was added dropwise and the reaction mixture was stirred overnight. After evaporation of all volatile materials, the solid residue was purified on silica gel column {eluent: stepwise gradient of MeOH (0-10%) in CH$_2$Cl$_2$}, giving the desired compound 1 (1.02 g, 46.5%) as a foam. $^1$H NMR (DMSO-d$_6$) δ ppm 8.39 (br s, 1H, NH, D$_2$O exchangeable), 7.70 (d, 1H, H-6, J=7.3 Hz ), 7.4-6.8 (m, 14H, (C$_6$H$_5$)$_2$C(C$_6$H$_4$)OCH$_3$), 6.23 (d, 1H, H-5, J=7.3 Hz ), 6.02 (t, 1H, H-1', J=6.5 Hz ), 5.16 (d, 1H, OH-3', J=3.8 Hz , D$_2$O exchangeable), 4.9 (br s, 1H, OH-5', D$_2$O exchangeable), 4.1 (m, 1H, H-3'), 3.7 (m, 4H, H-4', OCH$_3$), 3.5 (m, 2H, H-5', H-5"), 2.1-1.8 (2 m, 2H, H-2', H-2"); FAB<0, (GT) m/e 498 (M–H)$^-$, 382 (B)$^-$; 226 (M–mMTr)$^-$; FAB>0 (GT) 500 (M+H)$^+$, 273 (mMTr)$^+$; UV (EtOH 95) λ$_{max}$=279 nm; λ$_{min}$=250 nm.

Example 6

5'-L-N-(tert-butoxycarbonyl)valine ester of $^4$N-mMTr-2'-deoxy-β-cytidine (2, FIG. 1)

To a solution of compound 1 (1 g, 2.00 mmol) in dry DMF (34 ml) were added successively 4-dimethylaminopyridine (DMAP, 37 mg, 0.3 mmol), N-(tert-butoxy-carbonyl)-L-valine (Boc-Val-OH, 587 mg, 2.7 mmol), and N,N'-dicyclohexylcarbodiimide (DCC, 660 mg, 3.2 mmol) {L. M. Beauchamp; G. F. Orr; P. De Miranda; T. Burnette; T. A. Krenitsky; *Antiviral Chem. Chemother.* 1992, 39 157-164.}. The solution was stirred at room temperature. After 40 h, the reaction mixture was recharged with additional DMAP (37 mg, 0.3 mmol), Boc-Val-OH (587 mg, 2.7 mmol) and DCC (660 mg, 3.2 mmol) and stirred at room temperature for 40 h. The mixture was filtered, the DMF was removed from the filtrate under reduced pressure, and the residue was chromatographed on a silica gel column {eluent: stepwise gradient of MeOH (0-10%) in CH$_2$Cl$_2$} to afford the desired compound 2 (515 mg, 37%) as a foam.

$^1$H NMR (DMSO-d$_6$) δ ppm 8.44 (br s, 1H, NH, D$_2$O exchangeable), 7.7-6.8 (m, 15H, H-6 and (C$_6$H$_5$)$_2$C(C$_6$H$_4$)OCH$_3$), 6.26 (d, 1H, H-5, J=7.3 Hz ), 6.06 (t, 1H, H-1', J=6.6 Hz), 5.7 (bs, 1H, OH-3', D$_2$O exchangeable), 4.2-4.0 (m, 3H, H-3', H-4' and CH), 3.8-3.9 (m, 2H, H-5', H-5"), 3.7 (s, 3H,, OCH$_3$), 2.0-1.9 (m, 3H, H-2', H-2", CH), 1.36 (s, 9H, (CH$_3$)$_3$C), 0.86 (m, 6H, (CH$_3$)$_2$CH); FAB<0, (GT) m/e 1395 (2M−H)$^-$, 697 (M−H)$^-$, 425 (M−mMTr)$^-$, 382 (B)$^-$; 216 (BocVal-H)$^-$; FAB>0 (GT) 384 (B+2H)$^+$, 273 (mMTr)$^+$; 57 (CH$_3$)$_3$C)$^+$; UV (EtOH 95) λ$_{max}$=279 nm; λ$_{min}$=249 nm.

Example 7

5'-L-valine ester of 2'-deoxy-β-L-cytidine hydrochloride (3, FIG. 1)

Compound 2 (500 mg, 0.715 mmol) was dissolved in a 20% solution of trifluoroacetic acid in CH$_2$Cl$_2$ (25 ml) and triisopropylsilane (1.47 ml, 71.5 mmol) was added. The reaction mixture was stirred at room temperature for 1 h and the valine ester was precipitated in Et$_2$O as the trifluoroacetate salt. After several coevaporations with water, the precipitate was taken up in water (2 ml), treated with a saturated solution of HCl in dioxane (20 ml) and evaporated under reduced pressure. This treatment was repeated 3 times and the desired compound 3 was finally precipitated in ether (207 mg, 73%) as the hydrochloride salt. $^1$H NMR (DMSO-d$_6$) δ ppm 9.7 (br s, 1H, 1/2NH$_2$, D$_2$O exchangeable), 8.6 (br s, 4H, 1/2NH$_2$, NH$_3$, D$_2$O exchangeable), 7.98 (d, 1H, H-6 J=7.8 Hz ), 6.17 (d, 1H, H-5, J=7.8 Hz ), 6.11 (pt, 1H, H-1'), 5.5 (bs, <1H, OH-3', D$_2$O exchangeable), 4.4 (m, 2H, H-5', H-5"), 4.3 (m, 1H, H-3'), 4.2-4.0 (m, 2H, H-4', CH), 3.8-3.9, 3.7 (s, 3H, OCH$_3$), 2.3-2.1 (m, 3H, H-2', H-2", CH), 0.94 (dd, 6H, (CH$_3$)$_2$CH, J=3.7 and 6.6 Hz ); FAB<0, (GT) m/e 361 (M+Cl)$^-$, 325 (M−H)$^-$, 116 (Val-H)$^-$, 110 (B)$^-$; 216 (BocVal-H)$^-$; FAB>0 (GT) 653 (2M+H)$^+$, 327 (M+H)$^+$; 112 (B+2H)$^+$; )$^+$; {α}$_D^{20}$−28.57 (c=0.49 in DMSO); UV (EtOH 95) λ$_{max}$=272 nm (ϵ 8700); λ$_{min}$=255 nm (ϵ 7600); HPLC rt=8.37 min (gradient from 0 to 50% CH$_3$N in 20 mM triethyl ammonium acetate buffer programmed over a 30 min period with a flow rate of 1 ml/min).

Example 8

N$^4$-Acetyl-2'-deoxy-β-L-cytidine (4, FIG. 2)

To a suspension of the nucleoside, β-L-dC (415 mg, 1.83 mmol) in N,N-dimethylformamide (9.2 ml) was added acetic anhydride (207 μl, 2.20 mmol) and the mixture was stirred at room temperature for 24 h [V. Bhat; B. G. Ugarkar; V. A. Sayeed, K. Grimm; N. Kosora; P. A. Domenico; E. Stocker, *Nucleosides & Nucleotides*, 1989, 8 (2), 179-183]. After removal of the DMF under reduced pressure, the resulting residue was purified by silica gel column chromatography [eluant: 15% MeOH in CH$_2$Cl$_2$] to afford the desired compound (310 mg, 63%) which was crystallized from ethanol; rap 128-170° C.; $^1$H NMR (DMSO-d$_6$) δ ppm 10.86 (s, 1H, NH, D$_2$O exchangeable), 8.31 (d, 1H, , H-6, J=7.5 Hz ), 7.18 (d, 1H, H-5, J=7.5 Hz ), 6.09 (t, 1H, H-1', J=6.3 Hz ), 5.25 (d, 1H, OH-3', D$_2$O exchangeable, J=4.2 Hz ), 5.03 (t, 1H, OH-5', D$_2$O exchangeable, J=5.0 Hz ), 4.1-4.2 (m, 1H, H-3'), 3.8 (m, 1H, H-4'), 3.4-3.6 (m, 2H, H-5', H-5"), 2.2-2.3 (m, 1H, H-2'), 2.08 (s, 3H, CH$_3$), 2.0-1.9 (m, 1H, H-2"); FAB<0, (GT) m/e 806 (3M−H)$^-$, 537 (2M−H)$^-$, 360 (M+G−H)$^-$, 268 (M−H)$^-$, 152 (B)$^-$; FAB>0 (GT) 808 (3M+H)$^+$, 539 (2M+H)$^+$, 362 (M+G+H)$^+$, 270 (M+H)$^+$, 154 (B+2H)$^+$, 117 (S)$^+$; UV (H$_2$O) λ$_{max}$=297 nm (ϵ 8300); λ$_{min}$=270 nm (ϵ 3500);. λ$_{max}$=245 nm (ϵ 14400); λ$_{min}$=226 nm (ϵ 5800); [α]$_D^{20}$−81.31 (c=1.07 in DMSO).

Example 9

N$^4$-[(Dimethylamino)methylene]-2'-deoxy-β-L-cytidine (5, FIG. 3)

The title compound was prepared according to a published procedure developed for the preparation of the corresponding D-enantiomer [S. G. Kerr, and T. I. Kalman, *J. Pharm. Sci.* 1994, 83, 582-586]. A solution of L-dC (500 mg, 2.20 mmol) in DMF (4.8 ml) was treated with dimethylformamide dimethylacetal (2.8 ml, 21.08 mmol), and stirred at room temperature overnight. The solution was evaporated under reduced pressure, and coevaporated with ethanol. Crystallization from ethanol/ether yielded the title compound (501.2 mg, 81%) as light yellow crystals. mp 174-176° C. (lit.: 188-190° C. for the D-enantiomer); $^1$H NMR (DMSO-d$_6$) δ ppm 8.60 (s, 1H, N=CH), 8.00 (d, 1H, H-6), 6.15 (t, J=6.6 Hz , 1H, H-1'), 5.96 (d, J=7.2 Hz , 1H, H-5), 5.22 (d, J=4.2 Hz, 1H, OH-3'), 5.01 (t, J=5.2 Hz, 1H, OH-5'), 4.20 (m, 1H, H-4'), 3.80 (m, 1H, H-3'), 3.56 (m, 2H, H-5' and H-5"), 3.15 and 3.02 (2 s, 3H and 3H, N(CH$_3$)$_2$), 2.22-1.90 (2 m, 1H and 1H, H-2' and H-2"); FAB>0 (GT) 847 (3M+H)$^+$, 565 (2M+H)$^+$, 283 (M+H); FAB<0, (GT) m/z 599 (2M+Cl)$^-$, 317 (M+Cl)$^-$, 165 (B)$^-$.

Example 10

3',5'-Di-O-acetyl-2'-deoxy-β-L-cytidine (6, FIG. 4)

The title compound has been synthesized in one step starting from the L-dC and following a procedure developed by Breiner et al [R. G. Breiner; W. Rose; J. A. Dunn; J. E. Mae Diarmid and J. Bardos; *J. Med Chem.* 1990, 33, 2596-2603] for the preparation of the D-enantiomer. A solution of L-dC (765 mg, 3.37 mmol) and acetyl chloride (960 μl, 13.48 mmol) in glacial acetic acid (4.8 ml) was stirred at room temperature for 10 min, then dry chloroform (3.5 ml) was added and the stirring was continued for 24 h. The solution was evaporated under reduced pressure and coevaporated with ethanol. Crystallization from ethanol yielded 78% of the desired compound, mp 192.193° C. (lit: 187-189° C. for the D-enantiomer [Breiner et al. *J. Med. Chem.* 1990, 33, 2596-2603]); $^1$H, NMR (DMSO-d$_6$) δ ppm 9.8 and 8.7 (2 br s, <3H, NH$_3$+, D$_2$O exchangeable), 8.0 (d, 1H, H-6 J=7.8 Hz ), 6.18 (d, 1H, H-5, J=7.8 Hz ), 6.08 (t, 1H, H-1', J=6.7 Hz ), 5.2 (m, 1H, H-3'), 4.3-4.1 (m, 3H, H-4', H-5', H-5"), 2,4-2,5 (m, 2H, H-2', H-2"), 2.06 and 2.03 (2 s, 6H, 2 CH$_3$); FAB<0, (GT) m/e 968 (3M+Cl)$^-$, 657 (2M+Cl)$^-$, 438 (M+G+Cl)$^-$, 346 (M+Cl)$^-$, 310 (M−H)$^-$, 110 (B)$^-$; 59 (CH$_3$COO)$^-$; FAB>0 (GT) 623 (2M+H)+, 312 (M+H)$^+$, 201 (S)$^+$, 112 (B+2H)$^+$, 43 (CH$_3$CO)+; [α]$_D^{20}$ 36.27 (c=1.02 in DMSO); UV (MeOH) λ$_{max}$=277 nm (ϵ 9900); λ$_{min}$=246 nm (ϵ 5000).

Example 11

3',5'-L-N-(t-Butoxycarbonyl)valine diester of 2'-deoxy-β-L-cytidine (9, FIG. 5)

A solution of N$^4$-[(dimethylamino)methylene]-2'-deoxy-β-L-cytidine (7, 500 mg, 1.77 mmol) in DMF (35 ml) was treated with Boc-Val-OH (1.31 g, 6.03 mmol), DMAP (86.5 mg, 0.71 mmol), 1-(3-dimethylaminopropyl)-3-ethylcarbodiimide hydrochloride (EDC) (1.36 g, 7.09 mmol), and stirred at room temperature for 40 hours. Additional quantities of Boc-Val-OH (655 mg, 3.01 mmol), DMAP (43.2 mg, 0.35 mmol), EDC (680 mg, 3.55 mmol) were added, and the solution was stirred for an additional 20 hours. After evaporation under reduced pressure, the residue was taken up in $CH_2Cl_2$, and extracted several times with water. The organic layer was washed with brine (100 ml), dried ($Na_2SO_4$), and evaporated under reduced pressure to give 8 as a crude material, which was used for the next step without further purification. The residue was taken up in dioxane (18 ml), treated with aq. 26% $NH_4OH$, and stirred at room temperature for 1 hour. The solution was evaporated under reduced pressure, and the residue was purified by chromatography on silica gel using a stepwise gradient of MeOH (0-5%) in $CH_2Cl_2$, to give the title compound (698.7 mg, 58% from 2). $^1H$ NMR (DMSO-$d_6$) δ ppm 7.58 (d, 1H, H-6), 7.29-7.18 (m, 4H, NH-Boc and $NH_2$), 6.20 (t, J=6.6 Hz, 1H, H-1'), 5.75 (d, J=7.3 Hz, 1H, H-5), 5.20 (br. s, 1H, H-3'), 4.29 (m, 2H, H-5' and H-5"), 4.14 (br. s, 1H, H-4'), 3.86 (m, 2H, CH—NH-Boc), 2.31-2.21 (m, 2H, H-2' and H-2"), 2.13-1.98 (m, 2H, CH(iPr)), 1.38 and 1.36 (2 s, 18H, tBu), 0.88 and 0.85 (2 d, J=6.8 Hz, 12H, $CH(CH_3)_2$); $^{13}C$ NMR (DMSO-$d_6$) δ ppm 172.67 and 172.46, 166.41, 156.64 and 155.70, 141.39, 95.43, 85.78, 82.03, 79.14, 75.57, 64.90, 60.37 and 60.11, 37.40, 30.33, 29.00, 19.83-19.12; FAB>0 (GT) 626 (M+H)+, 112 (B+2H)$^+$, 255 (M-Boc)$^+$; FAB<0, (GT) m/z 1249 (2M−H)$^−$, 624 (M−H)$^−$.

Example 12

3,5'-L-Valine ester of 2'-deoxy-β-L-cytidine hydrochloride (10, FIG. 5)

A solution of 2 (675 mg, 1.08 mmol) in dioxane (30 ml) was treated with a solution of 26% HCl in dioxane (30 ml), and stirred at room temperature for 1 hr 55. The resulting white suspension was evaporated under reduced pressure. The white solid residue was taken up in the minimal amount of MeOH and precipitated in ether to give the title compound 10 as a white solid. mp 187° C. (decomp.); $^1H$ NMR (DMSO-$d_6$) δ ppm 9.79 (br s, 1H, 1/2$NH_2$), 8.72 (br s, 7H, 1/2$NH_2$ and $NH_3^+$), 8.04 (d, 1H, H-6), 6.21 (d, J=7.8 Hz, 1H, H-5), 6.16 (t, J=6.9 Hz, 1H, H-1'), 5.39 (m, 1H, H-3'), 4.50-4.40 (m, 3H, H-4', H-5' and H-5"), 3.90 (2 br. d, 2H, CH—$NH_3^+$), 2.63-2.50 (2 m, 2H, H-2' and H-2"), 2.21 (m, 2H, CH(iPr)), 1.02-0.94 (m, 12H, $CH(CH_3)_2$); $^{13}C$ NMR (DMSO-$d_6$) δ ppm 169.50 and 168.94, 161.02, 148.50, 145.26, 95.18, 87.19, 82.15, 76.14, 65.77 and 65.59, 58.12 and 58.07, 37.00, 30.16, 19.26-18.51; FAB>0 (GT) 426 (M+H)$^+$, 112 (B+2H)$^+$; FAB<0, (GT) m/z 885 (2M+Cl)$^−$, 460 (M+Cl); UV ($H_2O$) $\lambda_{max}$=270 nm (ε 7600).

Example 13

$N^4$-Boc-Valinyl ester of 2'-deoxy-β-L-cytidine (13, FIG. 6)

A mixture of L-dC (1.80 g, 7.92 mmol) and triethylamine (8.8 ml, 63.14 mmol) in anhydrous THF (80 ml) was treated with chlorotrimethylsilane (6 ml, 47.28 mmol) and stirred at room temperature overnight. The reaction was quenched by addition of an aqueous saturated solution of $NH_4Cl$ (26 ml) and water (10 mL). The aqueous layer was extracted three times with EtOAc. The organic layers were combined, washed with brine, dried ($Na_2SO_4$) and evaporated under reduced pressure to give a crude light yellow foam-oil containing 11, which was used for the next step without further purification. This residue was taken up in $CH_2Cl_2$ (104 ml), treated with N-(tert-butoxycarbonyl)-L-valine (Boc-Val-OH, 1.72 g, 7.90 mmol), benzotriazol-1-yloxy-tris(dimethylamino)phosphonium hexafluorophosphate (BOP, 4.20 g, 9.50 mmol), triethylamine (2.2 ml, 15.78 mmol), and stirred at room temperature for 2 days. The solution was diluted with EtOAc and extracted twice with sat. $NaHCO_3$. The organic layer was dried ($Na_2SO_4$) and evaporated under reduced pressure to give 12 as a crude material, which was used for the next step without further purification. This residue was taken up in dioxane (80 ml), treated with aq. 26% $NH_4OH$ solution, and stirred at room temperature for 6h45. The solution was evaporated under reduced pressure, coevaporated with absolute EtOH, and the residue was purified by chromatography on silica gel, using a stepwise gradient of MeOH (5-10%) in $CH_2Cl_2$, to give the title compound 13 as a foam (1.64 g, 48.5% overall yield). $^1H$ NMR (DMSO-$d_6$) δ ppm 10.88 (s, 1H, NH-4), 8.40 (d, 1H, H-6), 7.26 (d, J=7.4 Hz, 1H, H-5), 7.06 (d, J=8.2 Hz, 1H, CH—NH-Boc), 6.15 (t, J=6.3 Hz, 1H, H-1'), 5.32 (d, J=4.2 Hz, 1H, OH-3'), 5.09 (t, J=5.2 Hz, 1H, OH-5'), 4.27 (m, 1H, H-3'), 4.06 (pt, J=7.5 Hz, 1H, CH—NH-Boc), 3.91 (m, 1H, H-4'), 3.63 (m, 2H, H-5' and H-5"), 235 (m, 1H, H-2"), 2.06 (m, 2H, H-2' and $CH(CH_3)_2$), 1.43 (s, 9H, tBu), 0.92 (pt, J=6.6 Hz, 6H, $CH(CH_3)_2$); $^{13}C$ NMR (DMSO-$d_6$) δ ppm 174.41, 162.94, 156.47, 155.24, 146.10, 96.06, 88.79, 87.10, 79.09, 70.75, 61.78, 61.55, 41.74, 30.63, 29.02, 19.91 and 19.10; FAB>0 (GT) 853 (2M+H)$^+$, 427 (M+H)$^+$ 311 (B+2H)$^+$, 255 (M-Boc)$^+$; FAB<0, (GT) m/z 851 (2M−H)$^−$, 425 (M−H)$^−$, 309 (B)$^−$.

Example 14

3',5'-$N^4$-Trivalyl-2'-deoxycytidine (14, FIG. 7)

The starting material, 3',5'-N4-tri(Boc-valyl)-2'-deoxycytidine was dissolved in $CH_2Cl_2$, but there was some insoluble material so the sample was filtered through Perlita. This resulted in an increase in the volume of the $CH_2Cl_2$ used. The HCl/dioxane reagent was then added with stirring. Within a few seconds some bubbling could be observed in the solution and then the mixture became cloudy. The mixture was stirred at room temperature for about 1 hr. During this time the precipitate became more crystalline. The mixture was quickly filtered, the filtercake was washed with $CH_2Cl_2$, and then it was dried on the pump to give, 0.16 g (69%) of cream-white crystals. The reagents and conditions are more explicitly described below in Table 1.

TABLE 1

| Reagent | Mol. Unit | Wt./Vol calc | Mol/pts | Wt/Vol used | Mol/pts | Equiv |
| --- | --- | --- | --- | --- | --- | --- |
| 3',5',$N^4$-triBoc-Val-2'-dC (CyVal2a-2a) | 825.0 FW | 0.30 g | 0.00036 | 0.3 g | 0.00036 | 1.00 |
| $CH_2Cl_2$ | 5.0 parts | 1.5 mL | 5 | 3.0 mL | 10 | 10.0 |
| HCl, 3.9 M in dioxane$^−$ | 256.0 mL/mol | 0.47 g | 0.00182 | 0.5 g | 0.00195 | 5.37 |

TABLE 1-continued

| Reagent | Mol. Unit | Wt./Vol calc | Mol/pts | Wt/Vol used | Mol/pts Equiv |
|---|---|---|---|---|---|
| 3',5',N⁴-triVal-2'-dC, crude | 634.0 FW | 0.23 g | calc-obt | 0.16 g | 69.4% |

Example 15

HPLC Assay Method for DiBocValyl-2'-dC and DiBocValyl-2'-dU

A 1.0 mg/mL sample was made by dissolving the desired compound in absolute ethanol. The solution was then diluted with a solution that contained 50% MeOH and 50% $KH_2PO_4$ (0.015M, pH=3.30-3.50) until a concentration of 0.16 mg/mL was obtained. (Note: all solvents used were degasified before use.) 20 μL of the solution was then immediately injected into an HPLC column from WATERS (NOVAPAK C18-4 pm-3, 9×150 mm). The flow rate was set at 1 mL/min with a column temperature of 35° C. To detect the compounds, the wavelength detection was set at 275 nm for Di-Boc 2'dC, 260 nm for Di-Boc2'dU and 204 for impurities after 15 minutes. The column was run with $KH_2PO_4$ (0.015M, pH=3.30-3.50, adjusted with $H_3PO_4$ 10% v/v) in Pump A and HPLC grade acetonitrile in Pump B. The gradient pattern is indicated in Table 2.

TABLE 2

| # | Time | Module | Event | Volume |
|---|---|---|---|---|
| 1 | 0.01 | Pumps | T. Flow | 1 |
| 2 | 0.01 | Pumps | B. Conc. | 45 |
| 3 | 12.00 | Pumps | B. Conc. | 45 |
| 4 | 20.00 | Pumps | B. Conc. | 70 |
| 5 | 28.00 | Pumps | B. Conc. | 70 |
| 6 | 28.00 | Pumps | B. Conc. | 45 |
| 7 | 32.00 | Pumps | B. Conc. | 45 |
| 8 | 32.01 | SCL-10Avp | STOP | 0 |

IX. Pharmacokinetics of the Active Compounds

Human DNA polymerases and mitochondrial function were not affected by L-dC in vitro. L-dC was non-cytotoxic to human peripheral blood mononuclear cells (PBMCs), bone marrow progenitor cells and numerous cell lines of human and other non-human mammalian origin.

Antiviral nucleosides and nucleoside analogs exert their antiviral effect as intracellular triphosphate derivatives at the level of the viral polymerase during virus replication. Like natural nucleosides (D-deoxycytidine and D-thymidine) and antiviral nucleoside analogs (e.g., lamivudine and zidovudine), L-dC was activated intracellularly by phosphorylation. In human hepatocytes, deoxycytidine kinase (dCK) was responsible for the dose-dependent initial conversion of L-dC to a 5'-monophosphate (MP) derivative. L-dC-MP was then converted to a 5'-diphosphate (DP) form, which was subsequently converted to the predominant intracellular 5'-triphosphate (TP) metabolite. The L-dC-TP level reached 72.4 μM in HepG2 cells exposed to 10 μM L-dC (90.1 μM in primary human hepatocytes) at 24 hours and had an intracellular half-life of 15.5 hours. Exposure of HepG2 cells or human hepatocytes in primary culture to L-dC also produced a second TP derivative, β-L-2'-deoxyuridine 5'-triphosphate (L-dU-TP). The L-dU-TP level reached 18.2 μM in HepG2 cells exposed to 10 μM L-dC (43.5 μM in primary human hepatocytes) at 24 hours.

In primary human hepatocyte cultures and in a human hepatoma cell line (HepG2), the major metabolite of L-dC was L-dC-TP. Exposure of these cells to L-dC also led to the formation of L-dU-TP. L-dC-TP and L-dU-TP did not inhibit human DNA polymerases α, β and γ up to concentrations of 100 μM, the highest concentration tested.

Example 16

Solubility Study

The solubility of natural deoxyribocytosine (D-dC), the 3'-valinyl ester of L-dC and the 3',5'-divalinyl ester of L-dC in water was compared. The solubility of L-dC was assessed first by analyzing the HPLC data (i.e., area under the curve) by successive injections of various well-known concentrations of β-L-dC, as shown in Table 3. The HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute. The concentration of the solution versus the area under the curve produced a linear relationship with y=4150049477 x−4334.46845 (FIG. 8a).

TABLE 3

| | Concentration (mol/l) | | | |
|---|---|---|---|---|
| | $10^{-3}$ | $5 \times 10^{-4}$ | $10^{-4}$ | $10^{-5}$ |
| Area | 4175916 | 2031950 | 440122 | 55264 |

From this, a saturated solution was prepared with natural deoxyribocytosine (D-dC); 3 samples were taken and injected into the HPLC. The concentration of this saturated solution was determined to be 1.07, 1.08 and 0.96 mol/L; therefore, the saturated solution had an average saturated concentration of 1.03 mol/L or 272 g/L. The results are tabulated in Table 4.

TABLE 4

| Results | Area | Concentration (mol/L) |
|---|---|---|
| 1st Sample | 4420674000 | 1.07 |
| 2nd Sample | 4475191000 | 1.08 |
| 3rd Sample | 3983845000 | 0.96 |

Similarly, the solubility of 3'-valinyl ester hydrochloride of β-L-dC in water was evaluated. The calibration curve was determined by successive injections of various concentrations of the 3'-Valinyl ester hydrochloride of β-L-dC into the HPLC and measuring the area under the curve, as shown in Table 5. Again, the HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute. The concentration of the solution versus the area under the curve produced a linear relationship with y=3176423963 x−33051.63.

TABLE 5

| | Concentration (mol/L) | | | | |
|---|---|---|---|---|---|
| | $10^{-3}$ | $5 \times 10^{-4}$ | $10^{-4}$ | $5 \times 10^{-5}$ | $10^{-5}$ |
| Area | 3,166,842 | 1,514,479 | 254,296 | 119,668 | 19,269 |

From this, a saturated solution was attempted for 3'-valinyl ester hydrochloride of β-L-dC; however, one was not obtained. Therefore, the maximum quantity of 3'-valinyl ester hydrochloride of β-L-dC readily available in the laboratory was dissolved in water. 3 samples were collected, and were determined from the area under the curve from the HPLC, to have an average concentration of 1.013, 0.996 and 1.059 mol/L. The results are tabulated in Table 6.

TABLE 6

| Results | Area | Concentration (mol/L) |
|---|---|---|
| $1^{st}$ Sample | 3218013000 | 1.013 |
| $2^{nd}$ Sample | 3162471000 | 0.996 |
| $3^{rd}$ Sample | 3362725000 | 1.059 |

All three results fell within the predicted range calculated from the calibration curve, indicating complete solubility of the compound at those high concentrations, indicating that a saturated solution of this sample is greater than the average of the three samples, i.e., greater than 1.023 mol/L or 408 g/L.

The solubility of 3',5'-divalinyl ester hydrochloride of β-L-dC in water was evaluated. The calibration curve was determined by successive injections of various concentrations of the 3',5'-divalinyl ester hydrochloride of β-L-dC into the HPLC and measuring the area under the curve, as shown in Table 7. The HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute. The concentration of the solution versus the area under the curve produced a linear relationship with y=3176423963 x−33051.63 (FIG. 8b).

TABLE 7

| | Concentration (mol/l) | | | | |
|---|---|---|---|---|---|
| | $10^{-3}$ | $5 \times 10^{-4}$ | $10^{-4}$ | $5 \times 10^{-5}$ | $10^{-5}$ |
| Area | 2863372 | 1466574 | 211046 | 115678 | 14435 |

From this, a saturated solution was attempted for 3',5'-divalinyl ester hydrochloride of β-L-dC; however, one was not obtained. Therefore, the maximum quantity of 3',5'-divalinyl ester hydrochloride of β-L-dC readily available in the laboratory was dissolved in water. 3 samples were collected, and were determined from the area under the curve from the HPLC, to have an average concentration of 2.8, 2.4 and 2.4 mol/L. The results are tabulated in Table 8.

TABLE 8

| Results | Area | Concentration (mol/L) |
|---|---|---|
| $1^{st}$ Sample | 8336188000 | 2.8 |
| $2^{nd}$ Sample | 7054012000 | 2.4 |
| $3^{rd}$ Sample | 6970838000 | 2.4 |

All three results fell within the predicted range calculated from the calibration curve, indicating complete solubility of the compound at those high concentrations, indicating that a saturated solution of this sample is greater than the average of the three samples, i.e., more than 2.5 mol/L or 1337 g/L.

Similar solubility studies were done on 5'-valinyl ester hydrochloride of β-L-dC (more than 5.1 mol/L or 1664 g/L) and 3'5'-diacetyl ester hydrochloride of β-L-dC (3.3 mol/L or 1148 g/L). The cumulative results are tabulated in Table 9.

TABLE 9

| Compound | Solubility (mol/L) | Solubility (g/L) |
|---|---|---|
| D-dC | 1.03 | 272 |
| 5'-val-L-dC | >5.1 | >1664 |
| 3'-val-L-dC | >1.023 | >408 |
| 3'5'-diacetyl-L-dC | 3.3 | 1148 |
| 3'5'-dival-L-dC | >2.5 | >1337 |

Log P Study—Phosphate Buffer

Approximately 1.5 mg of D-dC was dissolved in 2.2 mL of 0.02 M phosphate buffer solution (A, 100 mL, pH 7.2), made from a mixture of monobasic potassium phosphate solution (28.5 mL) and dibasic potassium phosphate solution (71.5 mL), saturated with octanol-1 (B). To 1 mL of this solution, 1 mL of octanol-1 (B) saturated with 0.02 M phosphate buffer solution (A) was added. The resultant mixture was shaken and centrifuged; three samples from each phase was collected and analyzed by HPLC, as shown in Table 10. The HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute. It was found that the log P of D-dC is −1.41; therefore, D-dC prefers water to octanol.

TABLE 10

| | STUDY 1 | | | | | | STUDY 2 | | | | | |
|---|---|---|---|---|---|---|---|---|---|---|---|---|
| | $A^1$ | $A^2$ | $A^3$ | $B^1$ | $B^2$ | $B^3$ | $A^1$ | $A^2$ | $A^3$ | $B^1$ | $B^2$ | $B^3$ |
| AREA | 1948481 | 2130720 | 2197377 | 79838 | 82172 | 80159 | 2380141 | 2326654 | 2339059 | 93123 | 90275 | 89651 |
| AVE. | | 2092193 | | | 80723 | | | 2348618 | | | 91016 | |
| P (B/A) | | | 0.039 | | | | | | 0.039 | | | |
| LOGP | | | −1.41 | | | | | | −1.41 | | | |

Similarly, approximately 1.5 mg of L-dC-3'-valine ester hydrochloride was dissolved in 2.5 mL of 0.02 M phosphate buffer solution (A, 100 mL, pH 7.2), made from a mixture of monobasic potassium phosphate solution (28.5 mL) and dibasic potassium phosphate solution (71.5 mL). The solution was then saturated with octanol-1 (B). To 1 mL of this solution, 1 mL of octanol-1(B) saturated with 0.02 M phosphate buffer solution (A) was added. The resultant mixture was shaken and centrifuged; three samples from each phase was collected and analyzed by HPLC, as shown in Table 11. The HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute.

TABLE 11

|  | Study 1 | | | | | | Study 2 | | | | | |
| --- | --- | --- | --- | --- | --- | --- | --- | --- | --- | --- | --- | --- |
|  | $A^1$ | $A^2$ | $A^3$ | $B^1$ | $B^2$ | $B^3$ | $A^1$ | $A^2$ | $A^3$ | $B^1$ | $B^2$ | $B^3$ |
| Area | 3352735 | / | 3417723 | 100544 | 96843 | 103466 | 3458180 | 3448062 | 3412971 | 100179 | / | 101731 |
| Ave. | | 3385227 | | | 100284 | | | 3439738 | | | 100955 | |
| P (B/A) | | | 0.0296 | | | | | | 0.0293 | | | |
| logP | | | −1.53 | | | | | | −1.53 | | | |

It was found that the log P of L-dC-3'-valine ester hydrochloride is -1.53; therefore, L-dC-3'-valine ester prefers water to octanol to a greater degree than D-dC.

Log P values were calculated for L-dC-5'-valine ester hydrochloride and L-dC-3',5'-divaline ester hydrochloride. The results are tabulated in Table 12. However, it should be noted that the log P value for L-dC-3',5'-divaline ester hydrochloride is probably lower than the one measured (−0.86). Significant conversion of the divaline ester into the 3'- or 5'-monovalinyl ester or even L-dC was observed during the experiment. 50% of conversion of L-dC-3',5'-divaline ester hydrochloride was detected in the aqueous phase and 14% in the organic phase. This conversion is due to the instability of the esters in the phosphate buffer at a pH of 7 (see examples 15 and 16).

TABLE 12

| Compound | log P (octanol/water) |
| --- | --- |
| D-dC | −1.41 |
| L-dC-3'-valine ester hydrochloride | −1.53 |
| L-dC-5'-valine ester hydrochloride | −1.42 |
| L-dC-3',5'-divaline ester hydrochloride | −0.86 |
| L-dC-3',5'-diacetyl ester hydrochloride | −0.74 |

Log P' Study—MilliQ Water

In order to avoid the conversion of the divaline ester into the mono esters and L-dC, an alternate log P study was performed using MilliQ water (A') instead of the phosphate buffer (pH of 6.5 instead of 7.2). It is important to note that only the hydrochloride form of the divalinyl ester can be considered in water. Approximately 1.5 mg of L-dC-3',5'-divalinyl ester hydrochloride was dissolved in 2.2 mL of MilliQ water (A', pH 6.5) saturated with octanol-1 (B). To 1 mL of this solution, 1 mL of octanol-1 (B) saturated with MilliQ water (A') was added. The resultant mixture was shaken and centrifuged; three samples from each phase was collected and analyzed by HPLC, as shown in Table 13. The HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute. It was found that the log P' of the 3',5'-divaline under these conditions was −2.72, indicating the strong effect of the counter ions in the phosphate buffer. No conversion of the divaline to the monoesters or L-dC was observed in either the aqueous or organic phases.

TABLE 13

|  | STUDY 1 | | | | | | STUDY 2 | | | | | |
| --- | --- | --- | --- | --- | --- | --- | --- | --- | --- | --- | --- | --- |
|  | $A^{1'}$ | $A^{2'}$ | $A^{3'}$ | $B^1$ | $B^2$ | $B^3$ | $A^{1'}$ | $A^{2'}$ | $A^{3'}$ | $B^1$ | $B^2$ | $B^3$ |
| AREA | 3278293 | 3292150 | 3282281 | 5484 | 5776 | 6496 | 3282927 | 3327122 | 3297985 | 5829 | 5615 | 6139 |
| AVE. | | 3284241 | | | 5919 | | | 3302678 | | | 5861 | |
| P' (B/A') | | | $1.80 \times 10^{-3}$ | | | | | | $1.77 \times 10^{-3}$ | | | |
| LOG P' | | | −2.7 | | | | | | −2.75 | | | |

Similarly, approximately 1.5 mg of L-dC-5'-valinyl ester hydrochloride was dissolved in 2.2 mL of MilliQ water (A', pH 6.5) saturated with octanol-1 (B). To 1 mL of this solution, 1 mL of octanol-1 (B) saturated with MilliQ water (A') was added. The resultant mixture was shaken and centrifuged; three samples from each phase was collected and analyzed by HPLC, as shown in Table 14. The HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute. It was found that the log P of the 5'-valine under these conditions was −2.75, again a value lower than found in the log P study using the phosphate buffer.

TABLE 14

| | STUDY 1 | | | | | | STUDY 2 | | | | | |
|---|---|---|---|---|---|---|---|---|---|---|---|---|
| | A[1'] | A[2'] | A[3'] | B[1] | B[2] | B[3] | A[1'] | A[2'] | A[3'] | B[1] | B[2] | B[3] |
| AREA | 3722494 | 3771963 | 3788317 | 6545 | 5082 | / | 3619900 | 3975353 | 4062284 | 8484 | 9454 | 5877 |
| AVE | | 3760924 | | | 5813 | | | 3885845 | | | 7938 | |
| P' (B/A') | | $1.54 \times 10^{-3}$ | | | | | | $2.04 \times 10^{-3}$ | | | | |
| LOG P' | | −2.81 | | | | | | −2.69 | | | | |

Under these conditions, the log P' values for L-dC-5'-valinyl ester hydrochloride and L-dC-3',5'-divalinyl ester hydrochloride are very similar (Table 15).

TABLE 15

| Compound | log P (octanol/water) | log P' (octanol/water) |
|---|---|---|
| L-dC-5'-valine ester hydrochloride | −1.42 | −2.75 |
| L-dC-3',5'-divaline ester hydrochloride | −0.86 | −2.72 |

Stability Study at pH 7.4

The rate of decomposition of each metabolite of L-dC-3'-valine ester hydrochloride was calculated. The half-life of L-dC-3'-valine ester hydrochloride at pH of 7.40 was determined to be 7 hours in a 0.2M Tris-HCl solution at 37° C. In these conditions, L-dC-3'-valine ester hydrochloride is simply transformed to L-dC. No cytosine was detected, thus, there was no detectable glycoside bond breakage.

Similarly, the rate of decomposition of each metabolite of L-dC-3',5'-divaline ester hydrochloride was calculated. The half-life of L-dC-3',5'-divaline ester hydrochloride at pH of 7.42 was determined to be 2.4 hours in a 0.2M Tris-HCl solution at 37° C. In these conditions, L-dC-3',5'-divaline ester hydrochloride is partially hydrolyzed into the 3'- and 5'-valinyl-L-dC, which are later transformed into L-dC. No cytosine was detected, thus, there was no detectable glycoside bond breakage (Scheme 4, FIGS. 9a and 9b).

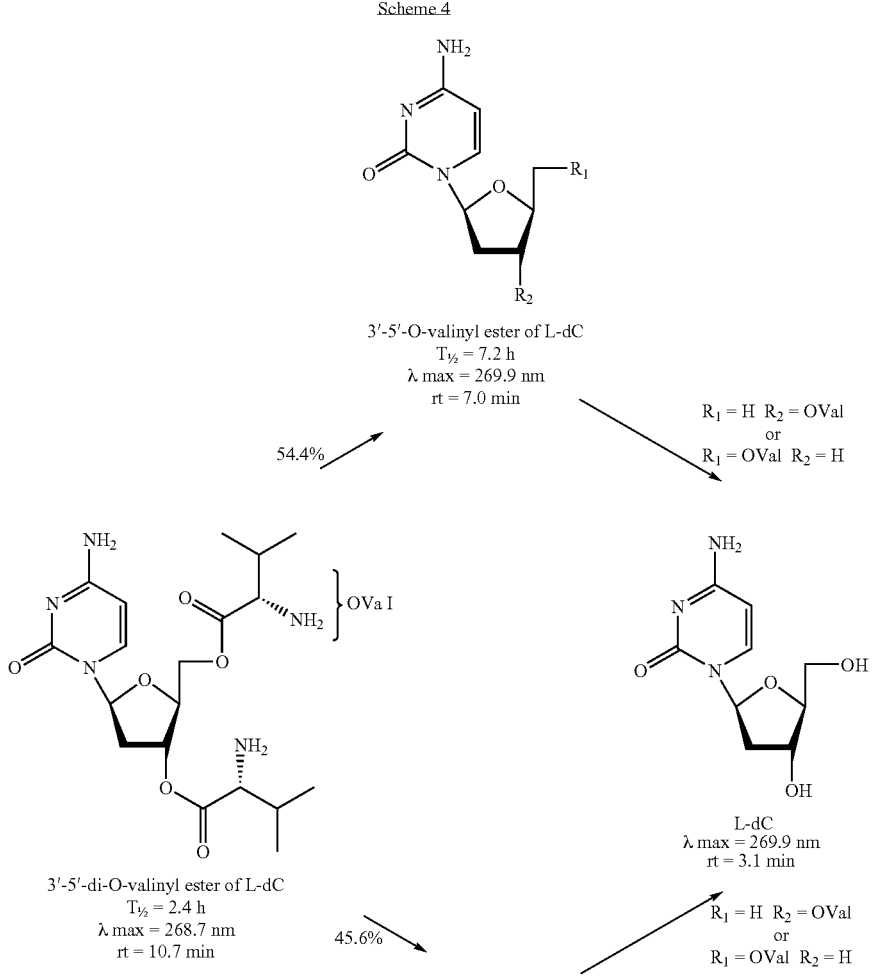

-continued

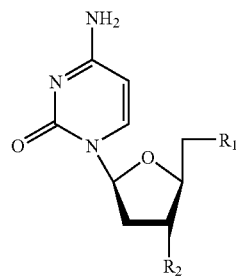

3'- or 5'-O-valinyl ester of L-dC
T½ = 6.9 h
λ max = 268.7 nm
rt = 7.2 min

Stability Study at pH 7.20

The half-life of L-dC-3',5'-divaline ester hydrochloride at pH of 7.20 was determined to be 2.2 hours in a 20 mM phosphate buffer. In these conditions, L-dC-3',5'-divaline ester hydrochloride is partially hydrolyzed into the 3'- and 5'-valinyl-L-dC, which are later transformed into L-dC. No cytosine was detected, thus, there was no detectable glycoside bond breakage (Scheme 5, FIGS. 10a and 10b).

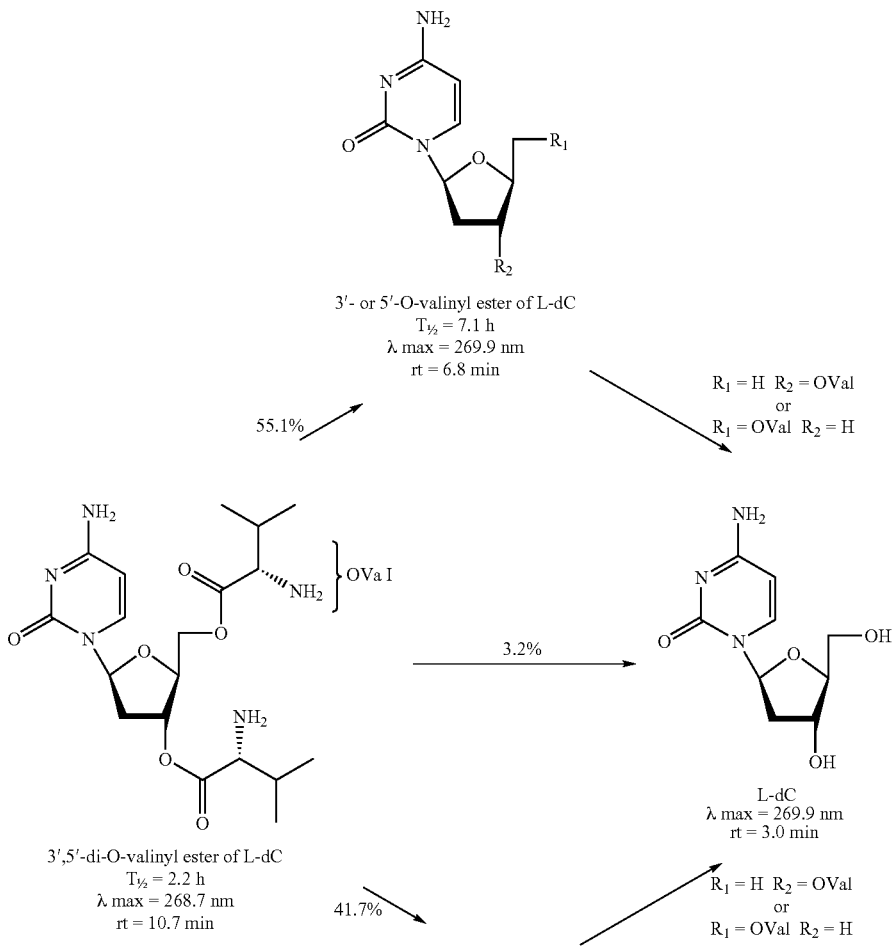

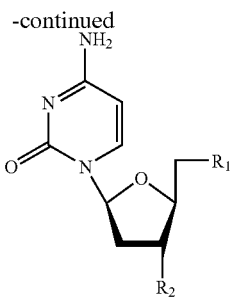

3'- or 5'-O-valinyl ester of L-dC
$T_{1/2}$ = 7 h
λ max = 268.7 nm
rt = 7.1 min

Stability Study at pH 4.5

The half-life of L-dC-3'-valine ester hydrochloride at pH of 4.5 was determined to be 8.6 days in a 20 mM acetate buffer. Again, L-dC-3'-valine ester hydrochloride is simply transformed to L-dC. No cytosine was detected, thus, there was no detectable glycoside bond breakage.

Similarly, the half-life of L-dC-3',5'-divaline ester hydrochloride at pH of 4.51 was determined to be 44 hours in a 20 mM acetate buffer. In these conditions, L-dC-3',5'-divaline ester hydrochloride is partially hydrolyzed into the 3'- and 5'-valinyl-L-dC, which are later transformed into L-dC. No cytosine was detected, thus, there was no detectable glycoside bond breakage (FIGS. 11a and 11b).

Stability Study at pH 1.2

The half-life of L-dC-3'-valine ester hydrochloride at pH of 1.2 was determined to be greater than 48 hours in a 135 mM KCl—HCl buffer solution. No cytosine was detected, thus, there was no detectable glycoside bond breakage.

Similarly, stability studies were done on L-dC-5'-valine ester hydrochloride. This compound is fully stable at a pH of 1.2, with no other metabolites or decomposition products detected for up to 23 hours. No glycosidic bond breakage was detected up to 2 days in solution.

The 3',5'-diacetyl ester of L-dC was found to have a half life at a pH of 1.2 of 11.2 hours. Under these conditions the compound was partially hydrolyzed into the 3'- or 5'-derivatives, which were later transformed into L-dC. No glycosidic bond breakage was detected up to 2 days in solution.

The 3',5'-divalinyl ester of L-dC was found to be fully stable at a pH of 1.23 since no other compounds were detected up to 48 hours in these conditions. No glycosidic bond breakage was detected up to 2 days in solution (FIG. 12).

Alternatively, when the $N^4$ position of L-dC is masked with dimethylamino-methylene or acetyl, the half-life of the compound at a pH of 1.2 is only 26 minutes or 50 minutes, respectively.

Single Dose Bioavailability of L-dC in the Cynomologus Monkey

The pharmacokinetics of L-dC following IV and oral administration of L-dC to cynomologus monkeys was determined. In this study, 10 mg/kg tritium ([3H]) radiolabeled L-dC was administered to three cynomologus monkeys as a single IV dose. Following a six week washout period, the same three monkeys received an identical oral dose of L-dC. Blood samples for pharmacokinetic analysis were collected pre-dose and at 0.25, 0.5, 1, 2, 3, 6, 8 and 24 hours after dosing. Urine samples for pharmacokinetic analyses were collected via pan catch pre-dose and over the following intervals post-dose: 0-2, 2-4, 4-8, and 8-12 hours, and then over 12-hour intervals thereafter through 336 hours post-dose. The drug was detected and the concentration determined using a reverse-phase high-performance liquid chromatography technique. The blood and urine drug level data were analyzed by a non-modeling mathematical method and AUC's derived by the linear trapezoidal rule.

Intravenous administration of L-dC. The mean $C_{max}$ of L-dC after IV administration was 95.7 µM and occurred at the earliest sampling time (15 minutes post-dose) for all animals. L-dC plasma concentrations decreased over time following the IV bolus with a mean $t_{1/2}$ of 1.59 hours. The total clearance (CL) and renal clearance (CLR) of L-dC following IV administration averaged 0.53 L/h/kg and 0.46 L/h/kg, respectively. The mean apparent volume of distribution ($V_d$) of 1.22 L/kg indicated that L-dC had a significant extravascular tissue distribution.

Urinary excretion was rapid, with 71% of the administered dose recovered within 2 hours. L-dC accounted for the majority (94%) of the dose recovered in the urine. The renal clearance (0.46 L/h/kg) accounted for 87% of total L-dC clearance and suggested that renal excretion was the major route of elimination.

L-dU was detected in the plasma and urine, indicating that metabolic elimination of L-dC also occurred following IV administration. Low levels of L-dU were detected in plasma at the limit of detection (lower limit of detection (LLOD)=0.1 µM). Renal excretion of L-dU was 4.0% of the total dose recovered in urine. With the exception of L-dU, no other metabolites were detected in the plasma or urine.

Oral administration of L-dC. The $C_{max}$ was 3.38 µM and occurred at a $T_{max}$ of 2.33 hours. The plasma concentration of L-dC declined in a biphasic manner with a mean terminal $t_{1/2}$ of 2.95 hours and was below detection limits by 24 hours in all monkeys. L-dC was absorbed from the gastrointestinal tract with a mean oral bioavailability (F) of 16.4%.

L-dU was detected in the plasma and urine, which suggested that metabolic elimination of L-dC occurred following oral administration. Low levels of L-dU were detected in plasma at the LLOD. With the exception of L-dU, no other metabolites were detected in the plasma or urine.

Approximately 8.5% of the administered oral dose was recovered in the urine within 12 hours. After 72 hours 15.5%±8% was recovered. L-dC accounted for the majority (~69%) of drug excreted in the urine. Renal excretion of L-dU was 29% of the total recovered dose. Feces were not collected.

Table 16 presents a summary of pharmacokinetic results for IV and oral administration of L-dC in cynomologus monkeys.

TABLE 16

Pharmacokinetic Analysis after Intravenous and Oral Administration of L-dC (10 mg/kg) in the Cynomologus Monkey

| Route (n) | $AUC_{last}$ (mM-h) | $t_{1/2}$ (h) | $C_{max}$ (mM) | $T_{max}$ (h) | CL (L/h/kg) | $CL_R$ (L/h/kg) | $V_d$ (L/kg) | F (%) |
|---|---|---|---|---|---|---|---|---|
| IV (3) | 81.1 (±5.7) | 1.59 (±0.09) | 95.7 (±13) | 0 | 0.53 (±0.04) | 0.46 | 1.22 (±0.11) | — |
| Oral (3) | 13.7 (±4.3) | 2.95 (±1.3) | 3.38 (±1.3) | 2.33 (±1.5) | — | — | — | 16.4 (±5.0) |

Mean value (±SD).

Single-Dose Bioavailability of L-dC in the Rhesus Monkey

The pharmacokinetics of L-dC following oral administration in the rhesus monkey was determined. In this study, 10 mg/kg [3H] radiolabeled L-dC was administered to three rhesus monkeys as a single oral dose. Blood samples for pharmacokinetic analysis were collected pre-dose and at 0.25, 0.5, 1, 2, 3, 6, 8 and 24 hours after dosing. Urine samples for pharmacokinetic analyses were collected via pan catch pre-dose and over the following intervals post-dose: 0-2, 2-4, 4-8 and 8-12 hours, and then at 12-hour intervals thereafter through 336 hours post-dose. The drug was detected and concentration determined using a reverse-phase HPLC technique. The blood and urine drug level data were analyzed by a non-modeling mathematical method and AUCs derived by the linear trapezoidal rule.

The average $AUC_{0.25\to8}$ and $C_{max}$ values were 12.2 mgM.h and 3.23 mgM, respectively. The $C_{max}$ occurred at a $T_{max}$ of 0.83 hours. The mean $t_{1/2}$ was 3.34 hours and the L-dC plasma concentration was below detection levels by 24 hours in all monkeys. The mean renal clearance of L-dC was 0.273 L/h/kg. No metabolites were observed in the plasma of monkeys receiving L-dC.

Approximately 8.5% of the administered oral dose (oral bioavailability of L-dC ~16%) was recovered in the urine within 8 hours. After 48 hours 15% was recovered. L-dC accounted for the majority (~77%) of drug excreted in the urine. Renal excretion of L-dU was 23% of the total recovered dose. With the exception of L-dU, no other metabolites were detected.

The AUC and $C_{max}$ for L-dC after oral administration to rhesus monkeys were similar to that observed in cynomolgus monkeys.

Single-Dose Bioavailability of L-dC in the Rat

The pharmacokinetics and bioavailability of L-dC in rats was determined. In this study, 10 mg/kg [3H] radiolabeled L-dC was administered to three female Sprague-Dawley rats as a single IV dose. A second group of three animals received an identical oral dose of L-dC. Blood samples for pharmacokinetic analyses were collected at 0.17, 0.33, 0.5, 1, 2, 3, 4, 6, 8 and 24 hours after dosing. Urine was also collected at 8 and 24 hours after dosing. The drug was detected and the concentration determined in plasma and urine using a reverse-phase HPLC technique. The data were analyzed by a non-modeling mathematical method and the AUCs derived by the linear trapezoidal rule.

Intravenous administration of L-dC. The average $AUC_{0.25\to8}$ value was 30.1 mM.h. The $C_{max}$ of L-dC was 91.1 mgM and occurred at the earliest sampling time (10 minutes post-dose) for all animals. L-dC plasma concentrations declined in a biphasic manner following the IV bolus with a mean t½ of 1.21 hours. The CL of L-dC averaged 1.44 L/h/kg. The mean $V_d$ of 2.53 L/kg indicated that L-dC had a significant extravascular tissue distribution. No metabolites were observed in the plasma of rats receiving L-dC.

L-dC accounted for the majority of radioactivity recovered in the urine. L-dU was detected in the urine, which suggested that metabolic elimination of L-dC occurred following IV administration.

Oral administration of L-dC. The average $AUC_{0.25\to8}$ value was 4.77 mM.h. The mean $C_{max}$ was 1.50 mgM and occurred at a $T_{max}$ of 1.0 hour. The plasma concentration of L-dC declined with a t½ of 2.52 hours. L-dC had limited uptake from the gastrointestinal tract with a mean oral bioavailability (F) of 15.4%. No metabolites were observed in the plasma of rats following oral administration of L-dC.

L-dC accounted for the majority of radioactivity recovered in the urine. L-dU was detected in the plasma and urine, which suggested that metabolic elimination of L-dC occurs following oral administration.

Table 17 presents a summary of pharmacokinetic results for both IV and oral L-dC.

TABLE 17

Pharmacokinetic Analysis after Intravenous and Oral Administration of L-dC (10 mg/kg) in the Rat

| Route (n) | $AUC_{0-25-28}$ (mM-h) | $t_{1/2}$ (h) | $C_{max}$ (mM) | $T_{max}$ (h) | CL (L/h/kg) | $V_d$ (L/kg) | F (%) |
|---|---|---|---|---|---|---|---|
| IV (3) | 30.1 (±4.7) | 1.21 (±0.06) | 91.1 (±6.6) | 0 | 1.44 (±0.29) | 2.53 (±0.60) | — |
| Oral (3) | 4.77 (±2.1) | 2.52 (±1.3) | 1.50 (±0.68) | 1.0 | — | — | 15.4 (±4.6) |

Mean value (±SD).

Single-Dose Bioavailability of L-dC in the Woodchuck

The pharmacokinetics and bioavailability of L-dC in woodchucks was determined. In this study, 10 mg/kg [3H] radiolabeled L-dC was administered to three woodchucks as a single IV dose. Blood samples for pharmacokinetic analyses were collected at 2, 5, 15, and 30 minutes and 1.0, 1.5, 2.0, 3.0, 4.0, and 24 hours post-dose. After a seven-day washout period, the same animals received 10 mg/kg L-dC as a single oral dose. Blood samples for pharmacokinetic analyses were collected at 15 and 30 minutes and 1.0, 1.5, 2.0, 3.0, 4.0, 8.0, and 24 hours post-dose. Urine was collected over the 24-hour post-dose period. Plasma drug levels, CL, $t_{1/2}$ and F were determined. Drug levels were determined using an HPLC method with in-line radioactivity detection and scintillation counting.

Intravenous administration of L-dC. The mean $C_{max}$ of L-dC was 112 μM and occurred at the earliest sampling time (2 minutes post-dose) for all animals. L-dC plasma concentrations declined in a biphasic manner following the IV bolus with a mean $t_{1/2}$ of 2.85 hours. The CL of L-dC averaged 0.39 L/h/kg. The mean $V_d$ was 1.17 L/kg. L-dC accounted for the majority of radioactivity recovered in the urine. L-dU was detected in the plasma and urine, indicating that metabolic elimination of L-dC occurred following IV administration. The levels of L-dU detected intermittently in plasma were at or below the limit of assay quantitation with a mean $C_{max}$ of 0.75 μM.

Oral administration of L-dC. The $C_{max}$ was 1.37 μM and occurred at a $T_{max}$ of 3 hours. L-dC plasma concentrations decreased with a mean t½ of 5.22 hours. L-dC was absorbed from the gastrointestinal tract with an oral bioavailability ranging from 5.60 to 16.9% with an average of 9.57%. L-dC accounted for the majority of radioactivity recovered in the urine. L-dU was detected in the plasma and urine, indicating that metabolic elimination of L-dC occurred following oral administration. L-dU in the plasma was near the limit of quantitation with a mean $C_{max}$ of 0.19 μM.

Table 18 presents a summary of pharmacokinetic results for both IV and oral L-dC.

Bioavailability of the Prodrugs of L-dC

The bioavailability of L-dC, the 5'-monoester of L-dC, the divaline ester of L-dC, and the diacetyl ester of L-dC was evaluated in cynomolgus monkeys, with and without L-dT. When the divaline ester of L-dC was orally administered to monkeys, approximately 73% of the dose was absorbed. Of the absorbed divaline ester of L-dC, more than 99% was rapidly converted to L-dC to give a high concentration of L-dC in the plasma and no detectable divaline ester of L-dC. A low plasma concentration of the monovaline ester of L-dC was detected early after oral administration of divaline ester of L-dC. A low plasma concentration of β-L-2'-deoxyuridine (L-dU) was detected intermittently. No other metabolites were detected. The results are provided in Table 19. As indicated, the combination of the 3',5'-divalyl ester of L-dC with L-dT provided the largest bioavailability of L-dC.

TABLE 19

|  | L-dC parent (mw = 227.22) | L-dC[3] 5'-valine (mw = 399.27) | L-dC 3'-valine (mw = 399.27) | L-dC di-valine (mw = 534.87) | L-dC di-acetyl (mw = 347.75) |
|---|---|---|---|---|---|
| % BA[1] | 16.4 ± 5.0 | 39.0 ± 11.4 | 85.1 ± 24.5 | 72.7 ± 22.0 | 23.0 ± 6.5 |
| % BA w/ L-dT[2] | 11.9 ± 1.7 | ND | ND | 74.6 ± 9.9 | 24.9 ± 4.0 |

[1] estimated relative to AUC of L-dC (oral dose)
[2] coadministered with 10 mg/kg L-dT
[3] Specific Activity 5'-mono-valine study based on total radioactive dose
ND, not determined
Purity = 87% L-dC-mono-valine, 12% L-dC Single Dose Bioavailability of Dival-L-dC in Cynomolgus Monkey Three make non-naive cynomolgus monkeys (*Macaca fascicularis*) received 10 mg/kg of dival-L-dC intravenously with a tracer amount of tritium ([3H]⁻) labeled drub (250 μCi) dissolved in sterile 9.0% saline. Following a 6 week washout period, the same three animals received an identical oral dose of dival-L-dC. Blood samples were collected in heparinized tubes at pre-dose (~18 hours) and 0.25, 0.50, 1, 2, 3, 4, 6, 8, and 24 hours after dosing. Urine was also collected from 0-2, 2-4, 4-8, 8-12 and then at 12-hour intervals until 336 hours post-dose. The drug was quantitated in plasma and urine with a liquid chromatography-mass spectrometry (LC-MS) technique. After administration of dival-L-dC, the plasma concentration time course of L-dC was analyzed by a non-modeling mathematical method and the area under the time-concentration curves (AUC) derived by the linear trapezoidal rule. The bioavailability (F) of L-dC following IV and PO administration of dival-L-dC was calculated from the L-dC AUCs, where F=$AUC_{po}/AUC_{iv}$×doseiv/dosepo.

Intravenously administered dival-L-dC was converted rapidly to L-dC following intravenous administration. Dival-L-dC was detected in the plasma at 15 minutes (1.39 μM) and at 30 minutes (0.36 M, 1 of 3 animals) [lower limit of quantitation (LLOQ)=0.23 μM or 100 ng/mL]. Dival-L-dC was not

TABLE 18

Pharmacokinetic Analysis of L-dC (10 mg/kg) after Intravenous and Oral Administration in the Woodchuck

| Route (n) | $AUC_{t\to24}{}^{a}$ (μM · h)) | $t_{1/2}$ (h) | $C_{max}$ (μM) | $T_{max}$ (h) | CL (L/h/kg) | $V_d$ (L/kg) | F (%) |
|---|---|---|---|---|---|---|---|
| IV (3) | 174 (±120)[b] | 2.85 (±130) | 112 (±33) | 0 | 0.39 (±0.3) | 1.17 (±0.36) | — |
| PO (3) | 11.3 (±4.7) | 5.22 (±2.7) | 1.37 (±0.22) | 3.0 (±1) | — | — | 9.57 (±6.4) |

[a] t = 0.033 hours for IV administration and 0.25 hours for PO administration
[b] Mean value (±SD)

detected in the plasma after 30 minutes post-dosing. The partially de-esterified form of dival-L-dC, β-L-2'-deoxycytidine-5'-valine ester, was detected in plasma at 15 minutes (3.23 μM) and decreased in concentration to 0.08 μM by 2 hours (LLOQ=0.031 μM or 10 ng/mL). L-dC represented the majority of drug present in the plasma following intravenous administration. The average $AUC_{0.25 \to 8}$ value for L-dC was 19.8 μM·h. The mean peak plasma concentration ($C_{max}$) of L-dC was 24.6 μM (LLOQ=0.088 μM or 20 ng/mL) and occurred at the earliest sampling time (15 minutes post-dose) in all animals. The plasma concentration of L-dC declined in a biphasic manner with a mean $t_{1/2}$ of 1.73 hours. The total body clearance (CL) and apparent volume of distribution ($V_d$) of L-dC averaged 1.01 L/h/kg and 2.46 L/kg, respectively, indicating that L-dC had significant extravascular tissue distribution. The binding of dival-L-dC and L-dC to human plasma proteins ex vivo was 13.3%±2.6% and 19.7%±5.9%, respectively. The impact of human plasma protein binding on dival-L-dC and L-dC free-drug levels was minimal, suggesting that drug interactions involving binding site displacement are not anticipated.

Urinary excretion was rapid with 58±3% of the administered dose of dival-L-dC excreted within 2 hours following intravenous administration. L-dC accounted for the majority (~93%) of drug excreted in the urine. L-dU was also detected in the plasma and urine. This suggested that metabolic elimination of L-dC also occurs following administration of dival-L-dC. Low levels of L-dU were detected in plasma at intermittent time points in two of three animals at concentrations ranging from 0.22 μM to 0.88 μM (LLOQ=0.22 μM or 50 ng/mL). There were no detectable levels of L-dU at any time point in the third monkey. Renal excretion of L-dU and the partially de-esterfied form of dival-L-dC, β-L-2'-deoxycytidine-5'-valine ester was minor, accounting for approximately 2.5% and 3.7% of the total recovered dose, respectively. Dival-L-dC was detected in the urine of one of three animals at 2 hours following IV administration, which accounted for approximately 0.15% of the recovered dose.

Because of the intermittent low concentrations of both the monovaline esters and L-dU in the plasma and urine, it was not feasible to perform pharmacokinetic analysis of these metabolites. The appearance of the monovaline ester of dival-L-dC was not unexpected as it represents and intermediate in the conversion of dival-L-dC to L-dC. In addition, in vitro cellular metabolism studies in monkey, rat and human primary hepatocytes and in extracts of HepG2 cells demonstrated that L-dC was not directly deaminated to L-dU but that L-dC monophosphate (-MP) is converted to L-dU-MP, which is either activated to L-dU disphosphate (-DP), and triphosphate (-TP), or metabolized to L-dU, which is then detected in the extracellular compartment (plasma). L-dU was non-cytotoxic ($CC_{50}$>200 μM) and L-dU-TP had an $IC_{50}$ in vitro against hepatitis B virus deoxyribonucleic acid (DNA) polymerase of 5.26 μM (see Microbiology and Virology, Section 10).

Orally administered dival-L-dC also was converted rapidly to L-dC following oral administration and was not detectable in plasma samples at any time point (LLOQ of dival-L-dC in solution=0.23 μM or 100 ng/mL). The partially de-esterified metabolite of dival-L-dC, β-L-2'-deoxycytidine-5'-valine ester, was detected in plasma at 30 minutes and 1 hour at concentrations ranging from 0.034 β to 0.107 β (LLOQ of monoester in solution=0.031 μM or 10 ng/mL). Dival-L-dC was not detected in the plasma.

L-dC represented the majority (>99% at $C_{max}$) of the plasma drug levels following oral administration of dival-L-dC. The average $AUC_{0.25 \to 8}$ value for L-dC was 14.0 μM h. The $C_{max}$ of L-dC was 8.26 μM (LLOQ of L-dC in solution=0.088 μM or 20 ng/mL) and occurred at 0.67 hours following administration of dival-L-dC. The plasma concentration of L-dC declined in a biphasic manner with a mean $t_{1/2}$ of 2.28 hours. The mean oral bioavailability of L-dC following administration of dival-L-dC was 72.7%±22%.

L-dU was also detected in the plasma indicating the metabolic elimination of L-dC occurs following oral administration of dival-L-dC. Low levels of L-dU were detectable in the plasma from 30 minutes to 4 hours in two of three animals of concentrations ranging from 0.24 μM to 0.66 μM (LLOQ of L-dU in solution=0.22 μM or 50 ng/mL) and in one animal only at 8 hours at a concentration of 0.39 μM.

After oral administration, dival-L-dC was rapidly absorbed from the gastrointestinal tract and converted to L-dC by first-pass intestinal and/or hepatic metabolism. Neither dival-L-dC nor L-dC metabolism was associated with liver microsomal enzymes. Following administration of high dose levels of dival-L-dC, the monovaline ester of L-dC was transiently detected prior to conversion to L-dC. No dival-L-dC was detected after oral administration. Intermittent low plasma levels of L-dU were detected at, or below, the lower limit of assay quantitation. L-dU was formed by deamination of L-dC following cellular uptake of L-dC.

Approximately 31±8% of the administered oral dose was recovered in the urine within 4 hours. After 72 hours 39±8% was recovered. L-dC accounted for the majority (~95%) of drug excreted in the urine. Renal excretion of L-dU and the partially de-esterified form of dival-L-dC, β-L-2'-deoxycytidine-5'-valine ester was minor, accounting for approximately 2.5% and 0.2% of the total recovered dose, respectively. No dival-L-dC was detected in the urine.

Table 20 represents a summary of pharmacokinetic results for L-dC following both IV and oral dosing of dival-L-dC.

TABLE 20

Pharmacokinetic Analysis after Intravenous and Oral Administration of Dival-L-dC (10 mg/kg) in Cynomologus Monkeys
Pharmacokinetic Parameter[2]

| Route (n) | $AUC_{0.25 \to 8}$ (μM h) | $t_{1/2}$ (h) | $C_{max}$ (μM) | $T_{max}$ (h) | CL (L/h/kg) | $V_d$ (L/kg) | F (%) |
|---|---|---|---|---|---|---|---|
| IV (3) | 19.8 (±5.2) | 1.73 (±0.33) | 24.6 (±2.6) | 0 | 1.01 (±0.32) | 2.46 (±0.47) | |
| Oral (3) | 14.0 (±2.4) | 2.28 (±1.4) | 8.26 (±0.71) | 0.67 (±0.3) | | | 72.7 (±22) |

(3) Mean value [±standard deviation (SD)].

Table 21 presents a schematic of metabolite formation form dival-L-dC, the monovaline derivative of L-dC, L-dC and L-dU following IV and oral administration of dival-L-dC. The $C_{max}$ of each metabolite is also noted.

TABLE 21

Metabolite Formation for IV and PO Administration of Dival-L-dC

Intravenous (10 mg/kg Dival-L-dC)

|  | dival-L-dC→ | mono-val-L-dC→ | L-dC→→ | L-dU |
|---|---|---|---|---|
| $C_{max}$ | 1.39 µM | 3.23 µM | 24.6 µM | 0.88 µM |

Oral (10 mg/kg dival-L-dC)

|  | val-L-dC→ | mono-val-L-dC→ | L-dC→→ | L-dU |
|---|---|---|---|---|
| $C_{max}$ | Not detected | 0.11 µM | 8.26 µM | 0.66 µM |

Oral Bioavailability of L-dC via Dival-L-dC in Cynomolgus Monkey

Three male non-naive cynomolgus monkeys (*Macaca fascicularis*) received 10 mg/kg of dival-L-dC orally with a tracer amount of [3H]-labeled drug (250 µCi) dissolved in sterile 0.9% saline. Blood samples were collected in heparinized tubes at pre-dose (~18 hours) and 0.25, 0.50, 1, 2, 3, 4, 6, 8 and 24 hours after dosing. Urine was collected from 0-2, 2-4, 4-8, 8-12 and then at 12-hour intervals until 336 hours post-dose. The drug was quantitated in plasma and in urine using HPLC analysis. After administration of dival-L-dC the plasma concentration time course of L-dC was analyzed by a non-modeling mathematical method and the area under the time-concentration curves (AUC) derived by the linear trapezoidal rule. Dival-L-dC was rapidly absorbed and converted to L-dC following oral administration. Radiochromatographic high pressure liquid chromatography (HPLC) analysis of plasma samples confirmed that the majority of the recovered radioactivity was L-dC. Dival-L-dC was detected in only one animal at 15 minutes post-dose at a concentration of 0.35 µM. The partially de-esterified form of dival-L-dC, β-L-2'-deoxycytidine-5'-valine ester, was not detected in the plasma or urine. Approximately 26% of the administered oral dose was recovered in the urine within 8 hours. After 72 hours 31% was recovered. L-dC accounted for the majority (~89%) of drug excreted in the urine. Renal excretion of L-dU was minor, accounting for approximately 10% of the recovered dose. No dival-L-dC or its partially de-esterified form, and no other metabolites were detected in the urine.

The overall pharmacokinetic profile was comparable to that determined in the pharmacokinetic study as demonstrated by similar $C_{max}$ to AUC ratios. Low levels of L-dU were detected in the plasma in two of three animals with an average $C_{max}$ of 0.33 µM. No L-dU was detected in the plasma of the third animal. The level of L-dU was at or below the limit of quantitation, precluding pharmacokinetic analysis.

In vitro metabolism of Dival-L-dC

Studies were conducted to determine the stability and protein binding of dival-L-dC and its de-esterified metabolites in human plasma. Dival-L-dC was incubated in human plasma at 37° C. and samples analyzed at various time points up to 24 hours (FIG. 13). No dival-L-dC was detectable at 24 horns with complete conversion to L-dC. Two additional metabolites (β-L-2'-deoxycytidine-5'-valine ester and β-L-2'-deoxycytidine-valine ester) were also noted. The transient nature of these metabolites indicated that they are intermediates in the conversion of dival-L-dC to L-dC. The in vitro half-life of dival-L-dC in human plasma at 37° C. was determined to be approximately 39 min.

The impact of human plasma protein binding on free levels of dival-L-dC and L-dC was also investigated using an ultrafiltration method. Plasma protein binding of dival-L-dC was 13.3%±2.6%. The binding of L-dC to plasma proteins was 19.7%±5.9%. This study shows that the impact of human plasma protein binding on dival-L-dC and L-dC is minimal and suggests that drug interactions involving binding site displacement are not anticipated.

Metabolic Activation and Intracellular Profile of L-dC

The cellular metabolism of L-dC was examined using HepG2 cells and human primary hepatocytes. High pressure liquid chromatography (HPLC) analysis demonstrated that L-dC was extensively phosphorylated in hepatocytes. The predominant metabolite in HepG2 cells exposed to 10 µM L-dC for 24 hours was L-dC-TP which reached 72.4±1.8 µM (see Table 23). In primary human hepatocytes, the L-dC-TP concentration at 24 hours was 90.1±37 µM, similar to the level of phosphorylation in HepG2 cells. Exposure of hepatocytes to L-dC led to activation of a second 5'-triphosphate derivative, L-dU-TP. In HepG2 cells exposed to 10 µM L-dC, the L-dU-TP level reached 18.2 µM (43.5 pM in primary human hepatocytes) at 24 hours. In primary rat and monkey hepatocytes the extent of phosphorylation of L-dC was slightly lower.

TABLE 23

Activation of L-dC(10 µM) in Hepatocytes

| Cells[a] | n | L-dC-MP | L-dU-MP | L-dC-DP | L-dC-DP-choline | L-dU-DP | L-dC-TP | L-dU-TP |
|---|---|---|---|---|---|---|---|---|
| HepG2 | 3 | 23.3 ± 0.86 | 6.73 ± 0.41 | 10.2 ± 1.9 | 25.6 ± 0.08 | 2.69 ± 0.45 | 72.4 ± 1.8 | 18.2 ± 1.0 |
| Human Primary Hepatocytes | 3 | 27.6 ± 15 | 5.74 ± 2.4 | 7.19 ± 2.3 | 15.8 ± 1.8 | 3.93 ± 1.6 | 90.1 ± 37 | 43.5 ± 27 |
| Monkey Primary Hepatocytes | 1 | 11.2 | 2.54 | 7.66 | 10.4 | 3.11 | 39.3 | 21.9 |
| Rats Primary Hepatocytes | 3 | 5.09 ± 2.1 | 3.53 ± 0.97 | 1.52 ± 0.38 | 8.82 ± 3.1 | 7.90 ± 1.4 | 14.2 ± 3.1 | 46.9 ± 5.2 |

[a]Cells were incubated for 24 hours with [3H]-L-dC, specific activity: HepG2 assay = 0.5 Ci/mmol; human, monkey and rat hepatocyte assay = 1.0 Ci/mmol.

In addition to the phosphorylated derivatives of L-dC and L-dU, formation of a [β-L-2'-deoxyliponucleotide metabolite was noted. In HepG2 cells and primary hepatocyte cultures exposed to 10 μM L-dC for 24 hours, [3-L-2'-deoxycytidine-5'-diphosphocholine (L-dC-DP-choline) was detected at a concentration of 25.6 μM (range 25.6-25.7 μM) and 12.3 μM (range 8.82-15.8 μM), respectively.

The metabolic profile obtained after a 24-hour exposure of HepG2 cells to 10 μM [3H]-L-dC is shown in FIG. 14. The apparent intracellular half-life of the L-dC-TP was 15.5±0.34 hours, which correlated with prolonged antiviral activity following drug withdrawal in the virus rebound experiments. The phosphorylation pattern detected in primary human hepatocytes was qualitatively and quantitatively similar to that obtained using HepG2 cells (FIG. 15).

Cellular Kinases Associated with Metabolic Activation

D-Deoxycytidine (dcyd) is a natural substrate of cytosolic dCyd kinase (dCK) and mitochondrial thymidine kinase (TK2) for conversion to dCyd-5'-monophosphate (dCMP). Cytosolic thymidine kinase (TK1) and TK2 utilize D-thymidine (Thd) as a natural substrate for conversion to Thd-5'-monophosphate (TMP). The cellular kinase involved in the initial phosphorylation of L-dC was identified in competition studies using L-dC and the natural endogenous Thd and dcyd. Intracellular phosphorylation of L-dC was decreased in a dose-dependent fashion by dCyd but not by Thd. Thus, dCyd acted as an inhibitor of L-dC phosphorylation. The change in intracellular phosphorylation of L-dC was similar when HepG2 cells were exposed to both Thd and dCyd or dCyd alone. The inhibition of L-dC phosphorylation by only the natural deoxypyrimidine, dCyd, suggested that dCK was involved in L-dC phosphorylation.

The role of these pyrimidine nucleoside kinase activities in the phosphorylation of L-dC was further investigated in kinase deficient cell lines. There was a significant decrease in the mount of phosphorylated metabolites of L-dC in dCK deficient cells. However, no significant difference was observed in L-dC phosphorylation in TK1 deficient cells. These data were consistent with the competition studies described above and indicated that dCK plays a critical role in the phosphorylation of L-dC to L-dC-MP.

Using cytosolic extracts of HepG2 cells as an enzyme source, steady state kinetics for L-dC, Thd, and dcyd phosphorylation were similar as indicated by the apparent Michaelis-Menten constant ($K_m$) and maximum initial velocity ($V_{max}$) values (L-dC: $K_m$ of 5.75 mM and $V_{max}$ of 1.12 mmol/min/mg protein; Thd: $K_m$ of 4.06 mM and $V_{max}$ of 1.26 nmol/min/mg protein; dcyd: $K_m$ of 4.85 mM and $V_{max}$ of 2.15 nmol/min/mg protein). In addition, the efficiency of L-dC, Thd, and dCyd phosphorylation were similar as defined by their corresponding $V_{max}/K_m$ in values (0.19, 0.31, and 0.44, respectively).

In addition, the extent of intracellular phosphorylation of L-dC was compared to that of the natural endogenous substrates, Thd and dcyd in woodchuck liver extracts. This was done to support antiviral testing in the woodchuck model of chronic hepatitis B virus infection. Phosphorylation of L-dC was similar to that of the endogenous substrates. Furthermore, the level of phosphorylation of L-dC was comparable to that of L-dC and that of the endogenous substrates in human liver extracts.

X. Activity of the Active Compounds Against Drug-Resistant HBV

β-L-2'-deoxynucleosides, and in particular β-L-2'-deoxycytidine and β-L-2'-deoxythymidine, are potent and selective inhibitors of drug-resistant HBV (M552V). HBV recombinants containing the YMDD mutation (defined as amino acid substitutions in the tyrosine, methionine, aspartate, aspartate nucleotide-binding locus of HBV polymerase) can be used to generate cell lines expressing lamivudine-resistant HBV, although these genomes are often less replication-competent than wild-type HBV in vitro (Fu and Cheng, 1998). These recombinant systems provide the best approach to addressing the question of resistance. The determination of the activity of LdT (IND 60,459) against lamivudine-resistant HBV strains (YMDD mutants) through the use of transient transfection assays using Huh-7 liver cells, the preferred cellular system for such assessments, according to the approach described by Ono et al, 2001 was attempted. However, in Huh-7 cells, LdT exhibited poor activity against even wild-type HBV. While Huh-7 cells phosphorylate lamivudine quite well, there was minimal phosphorylation of LdT to the active triphosphate. These results were summarized in the materials submitted to the Agency for the LdT End of Phase 2 Meeting (IND 60,459; Serial 024). Therefore, the system of Ono et al is not appropriate for the analysis of these drugs.

As an alternative approach, mutated HBV genomes were introduced into HepG2 cells via transient transfection. These experiments were similarly unsuccessful, primarily due to the poor and variable transfectability of these cells, which precluded obtaining consistent values for antiviral efficacy.

A more appropriate way to address the resistance question for LdT and LdC is by using stable HepG2 cell lines expressing recombinant HBV viruses with wild-type genomes as well as lamivudine-resistance mutations at positions 552 and 515 or 528, respectively. Compared to the preceding methods, these stable cell lines offer consistent polymerase expression levels combined with a good signal-to-noise ratio.

The in vitro activity of the drugs LdT (telbivudine) and LdC were determined against lamivudine-resistant mutants of hepatitis B virus (HBV). The biologically relevant mutants of HBV (subtype ayw) that have been determined to confer resistance to lamivudine therapy in the clinical setting arise in the polymerase gene and comprise two single mutations, M552V and M552I, found in the key YMDD active site motif as well as two double mutants L515M/M552V and L515M/M552I. [The L515M mutant referred to herein is equivalent to the L526M or L528M mutations in the B domain often cited in HBV resistance studies: the difference in numbering reflects sequence insertions/deletions among different HBV genotypes].

Materials and Methods

Recombinant DNA constructs corresponding to these lamivudine-resistant mutants were created by site directed mutagenesis. The test system comprised stable cell lines harboring each of the transfected mutant genomes, as well as a wild-type control HBV genome. The antiviral activity of LdT (telbivudine) and LdC, together with the control drugs lamivudine and PMEA, was determined against the mutant and wild-type HBV genomes in the respective test cell lines.

LdT (telbivudine) and LdC demonstrated minimal activity against the M552I single mutant or the L515M/M552V and L515M/M552I double mutants, although LdC did reach an $EC_{50}$ against the L515M/M552V mutant. However, in contrast to lamivudine, both drugs retain almost full antiviral activity against the M552V single mutant HBV genome. The M552V mutation is significantly resistant to lamivudine and is thought to be a key intermediate in the major pathway for development of breakthrough resistance to lamivudine. In lamivudine-treated patients, the M552V mutant typically appears 4 to 8 weeks prior to the emergence of the highly resistant L515M/M552V double mutant (Gauthier et al, 1999), which reportedly accounts for 60-70% of all lamivudine resistance in hepatitis B patients (Ahmed et al, 2000).

These results suggest that the activity of LdT (telbivudine) and LdC against the M552V mutant may help suppress a major proportion of YMDD-mediated emergence of antiviral resistance in patients. Coupled with the better quantitative suppression of HBV replication observed for LdT treated patients (compared to lamivudine recipients) in the current Phase IIB clinical trial, these results suggest that YMDD-mediated HBV resistance to LdT is likely to be substantially less frequent than is observed with lamivudine treatment.

In controlled clinical studies of lamivudine (100 mg qd), administered to HBV-infected patients, the prevalence of YMDD-mutant HBV was 14 to 32% after one year of treatment and as much as 58% after two to three years of treatment. Mutant virus was associated with evidence of diminished treatment response relative to lamivudine-treated patients without YMDD mutations.

Genotypic analysis of viral isolates obtained from patients with renewed HBV replication while receiving lamivudine suggests that a reduction in HBV sensitivity to lamivudine is associated with mutations resulting in a methionine to valine or isoleucine substitution in the YMDD motif of the catalytic domain of HBV polymerase (position 552) and a leucine to methionine substitution at position 515 or 528 (depending on the genotype/subtype of HBV).

At the present time, there is no cell-based HBV infection system that can be used to assess the activity of antiviral agents against cells infected with lamivudine-resistant HBV isolates from patients. The DHBV in vitro model has not proved useful to select drug-resistant mutations because the primary duck hepatocytes used in this model cannot be sustained for more than a few weeks in cell culture. The relevance of selection of drug-resistant mutants in the woodchuck in vivo model is dubious because the spectrum of lamivudine-resistant mutants in the woodchuck does not match that identified in HBV-infected patients.

HBV recombinants containing the YMDD mutation can be used to generate cell lines expressing lamivudine-resistant HBV, although these genomes are often less replication-competent than wild-type HBV in vitro (Fu and Cheng, 1998). These recombinant systems provide the best approach to addressing the question of resistance. The activity of LdT (IND 60,459) against lamivudine-resistant HBV strains (YMDD mutants) through the use of transient transfection assays using Huh-7 liver cells, the preferred cellular system for such assessments, according to the approach described by Ono et al, 2001, was attempted. However, in Huh-7 cells, LdT exhibited poor activity against even wild-type HBV. Further investigation revealed that while Huh-7 cells phosphorylate larnivudine quite well, there was minimal phosphorylation of LdT to the active triphosphate. These results were summarized in the materials submitted to the Agency for the LdT End of Phase 2 Meeting (IND 60,459; Serial 024). Therefore the system of Ono et al is not appropriate for the analysis of this type of drug.

As an alternative approach mutated HBV genomes were introduced into HepG2 cells via transient transfection. These experiments were similarly unsuccessful, primarily due to the poor and variable transfectability of these cells, which precluded obtaining consistent values for antiviral efficacy.

A more appropriate way to address the resistance question for LdT and LdC is by using stable HepG2 cell lines expressing recombinant HBV viruses with wild-type genomes as well as lamivudine-resistance mutations at positions 552 and 515 or 528, respectively. Compared to the preceding methods, these stable cell lines offer consistent polymerase expression levels combined with a good signal-to-noise ratio.

Example 17

Transfections of HepG2 Cells to Create Lamividine-Resistant Stable Cell Lines

Stably transformed cells harboring the characteristics of lamivudine-resistant and wild type HBV genomes were obtained to test the activity of LdT and LdC against the mutants along with lamivudine and adefovir as controls.

HepG2 Growth Media
  EMEM (Mediatech, Cat#MT 10-010-CV)
  10% FBS (Mediatech, Cat#MT 35-011-CV)
  1×L-glutamine (2 mM final)
  1×Penicillin-Streptomycin (100 I.U./100 µg per ml final)
  1×Na-Pyruvate (1 mM final)
  1×Non-Essential Amino Acids (NEAA, 0.1 mM final)

HepG2 Transfection Media
  EMEM (Mediatech, Cat#MT 10-010-CV)
  10% FBS (Mediatech, Cat#MT 35-011-CV)
  1×L-glutamine (2 mM final)
  1×Na-Pyruvate (1 mM final)
  1×NEAA (0.1 mM final)

HepG2-Stable Cell Line Growth/Selection Media
  EMEM (Mediatech, Cat#MT 10-010-CV)
  10% FBS (Mediatech, Cat#MT 35-011-CV)
  1×L-glutamine (2 mM final)
  1×Penicillin-Streptomycin (100 I.U./µg per ml final)
  1×NaPyruvate (1 mM final)
  1×NEAA (0.1 mM final)
  500 µg/ml Geneticin (G-418, Life Technologies Cat #10131)

Constructs
  pCMV-WT (ayw)
  pCMV-M552V
  pCMV-M552I
  pCMV-L515M/M552V
  pCMV-L515M/M552I
  pCMV-neo All constructs contain the HBV genome cloned behind the CMV promoter. HBV plasmids containing point-mutated polymerase genes were derived by site-directed mutagenesis using pCMV-hbv as parent and a commercial kit (Stratagene's QuikChange kit, Cat. #200518-5) as described previously (Allen et al., 1998). pCMVhbv (kindly provided by Dr. C. Seeger, Fox Chase Cancer Institute) contains an over-length HBV genome subtype ayw. The construct containing a single L515M mutation was not generated, because this mutation is thought to confer only minimal resistance to lamivudine; rather it serves as a compensatory mutation (Gauthier et al, 1999).

Plasmid pCMV-neo was used to confer resistance to G-418 antibiotic (neomycin). This plasmid contains the backbone of pEGFP-N1 (Clontech Cat #6085-1) with the SV40-driven Kan$^r$/Neo$^r$ expression cassette but without the EGFP expression cassette.

Preparation of cells for transfection: Cells were plated in collagen-coated 6-well plates (Biocoat, Becton Dickinson, Cat-#35-4400) at 2×10$^5$ cells per well in 3 mL HepG2 growth media. Cells were incubated overnight at 37° C.

Preparation of Fugene:DNA complex: Each construct was used to transfect 2 wells of a 6-well collagen-coated plate. Controls included 1 well containing the pCMVhbv wild-type construct without pCMV-neo DNA and 1 well containing the neo$^R$-plasmid only. Cells were transfected with Fugene (Roche cat #1815091) according to the manufacturer's suggested protocol with a Fugene-to-DNA ratio of 3:1 (3 ul Fugene+1 ug of supercoiled plasmid DNA/well). Briefly, 6 µL of Fugene was diluted into 200 ul of serum free EMEM medium in a microcentrifuge tube. 2 µg of the respective HBV plasmid DNA along with 0.2 µg of pCMVneo DNA was then added. The solution was gently mixed and then incubated for 15 minutes at room temperature.

Transfection of cells: 6-well plates were aspirated and fed with 2 ml HepG2 transfection media. The Fugene:DNA complex solution was then added slowly to the cells while swirling the plate to evenly disperse the solution. The plates were incubated overnight at 37° C. HepG2-Stable Cell Line Growth/Selection Media was added the following day.

Example 18

Selection of Stable Cell Line Colonies and Subclones

Transfected cells were fed twice a week for 2½ weeks until distinct G418-resistant colonies formed. Colonies that appeared to be "clonal" (not in contact with any other colonies) were picked off the 6-well plate with a pipette tip and placed in a BD 96-well collagen plates in 150 µL of HepG2-Stable Cell Line Growth/Selection Media. 16 colonies were picked per construct.

Media was changed every 3-4 days. HBV expressing colonies were identified via testing of 100 µL of culture supernatant for presence of HBeAg via ELISA (see below). Positive colonies were subcloned by limiting dilution in collagen 96-well plates and culture supernatant was screened by ELISA 2 weeks later (media was changed every 3-4 days). Positive wells were expanded, frozen stocks were made and cell line was then subcloned again by limiting dilution and the culture supernatant was screened by ELISA 2 weeks later.

Example 19

Testing of Stable Transfected Cell Lines

Stable cell line clones were screened for expression of the viral genome by two tests. The first assay was a semi-quantitative ELISA assay that measures the production of hepatitis B virus e antigen (HBeAg), a viral protein marker that correlates well with viral replication. Cell lines that produced high levels of HBeAg were then tested for the production of replicative viral genomes using the endogenous polymerase assay.

HBeAg-ELISA of Stable Cell Line Culture Supernatant: The capture antibody was a mouse anti-HBeAg mAb used at 10 ug/ml. 100 ul of culture supernatant was used directly from 96-well cell culture plate. Detection antibody was a polyclonal (rabbit) anti-HBc/eAg-antibody (DAKO, Cat # B0586) at 1:3,000 dilution in 10% FCS/TNE). Peroxidase-conjugated goat anti-rabbit-IgG (1:10,000; Zymed Cat #81-6120)) was used to develop and substrate was o-phenylenediamine (Zymed Cat #00-2003) in citrate/phosphate buffer. Development was stopped with 2N $Na_2SO_4$ prior to reading the optical density (O.D.) at 490 nm in a Fusion plate reader (Packard Instruments).

Endogenous Polymerase Assay (EPA) of cell lysate: Cells were grown in 12-well collagen plates to 100% confluency for 3-4 days and cytosolic lysates were prepared in 1 ml of 50 mM Tris-HCl pH 7.4, 150 mM NaCl, 5 mM $MgCl_2$, 0.2%NP-40. EPAs were essentially performed as described (Seifer et al., 1998). Briefly, intracellular HBV nucleocapsids were immunoprecipitated from the cytoplasmic lysates overnight at 4° C. with a polyclonal rabbit anti-HBc/eAg antibody (DaKo Cat # B0586) and immobilized on protein A sepharose CL-4B beads (Amersham Pharmacia Cat #17-0780-01). The immobilized capsids were then washed, endogenous polymerase reactions were initiated in 50 ul reaction volume containing 50 mM Tris-HCl pH7.4, 75 mM $NH_4Cl$, 1 mM EDTA, 20 mM $MgCl_2$, 0.1 mM β-ME, 0.5%NP-40, 100 µM cold dGTP, TTP, dCTP, and 50 nM $^{33}$P-dATP (Perkin Elmer Life Sciences Cat # NEG 612H), and incubated overnight at 37° C. Following digestion with 1 mg/ml of Proteinase K (Roche, Cat #1373196) for 1 h at 37° C., $^{33}$P-labeled HBV DNA was liberated via phenol/chloroform extraction The nucleic acids were finally precipitated with equal volumes 5M $NH_4$-acetate and 2.5 volumes 100% EtOH and separated on a 1% native agarose gel in Tris-borate buffer. Gels were either fixed with 7%TCA, then dried, or blotted onto positively charged nylon membrane (Pall Biodyne Plus Cat #60406) overnight at room temperature via capillary transfer in 0.4 N NaOH. Dried gels/membranes were exposed to a phosphoimager screen (Molecular Dynamics) overnight at room temperature, then scanned (Storm 860, Molecular Dynamics) and quantitated with ImageQuant (Molecular Dynamics) software.

The clonal cell lines that were selected as having high HBeAg expression as well as high level production of replicative genomes were designated as follows:

| Cell line | Virus |
|-----------|-------|
| WT3/C1 | Wild-type (ayw) |
| V1/C9 | M552V |
| I2 | M552I |
| MV5/B3 | L515M/M552V |
| MI4 | L515M/M552I |

Example 20

Antiviral Testing
LdT (telbivudine, Idenix), LdC-HCl (Idenix), Lamivudine (Moravec) and PMEA (Moravec)
PMEA is the Active Component of the Prodrug Adefovir.

12-well Biocoat collagen I plates (Becton Dickinson Cat #35-4500) are seeded with cells at a density of 0.5-1×10$^6$ cells per well in 2 ml DMEM containing 5% FBS, 2 mM L-glutamine, 100 I.U. penicillin/100 µg/mL streptomycin, and 0.5 mg/mL G-418.

Drug dilutions are prepared freshly in 100% DMSO as 200× stocks. For each experiment, 4 aliquots of each drug dilution series are stored at −20° C. until used. Once cells reach confluency, drug treatment is initiated by adding 10 µL of drug dilution into 2 ml of fresh DMEM+5% FBS. Thus, the final DMSO concentration does not exceed 0.5%. The no-drug control well receives only 10 µl of DMSO. Cells are treated every other day with 2 mL of fresh drug/medium for a total of 8 days. Cell lysates are then collected on day 10 as described below:

Aspirate media and rinse cell monolayer carefully once with 1 mL of PBS.

Add 1 ml of lysis buffer (50 mM Tris-HCl pH 7.5/150 mM NaCl/5 mM $MgCl_2$/0.2% NP-40). Store on ice for 30 min to 4 h.

Harvest lysed cells. Transfer to 1.5 ml microfuge tubes.
Clarify lysate by spinning for 5 min at RT and 14,000 rpm.
Transfer clarified lysate to fresh tubes. Snap-freeze on dry-ice and store at −80° C. until ready to continue with endogenous polymerase assays essentially as described above.

$EC_{50}$'s were generated from the phosphorimager data by curve fitting using Xlfit software.

Table 24 summarizes the results obtained when LdT and LdC, as well as the lamivudine and PMEA controls, were tested for activity against the different mutant and wild-type HBV genomes expressed in stably transfected HepG2 cells. The antiviral activities are presented in Table 24a. The $EC_{50}$ values obtained for the different drugs against the wild-type virus generally accord well with literature-reported values, except that the mean $EC_{50}$ value for LdT is higher than the typical value of around 200 nM seen in most of our prior studies. The antiviral activity of LdT in cell culture is quite variable and that the potency of LdT in cell culture assays does not seem to be predictive of the efficacy seen in patients in the clinical setting.

With respect to the activity observed against lamivudine-resistant mutants, PMEA retained significant activity against all the mutants in agreement with prior reports (see Gilead FDA briefing document, 2002). Against the two double mutants or the M552I single mutant, LdT, LdC and lamivudine were largely inactive ($EC_{50}>1$ mM), although LdC showed marginal activity against the L515M/M552V mutant with an $EC_{50}$ of approximately 780 µM. The major finding from the present study was that LdT and LdC retained almost complete activity against the M552V single mutant, whereas the activity of lamivudine against this mutant was significantly diminished.

The effect of the lamivudine-resistant mutants on the observed efficacy of the drugs can best be seen from the fold-resistance analysis presented in Table 24b. The results obtained in this study are in broad agreement with prior studies (as summarized in the Gilead FDA Advisory Committee Briefing Document, 2002). It is clear from Table 24b that LdT, LdC and lamivudine show a substantial fold resistance when tested against either of the double mutants or the M552I single mutant. However, the status of the single M552V mutant is very different. LdT and LdC exhibit essentially unchanged antiviral activity against this mutant, with respective fold resistance changes of 1.2 and 2.1 fold, whereas lamivudine shows a 24.8 fold resistance in our hands and a 153 fold resistance according to the Glaxo group (Allen et al, 1998)

Both LdT and LdC were relatively inactive against the double-mutant HBV strains commonly found in hepatitis B patients with established larnivudine resistance. If these in vitro results are predictive of clinical activity, then the results suggest that LdT and the LdC prodrug currently being investigated in the clinic may have minimal anti-HBV activity in patients with established lamivudine resistance, harboring the double-mutant HBV strains. However, two recent abstract reports in the literature have highlighted the problem that results with laboratory transfectants sometimes have poor predictive value with regard to activity in the clinic. A report from Gilead virologists (Delaney et al., 2001) suggested minimal in vitro activity for entecavir against YMDD-mutant HBV strains, while another abstract at the same meeting (AASLD 2001) described the results of a large prospective trial conducted by entecavir's sponsor (Bristol Myers Squibb), in which entecavir treatment produced substantial HBV DNA reductions in lamivudine-resistant hepatitis B patients (REF xxx). Thus, in view of the problematic clinical predictive value for HBV-related laboratory results, it may be desirable to perform a small clinical trial for LdT (and LdC) in patients with lamivudine-resistant HBV, despite the minimal in vitro activity for these two compounds against double-mutant HBV strains.

The studies demonstrated essentially unaltered anti-viral activity for LdT and LdC against the M552V HBV mutant, in contrast to lamivudine. The M552V mutation is critical for the development of lamivudine resistance, as it is thought to be the first step in the pathway that leads to the M515L/M552V double mutant, which accounts for 60-70% of lamivudine resistance in hepatitis B patients (Ahmed et al, 2000). This in-vitro finding is important to the overall understanding of the potential resistance profile of LdT (telbivudine), as activity against the key M552V mutation may help to suppress the emergence of viral resistance in hepatitis B patients being treated with LdT (telbivudine).

While clinical antiviral resistance patterns can be established only from clinical trials, the unaltered activity of LdT and LdC against M552V HBV mutants, coupled with the better quantitative suppression of HBV replication observed for LdT treated patients in the current Phase IIB clinical trial, suggest that YMDD-mediated HBV resistance to LdT is likely to be substantially less frequent than is observed with lamivudine treatment.

Table 24. Inhibition Profile [(a) antiviral efficacy; and (b) fold resistance] of LdT, LdC, Lamivudine and PMEA against wild-type and lamivudine-resistant mutant HBV viruses derived from stable cell lines as determined by EPA of intracellular nucleocapsids.

TABLE 24a

Aniviral Efficacy

| Cell Line | Virus | LdT $EC_{50}$(uM) | LdC-HCl $EC_{50}$(uM) | Lam $EC_{50}$(uM) | PMEA $EC_{50}$(uM) |
|---|---|---|---|---|---|
| WT3/C1 | WT (ayw) | 0.65 ± 0.28 | 0.18 ± 0.09 | 0.05 ± 0.03 | 0.33 ± 0.17 |
| V1/C9 | M552V | 0.85 ± 0.48 | 0.36 ± 0.13 | 0.96 ± 0.36 | 1.02 ± 0.22 |
| I2 | M552I | ≧1000 | ≧1000 | ≧1000 | 1.6 ± 1.12 |
| MV5/B3 | L515M/M552V | ≧1000 | 777 ± 99 | ≧1000 | 0.62 ± 0.3 |
| MI4 | L515M/M552I | ≧823 ± 307 | ≧1000 | ≧1000 | 1.49 ± 0.3 |

TABLE 24b

Fold Resistance

| Cell Line | Virus | LdT x Resist. | LdC-HCl x Resist. | Lam x Resist. | PMEA x Resist. |
|---|---|---|---|---|---|
| WT3/C1 | WT (ayw) | 1 | 1 | 1 | 1 |
| V1/C9 | M552V | 1.2 ± 0.4 | 2.1 ± 0.5 | 24.8 ± 17.8 | 3.8 ± 2.3 |
| I2 | M552I | ≧1360 ± 363 | ≧6733 ± 4245 | ≧22922 ± 9063 | 4.6 ± 3.0 |

TABLE 24b-continued

| | | Fold Resistance | | | |
|---|---|---|---|---|---|
| | | Drug | | | |
| Cell Line | Virus | LdT × Resist. | LdC-HCl × Resist. | Lam × Resist. | PMEA × Resist. |
| MV5/B3 | L515M/M552V | ≧1360 ± 363 | 5051 ± 2717 | ≧22922 ± 9063 | 3.3 ± 2.9 |
| MI4 | L515M/M552I | ≧1049 ± 226 | ≧6733 ± 4245 | ≧22922 ± 9063 | 3.6 ± 1.1 |

All numbers in both tables represent average +/− SD derived from three to four independent experiments.
$EC_{50}$ = effective concentration that reduces virus production by 50% in cell culture
Fold resistance = $EC_{50}$ for the mutant HBV divided by the $EC_{50}$ for the wild-type HBV Ahmed S N S, Tavan D, Pichoud C, et al. "Early detection of viral resistance by determination of hepatitis B virus polymerase mutations in patients treated by lamivudine for chronic hepatitis B." *Hepatology* 2000, 32, 1078-1088.

Allen M I, Deslauriers M, Webster A, et al. "Identification and characterization of mutations in hepatitis B virus resistant to lamivudine." *Hepatology* 1998, 27 (6), 1670-1677.

Delaney W E, Huiling Y, Westland C E, et al. "In vitro cross resistance testing of adefovir, entecavir, and β-L-thymidine (L-DT) against drug-resistant strains of HBV." *Hepatology* 2001, 34 (No. 4, Pt 2), 628A, abstract #1825.

Fu L and Cheng, Y C. "Role of additional mutations outside the YMDD motif of hepatitis B virus polymerase in L(−) SddC (3TC) resistance." *Biochem Pharmacol.* 1998, 55, 1567-1572.

Gauthier J, Bourne E J, Lutz, M W et al. "Quantitation of hepatitis B viremia and emergence of YMDD variants in patients with chronic hepatitis B treated with lamivudine." *J. Infectious Dis* 1999, 180, 1757-62.

Gilead F D A Advisory Committee Briefing Document. "Adefovir dipivoxil for the treatment of chronic hepatitis B." NDA 21-449. Table 1 p 12. 5 Jul. 2002

Ono S K, Kato N, Shiratori Y, et al, "The polymerase L528M mutation cooperates with nucleotide binding-site mutations, increasing hepatitis B virus replication and drug resistance." *J. Clin Invest.* 2001, 107, 449-455.

Seifer M, Hamatake R, Bifano M, Standring D N. "Generation of replication-competent hepatitis B virus nucleocapsids in insect cells." *J. Virol.* 1998, 72, 2765-2776.

This invention has been described with reference to its preferred embodiments. Variations and modifications of the invention, will be obvious to those skilled in the art from the foregoing detailed description of the invention. It is intended that all of these variations and modifications be included within the scope of this invention.

---

We claim:

1. A method for the treatment of a host infected with a drug-resistant form of HBV, said HBV exhibiting a mutation at the 552 codon from methionine to valine in the DNA polymerase region, said method comprising administering an effective amount of a β-L-2'-deoxynucleoside having thymine or cytosine as base, or a pharmaceutically acceptable salt, ester or prodrug thereof; in combination or alternation with at least one other anti-HBV agent.

2. The method of claim 1, wherein the β-L-2'-doexynucleoside is β-L-2'-deoxythymidine, or a pharmaceutically acceptable salt, ester or prodrug thereof.

3. The method of claim 1, wherein the β-L-2'-doexynucleoside is β-L-2'-deoxycytidine, or a pharmaceutically acceptable salt, ester or prodrug thereof.

4. The method of claim 1, wherein the β-L-2'-doexynucleoside has the formula (I):

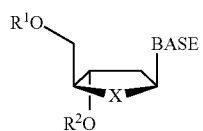

or a pharmaceutically acceptable salt, ester or prodrug thereof, wherein:
R$^1$ and R$^2$ are independently hydrogen, straight chained, branched or cyclic alkyl, acyl, acetyl, butyryl, CO-alkyl, CO-aryl, CO-aikoxyalkyl, CO-aryloxyalkyl, CO-substituted aryl, alkylsulfonyl, arylsulfonyl, aralkylsulfonyl, amino acid residue, mono, di, or triphosphate;
X is O, S, SO$_2$ or CH$_2$; and
BASE is a purine or pyrimidine base that may optionally be substituted.

5. The method of claim 1, wherein the β-L-2'-doexynudeoside has the formula:

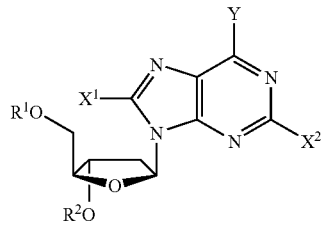

or a pharmaceutically acceptable salt, ester or prodrug thereof, wherein:
R$^1$ and R$^2$ are independently hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate;
Y is OR$^3$, NR$^3$R$^4$ or SR$^3$;
X$^1$ and X$^2$ are independently selected from the group consisting of H, straight chained, branched or cyclic alkyl, acyl, acetyl, butyryl, CO-alkyl, CO-aryl, CO-alkoxyalkyl, halogen, OR$^5$, NR$^5$R$^6$ or SR$^5$; and
R$^3$, R$^4$, R$^5$ and R$^6$ are independently H, straight chained, branched or cyclic alkyl, dialkylaminoalkylene, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate.

6. The method of claim 1, wherein the β-L-2'-doexynucleoside has the formula:

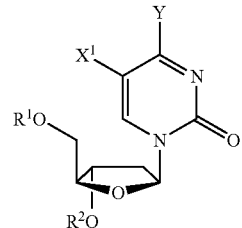

or a pharmaceutically acceptable salt, ester or prodrug thereof, wherein:
R$^1$ and R$^2$ are independently hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate;
Y is OR$^3$, NR$^3$R$^4$ or SR$^3$;
X$^1$ is selected from the group consisting of H, straight chained, branched or cyclic alkyl, acyl, acetyl, butyryl, CO-alkyl, CO-aryl, CO-alkoxyalkyl, halogen, OR$^5$, NR$^5$R$^6$ or SR$^5$; and
R$^3$, R$^4$, R$^5$ and R$^6$ are independently H, straight chained, branched or cyclic alkyl, dialkylaminoalkylene, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate.

7. The method of claim 6, wherein the β-L-2'-doexynucleoside has the formula:

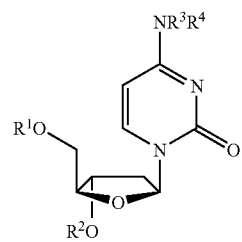

or a pharmaceutically acceptable salt, ester or prodrug thereof, wherein:
R$^1$ and R$^2$ are independently hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate; and
R$^3$ and R$^4$ are independently H, straight chained, branched or cyclic alkyl, dialkylaminoalkylene, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate.

8. The method of claim 7, wherein R$^3$ and/or R$^4$ is H.

9. The method of claim 7, wherein R$^1$ and/or R$^2$ is H.

10. The method of claim 7, wherein at least one of R$^1$, R$^2$ or R$^4$ is an amino acid residue of the formula:

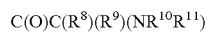

wherein:

R[8] is the side chain of an amino acid, alkyl, aryl, heteroaryl, heterocyclic, or can optionally attach to R[10] to form a ring structure;

R[9] is hydrogen, alkyl, or aryl; and

R[10] and R[11] are independently hydrogen, acyl, or alkyl.

11. The method of claim 10, wherein the amino acid residue is L-valinyl.

12. The method of claim 7, wherein the β-L-2'-doexynucleoside has the formula:

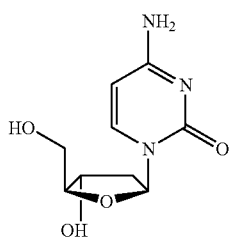

or a pharmaceutically acceptable salt, ester or prodrug thereof.

13. The method of claim 7, wherein the β-L-2'-doexynucleoside has the formula:

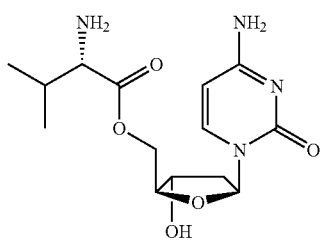

or a pharmaceutically acceptable salt, ester or prodrug thereof.

14. The method of claim 7, wherein the β-L-2'-doexynucleoside has the formula:

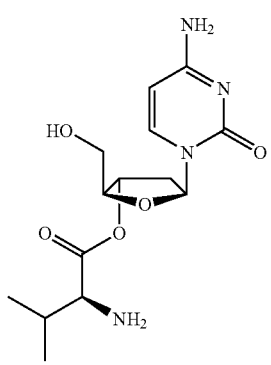

or a pharmaceutically acceptable salt, ester or prodrug thereof.

15. The method of claim 7, wherein the β-L-2'-doexynucleoside has the formula:

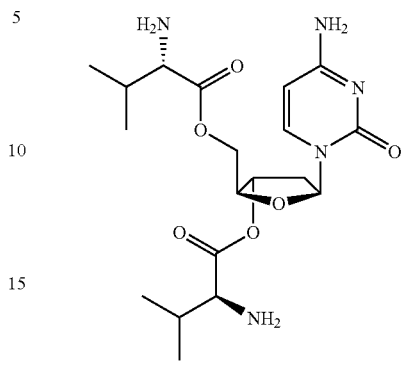

or a pharmaceutically acceptable salt, ester or prodrug thereof.

16. The method of claim 6, wherein the β-L-2'-doexynudeoside has the formula:

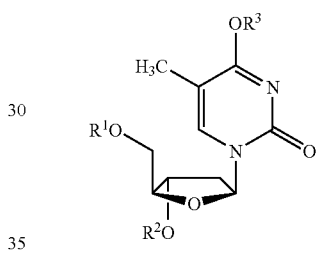

or a pharmaceutically acceptable salt, ester or prodrug thereof;

R[1] and R[2] are independently hydrogen, straight chained, branched or cyclic alkyl, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate; and R[3] is hydrogen, straight chained, branched or cyclic alkyl, dialkylaminoalkylene, acyl, acetyl, butyryl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate.

17. The method of claim 16, wherein R[3] is H.

18. The method of claim 16, wherein R[1] and/or R[2] is H.

19. The method of claim 16, wherein at least one of R[1] or R[2] is an amino acid residue of the formula:

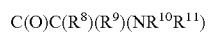

C(O)C(R[8])(R[9])(NR[10]R[11])

wherein:

R[8] is the side chain of an amino acid, alkyl, aryl, heteroaryl, heterocyclic, or can optionally attach to R[10] to form a ring structure;

R[9] is hydrogen, alkyl, or aryl; and

R[10] and R[11] are independently hydrogen, acyl, or alkyl.

20. The method of claim 19, wherein the amino acid residue is L-valinyl.

21. The method of claim 4, wherein the β-L-2'-doexy-nucleoside has the formula:

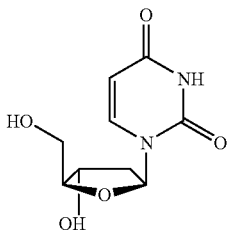

or a pharmaceutically acceptable salt, ester or prodrug thereof.

22. The method of claim 4, wherein the β-L-2'-doexy-nucleoside has the formula:

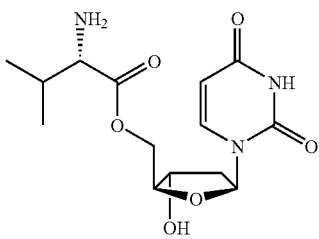

or a pharmaceutically acceptable salt, ester or prodrug thereof.

23. The method of claim 4, wherein the β-L-2'-doexy-nucleoside has the formula:

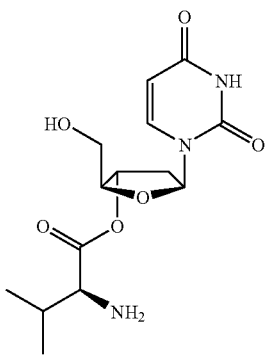

or a pharmaceutically acceptable salt, ester or prodrug thereof.

24. The method of claim 4, wherein the β-L-2'-doexy-nucleoside has the formula:

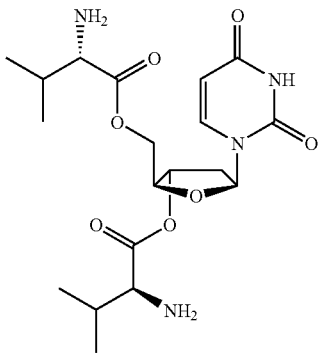

or a pharmaceutically acceptable salt, ester or prodrug thereof.

25. The method of claim 4, wherein the β-L-2'-doexy-nudeoside has the formula:

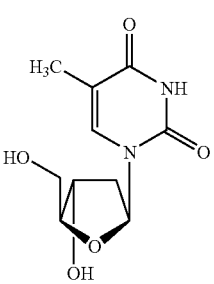

or a pharmaceutically acceptable salt, ester or prodrug thereof.

26. The method of claim 1 or 25 wherein the other anti-HBV agent is selected from the group consisting of 3TC, FTC, L-FMAU, DAPD, DXG, famciclovir, penciclovir, BMS-200475, bis pom PMEA (adefovir, dipivoxil), lobucavir, ganciclovir, tenofovir, Lfd4C, foscamet (trisodium phosphonoformate), isoprinosine, levamizole, N-acetylcystine (NAC), interferon, pegylated interferon, ISS, ribavirin, PC 1323 and polyadencyclic polyuridylic acid.

27. The method of claim 26 wherein the other anti-HBV agent is interferon.

28. The method of claim 27, wherein the interferon is selected from the group consisting of interferon alpha, pegylated interferon alpha, interferon alpha-2a, interferon alpha-2b, pegylated interferon alpha-2a, pegylated interferon alpha-2b interferon beta, interferon gamma, interferon tau, interferon omega, consensus interferon, interferon alphacon-1, natural interferon, interferon beta-1a, omega interferon, oral interferon alpha, interferon gamma-1b, natural human multi-subtype IFN-alpha, and human IFN-beta.

29. The method of claim 1 or 25, wherein the host is a human.

30. The method of claim 4, wherein the β-L-2'-doexy-nucleoside has the formula:

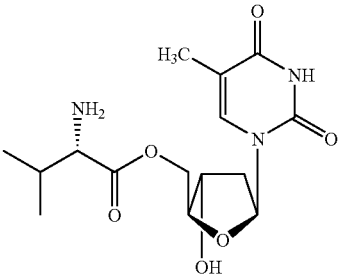

or a pharmaceutically acceptable salt, ester or prodrug thereof.

31. The method of claim 4, wherein the β-L-2'-doexy-nucleoside has the formula:
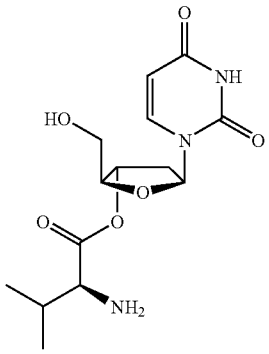
or a pharmaceutically acceptable salt, ester or prodrug thereof.
32. The method of claim 4, wherein the β-L-2'-doexy-nucleoside has the formula:
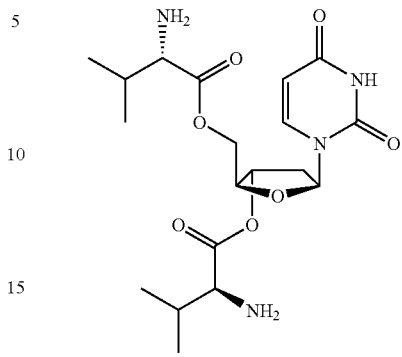
or a pharmaceutically acceptable salt, ester or prodrug thereof.
* * * * *

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial
<220> FEATURE:
<223> OTHER INFORMATION: Immunostimulatory sequence (ISS)

<400> SEQUENCE: 1
tgactgtgaa cgttcgagat ga                                            22

<210> SEQ ID NO 2
<211> LENGTH: 22
<212> TYPE: DNA
<213> ORGANISM: Artificial
<220> FEATURE:
<223> OTHER INFORMATION: Immunostimulatory sequence (ISS)

<400> SEQUENCE: 2
tgaccgtgaa cgttcgagat ga                                            22

<210> SEQ ID NO 3
<211> LENGTH: 23
<212> TYPE: DNA
<213> ORGANISM: Artificial
<220> FEATURE:
<223> OTHER INFORMATION: Immunostimulatory sequence (ISS)

<400> SEQUENCE: 3
tcatctcgaa cgttccacag tca                                           23
```

```
<210> SEQ ID NO 4
<211> LENGTH: 22
<212> TYPE: DNA
<213> ORGANISM: Artificial
<220> FEATURE:
<223> OTHER INFORMATION: Immunostimulatory sequence (ISS)

<400> SEQUENCE: 4
tgactgtgaa cgttccagat ga                                              22

<210> SEQ ID NO 5
<211> LENGTH: 26
<212> TYPE: DNA
<213> ORGANISM: Artificial
<220> FEATURE:
<223> OTHER INFORMATION: Immunostimulatory sequence (ISS)

<400> SEQUENCE: 5
tccataacgt tcgcctaacg ttcgtc                                          26

<210> SEQ ID NO 6
<211> LENGTH: 22
<212> TYPE: DNA
<213> ORGANISM: Artificial
<220> FEATURE:
<223> OTHER INFORMATION: Immunostimulatory sequence (ISS)
<220> FEATURE:
<221> NAME/KEY: misc_feature
<222> LOCATION: (11)..(11)
<223> OTHER INFORMATION: 5-bromocytosine

<400> SEQUENCE: 6
tgactgtgaa ngttccagat ga                                              22

<210> SEQ ID NO 7
<211> LENGTH: 22
<212> TYPE: DNA
<213> ORGANISM: Artificial
<220> FEATURE:
<223> OTHER INFORMATION: Immunostimulatory sequence (ISS)
<220> FEATURE:
<221> NAME/KEY: misc_feature
<222> LOCATION: (11)..(11)
<223> OTHER INFORMATION: 5-bromocytosine

<400> SEQUENCE: 7
tgactgtgaa ngttcgagat ga                                              22

<210> SEQ ID NO 8
<211> LENGTH: 22
<212> TYPE: DNA
<213> ORGANISM: Artificial
<220> FEATURE:
<223> OTHER INFORMATION: Immunostimulatory sequence (ISS)
<220> FEATURE:
<221> NAME/KEY: misc_feature
<222> LOCATION: (11)..(11)
<223> OTHER INFORMATION: 5-bromocytosine
<220> FEATURE:
<221> NAME/KEY: misc_feature
<222> LOCATION: (15)..(15)
<223> OTHER INFORMATION: 5-bromocytosine

<400> SEQUENCE: 8
tgactgtgaa ngttngagat ga                                              22
```